US006645933B1

(12) United States Patent
Alitalo et al.

(10) Patent No.: US 6,645,933 B1
(45) Date of Patent: *Nov. 11, 2003

(54) RECEPTOR LIGAND VEGF-C

(75) Inventors: Kari Alitalo, Espoo (FI); Vladimir Joukov, Helsinki (FI)

(73) Assignees: Helsinki University Licensing Ltd. Oy, Helsinki (FI); Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/671,573

(22) Filed: Jun. 28, 1996

Related U.S. Application Data

(63) Continuation-in-part of application No. 08/601,132, filed on Feb. 14, 1996, which is a continuation-in-part of application No. 08/585,895, filed on Jan. 12, 1996, now Pat. No. 6,245,530, which is a continuation-in-part of application No. 08/510,133, filed on Aug. 1, 1995, now Pat. No. 6,221,839.

(51) Int. Cl.[7] ............... A61K 38/18; C07K 14/475; C07K 14/49
(52) U.S. Cl. .............. 514/2; 514/12; 530/350; 530/399
(58) Field of Search ................ 530/399, 413; 435/69.4

(56) References Cited

U.S. PATENT DOCUMENTS

| | | | |
|---|---|---|---|
| 4,959,314 A | 9/1990 | Mark et al. | |
| 5,219,739 A | 6/1993 | Tischer et al. | |
| 5,326,695 A | 7/1994 | Andersson et al. | |
| 5,332,671 A | 7/1994 | Ferrara et al. | |
| 5,607,918 A | 3/1997 | Eriksson et al. | 514/12 |
| 5,932,540 A | 8/1999 | Hu et al. | |
| 5,935,820 A | 8/1999 | Hu et al. | |
| 6,040,157 A | 3/2000 | Hu et al. | |
| 6,130,071 A | 10/2000 | Altialo et al. | |
| 6,451,764 B1 | 9/2002 | Lee et al. | 514/12 |

FOREIGN PATENT DOCUMENTS

| | | |
|---|---|---|
| EP | 0 506 477 A1 | 3/1992 |
| WO | WO 91/09955 | 7/1991 |
| WO | WO 92/20808 | 11/1992 |
| WO | WO 94/12650 | 6/1994 |
| WO | 95/24473 A1 | 9/1995 |
| WO | 95/33050 | 12/1995 |
| WO | 95/33772 | 12/1995 |
| WO | 96/11269 A2 | 4/1996 |
| WO | 96/30046 | 10/1996 |
| WO | 96/39421 | 12/1996 |
| WO | 96/39515 | 12/1996 |
| WO | 97/05250 A | 2/1997 |
| WO | 97/09427 A | 3/1997 |
| WO | 97/17442 A | 5/1997 |

OTHER PUBLICATIONS

Reeck et al. Cell 50,667, 1987.*
Wells. Additivity of mutational effects in proteins. Biochemistry. Vol. 29, No. 37, pp. 8509–8517, Sep. 18, 1990.

Bowie et al. Deciphering the message in protein sequences: tolerance to amino acid substitutions. Science. Vol. 247, pp. 1306–1310, Mar. 16, 1990.

Achen, M.G. et al., "Vascular Endothelial Growth Factor D (VEGF–D) is a Ligand for the Tyrosine Kinases VEGF Receptor 2 (Flk1) and VEGF Receptor 3 (Flt4)," *Proceedings of the National Academy of Science, USA*, 95:548–553 (Jan., 1998).

Adams, M.D. et al., "Initial assessment of human gene diversity and expression patterns based upon 83 million nucleotides of cDNA sequence," *Nature*, 377(6547 Supplement):3–174 (Sep., 1995).

Cohen, T. et al., "VEGF121, A Vascular Endothelial Growth Factor (VEGF) Isoform Lacking Heparin Binding Ability, Requires Cell–Surface Heparan Sulfates for Efficient Binding to the VEGF Receptors of Human Melanoma Cells," *Journal of Biological Chemistry*, 270(190:11322–11326 (May 12, 1995).

Genbank AA151613, "z127h03.s1 Soares pregnant uterus NbHPU Homo sapiens cDNA clone 503189 3'," Hillier, L. et al., Dated May 14, 1997.

Genbank AA425486, "zw46b06.r1 Soares total fetus Nb2HF8 9w Homo sapiens cDNA clone 773075 5' similar to SW:VEGF_MOUSE Q00731 VASCULAR ENDOTHELIAL GROWTH FACTOR PRECURSOR," Deposited by Hillier, L. et al. Dated Oct. 16, 1997.

Genbank N31713, "yy15b12.s1 Homo sapiens cDNA clone 271295 3'," Deposited by Hillier, L. et al. Dated Jan. 10, 1996.

Genbank N31720, "yy15d12.s1 Homo sapiens cDNA clone 271319 3'," Deposited by Hillier, L. et al. Dated Jan. 10, 1996.

Genbank AA406492, "zv12g06.r1 Soares NhHMPu S1 Homo sapiens cDNA clone 75366 5'," Deposited by Hillier, L. et al. Dated May 17, 1997.

Genbank N50972, "yy94b08.s1 Homo sapiens cDNA clone 281175 3'," Deposited by Hillier, L. et al. Dated Feb. 14, 1996.

Genbank AA421713, "zu24b03.s1 Soares NhHMPu S1 Homo sapiens cDNA clone 738893 3'," Deposited by Hillier, L. et al. Dated Oct. 16, 1997.

Genbank N94399, "zb76f04.s1 Soares senescent fibroblasts NbHSF Homo sapiens cDNA clone 309535 3'," Deposited by Hillier, L et al. Dated Aug. 20, 1996.

(List continued on next page.)

*Primary Examiner*—Christine J. Saoud
(74) *Attorney, Agent, or Firm*—Marshall, Gerstein & Borun

(57) ABSTRACT

Provided are polypeptide ligands for the receptor tyrosine kinase, Flt4. Also provided are cDNAs and vectors encoding the ligands, pharmaceutical compositions and diagnostic reagents comprising the ligands, and methods of making and using the ligands.

46 Claims, 56 Drawing Sheets

OTHER PUBLICATIONS

Genbank H05177, "y185b08.r1 Homo sapiens cDNA clone 44993 5'," Deposited by Hillier, L. et al. Dated Jun. 21, 1995.
Genbank AA479987, "zv18h12.s1 Soares NhHMPu S1 Homo sapiens cDNA clone 754055 3'," Deposited by Hillier, L. et al. Dated Aug. 08, 1997.
Genbank H05134, "y185b08.s1 Homo sapiens cDNA clone 44993 3'," Deposited by Hillier, L. et al. Dated Jun. 21, 1995.
Genbank, AA298182 "EST113866 Bone VII Homo sapiens cDNA 5' end," Deposited by Adams, M.D. et al. Dated Apr. 18, 1997.
Genbank AA298283, "EST113896 Bone VII Homo sapiens cDNA 5' end similar to similar to vascular endothelial growth factor," Deposited by Adams, M.D. et al. Dated Apr. 18, 1997.
Genbank T81481, "yd29f07.s1 Homo sapiens cDNA clone 109669 3'," Deposited by Hillier, L. et al. Dated Mar. 15, 1995.
Genbank AA425303, "zw46b06.s1 Soares total fetus Nb2HF8 9w Homo sapiens cDNA clone 773075 3', mRNA sequence," Deposited by Hillier, L. et al. Dated Oct. 16, 1997.
Genbank Z40230, "H. sapiens partial cDNA sequence; clone c–1wf11," Deposited by Genexpress. Dated Sep. 21, 1995.
Genbank Z44272, "H. sapiens partial cDNA sequence; clone c–1wf11," Deposited by Genexpress, Dated Sep. 21, 1995.
Genbank AA478766,"zv18h12.r1 Soares NhHMPu S1 Homo sapiens cDNA clone 754055 5', " Deposited by Hillier, L. et al. Dated Aug. 08, 1997.
Genbank H96876, "yw04b12.s1 Soares melanocyte 2NbHM Homo sapiens cDNA clone 251231 3'," Deposited by Hillier, L. et al. Dated Nov. 25, 1996.
Genbank H96533, "yw04b12.r1 Soares melanocyte 2NbHM Homo sapiens cDNA clone 251231 5'," Deposited by Hillier, L. et al. Dated Nov. 25, 1996.
Genbank T81690, "yd29f07.r1 Homo sapiens cDNA clone 109669 5' similar to SP:BAR3_CHITE Q03376 BALBIANI RING PROTEIN 3," Deposited by Hillier, L. et al. Dated Mar. 15, 1995.
Genbank T84377, "yd37h08.r1 Homo sapiens cDNA clone 110463 5' similar to SP:BAR3_CHITE Q03376 BALBIANI RING PROTEIN 3," Deposited by Hillier, L. et al. Dated Mar. 16, 1995.
Genbank N42368, "yy15b11.r1 Homo sapiens cDNA clone 271293 5'," Deposited by Hillier, L. et al. Dated Jan. 25, 1996.
Genbank N42374, "yy15b11.r1 Homo sapiens cDNA clone 271317 5'," Deposited by Hillier, L. et al. Dated Jan. 25, 1996.
Genbank H81868, "yy83d09.r1 Homo sapiens cDNA clone 249329 5'," Deposited by Hillier, L. et al. Dated Nov. 9, 1995.
Genbank H81867, "yv83d09.r1 Homo sapiens cDNA clone 249329 5'," Deposited bu Hillier, L. et al. Dated Nov. 9, 1995.
Genbank AA149461, "z127h03.r1 Soares pregnant uterus NbHPU Homo sapiens cDNA clone 503189 5' similar to SW:BAR3_CHITE Q03376 BALBIANI RING PROTEIN 3 PRECURSOR," Deposited by Hillier, L. et al. Dated May 14, 1997.

Genbank R77495, "yi79e04.s1 Homo sapiens cDNA clone 145470 3'," Deposited by Hillier, L. et al. Dated Jun. 7, 1995.
Genbank H07899, "y186g06.s1 Homo sapiens cDNA clone 45138 3'," Deposited by Hillier, L. et al. Dated Jun. 23, 1995.
Genbank T89295, "y37h08.s1 Homo sapiens cDNA clone 110463 3'," Deposited by Hillier, L. et al. Dated Mar. 20, 1995.
Genbank C21512, "HUMGS0010510, Human Gene Signature, 3'–directed cDNA sequence," Deposited by Okubo, K. Dated Oct. 1, 1996.
Genbank N82975, "TgESTzy53h10.r1 TgRH Tachyzoite cDNA Toxoplasma gondii cDNA clone tgzy53h10.r1 5'," Deposited by Hehl, A. et al. Dated Sep. 10, 1997.
Genbank AA549856, "0929m3 gmbPfHB3.1, G. Roman Reddy Plasmodium falciparum genomic clone 0929m," Deposited by Dame, J.B. et al. Dated Aug. 11, 1997.
Jeltsch, M. et al., "Hyperplasia of Lymphatic Vessels in VEGF–C Transgenic Mice," *Science,* *276*:1423–1425 (May, 1997).
Joukov, V. et al., "Proteolytic Processing Regulates Receptor Specificity and Activity of VEGF–C," *EMBO Journal,* *16*(13):3898–3911 (Jun., 1997).
Joukov, V. et al., "A Recombinant Mutant Vascular Endothelial Growth Factor–C that has Lost Vascular Endothelial Growth Factor Receptor–2 Binding, Activation, and Vascular Permeability Activties," *Journal of Biological Chemistry,* *273*(12):6599–6602 (Mar. 20, 1998).
Lee, J. et al., "Vascular Endothelial Growth Factor Related Protein (vrp): A Ligand and Specific Activator of the Tyrosine Kinase Receptor Flt4," EMBL Sequence Data Library, XP002066361, accession No. U4142. Dated Jan. 10, 1996.
U.S. patent application Ser. No. 09/534,376, Altialo et al., filed Mar. 24, 2000.
U.S. patent application Ser. No. 09/375,248, Altialo et al., filed Aug. 16, 1999.
U.S. patent application Ser. No. 09/355,700, Altialo et al.
Bowie, et al., "Deciphering the Message in Protein Sequences: tolerance to amino acid substitutions," *Science* 247:1306–1310(1990).
Capecchi, M.R., "Altering the Genome by Homologous Recombination," *Science* 244:1288–1292 (1989).
Chen, et al., "Selective Degradation of Early–Response–Gene mRNAs: Functional Analyses of Sequence Features of the AU–Rich Elements," *Mol. Cell Biol.* 14:8471–8482 (1994).
Claesson–Welsh, et al., "cDNA Cloning and Expression of the Human A–type Platelet–Derived Growth Factor (PDGF) Receptor Establishes Structural Similarity to the B–type PDGF Receptor," *Proc. Natl. Acad. Sci. USA* 86:4917–4921 (1989).
Claesson–Welsh, et al., "cDNA Cloning and Expression of the Human A–type Platelet–Derived Growth Factor (PDGF) Receptor Specific for B–Chain–Containing PDGF Molecules," *Mol. Cell Biol.* 8:3476–3486(1988).
Collins, et al., "Cultured Human Endothelial Cells Express Platelet–Derived Growth Factor B Chain: cDNA Cloning and Structural Analysis," *Nature* 316:748–750 (1985).
Fukumura, et al., "Tumor Necrosis Factor β–induced Leukocyte Adhesion in Normal and Tumor Vessels: Effect of Tumor Type, Transplantation Site, and Host Strain," *Cancer Research* 55:4824–4829 (1995).

Genbank AAA85214, "Vascualr Endothelial Growth Factor Related Protein," Lee, et al., Dated Jan. 9, 1996.

Genbank M21616, "Human Platelet–derived Growth Factor (PDGF) Receptor mRNA, Complete cds." Deposited by Claesson–Welsh et al., Dated Sep. 28, 1992.

Genbank M22734, "Human Platlet–derived Growth Factor A Type Receptor mRNA, Complete cds.," Deposited by Claesson–Welsh, et al., Dated Jan. 7, 1995.

Genbank M32977, "Human Heparin–binding Vascular Endothelial Growth Factor (VEGF) mRNA, Complete cds." Deposited by Leung et al., Dated Feb. 28, 1991.

Genbank U48801, "Human Vascular Endothelial Growth Factor B Precursor (VEGF–B) mRNA, Complete cds." Deposited by Olofsson et al., Dated Aug. 19, 1996.

Genbank X02811, "Human mRNA for Platelet–derived Growth Factor B Chain (PDGF–B)," Deposited by Collins et al. Dated Mar. 27, 1995.

Genbank X15997, "Human Vascular Permeability Factor mRNA, Complete Cds.," Deposited by Keck et al., Dated Jun. 15, 1990.

Genbank X54936, "H. sapiens mRNA for Placenta Growth Factor (PIGF)", Deposited by Persico, M.G., Dated Nov. 12, 1991.

Hillier, et al., y185b08.21 Homo sapiens cDNA clone 44993 5'. EST–STS Accession No. H05177 (Jun. 21, 1995).

Hillier, et al., y186g06.r1 Homo sapiens cDNA clone 45138 5'. EST–STS Accession No. H07991 (Jun. 23, 1995).

Hillier, et al., yd29f07.r1 Homo sapiens cDNA clone 109669 5' similar to SP:BAR3_CHITE Q03376 BALBIANI RING PROTEIN 3. EST–STS Accession No. T81690 (Mar. 15, 1995).

Keyt, et al. "Identification of Vascular Endothelial Growth Factor Determinants for Binding KDR and FLT–1 Receptors," *J. Biol. Chem.* 271:5638–5646 (1996).

Kim, et al. "The Vascular Endothelial Growth Factor Proteins: Identification of Biologically Relevant Regions by Neutralizing Monoclonal Antibodies," *Growth Factors* 7:53–64 (1992).

Korhonen, et al. "The Mouse Tie Receptor Tyrosine Kinase Gene: Expression During Ambryonic Angiogenesis," *Oncogene* 9:395–403 (1994).

Leak, L.V., "Electron Microscopic Observations on Lymphatic Capillaries and the Structural Components of the Connective Tissue–Lymph Interface" *Micsovasc. Res.* 2:361–391 (1970).

Leu, et al. "Flow Velocity in the Superficial Lymphatic Network of the Mouse Tail," *Am. J. Physiol.* 267:H1507–H1513 (1994).

Miles, et al. "Vascular reactions to Histamine, Histamine–Liberator and Leukotaxine in the Skin of Guinea–Pigs," *J. Physiol.* 118:228–257 (1952).

Muragaki, et al. "Mouse Col18a1 is expressed in a tissue–specific manner as three alternative variants and is localized in basement membrane zones," *Proc. Nat'l Acad. Sci. USA* 92:7683–8776 (1995).

Orlandini, et al., "Identification of a c–fos–induced gene that is related to the platelet–derived growth factor/vascular endothelial growth factor family," *Proc. Nat'l Acad. Sci., USA* 93:11675–11680 (1996).

Schmelz, et al., "*Complexus adhaerentes*, A New Group of Desmoplakin–Containing Junctions in Endothelial Cells:II. Different Types of Lymphatic Vessels," *Differentiation* 57:97–117 (1994).

Swartz, et al., "Transport in Lymphatic Capillaries. I. Macroscopic Measurements Using Residue Time Distribution Theory," *Am. J. Physiol.* 270:H324–329 (1996).

Udaka, et al., "Simple Method for Quantitation of Enhanced Vascular Permeability," *Proc. Soc. Exp. Biol. Med.* 133:1384–1387 (1970).

Vassbotn, et al., "Reversion of Autocrine Transformation by a Dominant Negative Platelet–Derived Growth Factor Mutant," *Mol. Cell. Biol.*, 13:4066–4976 (1993).

Wells, "Additivity of Mutational Effects in Proteins," *Biochemistry* 29:8509–8517 (1990).

Andersson et al., "Assignment of Interchain Disulfide Bonds in platelet–Derived Growth Factor (PDGF) and Evidence for Agonist Activity of Monomeric PDGF," *J. Biol. Chem.*, 267(16):11260–11266 (Jun. 5, 1992).

Aprelikova et al., "FLT4, A Novel Class III Receptor Tyrosine Kinase in Chromosome 5q33–qter," *Cancer Research*, 52:746–748 (Feb. 1, 1992).

Ausprunk, et al., "Migration and Proliferation of Endothelial Cells in Preformed and Newly Formed Blood Vessels during Tumor Angiogenesis," *Microvasc. Res.*, 14:53–65 (1977).

Basilico et al., "The FGF Family of Growth Factors and Oncogenes," *Adv. Cancer Res.*, 59:145–165 (1992).

Berse et al., "Vascular Permeability Factor (Vascular Endothelial Growth Factor) Gene is Expressed Differentially in Normal Tissues, Macrophages, and Tumors," *Mol. Biol. Cell.*, 3:211–220 (Feb., 1992).

Betsholtz et al., "cDNA Sequence and Chromosomal Localization of Human Platelet–Derived Growth Factor A–Chain and Its Expression in Tumor Cell Lines," *Nature*, 320:695–699 (Apr., 1986).

Borg et al., "Biochemical Characterization of Two Isoforms of FLT4, a VEGF Receptor–Related Tyrosine Kinase," *Oncogene*, 10:973–84 (1995).

Breier et al., "Expression of Vascular Endothelial Growth Factor During Ebryonic Angiogenesis and Endothelial Cell Differentiation," *Development*, 114:521–532 (1992).

Cao et al., "Heterodimers of Placenta Growth Factor/Vascular Endothelial Growth Factor," *J. Biol. Chem.*, 271(6):3154–3162 (Feb. 9, 1996).

Cheng and Flanagan, "Identification and Cloning of ELF–1, A Developmentally Expressed Ligand for the Mek4 and Sek Receptor Tyrosine Kinases," *Cell* 79:157–168 (Oct. 7, 1994).

Claesson–Welsh et al., "Identification and Structural Analysis of the A Type Receptor for Platelet–derived Growth Factor," *J. Biol. Chem.*, 264(3):1742–1747 (Jan. 25, 1989).

Coffin et al., "Angioblast Differentiation and Morphogenesis of the Vascular Endothelium in the Mouse Embryo," *Devel. Biol.*, 148:51–62 (1991).

Curran and Franza, "Fos and Jun: The AP–1 Connection," *Cell*, 55:395–397 (Nov. 4, 1988).

De Vries et al., "The fms–Like Tyrosine Kinase, a Receptor for Vascular Endothelial Growth Factor," *Science*, 255:989–991 (Feb. 21, 1992).

Dignam et al., "Balbiani Ring 3 in *Chironomus tentans* Encodes a 185–kDa Secretory Protein Which is Synthesized Throughout the Fourth Larval Instar," *Gene*, 88:133–140 (1990).

DiSalvo et al., "Purification and Characterization of a Naturally Occurring Vascular Endothelial Growth Factor: Placenta Growth Factor Heterodimer," *J. Biol. Chem.*, 270(13):7717–7723 (Mar. 31, 1995).

Don et al., "'Touchdown' PCR to Circumvent Spurious Priming During Gene Amplification," *Nucl. Acids Res.,* 19:4008 (1991).

Dumont et al., "Dominant–negative and Targeted Null Mutations in the Endothelial Receptor Tyrosine Kinase, tek, Reveal a Critical Role in Vasculogenesis of the Embryo," *Genes Dev.,* 8:1897–1909 (1994).

Dumont et al., "Vascularization of the Mouse Embryo: A Study of flk–1, tek, tie and Vascular Endothelial Growth Factor Expression During Development," *Development Dynamics,* 203:80–92 (1995).

Dvorak et al., "Review: Vascular Permeability Factor/Vascular Endothelial Growth Factor, Microvascular Hyperpermeability, and Angiogenesis," *Amer. J. Path.,* 146:1029–1039 (1995).

Eichmann et al., "Two Molecules Related to the VEGF Receptor are Expressed in Early Endothelial Cells During Avian Embryonic Development," *Mech. Dev.,* 42:33–48 (1993).

Ferrara et al., "Molecular and Biological Properties of the Vascular Endothelial Growth Factor Family of Proteins," *Endocrine Rev.,* 13(1):18–32 (1992).

Finnerty et al., "Molecular Cloning of Murine FLT and FLT4," *Oncogene,* 8(11):2293–2298 (1993).

Flamme et al., "Vascular Endothelial Growth Factor (VEGF) and VEGF–Receptor 2 (flk–1) are Expressed During Vasculogenesis and Vascular Differentiation in the Quail Embryo," *Devel. Biol.,* 169:699–712 (1995).

Flanagan and Leder, "The kit Ligand: A Cell Surface Molecule Altered in Steel Mutant Fibroblasts," *Cell,* 63:185–194 (Oct. 5, 1990).

Folkman, "Angiogenesis in Cancer, Vascular, Rheumatoid and Other Disease," *Nature Med.,* 1(1):27–31 (1995).

Folkman et al., "Angiogenesis," *J. Biol. Chem.,* 267(16):10931–10934 (Jun. 5, 1992).

Folkman et al., "Long–term Culture of Capillary Endothelial Cells," *Proc. Nat'l Acad. Sci., USA,* 76(10):5217–5221 (Oct., 1979).

Fong et al., "Role of the Flt–1 Receptor Tyrosine Kinase in Regulating the Assembly of Vascular Endothelium," *Nature,* 376:66–70 (Jul. 6, 1995).

Fournier et al., "Mutation of Tyrosine Residue 1337 Abrogates Ligand–Dependent Transforming Capacity of the FLT4 Receptor," *Oncogene,* 11(5):921–931 (Sep. 7, 1995).

Friesel et al., "Molecular Mechanisms of Angiogenesis: Fibroblast Growth Factor Signal Transduction," *FASEB J.,* 9:919–25 (1995).

Galland et al., "The Flt4 Gene Encodes a Transmembrane Tyrosine Kinase Related to the Vascular Endothelial Growth Factor Receptor," *Oncogene,* 8:1233–1240 (1993).

Genbank S66407, "FLT4 Receptor Tyrosine Kinase Isoform FLT4 Long (3' Region, Alternatively Spliced) [Human, mRNA Partial, 216 nt].," Deposited by Pajusola et al., Dated Dec. 17, 1993.

Genbank U48800, "Mus Musculus Vascular Endothelial Growth Factor B Precursor (VEGF–B) mRNA, Complete Cds.," Deposited by Olofsson et al., Dated Aug. 19, 1996.

Genbank X15997, "Human Vascular Permeability Factor mRNA, Complete Cds.," Deposited by Keck et al., Dated Jun. 15, 1990.

Genbank X60280, "Vector Plasmid pLTRpoly DNA.," Deposted by Maekelae, T.P., Dated Jul. 16, 1996.

Genbank X68203, "H. sapiens mRNA for FLT4, Class III Receptor Tyrosine Kinase.," Deposited by Aprelikova, O., Dated Nov. 30, 1993.

Genbank X94216, "Homo sapiens mRNA for VEGF–C protein," Deposited by Joukov et al., Dated Feb. 6, 1996.

Harlow et al., *Antibodies, a Laboratory Manual,* Cold Spring Harbor Laboratory Press, pp. 72–137, 141–157, 287 & 321–358 (1988).

Heldin et al., "Structure of Platelet–Derived Growth Factor: Implications for Functional Properties," *Growth Factors,* 8:245–252 (1993).

Joukov et al., "A Novel Vascular Endothelial Growth Factor, VEGF–C, Is a Ligand for the Flt4 (VEGFR–3) and KDR (VEGFR–2) Receptor Tyrosine Kinases," *EMBO J.,* 15(2):290–298 (1996).

Kaipainen et al., "Expression of the FMS–Like Tyrosine Kinase 4 Gene Becomes Restricted to Lymphatic Endothelium During Development," *Proc. Nat'l Acad. Sci., USA,* 92:3566–3570 (Apr., 1995).

Kaipainen et al., "The Related FLT4, FLT1 and KDR Receptor Tyrosine Kinases Show Distinct Expression Patterns in Human Fetal Endothelial Cells," *J. Exp. Med.,* 178:2077–2088 (Dec., 1993).

Kaipainen et al., "Enhanced Expression of the Tie Receptor Tyrosine Kinase Messenger RNA in the Vascular Endothelium of Metastatic Melanomas," *Cancer Res.,* 54:6571–6577 (Dec. 15, 1994).

Kozak, "An Analysis of 5'–Non–Coding Sequences from 699 Vertebrate Messenger RNAs," *Nucl. Acids Res.* 15:8125–8148 (1987).

Lee et al., "Vascular Endothelial Growth Factor–Related Protein: A Ligand and Specific Activator of the Tyroisne Kinase Receptor Flt4," *Proc. Nat'l Acad. Sci., USA,* 93: 1988–1992 (Mar., 1996).

Leung et al., "Vascular Endothelial Growth Factor Is a Secreted Angiogenic Mitogen," *Science,* 246:1306–1309 (Dec. 8, 1989).

Levy et al., "Post–transcriptional Regulation of Vascular Endothelial Growth Factor by Hypoxia," *J. Biol. Chem.,* 271(5):2746–4753 (Feb. 2, 1996).

Levy et al., "Transcriptional Regulation of the Rat Vascular Endothelial Growth Factor Gene by Hypoxia," *J. Biol. Chem.,* 270(22):13333–13340 (Jun. 2, 1995).

Lyman et al., "Molecular Cloning of a Ligand for the flt3/ftk–2 Tyrosine Kinase Receptor: A Proliferative Factor for Primitive Hematopoietic Cells," *Cell,* 75:1157–1167 (Dec. 17, 1993).

Maglione et al., "Isolation of a Human Placenta cDNA Coding for a Protein Related to the Vascular Permeability Factor," *Proc. Nat'l Acad. Sci., USA,* 88:9267–9271 (Oct., 1991).

Maglione et al., "Two Alternative mRNAs Coding for the Angiogenic Factor, Placenta Growth Factor (PIGF) are Transcribed from a Single Gene of Chromosome 14," *Oncogene,* 8:925–931 (1993).

Mäkelä et al., "Plasmid pLTRpoly: A Versatile High–Efficiency Mammalian Expression Vector," *Gene,* 118:293–294 (1992).

Matthews et al., "A Receptor Tyrosine Kinase cDNA Isolated from a Population of Enriched Primitive Hematopoietic Cells and Exhibiting Close Genetic Linkage to c–kit," *Proc. Nat'l Acad. Sci., USA,* 88:9026–9030 (Oct., 1991).

Metzelaar et al., "CD63 Antigen," *J. of Biol. Chem.,* 266(5):3239–3245 (Feb. 15, 1991).

Millauer et al., "Glioblastoma Growth Inhibited in vivo by a Dominant–Negative Flk–1 Mutant," *Nature, 367*:576–579 (Feb. 10, 1994).

Millauer et al., "High Affinity VEGF Binding and Developmental Expression Suggest Flk–1 as a Major Regulator of Vasculogenesis and Angiogenesis," *Cell, 72*:835–846 (Mar. 26, 1993).

Mitchell et al., "Transcription Factor AP–2 is Expressed in Neural Crest Cell Lineages During Mouse Embryogenesis," *Genes and Dev., 5*:105–119 (1991).

Morgenstern et al., "Advanced Mammalian Gene Transfer: High Titre Retroviral Vectors With Multiple Drug Selection Markers and a Complementary Helper–Free Packaging Cell Line," *Nucl. Acids Res., 18(12)*:3587–3595 (1990).

Mount, S.M., "A Catalogue of Splice Junction Sequences," *Nucl. Acids Res., 10(2)*:459–472 (1982).

Mustonen et al., "Endothelial Receptor Tyrosine Kinases Involved in Angiogenesis," *J. Cell Biol., 129*:895–898 (May, 1995).

Nelson and Sun, "The 50– and 58–kdalton Keratin Classes as Molecular Markers for Stratified Squamous Epithelia: Cell Culture Studies," *J. Cell Biol., 97*:244–251 (Jul., 1983).

Neufeld et al., "Vascular Endothelial Growth Factor and Its Receptors," *Prog. Growth Fact. Res., 5*:89–97 (1994).

Oefner et al., "Crystal Structue of Human Platelet–derived Growth Factor BB," *EMBO J., 11(11)*:3921–3926 (1992).

Oelrichs et al., "NYK/FLK–1: A Putative Receptor Tyrosine Kinase Isolated from E10 Embryonic Neuroepithelium is Expressed in Endothelial Cells of the Developing Embryo," *Oncogene, 8*:11–18 (1993).

Olofsson et al., "Vascular Endothelial Growth Factor B, A Novel Growth Factor for Endothelial Cells," *Proc. Nat'l Acad. Sci., USA, 93*:2576–2581 (Mar., 1996).

Paavonen et al., "Novel Human Vascular Endothelial Growth Factor Genes VEGF–B and VEGF–C Localized to Chromosomes 11q13 and 4q34, Respectively," *Circulation 93(6)*:1079–1082 (Mar. 15, 1996).

Pajusola et al., "FLT4 Receptor Tyrosine Kinase Contains Seven Immunoglobulin–Like Loops and Is Expressed in Multiple Human Tissues and Cell Lines," *Cancer Res., 52*:5738–5743 (Oct. 15, 1992).

Pajusola et al., "Signalling Properties of FLT4, a Proteolytically Processed Receptor Tyrosine Kinase Related to Two VEGF Receptors," *Oncogene, 9*:3545–3555 (1994).

Pajusola et al., "Two Human FLT4 Receptor Tyrosine Kinase Isoforms With Distinct Carboxy Terminal Tails are Produced by Alternative Processing of Primary Transcripts," *Oncogene, 8*: 2931–2937 (1993).

Park et al., "Placenta Growth Factor, Potentiation of Vascular Endothelial Growth Factor Bioactivity In vitro and In vivo, and High Affintiy Binding to Flt–1 but not to Flk–1/KDR," *J. Biol. Chem., 269(41)*:25646–25654 (Oct. 14, 1994).

Partanen et al., "A Novel Endothelial Cell Surface Receptor Tyrosine Kinase with Extracellular Epidermal Growth Factor Homology Domains," *Mol. & Cell. Biol., 12(4)*:1698–1707 (Apr., 1992).

Partanen et al., "Putative Tyrosine Kinases Expressed in K–562 Human Leukemia Cells," *Proc. Nat'l Acad. Sci., USA, 87*:8913–8917 (Nov., 1990).

Paulsson et al., "The Balbiani Ring 3 Gene in *Chironomus tentans* has a Diverged Repetitive Structure Split by Many Introns," *J. Mol. Biol., 211*:331–349 (1990).

Pear et al., "Production of High–titer Helper–free Retroviruses by Transient Transfection," *Proc. Nat'l Acad. Sci., USA, 90*:8392–8396 (Sep., 1993).

Pertovaara et al., "Vascular Endothelial Growth Factor Is Induced in Response to Transforming Growth Factor–β in Fibroblastic and Epithelial Cells," *J. Biol. Chem., 269(9)*:6271–6274 (Mar. 4, 1994).

Peters et al., "Vascular Endothelial Growth Factor Receptor Expression during Embryogenesis and Tissue Repair Suggests a Role in Endothelial Differentiation and Blood Vessel Growth," *Proc. Nat'l Acad. Sci., USA, 90*:8915–8918 (Oct., 1993).

Pötgens et al., "Covalent Dimerization of Vascular Permeability Factor/Vascular Endothelial Growth Factor Is Essential for Its Biological Activity," *J. Biol. Chem., 269(52)*:32879–32885 (Dec. 30, 1994).

Puri et al., "The Receptor Tyrosine Kinase TIE is Required for Integrity and Survival of Vascular Endothelial Cells," *EMBO J., 14*:5884–5891 (1995).

Quinn et al., "Fetal Liver Kinase 1 is a Receptor for Vascular Endothelial Growth Factor and is Selectively Expressed in Vascular Endothelium," *Proc. Nat'l Acad. Sci., USA, 90*:7533–7537 (Aug., 1993).

Risau et al., "Changes on the Vascular Extracellular Matrix During Embryonic Vasculogenesis and Angiogenesis," *Devel. Biol., 125*:441–450 (1988).

Risau et al., "Platelet–Derived Growth Factor is Angiogenic In Vivo," *Growth Factors, 7*:261–266 (1992).

Risau, W., "Differentiation of Endothelium," *FASEB J., 9*:926–933 (1995).

Sabin, F.R., "The Lymphatic System in Human Embryos, With A Consideration of the Morphology of the System as a Whole," *Am. J. Anat., 9(1)*:43–91 (1909).

Saksela et al., "Cell–Associated Plasminogen Activation: Regulation and Physiological Function," *Ann. Rev. Cell Biol., 4*:93–126 (1988).

Sambrook et al., *Molecular Cloning: a Laboratory Manual*, Second Edition, Cold Spring Harbor, New York: Cold Spring Harbor Laboratory (1989), pp. 2.60–2.79, 4.21–4.32, 7.3–7.36, and 9.47–9.51.

Sato et al., "Distinct Roles of the Receptor Tyrosine Kinases Tie–1 and Tie–2 in Blood Vessel Formation," *Nature, 376*:70–74 (Jul. 6, 1995).

Schneider et al., "A One–step Purification of Membrane Proteins Using a High Efficiency Immunomatrix," *J. Biol. Chem., 257(18)*:10766–70769 (Sep. 25, 1982).

Seetharam et al., "A Unique Signal Transduction from FLT Tyrosine Kinase, a Receptor for Vascular Endothelial Growth Factor VEGF," *Oncogene, 10*:135–147 (1995).

Senger et al., "Tumor Cells Secrete a Vascular Permeability Factor That Promotes Accumulation of Ascites Fluid," *Science, 219*:983–985 (Feb. 25, 1983).

Shalaby et al., "Failure of Blood–Island Formation and Vasculogenesis in Flk–1–deficient Mice," *Nature, 376*:62–66 (Jul. 6, 1995).

Shibuya et al., "Nucleotide Sequence and Expression of a Novel Human Receptor–Type Tyrosine Kinase Gene (flt) Closely Related to the fms Family," *Oncogene, 5*:519–524 (1990).

Shibuya, M., "Role of VEGF–FLT Receptor System in Normal and Tumor Angiogenesis," *Adv. Cancer Res., 67*:281–316 (1995).

Shweiki et al., "Patterns of Expression of Vascular Endothelial Growth Factor (VEGF) and VEGF Receptors in Mice Suggest a Role in Hormonally Regulated Angiogenesis," *J. Clin. Invest.*, 91:2235–2243 (May, 1993).

Sitaras et al., "Constitutive Production of Platelet–Derived Growth Factor–Like Proteins by Human Prostate Carcinoma Cell Lines," *Cancer Research*, 48(7):1930–1935 (Apr. 1, 1988).

Southern and Berg, "Transformation of Mammalian Cells to Antibiotic Resistance with a Bacterial Gene Under Control of the SV40 Early Region Promoter," *J. Mol. Appl. Genet.*, 1, 327–341 (1982).

Terman et al., "Identification of New Endothelial Cell Growth Factor Receptor Tyrosine Kinase," *Oncogene*, 6:1677–1683 (1991).

Terman et al., "Identification of the KDR Tyrosine Kinase as a Receptor for Vascular Endothelial Cell Growth Factor," *Biochem. Biophys. Res. Commun.*, 187:1579–1586 (Sep. 30, 1992).

Terman et al., "VEGF Receptor Subtypes KDR and FLT1 Show Different Sensitivities to Heparin and Placenta Growth Factor," *Growth Factors*, 11(3):187–195 (1994).

Tessier et al., "Enhanced Secretion From Insect Cells of a Foreign Protein Fused to the Honeybee Melittin Signal Peptide," *Gene*, 98:177–183 (1991).

Tischer et al., "The Human Gene for Vascular Endothelial Growth Factor. Multiple Protein Forms are Encoded Through Alternative Exon Splicing," *J. Biol. Chem.*, 266(18):11947–11954 (Jun. 25, 1991).

Van der Geer et al., "Receptor–Tyrosine Kinases and Their Signal Transduction Pathways," *Ann. Rev. Cell Biol.*, 10:251–337 (1994).

Vassar et al., "Tissue–specific and Differentiation –specific Expression of a Human K14 Keratin Gene in Transgenic Mice," *Proc. Nat'l Acad,. Sci., USA*, 86:1563–1567 (Mar., 1989).

Vassar et al., "Transgenic Mice Provide New Insights Into the Role of TGF–α During Epidermal Development and Differentiation," *Genes & Dev.*, 5:714–727 (1991).

Västrik et al., "Expression of the Mad Gene During Cell Differentiation In Vivo and Its Inhibition of the Cell Growth In Vitro," *J. Cell. Biol.*, 128(6):1197–1208, (Mar., 1998).

von Heijne, G., "A New Method for Predicting Signal Sequence Cleavage Sites," *Nucleic Acids Res.*, 14(11):4683–4690 (1986).

Waltenberger et al., "Different Signal Transduction Properties of KDR and Flt1, Two Receptors for Vascular Endothelial Growth Factor," *J. Biol. Chem*, 269(43):26988–26995 (Oct. 28, 1994).

Wanaka et al., "Expression of FGF Receptor Gene in Rat Development," *Development*, 111:455–468 (1991).

Wen et al., "Neu Differentiation Factor: A Transmembrane Glycoprotein Containing an EGF Domain and an Immunoglobulin Homology Unit," *Cell* 69:559–572 (May 1, 1992).

Yamane et al., "A New Communication System Between Hepatocytes and Sinusoidal Endothelial Cells in Liver Through Vascular Endothelial Growth Factor and Flt Tyrosine Kinase Receptor Family (Flt–1 and KDR/Flk–1)," *Oncogene*, 9:2683–2690 (1994).

Alitalo et al., "Vascular Endothelial Growth Factors and Receptors Involved in Angiogenesis," *The 9th International Conference of the International Society of Differentiation (ISD), Development, Cell Differentiation and Cancer*, Pisa (Italy), Sep. 28–Oct. 2, 1996, p. 66 (ABSTRACT S22).

Alitalo et al., "Vascular Endothelial Growth Factors B and C and Receptors Involved in Angiogenesis," *German–American Academic Council Foundation (GAAC)/ Stiftung Deutsch–Amerikanisches Akademisches Konzil (DAAK), 2nd Symposium on Current Problems in Molecular Medicine: The Role of Cytokines in Human Disease*, Nov. 17–20, 1996, Ringberg Castle, Germany, p. 1 (ABSTRACT).

Kukk et al., "VEGF–C Receptor Binding and Pattern of Expression with VEGFR–3 Suggests a Role in Lymphatic Vascular Development," *Development*, 122:3829–3837 (1996).

Paavonen et al., "Chromosomal Localization and Regulation of Human Vascular Endothelial Growth Factors B and C (VEGF–B and VEGF–C)," *IX International Vascular Biology Meeting*, Seattle, Washington, Sep. 4–8, 1996, p. 76 (ABSTRACT 299).

Pajusola, "Cloning and Characterization of a New Endothelial Receptor Tyrosine Kinase Flt4 and Two Novel VEGF–Like Growth Factors VEGF–B and VEGF–C," Academic Dissertation, Molecular/Cancer Biology Laboratory and Department of Pathlogy, Hoartman Instutute and Deparment of Biosciences Division of Genetics, University of Helsinki, (Jan. 26, 1996).

Hillier et al., "The WashU–Merck EST Project," EMBL Database entry HS991157, accession No. H07991, Jul. 2, 1995.

* cited by examiner

*FIG. 5A* *FIG. 5B*
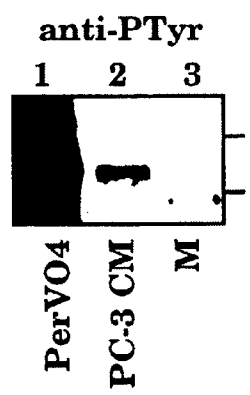 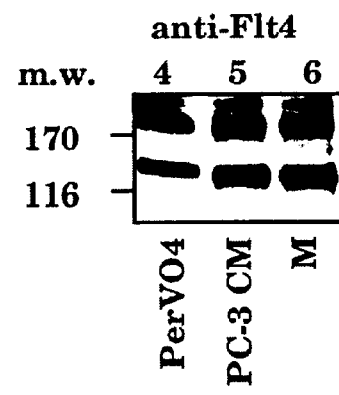 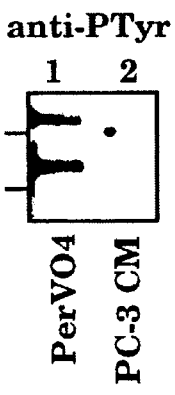
*FIG. 5C*
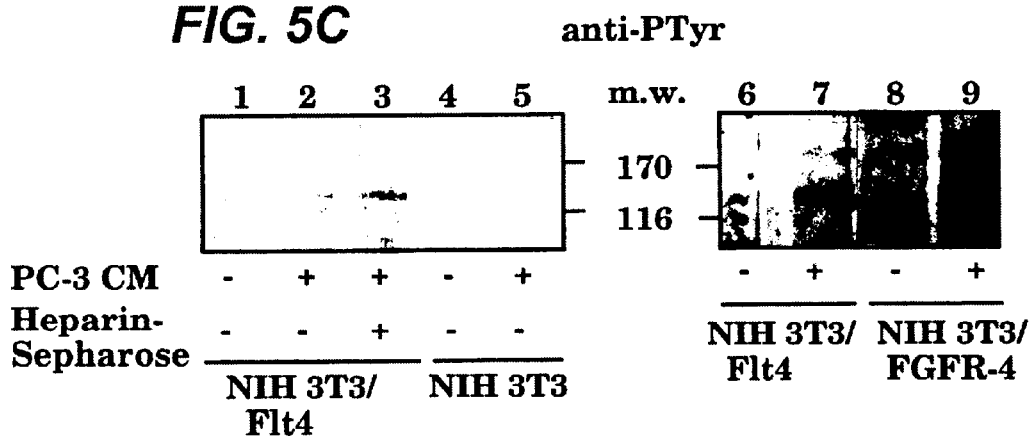

FIG. 10A

```
              1                                                           50
   PDGF-A     ..........  ..........  ..........  ..........  .MRTLACLLL
   PDGF-B     ..........  ..........  ..........  ..........  MNRCWA.LFL
   PlGF-1     ..........  ..........  ..........  ..........  ..........
  VEGF165     ..........  ..........  ..........  ..........  ..........
 VEGF-B167    ..........  ..........  ..........  ..........  ..........
   VEGF-C     MHLLGFFSVA  CSLLAAALLP  GPREAPAAAA  AFESGLDLSD  AEPDAGEATA 51                                                         100
   PDGF-A     LGCGYLAHVL  AEEAEIPREV  IERLARSQIH  SIRDLQRLLE  IDSVGSEDSL
   PDGF-B     SLCCYLRLVS  AEGDPIPEEL  YEMLSDHSIR  SFDDLQRLLH  GDP.GEEDGA
   PlGF-1     ..........  ......MPVM  RLFPC..FLQ  LLAGLAL...  PAVPPQQW..
  VEGF165     ..........  .........M  NFLLS..WVH  WSLALLLYLH  HAKWSQAA..
 VEGF-B167    ..........  .........M  SPLLR..RLL  LAALLQLAPA  QAPVSQP...
   VEGF-C     YASKDLEEQL  RSVSSVDELM  TVLYPEYWKM  YKCQLRKGGW  QHNREQANLN 101                                                        150
   PDGF-A     DTSLRAHGVH  ATKHVPEKRP  LPIRRKRSI.  .....EEAVP  AVCKTRTVIY
   PDGF-B     ELDLNMTRSH  SGGELES...  .LARGRRSLG  SLTIAEPAMI  AECKTRTEVF
   PlGF-1     .....ALSAG  NGSSEVEVVP  FQE.VWGR..  ..........  SYCRALERLV
  VEGF165     .....PMAEG  GGQNHHEVVK  FMD.VYQR..  ..........  SYCHPIETLV
 VEGF-B167    .........D  APGHQRKVVS  WID.VYTR..  ..........  ATCQPREVVV
   VEGF-C     SRTEETIKFA  AAHYNTEILK  SIDNEWRK..  ..........  TQCMPREVCI 151                                                        200
   PDGF-A     EIPRSQVDPT  SANFLIWPPC  VEVKRCTGCC  NTSSVKCQPS  RVHHRSVKVA
   PDGF-B     EISRRLIDRT  NANFLVWPPC  VEVQRCSGCC  NNRNVQCRPT  QVQLRPVQVR
   PlGF-1     DVVSEYPSEV  ..EHMFSPSC  VSLLRCTGCC  GDENLHCVPV  ETANVTMQLL
  VEGF165     DIFQEYPDEI  ..EYIFKPSC  VPLMRCGGCC  NDEGLECVPT  EESNITMQIM
 VEGF-B167    PLTVELMGTV  ..AKQLVPSC  VTVQRCGGCC  PDDGLECVPT  GQHQVRMQIL
   VEGF-C     DVGKEFGVAT  ..NTFFKPPC  VSVYRCGGCC  NSEGLQCMNT  STSYLSKTLF
```

FIG. 10B

```
              201                                                              250
   PDGF-A     KVEYVRKKPK LKEVQVRLEE HLECACAT.. .......... TSLNPDYREE
   PDGF-B     KIEIVRKKPI FKKATVTLED HLACKCETVA AARPVTRSPG GSQEQRAKTP
   P1GF-1     KIRSG..DRP .SYVELTFSQ HVRCECRPLR EK........ ..........
   VEGF165    RIKPH..QGQ .HIGEMSFLQ HNKCECRPKK DR........ ..........
   VEGF-B167  MIRYP..SSQ ..LGEMSLEE HSQCECRPKK KD........ ..........
   VEGF-C     EITVPLSQGP .KPVTISFAN HTSCRCMSKL DVYRQVHSII RRSLPATLPQ 251                                                              300
   PDGF-A     DTDVR..... .......... .......... .......... ..........
   PDGF-B     QTRVTIRTVR VRRPPKGKHR KFKHTHDKTA LKETLGA... ..........
   P1GF-1     .......... .......... .......... .MKPERCGDA VPRR......
   VEGF165    .......... .......... .......... .ARQENPCGP CSERRKHLFV
   VEGF-B167  .......... .......... ..........S AVKPDSPRPL CPRCTQHHQR
   VEGF-C     CQAANKTCPT NYMWNNHICR CLAQEDFMFS SDAGDDSTDG FHDICGPNKE 301                                                              350
   PDGF-A     .......... .......... .......... .......... ..........
   PDGF-B     .......... .......... .......... .......... ..........
   P1GF-1     .......... .......... .......... .......... ..........
   VEGF165    QDPQTCKCSC KNTDS.RCKA RQLELNERTC RCDKPRR... ..........
   VEGF-B167  PDPRTCRCRC RRRSFLRCQG RGLELNPDTC RCRKLRR... ..........
   VEGF-C     LDEETCQCVC RAGLRPASCG PHKELDRNSC QCVCKNKLFP SQCGANREFD
```

FIG. 10C

```
              351                                                          400
    PDGF-A    ..........  ..........  ..........  ..........  ..........
    PDGF-B    ..........  ..........  ..........  ..........  ..........
     PlGF-1   ..........  ..........  ..........  ..........  ..........
    VEGF165   ..........  ..........  ..........  ..........  ..........
   VEGF-B167  ..........  ..........  ..........  ..........  ..........
     VEGF-C   ENTCQCVCKR  TCPRNQPLNP  GKCACECTES  PQKCLLKGKK  FHHQTCSCYR 401                                  434
    PDGF-A    ..........  ..........  ..........  ....
    PDGF-B    ..........  ..........  ..........  ....
     PlGF-1   ..........  ..........  ..........  ....
    VEGF165   ..........  ..........  ..........  ....
   VEGF-B167  ..........  ..........  ..........  ....
     VEGF-C   RPCTNRQKAC  EPGFSYSEEV  CRCVPSYWKR  PQMS
```

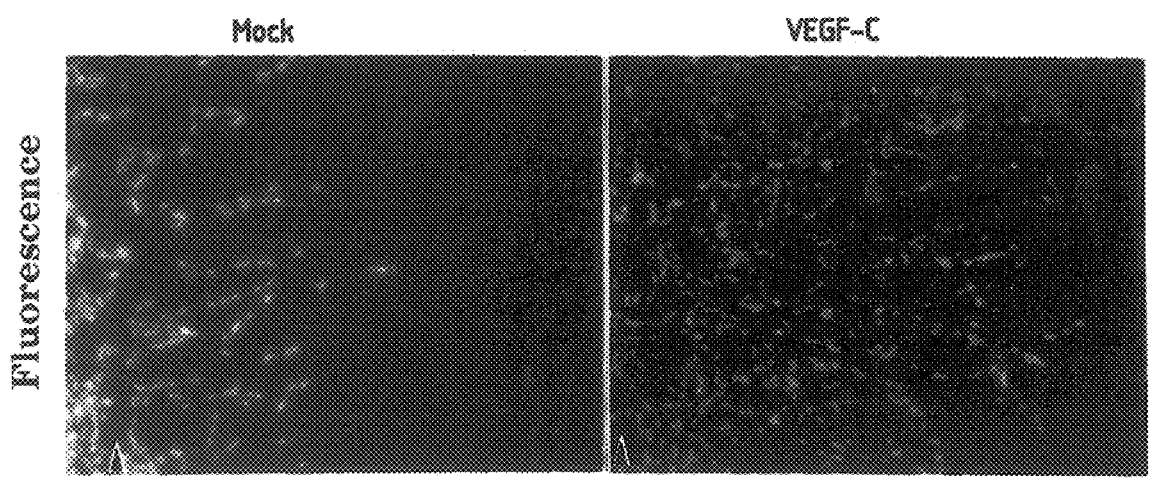

Chr 4

VEGF-C, q34

FIG. 21A
Reducing
FIG. 21B
Non-reducing
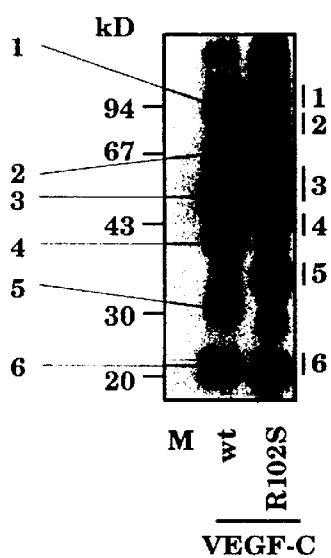
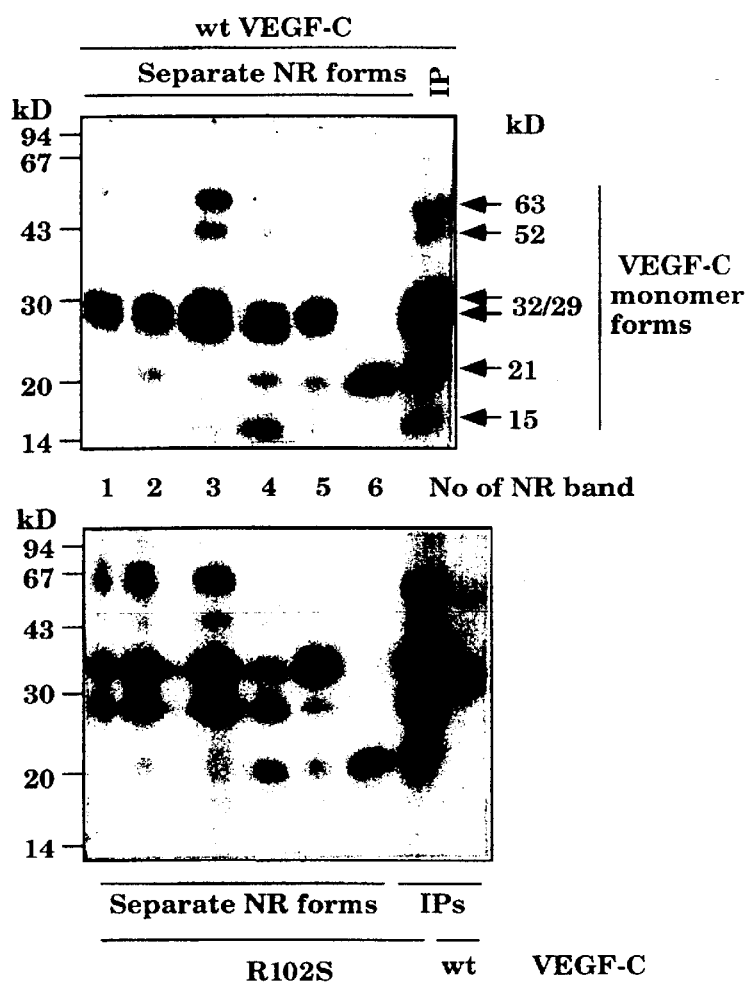
FIG. 21C

FIG. 25

VEGFC gene —[////]══▼══════════════════════════╗ STOP 991
         SacI  Signal peptide  PstI BglII AccI   RCMSK LDV         BspMI Clone SacI-AccI frament into pBS
Delete BglII site Using mutagenic primer
with PstI site and AccI primer. To Give:

—[////]══▼══—
SacI    PstI AccI

EETIKF.....
SacI-XhoI→        ←AccI

PCR to create XhoI site for in-frame
Fusion to XhoI site Of Pichia PHO1
Signal Sequence.

—[////]══▼══════════════════════════╗—
SacI   PstI BglII AccI    STOP 991    XhoI
                          RCMSK LDV        pVC-Stop SacI-BspMI fragment of STOP codon mutated VEGFC
cloned in pBS Clone SacI -XhoI and AccI primer PCR product
into pVC-Stop to give:

—│—│—▼══════════════════════════—│—
SacI XhoI PstI AccI   STOP 991   XhoI
         EETIKFAAA...    RCMSK

Clone XhoI fragment into Pichia vector, pHIL-S

NIH 3T3/
VEGFR-3

Anti-PTyr

M  wt  4G  ΔNΔCHis  NHis

PAE/
VEGFR-2

Anti-PTyr

M  wt  4G  ΔNΔCHis  NHis

```
          1  Signal sequence           31 ↓ 32    N-terminal propeptide                                                                                    98
mouse       MHLLCFLSLACLLAAALLPSREAPATVAA        FESGLGFSEAEPDGGEVTAPEGMNLEEQLRSVSSVDELMSVLYPDYWMYKCQLRKGGWQ....QPTLNTR
human       ....G.F.V......L.G......AA..         ....DL.D....A.AT.YAS.D.........T....E..............HNRE.AN..S.
```

VEGF homology

```
99                                                                                                                                                          222
TGDSVKFAAAHYNTELLKSIDNEWRKTQCMPREVCIDVGKEFGAATNTFFKPPCVSVYRCGGCCNSEGLQCMNTSTGYLSKTLFEITVPLSQGPKPVTISFANHTSCRCMSKLDVYRQVHSIIR
.EETI.............C..........................C....RC..CC....C...........C.C..........................)......
.................................V.....................................S......................................
```

BR3P homology

```
223
RSLPATLQCQAANKTCPTNYVWNNYM CRC LAQQDFIFYSNVEDDSTNGFHDV   C...C.C.C.........  CGPHKELDEDTCQCVC  KGGLRPSS
..........................     ...M..HI..E..M.S.DAG....I........................RA....A.
                                                                                  CGPHKELDRDSCQCVC  KNKLPPNS
                                                                                  ........N............SQ
                                                                                  CGANRFFDENTCQCVC  KRT
                                                                                  ........R............
                                                                                  CPRNQPLNPCKCACEC
```

```
                                                                                                      415
....TENTQKCFLAGKKFHHQT CSC YRRP
.........SP....L..............
                              CANRLHCDPGLSFSEKV CRC VPSYWKRPHLN
                              .......T..Q.A.E..GF.Y.........QMS
```

FIG. 31B

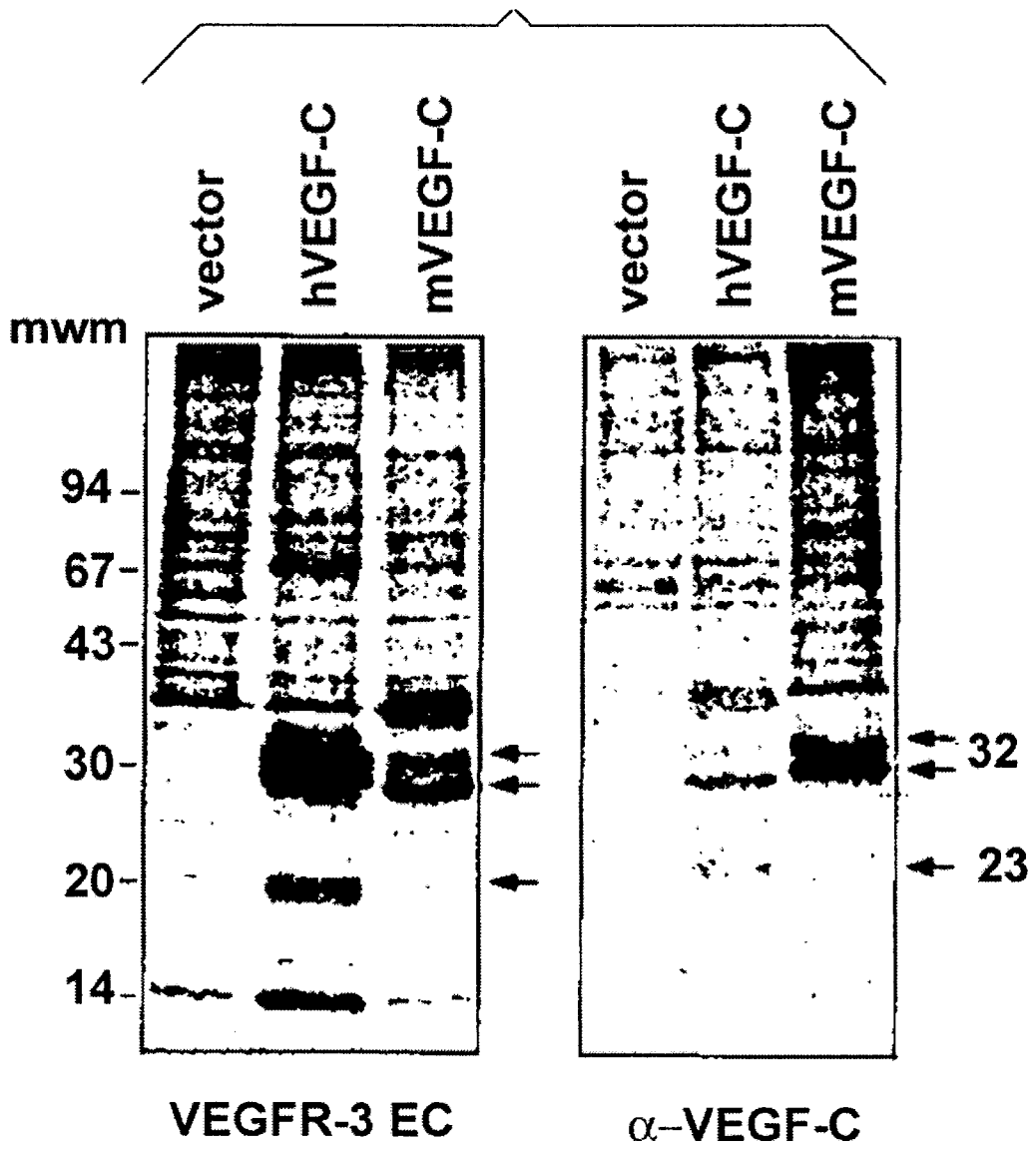

α-VEGFR-3

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
TGTCCTCGCT GTCCTTGTCT                                               20
```

(2) INFORMATION FOR SEQ ID NO:2:

(i) SEQUENCE CHARACTERISTICS:
      (A) LENGTH: 70 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
ACATGCATGC CACCATGCAG CGGGGCGCCG CGCTGTGCCT GCGACTGTGG CTCTGCCTGG   60

GACTCCTGGA                                                          70
```

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

```
ACATGCATGC CCCGCCGGTC ATCC                                          24
```

(2) INFORMATION FOR SEQ ID NO:4:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:4:

```
CGGAATTCCC CATGACCCCA AC                                            22
```

(2) INFORMATION FOR SEQ ID NO:5:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:5:

CCATCGATGG ATCCTACCTG AAGCCGCTTT CTT                                       33

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

ATTTAGGTGA CACTATA                                                         17

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CCATCGATGG ATCCCGATGC TGCTTAGTAG CTGT                                      34

(2) INFORMATION FOR SEQ ID NO:8:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Pro Met Thr Pro Thr Thr Tyr Lys Gly Ser Val Asp Asn Gln Thr Asp
1               5                   10                  15

Ser Gly Met Val Leu Ala Ser Glu Glu Phe Glu Gln Ile Glu Ser Arg
            20                  25                  30

His Arg Gln Glu Ser Gly Phe Arg
        35                  40

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CTGGAGTCGA CTTGGCGGAC T                                                    21

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: single

```
        (D) TOPOLOGY: linear (ii) MOLECULE TYPE: cDNA (xi) SEQUENCE DESCRIPTION: SEQ ID NO:10:

CGCGGATCCC TAGTGATGGT GATGGTGATG TCTACCTTCG ATCATGCTGC CCTTATCCTC      60

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCCAAGCTTG GATCCAAGTG GCTACTCCAT GACC      34

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTTGCCTGTG ATGTGCACCA      20

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Xaa Glu Glu Thr Ile Lys Phe Ala Ala Ala His Tyr Asn Thr Glu Ile
 1               5                  10                  15

Leu Lys (2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCAGARGARA CNATHAA      17

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:15:

Glu Glu Thr Ile Lys
1               5

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCAYTTNARD ATYTCNGT                                                         18

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Thr Glu Ile Leu Lys
1               5

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

ATTCGCTGCA GCACACTACA AC                                                    22

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TCNGTGTTGT AGTGTGCTG                                                        19

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Ala Ala His Tyr Asn Thr Glu
1               5

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TAATACGACT CACTATAGGG                                                    20

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GTTGTAGTGT GCTGCAGCGA ATTT                                               24

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Lys Phe Ala Ala Ala His Tyr Asn
1               5

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TCACTATAGG GAGACCCAAG C                                                  21

(2) INFORMATION FOR SEQ ID NO:25:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
TCACTATAGG GAGACCCAAG CTTGGTACCG AGCTCGGATC CACTAGTAAC GGCCGCCAGT      60

GTGGTGGAAT TCGACGAACT CATGACTGTA CTCTACCCAG AATATTGGAA AATGTACAAG    120

TGTCAGCTAA GGCAAGGAGG CTGGCAACAT AACAGAGAAC AGGCCAACCT CAACTCAAGG    180

ACAGAAGAGA CTATAAAATT CGCTGCAGCA CACTACAAC                           219
```

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
ACAGAGAACA GGCCAACC                                                   18
```

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
TCTAGCATTT AGGTGACAC                                                  19
```

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
AAGAGACTAT AAAATTCGCT GCAGC                                           25
```

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
CCCTCTAGAT GCATGCTCGA                                                 20
```

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
GTTGTAGTGT GCTGCAGCGA ATTT                                          24
```

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
TCACTATAGG GAGACCCAAG C                                             21
```

(2) INFORMATION FOR SEQ ID NO:32:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 352..1608

(xi) SEQUENCE DESCRIPTION: SEQ ID NO:32:

```
CCCGCCCCGC CTCTCCAAAA AGCTACACCG ACGCGGACCG CGGCGGCGTC CTCCCTCGCC    60

CTCGCTTCAC CTCGCGGGCT CCGAATGCGG GGAGCTCGGA TGTCCGGTTT CCTGTGAGGC   120

TTTTACCTGA CACCCGCCGC CTTTCCCCGG CACTGGCTGG GAGGGCGCCC TGCAAAGTTG   180

GGAACGCGGA GCCCCGGACC CGCTCCCGCC GCCTCCGGCT CGCCCAGGGG GGGTCGCCGG   240

GAGGAGCCCG GGGGAGAGGG ACCAGGAGGG GCCCGCGGCC TCGCAGGGGC GCCCGCGCCC   300

CCACCCCTGC CCCCGCCAGC GGACCGGTCC CCCACCCCCG GTCCTTCCAC C ATG CAC   357
                                                        Met His
                                                          1

TTG CTG GGC TTC TTC TCT GTG GCG TGT TCT CTG CTC GCC GCT GCG CTG   405
Leu Leu Gly Phe Phe Ser Val Ala Cys Ser Leu Leu Ala Ala Ala Leu
      5                  10                  15

CTC CCG GGT CCT CGC GAG GCG CCC GCC GCC GCC GCC TTC GAG TCC       453
Leu Pro Gly Pro Arg Glu Ala Pro Ala Ala Ala Ala Phe Glu Ser
 20                  25                  30

GGA CTC GAC CTC TCG GAC GCG GAG CCC GAC GCG GGC GAG GCC ACG GCT   501
Gly Leu Asp Leu Ser Asp Ala Glu Pro Asp Ala Gly Glu Ala Thr Ala
 35                  40                  45                  50

TAT GCA AGC AAA GAT CTG GAG GAG CAG TTA CGG TCT GTG TCC AGT GTA   549
Tyr Ala Ser Lys Asp Leu Glu Glu Gln Leu Arg Ser Val Ser Ser Val
              55                  60                  65

GAT GAA CTC ATG ACT GTA CTC TAC CCA GAA TAT TGG AAA ATG TAC AAG   597
Asp Glu Leu Met Thr Val Leu Tyr Pro Glu Tyr Trp Lys Met Tyr Lys
         70                  75                  80

TGT CAG CTA AGG AAA GGA GGC TGG CAA CAT AAC AGA GAA CAG GCC AAC   645
Cys Gln Leu Arg Lys Gly Gly Trp Gln His Asn Arg Glu Gln Ala Asn
     85                  90                  95

CTC AAC TCA AGG ACA GAA GAG ACT ATA AAA TTT GCT GCA GCA CAT TAT   693
Leu Asn Ser Arg Thr Glu Glu Thr Ile Lys Phe Ala Ala Ala His Tyr
    100                 105                 110
```

-continued

```
AAT ACA GAG ATC TTG AAA AGT ATT GAT AAT GAG TGG AGA AAG ACT CAA        741
Asn Thr Glu Ile Leu Lys Ser Ile Asp Asn Glu Trp Arg Lys Thr Gln
115                 120                 125                 130

TGC ATG CCA CGG GAG GTG TGT ATA GAT GTG GGG AAG GAG TTT GGA GTC        789
Cys Met Pro Arg Glu Val Cys Ile Asp Val Gly Lys Glu Phe Gly Val
                135                 140                 145

GCG ACA AAC ACC TTC TTT AAA CCT CCA TGT GTG TCC GTC TAC AGA TGT        837
Ala Thr Asn Thr Phe Phe Lys Pro Pro Cys Val Ser Val Tyr Arg Cys
            150                 155                 160

GGG GGT TGC TGC AAT AGT GAG GGG CTG CAG TGC ATG AAC ACC AGC ACG        885
Gly Gly Cys Cys Asn Ser Glu Gly Leu Gln Cys Met Asn Thr Ser Thr
        165                 170                 175

AGC TAC CTC AGC AAG ACG TTA TTT GAA ATT ACA GTG CCT CTC TCT CAA        933
Ser Tyr Leu Ser Lys Thr Leu Phe Glu Ile Thr Val Pro Leu Ser Gln
    180                 185                 190

GGC CCC AAA CCA GTA ACA ATC AGT TTT GCC AAT CAC ACT TCC TGC CGA        981
Gly Pro Lys Pro Val Thr Ile Ser Phe Ala Asn His Thr Ser Cys Arg
195                 200                 205                 210

TGC ATG TCT AAA CTG GAT GTT TAC AGA CAA GTT CAT TCC ATT ATT AGA       1029
Cys Met Ser Lys Leu Asp Val Tyr Arg Gln Val His Ser Ile Ile Arg
                215                 220                 225

CGT TCC CTG CCA GCA ACA CTA CCA CAG TGT CAG GCA GCG AAC AAG ACC       1077
Arg Ser Leu Pro Ala Thr Leu Pro Gln Cys Gln Ala Ala Asn Lys Thr
                230                 235                 240

TGC CCC ACC AAT TAC ATG TGG AAT AAT CAC ATC TGC AGA TGC CTG GCT       1125
Cys Pro Thr Asn Tyr Met Trp Asn Asn His Ile Cys Arg Cys Leu Ala
            245                 250                 255

CAG GAA GAT TTT ATG TTT TCC TCG GAT GCT GGA GAT GAC TCA ACA GAT       1173
Gln Glu Asp Phe Met Phe Ser Ser Asp Ala Gly Asp Asp Ser Thr Asp
        260                 265                 270

GGA TTC CAT GAC ATC TGT GGA CCA AAC AAG GAG CTG GAT GAA GAG ACC       1221
Gly Phe His Asp Ile Cys Gly Pro Asn Lys Glu Leu Asp Glu Glu Thr
275                 280                 285                 290

TGT CAG TGT GTC TGC AGA GCG GGG CTT CGG CCT GCC AGC TGT GGA CCC       1269
Cys Gln Cys Val Cys Arg Ala Gly Leu Arg Pro Ala Ser Cys Gly Pro
                295                 300                 305

CAC AAA GAA CTA GAC AGA AAC TCA TGC CAG TGT GTC TGT AAA AAC AAA       1317
His Lys Glu Leu Asp Arg Asn Ser Cys Gln Cys Val Cys Lys Asn Lys
                310                 315                 320

CTC TTC CCC AGC CAA TGT GGG GCC AAC CGA GAA TTT GAT GAA AAC ACA       1365
Leu Phe Pro Ser Gln Cys Gly Ala Asn Arg Glu Phe Asp Glu Asn Thr
            325                 330                 335

TGC CAG TGT GTA TGT AAA AGA ACC TGC CCC AGA AAT CAA CCC CTA AAT       1413
Cys Gln Cys Val Cys Lys Arg Thr Cys Pro Arg Asn Gln Pro Leu Asn
        340                 345                 350

CCT GGA AAA TGT GCC TGT GAA TGT ACA GAA AGT CCA CAG AAA TGC TTG       1461
Pro Gly Lys Cys Ala Cys Glu Cys Thr Glu Ser Pro Gln Lys Cys Leu
355                 360                 365                 370

TTA AAA GGA AAG AAG TTC CAC CAC CAA ACA TGC AGC TGT TAC AGA CGG       1509
Leu Lys Gly Lys Lys Phe His His Gln Thr Cys Ser Cys Tyr Arg Arg
                375                 380                 385

CCA TGT ACG AAC CGC CAG AAG GCT TGT GAG CCA GGA TTT TCA TAT AGT       1557
Pro Cys Thr Asn Arg Gln Lys Ala Cys Glu Pro Gly Phe Ser Tyr Ser
                390                 395                 400

GAA GAA GTG TGT CGT TGT GTC CCT TCA TAT TGG AAA AGA CCA CAA ATG       1605
Glu Glu Val Cys Arg Cys Val Pro Ser Tyr Trp Lys Arg Pro Gln Met
            405                 410                 415

AGC TAAGATTGTA CTGTTTTCCA GTTCATCGAT TTTCTATTAT GGAAAACTGT            1658
Ser
```

-continued

```
GTTGCCACAG TAGAACTGTC TGTGAACAGA GAGACCCTTG TGGGTCCATG CTAACAAAGA      1718

CAAAAGTCTG TCTTTCCTGA ACCATGTGGA TAACTTTACA GAAATGGACT GGAGCTCATC      1778

TGCAAAAGGC CTCTTGTAAA GACTGGTTTT CTGCCAATGA CCAAACAGCC AAGATTTTCC      1838

TCTTGTGATT TCTTTAAAAG AATGACTATA TAATTTATTT CCACTAAAAA TATTGTTTCT      1898

GCATTCATTT TTATAGCAAC AACAATTGGT AAAACTCACT GTGATCAATA TTTTTATATC      1958

ATGCAAAATA TGTTTAAAAT AAAATGAAAA TTGTATTAT                             1997
```

(2) INFORMATION FOR SEQ ID NO:33:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:33:

```
Met His Leu Leu Gly Phe Phe Ser Val Ala Cys Ser Leu Leu Ala Ala
 1               5                  10                  15

Ala Leu Leu Pro Gly Pro Arg Glu Ala Pro Ala Ala Ala Ala Ala Phe
             20                  25                  30

Glu Ser Gly Leu Asp Leu Ser Asp Ala Glu Pro Asp Ala Gly Glu Ala
         35                  40                  45

Thr Ala Tyr Ala Ser Lys Asp Leu Glu Glu Gln Leu Arg Ser Val Ser
     50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                 85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
```

```
                290                 295                 300
Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser (2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TGAGTGATTTGTAGCTGCTGTG                                              22

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TATTGCAGCAACCCCCACATCT                                              22

(2) INFORMATION FOR SEQ ID NO:36:

(i) SEQUENCE CHARACTERISTICS:
        (A) LENGTH: 4416 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

CCACGCGCAG CGGCCGGAGA TGCAGCGGGG CGCCGCGCTG TGCCTGCGAC TGTGGCTCTG      60

CCTGGGACTC CTGGACGGCC TGGTGAGTGG CTACTCCATG ACCCCCCCGA CCTTGAACAT     120

CACGGAGGAG TCACACGTCA TCGACACCGG TGACAGCCTG TCCATCTCCT GCAGGGGACA     180

GCACCCCCTC GAGTGGGCTT GGCCAGGAGC TCAGGAGGCG CCAGCCACCG GAGACAAGGA     240

CAGCGAGGAC ACGGGGGTGG TGCGAGACTG CGAGGGCACA GACGCCAGGC CCTACTGCAA     300

GGTGTTGCTG CTGCACGAGG TACATGCCAA CGACACAGGC AGCTACGTCT GCTACTACAA     360
```

```
GTACATCAAG GCACGCATCG AGGGCACCAC GGCCGCCAGC TCCTACGTGT TCGTGAGAGA      420

CTTTGAGCAG CCATTCATCA ACAAGCCTGA CACGCTCTTG GTCAACAGGA AGGACGCCAT      480

GTGGGTGCCC TGTCTGGTGT CCATCCCCGG CCTCAATGTC ACGCTGCGCT CGCAAAGCTC      540

GGTGCTGTGG CCAGACGGGC AGGAGGTGGT GTGGGATGAC CGGCGGGGCA TGCTCGTGTC      600

CACGCCACTG CTGCACGATG CCCTGTACCT GCAGTGCGAG ACCACCTGGG GAGACCAGGA      660

CTTCCTTTCC AACCCCTTCC TGGTGCACAT CACAGGCAAC GAGCTCTATG ACATCCAGCT      720

GTTGCCCAGG AAGTCGCTGG AGCTGCTGGT AGGGGAGAAG CTGGTCCTGA ACTGCACCGT      780

GTGGGCTGAG TTTAACTCAG GTGTCACCTT TGACTGGGAC TACCCAGGGA AGCAGGCAGA      840

GCGGGGTAAG TGGGTGCCCG AGCGACGCTC CCAGCAGACC CACACAGAAC TCTCCAGCAT      900

CCTGACCATC CACAACGTCA GCCAGCACGA CCTGGGCTCG TATGTGTGCA AGGCCAACAA      960

CGGCATCCAG CGATTTCGGG AGAGCACCGA GGTCATTGTG CATGAAAATC CCTTCATCAG     1020

CGTCGAGTGG CTCAAAGGAC CCATCCTGGA GGCCACGGCA GGAGACGAGC TGGTGAAGCT     1080

GCCCGTGAAG CTGGCAGCGT ACCCCCCGCC CGAGTTCCAG TGGTACAAGG ATGGAAAGGC     1140

ACTGTCCGGG CGCCACAGTC CACATGCCCT GGTGCTCAAG GAGGTGACAG AGGCCAGCAC     1200

AGGCACCTAC ACCCTCGCCC TGTGGAACTC CGCTGCTGGC CTGAGGCGCA ACATCAGCCT     1260

GGAGCTGGTG GTGAATGTGC CCCCCAGAT ACATGAGAAG GAGGCCTCCT CCCCCAGCAT      1320

CTACTCGCGT CACAGCCGCC AGGCCCTCAC CTGCACGGCC TACGGGGTGC CCCTGCCTCT     1380

CAGCATCCAG TGGCACTGGC GGCCCTGGAC ACCCTGCAAG ATGTTTGCCC AGCGTAGTCT     1440

CCGGCGGCGG CAGCAGCAAG ACCTCATGCC ACAGTGCCGT GACTGGAGGG CGGTGACCAC     1500

GCAGGATGCC GTGAACCCCA TCGAGAGCCT GGACACCTGG ACCGAGTTTG TGGAGGGAAA     1560

GAATAAGACT GTGAGCAAGC TGGTGATCCA GAATGCCAAC GTGTCTGCCA TGTACAAGTG     1620

TGTGGTCTCC AACAAGGTGG CCAGGATGA GCGGCTCATC TACTTCTATG TGACCACCAT      1680

CCCCGACGGC TTCACCATCG AATCCAAGCC ATCCGAGGAG CTACTAGAGG CCAGCCGGT      1740

GCTCCTGAGC TGCCAAGCCG ACAGCTACAA GTACGAGCAT CTGCGCTGGT ACCGCCTCAA     1800

CCTGTCCACG CTGCACGATG CGCACGGGAA CCCGCTTCTG CTCGACTGCA AGAACGTGCA     1860

TCTGTTCGCC ACCCCTCTGG CCGCCAGCCT GGAGGAGGTG GCACCTGGGG CGCGCCACGC     1920

CACGCTCAGC CTGAGTATCC CCCGCGTCGC GCCCGAGCAC GAGGGCCACT ATGTGTGCGA     1980

AGTGCAAGAC CGGCGCAGCC ATGACAAGCA CTGCCACAAG AAGTACCTGT CGGTGCAGGC     2040

CCTGGAAGCC CCTCGGCTCA CGCAGAACTT GACCGACCTC CTGGTGAACG TGAGCGACTC     2100

GCTGGAGATG CAGTGCTTGG TGGCCGGAGC GCACGCGCCC AGCATCGTGT GGTACAAAGA     2160

CGAGAGGCTG CTGGAGGAAA AGTCTGGAGT CGACTTGGCG GACTCCAACC AGAAGCTGAG     2220

CATCCAGCGC GTGCGCGAGG AGGATGCGGG ACGCTATCTG TGCAGCGTGT GCAACGCCAA     2280

GGGCTGCGTC AACTCCTCCG CCAGCGTGGC CGTGGAAGGC TCCGAGGATA AGGGCAGCAT     2340

GGAGATCGTG ATCCTTGTCG GTACCGGCGT CATCGCTGTC TTCTTCTGGG TCCTCCTCCT     2400

CCTCATCTTC TGTAACATGA GGAGGCCGGC CCACGCAGAC ATCAAGACGG GCTACCTGTC     2460

CATCATCATG GACCCCGGGG AGGTGCCTCT GGAGGAGCAA TGCGAATACC TGTCCTACGA     2520

TGCCAGCCAG TGGGAATTCC CCCGAGAGCG GCTGCACCTG GGGAGAGTGC TCGGCTACGG     2580

CGCCTTCGGG AAGGTGGTGG AAGCCTCCGC TTTCGGCATC CACAAGGGCA GCAGCTGTGA     2640

CACCGTGGCC GTGAAAATGC TGAAAGAGGG CGCCACGGCC AGCGAGCACC GCGCGCTGAT     2700
```

-continued

```
GTCGGAGCTC AAGATCCTCA TTCACATCGG CAACCACCTC AACGTGGTCA ACCTCCTCGG   2760

GGCGTGCACC AAGCCGCAGG GCCCCCTCAT GGTGATCGTG GAGTTCTGCA AGTACGGCAA   2820

CCTCTCCAAC TTCCTGCGCG CCAAGCGGGA CGCCTTCAGC CCCTGCGCGG AGAAGTCTCC   2880

CGAGCAGCGC GGACGCTTCC GCGCCATGGT GGAGCTCGCC AGGCTGGATC GGAGGCGGCC   2940

GGGGAGCAGC GACAGGGTCC TCTTCGCGCG GTTCTCGAAG ACCGAGGGCG GAGCGAGGCG   3000

GGCTTCTCCA GACCAAGAAG CTGAGGACCT GTGGCTGAGC CCGCTGACCA TGGAAGATCT   3060

TGTCTGCTAC AGCTTCCAGG TGGCCAGAGG GATGGAGTTC CTGGCTTCCC GAAAGTGCAT   3120

CCACAGAGAC CTGGCTGCTC GGAACATTCT GCTGTCGGAA AGCGACGTGG TGAAGATCTG   3180

TGACTTTGGC CTTGCCCGGG ACATCTACAA AGACCCTGAC TACGTCCGCA AGGGCAGTGC   3240

CCGGCTGCCC CTGAAGTGGA TGGCCCCTGA AAGCATCTTC GACAAGGTGT ACACCACGCA   3300

GAGTGACGTG TGGTCCTTTG GGGTGCTTCT CTGGGAGATC TTCTCTCTGG GGGCCTCCCC   3360

GTACCCTGGG GTGCAGATCA ATGAGGAGTT CTGCCAGCGG CTGAGAGACG GCACAAGGAT   3420

GAGGGCCCCG GAGCTGGCCA CTCCCGCCAT ACGCCGCATC ATGCTGAACT GCTGGTCCGG   3480

AGACCCCAAG GCGAGACCTG CATTCTCGGA GCTGGTGGAG ATCCTGGGGG ACCTGCTCCA   3540

GGGCAGGGGC CTGCAAGAGG AAGAGGAGGT CTGCATGGCC CCGCGCAGCT CTCAGAGCTC   3600

AGAAGAGGGC AGCTTCTCGC AGGTGTCCAC CATGGCCCTA CACATCGCCC AGGCTGACGC   3660

TGAGGACAGC CCGCCAAGCC TGCAGCGCCA CAGCCTGGCC GCCAGGTATT ACAACTGGGT   3720

GTCCTTTCCC GGGTGCCTGG CCAGAGGGGC TGAGACCCGT GGTTCCTCCA GGATGAAGAC   3780

ATTTGAGGAA TTCCCCATGA CCCCAACGAC CTACAAAGGC TCTGTGGACA ACCAGACAGA   3840

CAGTGGGATG GTGCTGGCCT CGGAGGAGTT TGAGCAGATA GAGAGCAGGC ATAGACAAGA   3900

AAGCGGCTTC AGGTAGCTGA AGCAGAGAGA GAGAAGGCAG CATACGTCAG CATTTTCTTC   3960

TCTGCACTTA TAAGAAAGAT CAAAGACTTT AAGACTTTCG CTATTTCTTC TACTGCTATC   4020

TACTACAAAC TTCAAAGAGG AACCAGGAGG ACAAGAGGAG CATGAAAGTG GACAAGGAGT   4080

GTGACCACTG AAGCACCACA GGGAAGGGGT TAGGCCTCCG GATGACTGCG GGCAGGCCTG   4140

GATAATATCC AGCCTCCCAC AAGAAGCTGG TGGAGCAGAG TGTTCCCTGA CTCCTCCAAG   4200

GAAAGGGAGA CGCCCTTTCA TGGTCTGCTG AGTAACAGGT GCNTTCCCAG ACACTGGCGT   4260

TACTGCTTGA CCAAAGAGCC CTCAAGCGGC CCTTATGCCA GCGTGACAGA GGGCTCACCT   4320

CTTGCCTTCT AGGTCACTTC TCACACAATG TCCCTTCAGC ACCTGACCCT GTGCCCGCCA   4380

GTTATTCCTT GGTAATATGA GTAATACATC AAAGAG                           4416
```

(2) INFORMATION FOR SEQ ID NO:37:

(i) SEQUENCE CHARACTERISTICS:
(A) LENGTH: 4273 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:37:

```
AAGCTTATCG ATTTCGAACC CGGGGGTACC GAATTCCTCG AGTCTAGAGG AGCATGCCTG     60

CAGGTCGACC GGGCTCGATC CCCTCGCGAG TTGGTTCAGC TGCTGCCTGA GGCTGGACGA    120

CCTCGCGGAG TTCTACCGGC AGTGCAAATC CGTCGGCATC CAGGAAACCA GCAGCGGCTA    180

TCCGCGCATC CATGCCCCCG AACTGCAGGA GTGGGGAGGC ACGATGGCCG CTTTGGTCCC    240
```

```
GGATCTTTGT GAAGGAACCT TACTTCTGTG GTGTGACATA ATTGGACAAA CTACCTACAG    300

AGATTTAAAG CTCTAAGGTA AATATAAAAT TTTTAAGTGT ATAATGTGTT AAACTACTGA    360

TTCTAATTGT TTGTGTATTT TAGATTCCAA CCTATGGAAC TGATGAATGG GAGCAGTGGT    420

GGAATGCCTT TAATGAGGAA AACCTGTTTT GCTCAGAAGA AATGCCATCT AGTGATGATG    480

AGGCTACTGC TGACTCTCAA CATTCTACTC CTCCAAAAAA GAAGAGAAAG GTAGAAGACC    540

CCAAGGACTT TCCTTCAGAA TTGCTAAGTT TTTTGAGTCA TGCTGTGTTT AGTAATAGAA    600

CTCTTGCTTG CTTTGCTATT TACACCACAA AGGAAAAAGC TGCACTGCTA TACAAGAAAA    660

TTATGGAAAA ATATTCTGTA ACCTTTATAA GTAGGCATAA CAGTTATAAT CATAACATAC    720

TGTTTTTTCT TACTCCACAC AGGCATAGAG TGTCTGCTAT TAATAACTAT GCTCAAAAAT    780

TGTGTACCTT TAGCTTTTTA ATTTGTAAAG GGGTTAATAA GGAATATTTG ATGTATAGTG    840

CCTTGACTAG AGATCATAAT CAGCCATACC ACATTTGTAG AGGTTTTACT TGCTTTAAAA    900

AACCTCCCAC ACCTCCCCCT GAACCTGAAA CATAAAATGA ATGCAATTGT TGTTGTTAAC    960

TTGTTTATTG CAGCTTATAA TGGTTACAAA TAAAGCAATA GCATCACAAA TTTCACAAAT   1020

AAAGCATTTT TTTCACTGCA TTCTAGTTGT GGTTTGTCCA AACTCATCAA TGTATCTTAT   1080

CATGTCTGGA TCTGCCGGTC TCCCTATAGT GAGTCGTATT AATTTCGATA AGCCAGGTTA   1140

ACCTGCATTA ATGAATCGGC CAACGCGCGG GGAGAGGCGG TTTGCGTATT GGGCGCTCTT   1200

CCGCTTCCTC GCTCACTGAC TCGCTGCGCT CGGTCGTTCG GCTGCGGCGA GCGGTATCAG   1260

CTCACTCAAA GGCGGTAATA CGGTTATCCA CAGAATCAGG GGATAACGCA GGAAAGAACA   1320

TGTGAGCAAA AGGCCAGCAA AAGGCCAGGA ACCGTAAAAA GGACGCGTTG CTGGCGTTTT   1380

TCCATAGGCT CCGCCCCCCT GACGAGCATC ACAAAAATCG ACGCTCAAGT CAGAGGTGGC   1440

GAAACCCGAC AGGACTATAA AGATACCAGG CGTTTCCCCC TGGAAGCTCC CTCGTGCGCT   1500

CTCCTGTTCC GACCCTGCCG CTTACCGGAT ACCTGTCCGC CTTTCTCCCT TCGGGAAGCG   1560

TGGCGCTTTC TCAATGCTCA CGCTGTAGGT ATCTCAGTTC GGTGTAGGTC GTTCGCTCCA   1620

AGCTGGGCTG TGTGCACGAA CCCCCCGTTC AGCCCGACCG CTGCGCCTTA TCCGGTAACT   1680

ATCGTCTTGA GTCCAACCCG GTAAGACACG ACTTATCGCC ACTGGCAGCA GCCACTGGTA   1740

ACAGGATTAG CAGAGCGAGG TATGTAGGCG GTGCTACAGA GTTCTTGAAG TGGTGGCCTA   1800

ACTACGGCTA CACTAGAAGG ACAGTATTTG GTATCTGCGC TCTGCTGAAG CCAGTTACCT   1860

TCGGAAAAAG AGTTGGTAGC TCTTGATCCG GCAAACAAAC CACCGCTGGT AGCGGTGGTT   1920

TTTTTGTTTG CAAGCAGCAG ATTACGCGCA GAAAAAAAGG ATCTCAAGAA GATCCTTTGA   1980

TCTTTTCTAC GGGGTCTGAC GCTCAGTGGA ACGAAAACTC ACGTTAAGGG ATTTTGGTCA   2040

TGAGATTATC AAAAAGGATC TTCACCTAGA TCCTTTTAAA TTAAAAATGA AGTTTTAAAT   2100

CAATCTAAAG TATATATGAG TAAACTTGGT CTGACAGTTA CCAATGCTTA ATCAGTGAGG   2160

CACCTATCTC AGCGATCTGT CTATTTCGTT CATCCATAGT TGCCTGACTC CCCGTCGTGT   2220

AGATAACTAC GATACGGGAG GGCTTACCAT CTGGCCCCAG TGCTGCAATG ATACCGCGAG   2280

ACCCACGCTC ACCGGCTCCA GATTTATCAG CAATAAACCA GCCAGCCGGA AGGGCCGAGC   2340

GCAGAAGTGG TCCTGCAACT TTATCCGCCT CCATCCAGTC TATTAATTGT TGCCGGGAAG   2400

CTAGAGTAAG TAGTTCGCCA GTTAATAGTT TGCGCAACGT TGTTGCCATT GCTACAGGCA   2460

TCGTGGTGTC ACGCTCGTCG TTTGGTATGG CTTCATTCAG CTCCGGTTCC CAACGATCAA   2520

GGCGAGTTAC ATGATCCCCC ATGTTGTGCA AAAAAGCGGT TAGCTCCTTC GGTCCTCCGA   2580

TCGTTGTCAG AAGTAAGTTG GCCGCAGTGT TATCACTCAT GGTTATGGCA GCACTGCATA   2640
```

```
ATTCTCTTAC TGTCATGCCA TCCGTAAGAT GCTTTTCTGT GACTGGTGAG TACTCAACCA    2700

AGTCATTCTG AGAATAGTGT ATGCGGCGAC CGAGTTGCTC TTGCCCGGCG TCAATACGGG    2760

ATAATACCGC GCCACATAGC AGAACTTTAA AAGTGCTCAT CATTGGAAAA CGTTCTTCGG    2820

GGCGAAAACT CTCAAGGATC TTACCGCTGT TGAGATCCAG TTCGATGTAA CCCACTCGTG    2880

CACCCAACTG ATCTTCAGCA TCTTTTACTT TCACCAGCGT TTCTGGGTGA GCAAAAACAG    2940

GAAGGCAAAA TGCCGCAAAA AAGGGAATAA GGGCGACACG GAAATGTTGA ATACTCATAC    3000

TCTTCCTTTT TCAATATTAT TGAAGCATTT ATCAGGGTTA TTGTCTCATG AGCGGATACA    3060

TATTTGAATG TATTTAGAAA AATAAACAAA TAGGGGTTCC GCGCACATTT CCCCGAAAAG    3120

TGCCACCTGA CGTCTAAGAA ACCATTATTA TCATGACATT AACCTATAAA AATAGGCGTA    3180

TCACGAGGCC CTTTCGTCTC GCGCGTTTCG GTGATGACGG TGAAAACCTC TGACACATGC    3240

AGCTCCCGGA GACGGTCACA GCTTGTCTGT AAGCGGATGC CGGGAGCAGA CAAGCCCGTC    3300

AGGGCGCGTC AGCGGGTGTT GGCGGGTGTC GGGGCTGGCT TAACTATGCG GCATCAGAGC    3360

AGATTGTACT GAGAGTGCAC CATATGGACA TATTGTCGTT AGAACGCGGC TACAATTAAT    3420

ACATAACCTT ATGTATCATA CACATACGAT TTAGGTGACA CTATAGAACT CGAGCAGAGC    3480

TTCCAAATTG AGAGAGAGGC TTAATCGAG ACAGAAACTG TTTGAGTCAA CTCAAGGATG    3540

GTTTGAGGGA CTGTTTAACA GATCCCCTTG GTTTACCACC TTGATATCTA CCATTATGGG    3600

ACCCCTCATT GTACTCCTAA TGATTTTGCT CTTCGGACCC TGCATTCTTA ATCGATTAGT    3660

CCAATTTGTT AAAGACAGGA TATCAGTGGT CCAGGCTCTA GTTTTGACTC AACAATATCA    3720

CCAGCTGAAG CCTATAGAGT ACGAGCCATA GATAAAATAA AAGATTTTAT TTAGTCTCCA    3780

GAAAAAGGGG GGAATGAAAG ACCCCACCTG TAGGTTTGGC AAGCTAGCTT AAGTAACGCC    3840

ATTTTGCAAG GCATGGAAAA ATACATAACT GAGAATAGAG AAGTTCAGAT CAAGGTCAGG    3900

AACAGATGGA ACAGCTGAAT ATGGGCCAAA CAGGATATCT GTGGTAAGCA GTTCCTGCCC    3960

CGGCTCAGGG CCAAGAACAG ATGGAACAGC TGAATATGGG CCAAACAGGA TATCTGTGGT    4020

AAGCAGTTCC TGCCCCGGCT CAGGGCCAAG AACAGATGGT CCCCAGATGC GGTCCAGCCC    4080

TCAGCAGTTT CTAGAGAACC ATCAGATGTT TCCAGGGTGC CCCAAGGACC TGAAATGACC    4140

CTGTGCCTTA TTTGAACTAA CCAATCAGTT CGCTTCTCGC TTCTGTTCGC GCGCTTCTGC    4200

TCCCCGAGCT CAATAAAAGA GCCCACAACC CCTCACTCGG GGCGCCAGTC CTCCGATTGA    4260

CTGAGTCGCC CGG                                                      4273
```

(2) INFORMATION FOR SEQ ID NO:38:

(i) SEQUENCE CHARACTERISTICS:
       (A) LENGTH: 216 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:38:

```
CAAGAAAGCG GCTTCAGCTG TAAAGGACCT GGCCAGAATG TGGCTGTGAC CAGGGCACAC      60

CCTGACTCCC AAGGGAGGCG GCGGCGGCCT GAGCGGGGGG CCCGAGGAGG CCAGGTGTTT     120

TACAACAGCG AGTATGGGGA GCTGTCGGAG CCAAGCGAGG AGGACCACTG CTCCCCGTCT     180

GCCCGCGTGA CTTTCTTCAC AGACAACAGC TACTAA                              216
```

(2) INFORMATION FOR SEQ ID NO:39:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Glu Glu Thr Ile Lys Phe Ala Ala Ala His Tyr Asn Thr Glu Ile Leu
1               5                   10                  15

Lys
```

(2) INFORMATION FOR SEQ ID NO:40:

(i) SEQUENCE CHARACTERISTICS:
        (A) LENGTH: 1836 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 168..1412

(xi) SEQUENCE DESCRIPTION: SEQ ID NO:40:

```
GCGGCCGCGT CGACGCAAAA GTTGCGAGCC GCCGAGTCCC GGGAGACGCT CGCCCAGGGG      60

GGTCCCCGGG AGGAAACCAC GGGACAGGGA CCAGGAGAGG ACCTCAGCCT CACGCCCCAG     120

CCTGCGCCAG CCAACGGACC GGCCTCCCTG CTCCCGGTCC ATCCACC ATG CAC TTG      176
                                                    Met His Leu
                                                      1

CTG TGC TTC TTG TCT CTG GCG TGT TCC CTG CTC GCC GCT GCG CTG ATC      224
Leu Cys Phe Leu Ser Leu Ala Cys Ser Leu Leu Ala Ala Ala Leu Ile
     5                  10                  15

CCC AGT CCG CGC GAG GCG CCC GCC ACC GTC GCC GCC TTC GAG TCG GGA      272
Pro Ser Pro Arg Glu Ala Pro Ala Thr Val Ala Ala Phe Glu Ser Gly
 20                  25                  30                  35

CTG GGC TTC TCG GAA GCG GAG CCC GAC GGG GGC GAG GTC AAG GCT TTT      320
Leu Gly Phe Ser Glu Ala Glu Pro Asp Gly Gly Glu Val Lys Ala Phe
                 40                  45                  50

GAA GGC AAA GAC CTG GAG GAG CAG TTG CGG TCT GTG TCC AGC GTA GAT      368
Glu Gly Lys Asp Leu Glu Glu Gln Leu Arg Ser Val Ser Ser Val Asp
             55                  60                  65

GAG CTG ATG TCT GTC CTG TAC CCA GAC TAC TGG AAA ATG TAC AAG TGC      416
Glu Leu Met Ser Val Leu Tyr Pro Asp Tyr Trp Lys Met Tyr Lys Cys
         70                  75                  80

CAG CTG CGG AAA GGC GGC TGG CAG CAG CCC ACC CTC AAT ACC AGG ACA      464
Gln Leu Arg Lys Gly Gly Trp Gln Gln Pro Thr Leu Asn Thr Arg Thr
     85                  90                  95

GGG GAC AGT GTA AAA TTT GCT GCT GCA CAT TAT AAC ACA GAG ATC CTG      512
Gly Asp Ser Val Lys Phe Ala Ala Ala His Tyr Asn Thr Glu Ile Leu
100                 105                 110                 115

AAA AGT ATT GAT AAT GAG TGG AGA AAG ACT CAA TGC ATG CCA CGT GAG      560
Lys Ser Ile Asp Asn Glu Trp Arg Lys Thr Gln Cys Met Pro Arg Glu
                120                 125                 130

GTG TGT ATA GAT GTG GGG AAG GAG TTT GGA GCA GCC ACA AAC ACC TTC      608
Val Cys Ile Asp Val Gly Lys Glu Phe Gly Ala Ala Thr Asn Thr Phe
            135                 140                 145

TTT AAA CCT CCA TGT GTG TCC GTC TAC AGA TGT GGG GGT TGC TGC AAC      656
```

```
Phe Lys Pro Pro Cys Val Ser Val Tyr Arg Cys Gly Gly Cys Cys Asn
            150                 155                 160

AGG GAG GGG CTG CAG TGC ATG AAC ACC AGC ACA GGT TAC CTC AGC AAG        704
Arg Glu Gly Leu Gln Cys Met Asn Thr Ser Thr Gly Tyr Leu Ser Lys
    165                 170                 175

ACG TTG TTT GAA ATT ACA GTG CCT CTC TCA CAA GGC CCC AAA CCA GTC        752
Thr Leu Phe Glu Ile Thr Val Pro Leu Ser Gln Gly Pro Lys Pro Val
180                 185                 190                 195

ACA ATC AGT TTT GCC AAT CAC ACT TCC TGC CGG TGC ATG TCT AAA CTG        800
Thr Ile Ser Phe Ala Asn His Thr Ser Cys Arg Cys Met Ser Lys Leu
                200                 205                 210

GAT GTT TAC AGA CAA GTT CAT TCA ATT ATT AGA CGT TCT CTG CCA GCA        848
Asp Val Tyr Arg Gln Val His Ser Ile Ile Arg Arg Ser Leu Pro Ala
            215                 220                 225

ACA TTA CCA CAG TGT CAG GCA GCT AAC AAG ACA TGT CCA ACA AAC TAT        896
Thr Leu Pro Gln Cys Gln Ala Ala Asn Lys Thr Cys Pro Thr Asn Tyr
        230                 235                 240

GTG TGG AAT AAC TAC ATG TGC CGA TGC CTG GCT CAG CAG GAT TTT ATC        944
Val Trp Asn Asn Tyr Met Cys Arg Cys Leu Ala Gln Gln Asp Phe Ile
    245                 250                 255

TTT TAT TCA AAT GTT GAA GAT GAC TCA ACC AAT GGA TTC CAT GAT GTC        992
Phe Tyr Ser Asn Val Glu Asp Asp Ser Thr Asn Gly Phe His Asp Val
260                 265                 270                 275

TGT GGA CCC AAC AAG GAG CTG GAT GAA GAC ACC TGT CAG TGT GTC TGC       1040
Cys Gly Pro Asn Lys Glu Leu Asp Glu Asp Thr Cys Gln Cys Val Cys
                280                 285                 290

AAG GGG GGG CTT CGG CCA TCT AGT TGT GGA CCC CAC AAA GAA CTA GAT       1088
Lys Gly Gly Leu Arg Pro Ser Ser Cys Gly Pro His Lys Glu Leu Asp
            295                 300                 305

AGA GAC TCA TGT CAG TGT GTC TGT AAA AAC AAA CTT TTC CCT AAT TCA       1136
Arg Asp Ser Cys Gln Cys Val Cys Lys Asn Lys Leu Phe Pro Asn Ser
        310                 315                 320

TGT GGA GCC AAC AGG GAA TTT GAT GAG AAT ACA TGT CAG TGT GTA TGT       1184
Cys Gly Ala Asn Arg Glu Phe Asp Glu Asn Thr Cys Gln Cys Val Cys
    325                 330                 335

AAA AGA ACG TGT CCA AGA AAT CAG CCC CTG AAT CCT GGG AAA TGT GCC       1232
Lys Arg Thr Cys Pro Arg Asn Gln Pro Leu Asn Pro Gly Lys Cys Ala
340                 345                 350                 355

TGT GAA TGT ACA GAA AAC ACA CAG AAG TGC TTC CTT AAA GGG AAG AAG       1280
Cys Glu Cys Thr Glu Asn Thr Gln Lys Cys Phe Leu Lys Gly Lys Lys
                360                 365                 370

TTC CAC CAT CAA ACA TGC AGT TGT TAC AGA AGA CCG TGT GCG AAT CGA       1328
Phe His His Gln Thr Cys Ser Cys Tyr Arg Arg Pro Cys Ala Asn Arg
            375                 380                 385

CTG AAG CAT TGT GAT CCA GGA CTG TCC TTT AGT GAA GAA GTA TGC CGC       1376
Leu Lys His Cys Asp Pro Gly Leu Ser Phe Ser Glu Glu Val Cys Arg
        390                 395                 400

TGT GTC CCA TCG TAT TGG AAA AGG CCA CAT CTG AAC TAAGATCATA            1422
Cys Val Pro Ser Tyr Trp Lys Arg Pro His Leu Asn
    405                 410                 415

CCAGTTTTCA GTCAGTCACA GTCATTTACT CTCTTGAAGA CTGTTGGAAC AGCACTTAGC     1482

ACTGTCTATG CACAGAAAGA CTCTGTGGGA CCACATGGTA ACAGAGGCCC AAGTCTGTGT     1542

TTATTGAACC ATGTGGATTA CTGCGGGAGA GGACTGGCAC TCATGTGCAA AAAAAACCTC    1602

TTCAAAGACT GGTTTTCTGC CAGGGACCAG ACAGCTGAGG TTTTTCTCTT GTGATTTAAA    1662

AAAAGAATGA CTATATAATT TATTTCCACT AAAAATATTG TTCCTGCATT CATTTTTATA    1722

GCAATAACAA TTGGTAAAGC TCACTGTGAT CAGTATTTTT ATAACATGCA AAACTATGTT    1782
```

TAAAATAAAA TGAAAATTGT ATTATAAAAA AAAAAAAAAA AAAAAAAAAA GCTT         1836

(2) INFORMATION FOR SEQ ID NO:41:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO:41:

```
Met His Leu Leu Cys Phe Leu Ser Leu Ala Cys Ser Leu Leu Ala Ala
 1               5                  10                  15

Ala Leu Ile Pro Ser Pro Arg Glu Ala Pro Ala Thr Val Ala Ala Phe
                20                  25                  30

Glu Ser Gly Leu Gly Phe Ser Glu Ala Glu Pro Asp Gly Gly Glu Val
            35                  40                  45

Lys Ala Phe Glu Gly Lys Asp Leu Glu Glu Gln Leu Arg Ser Val Ser
         50                  55                  60

Ser Val Asp Glu Leu Met Ser Val Leu Tyr Pro Asp Tyr Trp Lys Met
 65                  70                  75                  80

Tyr Lys Cys Gln Leu Arg Lys Gly Gly Trp Gln Gln Pro Thr Leu Asn
                 85                  90                  95

Thr Arg Thr Gly Asp Ser Val Lys Phe Ala Ala Ala His Tyr Asn Thr
               100                 105                 110

Glu Ile Leu Lys Ser Ile Asp Asn Glu Trp Arg Lys Thr Gln Cys Met
            115                 120                 125

Pro Arg Glu Val Cys Ile Asp Val Gly Lys Glu Phe Gly Ala Ala Thr
        130                 135                 140

Asn Thr Phe Phe Lys Pro Pro Cys Val Ser Val Tyr Arg Cys Gly Gly
145                 150                 155                 160

Cys Cys Asn Arg Glu Gly Leu Gln Cys Met Asn Thr Ser Thr Gly Tyr
                165                 170                 175

Leu Ser Lys Thr Leu Phe Glu Ile Thr Val Pro Leu Ser Gln Gly Pro
            180                 185                 190

Lys Pro Val Thr Ile Ser Phe Ala Asn His Thr Ser Cys Arg Cys Met
        195                 200                 205

Ser Lys Leu Asp Val Tyr Arg Gln Val His Ser Ile Ile Arg Arg Ser
210                 215                 220

Leu Pro Ala Thr Leu Pro Gln Cys Gln Ala Ala Asn Lys Thr Cys Pro
225                 230                 235                 240

Thr Asn Tyr Val Trp Asn Asn Tyr Met Cys Arg Cys Leu Ala Gln Gln
                245                 250                 255

Asp Phe Ile Phe Tyr Ser Asn Val Glu Asp Asp Ser Thr Asn Gly Phe
            260                 265                 270

His Asp Val Cys Gly Pro Asn Lys Glu Leu Asp Glu Asp Thr Cys Gln
        275                 280                 285

Cys Val Cys Lys Gly Gly Leu Arg Pro Ser Ser Cys Gly Pro His Lys
    290                 295                 300

Glu Leu Asp Arg Asp Ser Cys Gln Cys Val Cys Lys Asn Lys Leu Phe
305                 310                 315                 320

Pro Asn Ser Cys Gly Ala Asn Arg Glu Phe Asp Glu Asn Thr Cys Gln
                325                 330                 335

Cys Val Cys Lys Arg Thr Cys Pro Arg Asn Gln Pro Leu Asn Pro Gly
            340                 345                 350
```

```
Lys Cys Ala Cys Glu Cys Thr Glu Asn Thr Gln Lys Cys Phe Leu Lys
        355                 360                 365

Gly Lys Lys Phe His His Gln Thr Cys Ser Cys Tyr Arg Arg Pro Cys
    370                 375                 380

Ala Asn Arg Leu Lys His Cys Asp Pro Gly Leu Ser Phe Ser Glu Glu
385                 390                 395                 400

Val Cys Arg Cys Val Pro Ser Tyr Trp Lys Arg Pro His Leu Asn
                405                 410                 415
```

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

```
TCTCTTCTGT GCTTGAGTTG AG                                       22
```

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

```
TCTCTTCTGT CCCTGAGTTG AG                                       22
```

(2) INFORMATION FOR SEQ ID NO:44:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

```
TGTGCTGCAG CAAATTTTAT AGTCTCTTCT GTGGCGGCGG CGGCGGCGGG CGCCTCGCGA    60

GGACC                                                               65
```

(2) INFORMATION FOR SEQ ID NO:45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

```
CTGGCAGGGA ACTGCTAATA ATGGAATGAA                               30
```

(2) INFORMATION FOR SEQ ID NO:46:

(i) SEQUENCE CHARACTERISTICS:

(A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GGGCTCCGCG TCCGAGAGGT CGAGTCCGGA CTCGTGATGG TGATGGTGAT GGGCGGCGGC    60

GGCGGCGGGC GCCTCGCGAG GACC    84

(2) INFORMATION FOR SEQ ID NO:47:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

GTATTATAAT GTCCTCCACC AAATTTTATA G    31

(2) INFORMATION FOR SEQ ID NO:48:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GTTCGCTGCC TGACACTGTG GTAGTGTTGC TGGCGGCCGC TAGTGATGGT GATGGTGATG    60

AATAATGGAA TGAACTTGTC TGTAAACATC CAG    93

(2) INFORMATION FOR SEQ ID NO:49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

CATGTACGAA CCGCCAGG    18

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

AATGACCAGA GAGAGGCGAG    20

(2) INFORMATION FOR SEQ ID NO:51:

(i) SEQUENCE CHARACTERISTICS:

```
                (A) LENGTH: 10 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:51:

Ala Val Val Met Thr Gln Thr Pro Ala Ser
1               5                   10

(2) INFORMATION FOR SEQ ID NO:52:

(i) SEQUENCE CHARACTERISTICS:
                (A) LENGTH: 196 amino acids
                (B) TYPE: amino acid
                (C) STRANDEDNESS: Not Relevant
                (D) TOPOLOGY: linear (ii) MOLECULE TYPE: peptide (xi) SEQUENCE DESCRIPTION: SEQ ID NO:52:

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
                35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

(2) INFORMATION FOR SEQ ID NO:53:

(i) SEQUENCE CHARACTERISTICS:
                (A) LENGTH: 241 amino acids
                (B) TYPE: amino acid
                (C) STRANDEDNESS: Not Relevant
                (D) TOPOLOGY: linear (ii) MOLECULE TYPE: peptide (xi) SEQUENCE DESCRIPTION: SEQ ID NO:53:

Met Asn Arg Cys Trp Ala Leu Phe Leu Ser Leu Cys Cys Tyr Leu Arg
1               5                   10                  15
```

-continued

```
Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
            50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
            130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
                195                 200                 205

Thr Ile Arg Thr Val Arg Val Arg Arg Pro Pro Lys Gly Lys His Arg
            210                 215                 220

Lys Phe Lys His Thr His Asp Lys Thr Ala Leu Lys Glu Thr Leu Gly
225                 230                 235                 240

Ala
```

(2) INFORMATION FOR SEQ ID NO:54:

(i) SEQUENCE CHARACTERISTICS:
        (A) LENGTH: 149 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:54:

```
Met Pro Val Met Arg Leu Phe Pro Cys Phe Leu Gln Leu Leu Ala Gly
 1               5                  10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
            50                  55                  60

Tyr Pro Ser Glu Val Glu His Met Phe Ser Pro Ser Cys Val Ser Leu
 65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110
```

```
Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Cys Gly Asp
        130                 135                 140

Ala Val Pro Arg Arg
145
```

(2) INFORMATION FOR SEQ ID NO:55:

(i) SEQUENCE CHARACTERISTICS:
        (A) LENGTH: 191 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:55:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

(2) INFORMATION FOR SEQ ID NO:56:

(i) SEQUENCE CHARACTERISTICS:
        (A) LENGTH: 188 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:56:

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
            35                  40                  45
```

```
Pro Arg Glu Val Val Pro Leu Thr Val Glu Leu Met Gly Thr Val
    50              55                  60

Ala Lys Gln Leu Val Pro Ser Cys Val Thr Val Gln Arg Cys Gly Gly
65              70                  75              80

Cys Cys Pro Asp Asp Gly Leu Glu Cys Val Pro Thr Gly Gln His Gln
            85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
            130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185
```

(2) INFORMATION FOR SEQ ID NO:57:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CCCGAGGATC GAGAATTAAT TCCCC     25

(2) INFORMATION FOR SEQ ID NO:58:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

AAAAAGCGGC CGATCCTCTA GAG     23

RECEPTOR LIGAND VEGF-C

This application is a continuation-in-part of U.S. patent application Ser. No. 08/601,132, filed Feb. 14, 1996, which is a continuation-in-part of U.S. patent application Ser. No. 08/585,895, filed Jan. 12, 1996, now U.S. Pat. No. 6,245,530, which is a continuation-in-part of U.S. patent application Ser. No. 08/510,133, filed Aug. 1, 1995, now U.S. Pat. No. 6,221,839.

FIELD OF THE INVENTION

The present invention generally relates to the field of genetic engineering and more particularly to growth factors for endothelial cells and growth factor genes.

BACKGROUND OF THE INVENTION

Developmental growth, the remodelling and regeneration of adult tissues, as well as solid tumor growth, can only occur when accompanied by blood vessel formation. Angioblasts and hematopoietic precursor cells differentiate from the mesoderm and form the blood islands of the yolk sac and the primary vascular system of the embryo. The development of blood vessels from these early (in situ) differentiating endothelial cells is termed vasculogenesis. Major embryonic blood vessels are believed to arise via vasculogenesis, whereas the formation of the rest of the vascular tree is thought to occur as a result of vascular sprouting from pre-existing vessels, a process called angiogenesis, Risau et al., *Devel. Biol.,* 125:441–450 (1988).

Endothelial cells give rise to several types of functionally and morphologically distinct vessels. When organs differentiate and begin to perform their specific functions, the phenotypic heterogeneity of endothelial cells increases. Upon angiogenic stimulation, endothelial cells may re-enter the cell cycle, migrate, withdraw from the cell cycle and subsequently differentiate again to form new vessels that are functionally adapted to their tissue environment. Endothelial cells undergoing angiogenesis degrade the underlying basement membrane and migrate, forming capillary sprouts that project into the perivascular stroma. Ausprunk et al., *Microvasc. Rev.,* 14:51–65 (1977). Angiogenesis during tissue development and regeneration depends on the tightly controlled processes of endothelial cell proliferation, migration, differentiation, and survival. Dysfunction of the endothelial cell regulatory system is a key feature of many diseases. Most significantly, tumor growth and metastasis have been shown to be angiogenesis dependent. Folkman et al., *J. Biol. Chem.,* 267:10931–10934 (1992).

Key signals regulating cell growth and differentiation are mediated by polypeptide growth factors and their transmembrane receptors, many of which are tyrosine kinases. Autophosphorylated peptides within the tyrosine kinase insert and carboxyl-terminal sequences of activated receptors are commonly recognized by kinase substrates involved in signal transduction for the readjustment of gene expression in responding cells. Several families of receptor tyrosine kinases have been characterized. Van der Geer et al., *Ann. Rev. Cell Biol.,* 10:251–337 (1994). The major growth factors and receptors transducing angiogenic stimuli are schematically shown in FIG. 1.

Fibroblast growth factors are also known to be involved in the regulation of angiogenesis. They have been shown to be mitogenic and chemotactic for cultured endothelial cells. Fibroblast growth factors also stimulate the production of proteases, such as collagenases and plasminogen activators, and induce tube formation by endothelial cells. Saksela et al., *Ann. Rev. Cell Biol.,* 4:93–126 (1988). There are two general classes of fibroblast growth factors, FGF-1 and FGF-2, both of which lack conventional signal peptides. Both types have an affinity for heparin and FGF-2 is bound to heparin sulfate proteoglycans in the subendothelial extracellular matrix from which it may be released after injury. Heparin potentiates the stimulation of endothelial cell proliferation by angiogenic FGFs, both by protecting against denaturation and degradation and dimerizing the FGFs. Cultured endothelial cells express the FGF-1 receptor but no significant levels of other high-affinity fibroblast growth factor receptors.

Among other ligands for receptor tyrosine kinases, the platelet derived growth factor, PDGF-BB, has been shown to be weakly angiogenic in the chick chorioallantoic membrane. Risau et al., *Growth Factors,* 7:261–266 (1992). Transforming growth factor α (TGFα) is an angiogenic factor secreted by several tumor cell types and by macrophages. Hepatocyte growth factor (HGF), the ligand of the c-met proto-oncogene-encoded receptor, also is strongly angiogenic.

Recent evidence shows that there are endothelial cell specific growth factors and receptors that may be primarily responsible for the stimulation of endothelial cell growth, differentiation and certain differentiated functions. The best studied of these is vascular endothelial growth factor (VEGF), a member of the PDGF family. Vascular endothelial growth factor is a dimeric glycoprotein of disulfide-linked 23 kD subunits. Other reported effects of VEGF include the mobilization of intracellular calcium, the induction of plasminogen activator and plasminogen activator inhibitor-1 synthesis, stimulation of hexose transport in endothelial cells, and promotion of monocyte migration in vitro. Four VEGF isoforms, encoded by distinct mRNA splice variants, appear to be equally capable of stimulating mitogenesis in endothelial cells. However, each isoform has a different affinity for cell surface proteoglycans, which behave as low affinity receptors for VEGF. The 121 and 165 amino acid isoforms of VEGF (VEGF121 and VEGF165) are secreted in a soluble form, whereas the isoforms of 189 and 206 amino acid residues remain cell surface-associated and have a strong affinity for heparin. VEGF was originally purified from several sources on the basis of its mitogenic activity toward endothelial cells, and also by its ability to induce microvascular permeability, hence it is also called vascular permeability factor (VPF).

The pattern of VEGF expression suggests its involvement in the development and maintenance of the normal vascular system and in tumor angiogenesis. During murine development, the entire 7.5 day post-coital (p.c.) endoderm expresses VEGF and the ventricular neuroectoderm produces VEGF at the capillary ingrowth stage. See Breier et al., *Development,* 114:521–523 (1992). On day two of quail development, the vascularized area of the yolk sac as well as the whole embryo show expression of VEGF. In addition, epithelial cells next to fenestrated endothelia in adult mice show persistent VEGF expression, suggesting a role in the maintenance of this specific endothelial phenotype and function.

Two high affinity receptors for VEGF have been characterized. These are VEGFR-1/Flt-1 (fms-like tyrosine kinase-1) and VEGFR-2/Kdr/Flk-1 (kinase insert domain containing receptor/fetal liver kinase-1). Those receptors are classified in the PDGF-receptor family, but they have seven rather than five immunoglobulin-like loops in their extracellular domain and they possess a longer kinase insert than normally observed in this family. The expression of VEGF receptors occurs mainly in vascular endothelial cells, although some may be present on monocytes and melanoma cells. Only endothelial cells have been reported to proliferate in response to VEGF, and endothelial cells from different sources show different responses. Thus, the signals mediated through VEGFR-1 and VEGFR-2 appear to be cell type specific. The VEGF-related placenta growth factor (PlGF) was recently shown to bind to VEGFR-1 with high affinity. PlGF was able to enhance the growth factor activity of VEGF, but it did not stimulate endothelial cells on its own. Naturally occurring VEGF/PlGF heterodimers were nearly as potent mitogens as VEGF homodimers for endothelial cells.

The Flt4 receptor tyrosine kinase (VEGFR-3) is closely related in structure to the products of the VEGFR-1 and VEGFR-2 genes. Despite this similarity, the mature form of Flt4 differs from the VEGF receptors in that it is proteolytically cleaved in the extracellular domain into two disulfide-linked polypeptides. Pajusola et al., *Cancer Res.*, 52:5738–5743 (1992). The 4.5 and 5.8 kb Flt4 mRNAs encode polypeptides which differ in their C-termini due to the use of alternative 3' exons. The VEGFs do not show specific binding to Flt4 or induce its autophosphorylation.

Expression of Flt4 appears to be more restricted than expression of VEGFR-1 or VEGFR-2. The expression of Flt4 first becomes detectable by in situ hybridization in the angioblasts of head mesenchyme, the cardinal vein, and extraembryonically in the allantois of 8.5 day p.c. mouse embryos. In 12.5 day p.c. embryos the Flt4 signal is observed in developing venous and presumptive lymphatic endothelia, but arterial endothelia appear negative. During later stages of development, Flt4 mRNA becomes restricted to developing lymphatic vessels. Only the lymphatic endothelia and some high endothelial venules express Flt4 mRNA in adult human tissues and increased expression occurs in lymphatic sinuses in metastatic lymph nodes and in lymphangioma. These results support the theory of the venous origin of lymphatic vessels.

Five endothelial cell specific receptor tyrosine kinases, Flt-1 (VEGFR-1), KDR/Flk-1 (VEGFR-2), Flt4, Tie and Tek/Tie-2 have so far been described, which possess the intrinsic tyrosine kinase activity essential for signal transduction. Targeted mutations inactivating Flt-1, FLk-1, Tie and Tek in mouse embryos have indicated their essential and specific roles in vasculogenesis and angiogenesis at the molecular level. VEGFR-1 and VEGFR-2 bind VEGF with high affinity ($K_d$ 16 pM and 760 pM, respectively) and VEGFR-1 also binds the related placenta growth factor (PlGF; $K_d$ about 200 pM), while the ligands for Tie, Tek, and Flt4 have not heretofore been reported.

SUMMARY OF THE INVENTION

The present invention provides a ligand for the Flt4 receptor tyrosine kinase. Thus, the invention provides a purified and isolated polypeptide which is capable of binding to the Flt4 receptor tyrosine kinase. Preferably, an Flt4 ligand of the invention is capable of stimulating tyrosine phosphorylation of Flt4 receptor tyrosine kinase in a host cell expressing the Flt4 receptor tyrosine kinase. Preferred ligands of the invention are mammalian polypeptides. Highly preferred ligands are human polypeptides.

In one embodiment, an FlT4 ligand has a molecular weight of approximately 23 kD as determined by SDS-PAGE under reducing conditions. For example, the invention includes a ligand composed of one or more polypeptides of approximately 23 kD is purifyable from conditioned media from a PC-3 prostatic adenocarcinoma cell line, the cell line having ATCC Acc. No. CRL 1435. Amino acid sequencing of this PC-3 cell derived ligand revealed that the ligand comprises an amino terminal amino acid sequence set forth in SEQ ID NO: 13. A conditioned medium comprising an Flt4 ligand is itself an aspect of the invention.

In a highly preferred embodiment, the ligand comprises a fragment of the amino acid sequence shown in SEQ ID NO: 33 which specifically binds to the human Flt4 receptor tyrosine kinase. Exemplary fragments include: a polypeptide comprising an amino acid sequence set forth in SEQ ID NO: 33 from about residue 112 to about residue 213; a polypeptide comprising an amino acid sequence from about residue 104 to about residue 227 of SEQ ID NO: 33; and a polypeptide comprising an amino acid sequence from about residue 112 to about residue 227 of SEQ ID NO: 33. Other exemplary fragments include polypeptides comprising amino acid sequences of SEQ ID NO: 33 that span, approximately, the following residues: 31–213, 31–227, 32–227, 103–217, 103–225, 104–213, 113–213, 103–227, 113–227, 131–211, 161–211, 103–225, 227–419, 228–419, 31–419, and 1–419, as described in greater detail below.

The present invention also provides one or more polypeptide precursors of an Flt4 ligand, wherein one such precursor (designated "prepro-VEGF-C") comprises the complete amino acid sequence (amino acid residues 1 to 419) shown in SEQ ID NO: 33. Thus, the invention includes a purified and isolated polypeptide having the amino acid sequence of residues 1 to 419 shown in SEQ ID NO: 33. A putative 102 amino acid leader (prepro) peptide has been identified in the amino acid sequence shown in SEQ ID NO: 33. Thus, in a related aspect, the invention includes a purified and isolated polypeptide having the amino acids sequence of residues 103–419 shown in SEQ ID NO: 33.

In one embodiment, an expressed Flt4 ligand precursor is proteolytically cleaved upon expression to produce an approximately 23 kD polypeptide which is the Flt4 ligand (herein designated VEGF-C). Thus, an Flt4 ligand is provided which is the cleavage product of the precursor peptide shown in SEQ ID NO: 33 and which has a molecular weight of approximately 23 kD under reducing conditions.

A putative VEGF-C precursor or 'splice variant, consisting of polypeptides with molecular weights of about 29 and 32 kD, also is considered an aspect of the invention.

In another embodiment, an expressed Flt4 ligand precursor is proteolytically cleaved upon expression to produce an approximately 21 kD VEGF-C polypeptide. Sequence analysis has indicated that an observed 21 kD form has an amino terminus approximately 9 amino acids downstream from the amino terminus of the 23 kD form, suggesting alternative cleavage sites exist.

From the foregoing, it will be apparent that an aspect of the invention includes a fragment of the purified and isolated polypeptide having the amino acid sequence of residues 1 to 419 shown in SEQ ID NO: 33, the fragment being capable of specifically binding to Flt4 receptor tyrosine kinase. Preferred embodiments include fragments having an apparent molecular weight of approximately 21/23 kD and 29/32 kD as assessed by SDS-PAGE under reducing conditions.

Evidence suggests that the amino acids essential for retaining Flt4 ligand activity are contained within approximately amino acids 103/112–226/227 of SEQ ID NO: 33, and that a carboxy-terminal proteolytic cleavage to produce a mature, naturally-occurring Flt4 ligand occurs at the approximate position of amino acids 226–227 of SEQ ID NO: 33. Accordingly, a preferred Flt4 ligand comprises approximately amino acids 103–227 of SEQ ID NO: 33.

VEGF-C mutational analysis described herein indicates that a naturally occurring VEGF-C polypeptide spanning amino acids 103–227 of SEQ ID NO: 33, produced by a natural processing cleavage that defines the C-terminus, exists and is biologically active as an Flt4 ligand. A polypeptide fragment consisting of residues 104–213 of SEQ ID NO: 33 has been shown to retain VEGF-C biological activity. Additional mutational analyses indicate that a polypeptide spanning only amino acids 113–213 of SEQ ID NO: 33 retains Flt4 ligand activity. Accordingly, preferred polypeptides comprise sequences spanning, approximately, amino acid residues 103–227, 104–213, or 113–213, of SEQ ID NO: 33.

Moreover, sequence comparisons of members of the VEGF family of polypeptides provide an indication that still smaller fragments will retain biological activity, and such smaller fragments are intended as aspects of the invention. In particular, eight highly conserved cysteine residues of the VEGF family of polypeptides define a region from residues 131–211 of SEQ ID NO: 33 (see FIGS. 10 & 31B); therefore, a polypeptide spanning from about residue 131 to about residue 211 is expected to retain VEGF-C biological activity. In fact, a polypeptide comprising approximately residues 161–211, which retains an evolutionarily-conserved RCXXCC motif, is postulated to retain VEGF-C activity, and therefore is intended as an aspect of the invention. Some of the conserved cysteine residues in VEGF-C participate in interchain disulfide bonding to make homo- and heterodimers of the various naturally occurring VEGF-C polypeptides. Beyond the preceding considerations, evidence exists that VEGF-C polypeptides lacking interchain disulfide bonds retain VEGF-C biological activity. In particular, VEGF-C that has been reduced and alkylated (processes that prevent the formation of disulfide bonds by cysteine residues) retains biological activity. Consequently, the materials and methods of the invention include all VEGF-C fragments that retain at least one biological activity of VEGF-C, regardless of the presence or absence of interchain disulfide bonds. The invention also includes multimers comprising such fragments linked to each other or to other polypeptides. Fragment linkage may be by way of covalent bonding (e.g., disulfide bonding) or non-covalent bonding of polypeptide chains (e.g, hydrogen bonding, bonding due to stable or induced dipole-dipole interactions, bonding due to hydrophobic or hydrophilic interactions, combinations of these bonding mechanisms, and the like).

In yet another related aspect, the invention includes variants and analogs of the aforementioned polypeptides, including VEGF-C, precursors of VEGF-C, and fragments of VEGF-C. The variants contemplated by the invention include purified and isolated polypeptides having amino acid sequences that differ from the amino acid sequences of VEGF-C, VEGF-C precursors and VEGF-C fragments by conservative substitutions, as recognized by those of skill in the art, or by additions or deletions of amino acid residues that are compatible with the retention of at least one biological activity of VEGF-C.

Analogs contemplated by the invention include polypeptides having modifications to one or more amino acid residues that differ from the modifications found in VEGF-C, VEGF-C precursors, or VEGF-C fragments, but are compatible with the retention of at least one biological activity of VEGF-C, VEGF-C precursors, or VEGF-C fragments. For example, analogs within the scope of the invention include glycosylation variants and conjugants (attachment of the aforementioned polypeptides to compounds such as labels, toxins, etc.)

The present invention also provides purified and isolated polynucleotides (i.e., nucleic acids) encoding novel polypeptides, for example a cDNA or corresponding genomic DNA encoding VEGF-C. VEGF-C is a ligand for the FLT4 receptor tyrosine kinase (VEGFR-3), a receptor tyrosine kinase related to VEGFR-1 and VEGFR-2 that does not bind VEGF. VEGFR-3 is expressed in venous and lymphatic endothelia of fetal tissues and predominantly in lymphatic endothelia of adult tissues. Kaipainen al., *Cancer Res.,* 54:6571–77 (1994); Kaipainen, et al., *Proc. Natl. Acad. Sci. (USA),* 92:3566–70 (1995). A preferred nucleic acid of the invention encodes VEGF-C, for example a DNA encoding amino acid residues 1 to 419 of SEQ ID NO: 33. Other preferred nucleic acids encode one of the aforementioned fragments of VEGF-C. The invention also comprehends analogs of these polynucleotides, or derivatives of any one of these polynucleotides sufficiently duplicative of the corresponding naturally occurring polynucleotide such that the encoded polypeptide retains at least one biological property of the polypeptide encoded by the naturally occurring polynucleotide. DNA polynucleotides according to the invention include genomic DNAs, cDNAs, and oligonucleotides comprising the coding sequence for a fragment of VEGF-C, or an analog of a VEGF-C fragment that retains at least one of the biological activities of a VEGF-C fragment. Distinct polynucleotides encoding a polypeptide of the invention by virtue of the degeneracy of the genetic code are within the scope of the invention.

A preferred polynucleotide according to the invention comprises the human VEGF-C cDNA sequence set forth in SEQ ID NO: 32 from nucleotide 352 to 1611. Other polynucleotides according to the invention encode a VEGF-C polypeptide from, e.g., mammals other than humans. Still other polynucleotides of the invention comprise a coding sequence for a VEGF-C fragment, and allelic variants of those DNAs encoding part or all of VEGF-C. Moreover, the invention comprehends polynucleotides that differ from native VEGF-C-encoding polynucleotides by the deletion, insertion or substitution of nucleotides and which encode polypeptides that retain part or all of at least one of the biological activities associated with native VEGF-C-encoding polynucleotides. Further, the invention contemplates polynucleotides having sequences that differ from polynucleotides encoding a VEGF-C fragment in a manner that results in conservative amino acid differences between the encoded polypeptides, as understood by those of skill in the art.

The invention further comprises polynucleotides that hybridize to the above-defined polynucleotides under standard stringent hybridization conditions, or which would hybridize but for the degeneracy of the genetic code. Exemplary stringent hybridization conditions are as follows: hybridization at 42° C. in 50% formamide, 5×SSC, 20 mM $Na.PO_4$, pH 6.8 and washing in 0.2×SSC at 55° C. It is understood by those of skill in the art that variation in these conditions occurs based on the length and GC nucleotide content of the sequences to be hybridized. Formulas standard in the art are appropriate for determining exact hybridization conditions. See Sambrook et al., *Molecular Cloning: A Laboratory Manual* (Second ed., Cold Spring Harbor Laboratory Press 1989) §§9.47–9.51. These polynucleotides, capable of hybridizing to polynucleotides encoding VEGF-C, VEGF-C fragments, or VEGF-C analogs, are useful as nucleic acid probes for identifying, purifying and isolating polynucleotides encoding other (non-human) mammalian forms of VEGF-C. Additionally, these polynucleotides are useful in screening methods of the invention, as described below.

Preferred nucleic acid probes of the invention comprise nucleic acid sequences of at least about 16 continuous nucleotides of SEQ ID NO: 32. More preferably, these nucleic acid probes would have at least about 20 nucleotides found in a subsequence of SEQ ID NO: 32. In using these nucleic acids as probes, it is preferred that the nucleic acids specifically hybridize to a portion of the sequence set forth in SEQ ID NO: 32. Specific hybridization is herein defined as hybridization under standard stringent hybridization conditions. To identify and isolate other mammalian VEGF-C genes specifically, nucleic acid probes preferably are selected such that they fail to hybridize to genes related to VEGF-C (e.g., fail to hybridize to human VEGF or to human VEGF-B genes).

Thus, the invention comprehends polynucleotides comprising at least about 16 nucleotides wherein the polynucleotides are capable of specifically hybridizing to a gene encoding VEGF-C, e.g., a human gene. The specificity of hybridization ensures that a polynucleotide of the invention is able to hybridize to a nucleic acid encoding a VEGF-C under hybridization conditions that do not support hybridization of the polynucleotide to nucleic acids encoding, e.g., VEGF or VEGF-B. In one embodiment, polynucleotides of at least about 16 nucleotides, and preferably at least about 20 nucleotides, are selected as continuous nucleotide sequences found in SEQ ID NO: 32 or the complement of the nucleotide sequence set forth in SEQ ID NO: 32.

Thus, aspects of the invention include purified and isolated nucleic acids encoding polypeptides and polypeptide fragments of the invention; vectors which comprise nucleic acids of the invention; and host cells transformed or transfected with nucleic acids or vectors of the invention. For example, in a preferred embodiment, the invention includes a purified and isolated nucleic acid (e.g., a DNA or an RNA) encoding an Flt4 ligand precursor. Due to the degeneracy of the genetic code, numerous such coding sequences are possible, each having in common the coding of the amino acid sequence shown in SEQ ID NO: 33. As set forth above, the invention includes polypeptides which comprise a portion of the amino acid sequence shown in SEQ ID NO: 33 and which bind the Flt4 receptor tyrosine kinase (herein designated VEGFR-3); the invention also is intended to include nucleic acids encoding these polypeptides. Ligand precursors according to the invention, when expressed in an appropriate host cell, produce, via cleavage, a peptide which binds specifically to the Flt4 receptor tyrosine kinase (VEGFR-3). The nucleotide sequence shown in SEQ ID NO: 32 contains a preferred nucleotide sequence encoding the Flt4 ligand (VEGF-C).

The present invention also provides a cell line which produces an Flt4 ligand. In a preferred embodiment, the ligand may be purified and isolated directly from the cell culture medium. Also provided are vectors comprising a DNA encoding the Flt4 ligand, and host cells comprising the vectors. Preferred vectors of the invention are expression vectors wherein nucleic acids of the invention are operatively connected to appropriate promoters and other control sequences, such that appropriate host cells transformed or transfected with the vectors are capable of expressing the Flt4 ligand. A preferred vector of the invention is plasmid pFLT4-L, having ATCC accession no. 97231. Such vectors and host cells are useful for recombinantly producing VEGF-C polypeptides.

The invention further includes a method of making polypeptides of the invention. In a preferred method, a nucleic acid or vector of the invention is expressed in a host cell, and a polypeptide of the invention is purified from the host cell or the host cell's growth medium.

In a related embodiment, the invention includes a method of making a polypeptide capable of specifically binding to Flt4 receptor tyrosine kinase, comprising the steps of: (a) transforming or transfecting a host cell with a nucleic acid of the invention; (b) cultivating the host cell to express the nucleic acid; and (c) purifying a polypeptide capable of specifically binding to Flt4 receptor tyrosine kinase from the host cell or from the host cell's growth media.

The invention also is intended to include purified and isolated polypeptide ligands of Flt4 produced by methods of the invention.

In another aspect, the invention includes an antibody which is specifically reactive with polypeptides of the invention, such as an Flt4 receptor tyrosine kinase ligand. Antibodies, both monoclonal and polyclonal, may be made against a ligand of the invention according to standard techniques in the art. Such antibodies may be used in diagnostic applications to monitor angiogenesis, vascularization, lymphatic vessels and their disease states, wound healing, or certain hematopoietic or leukemia cells, or they may be used to block or activate the Flt4 receptor.

Ligands according to the invention may be labeled with a detectable label and used to identify their corresponding receptors in situ. Labeled Flt4 ligand and anti-Flt4 ligand antibodies may be used as imaging agents in the detection of lymphatic vessels, high endothelial venules, and Flt4 receptors expressed in histochemical tissue sections. The ligand or antibody may be covalently or non-covalently coupled to a suitable supermagnetic, paramagnetic, electron dense, echogenic, or radioactive agent for imaging. Other, non-radioactive labels, such as biotin and avidin, may also be used.

A related aspect of the invention is a method for the detection of specific cells, e.g., endothelial cells. These cells may be found in vivo, or in ex vivo biological tissue samples. The method of detection comprises the steps of exposing a biological tissue comprising, e.g., endothelial cells, to a polypeptide according to claim 1, under conditions wherein the polypeptide binds to the cells, optionally washing the biological tissue, and detecting the polypeptide bound to the cells in the biological tissue, thereby detecting the cells.

The present invention also provides diagnostic and clinical applications for claimed ligands. In a preferred embodiment, Flt4 ligands or precursors are used to accelerate angiogenesis, e.g., during wound healing, or to promote the endothelial functions of lymphatic vessels. A utility for VEGF-C is suggested as an inducer of angiogenesis also in tissue transplantation, in eye diseases, in the formation of collateral vessels around arterial stenoses and into injured tissues after infarction. Ligands may be applied in any suitable manner using an appropriate pharmaceutically-acceptable vehicle, e.g., a pharmaceutically-acceptable diluent, adjuvant, excipient or carrier. Ligands also may be used to quantify future metastatic risk by assaying biopsy material for the presence of active receptors or ligands in a binding assay or kit using detectably-labeled ligand. An Flt4 ligand according to the invention also may be used to promote re-growth or permeability of lymphatic vessels in, for example, organ transplant patients. In addition, an Flt4 ligand may be used to mitigate the loss of axillary lymphatic vessels following surgical interventions in the treatment of cancer (e.g., breast cancer). Ligands according to the invention also may be used to treat or prevent inflammation, edema, aplasia of the lymphatic vessels, lymphatic obstruction, elephantiasis, and Milroy's disease. Finally, Flt4 ligands may be used to stimulate lymphocyte production and maturation, and to promote or inhibit trafficking of leukocytes between tissues and lymphatic vessels or to affect migration in and out of the thymus.

An embodiment of this aspect of the invention is a method of screening for an endothelial cell disorder in a mammalian subject. The method comprises providing a sample of endothelial cells from the subject, contacting the sample of endothelial cells with a polypeptide according to claim 4, determining the growth rate of the cells, and correlating the growth rate with a disorder. In a preferred embodiment, the endothelial cells are lymphatic cells. In another preferred embodiment, the mammalian subject is a human being and the endothelial cells are human cells. In yet another preferred embodiment, the disorder is a vessel disorder, e.g., a lymphatic vessel disorder, such as the loss of lymphatic vessels through surgery or the reduction in function of existing lymphatic vessels due to blockages. In another embodiment, the endothelial cells are contacted with the polypeptide in vitro. The growth rate determined in the method is the rate of cell division per unit time, determined by any one of a number of techniques known in the art. The correlation of the growth rate with a disorder can involve a positive or negative correlation, e.g., whether the polypeptide has Flt4 ligand activity or is an inhibitor of such activity, as described below.

Inhibitors of the Flt4 ligand may be used to control endothelial cell proliferation and lymphangiomas. For example, such inhibitors may be used to arrest metastatic growth or spread, or to control other aspects of endothelial cell expression and growth. Inhibitors include antibodies, antisense oligonucleotides, and peptides which block the Flt4 receptor, all of which are intended as aspects of the invention.

In another embodiment, the invention provides a method for modulating the growth of endothelial cells in a mammalian subject comprising the steps of exposing mammalian endothelial cells to a polypeptide according to the invention in an amount effective to modulate the growth of the mammalian endothelial cells. In one embodiment, the modulation of growth is effected by using a polypeptide capable of stimulating tyrosine phosphorylation of Flt4 receptor tyrosine kinase in a host cell expressing the Flt4 receptor tyrosine kinase. In modulating the growth of endothelial cells, the invention contemplates the modulation of endothelial cell-related disorders. Endothelial cell disorders contemplated by the invention include, but are not limited to, physical loss of lymphatic vessels (e.g., surgical removal of axillary lymph tissue), lymphatic vessel occlusion (e.g., elephantiasis), and lymphangiomas. In a preferred embodiment, the subject, and endothelial cells, are human. The endothelial cells may be provided in vitro, or in vivo. An effective amount of a polypeptide is defined herein as that amount of polypeptide empirically determined to be necessary to achieve a reproducible change in cell growth rate (as determined by microscopic or macroscopic visualization and estimation of cell doubling time, or nucleic acid synthesis assays), as would be understood by one of ordinary skill in the art.

The present invention also provides methods for using the claimed nucleic acids (i.e., polynucleotides) in screening for endothelial cell disorders. In a preferred embodiment, the invention provides a method for screening an endothelial cell disorder in a mammalian subject comprising the steps of providing a sample of endothelial cell nucleic acids from the subject, contacting the sample of endothelial cell nucleic acids with a polynucleotide according to claim 35, determining the level of hybridization between the endothelial cell nucleic acids and the polynucleotide, and correlating the level of hybridization with a disorder. A preferred mammalian subject, and source of endothelial cell nucleic acids, is a human. The disorders contemplated by the method of screening with polynucleotides include, but are not limited to, vessel disorders such as the aforementioned lymphatic vessel disorders, and hypoxia.

Purified and isolated polynucleotides encoding other (non-human) mammalian VEGF-C forms also are aspects of the invention, as are the polypeptides encoded thereby, and antibodies that are specifically immunoreactive with the non-human VEGF-C variants. Thus, the invention includes a purified and isolated mammalian VEGF-C polypeptide, and also a purified and isolated polynucleotide encoding such a polypeptide.

In one embodiment, the invention includes a purified and isolated polypeptide having the amino acid sequence of residues 1 to 415 of SEQ ID NO: 41, which sequence corresponds to a putative mouse VEGF-C precursor. The putative mouse VEGF-C precursor is believed to be processed into a mature mouse VEGF-C in a manner analogous to the processing of the human prepro-polypeptide. Thus, in a related aspect, the invention includes a purified and isolated polypeptide capable of specifically binding to an Flt4 receptor tyrosine kinase (e.g., a human or mouse Flt-4 receptor tyrosine kinase), the polypeptide comprising a fragment of the purified and isolated polypeptide having the amino acid sequence of residues 1 to 415 of SEQ ID NO: 41, the fragment being capable of specifically binding to the Flt4 receptor tyrosine kinase. The invention further includes purified and isolated nucleic acids encoding the foregoing polypeptides, such as a nucleic acid comprising all or a portion of the sequence shown in SEQ ID NO: 40.

BRIEF DESCRIPTION OF THE DRAWING

FIGS. 5A, 5B, and 5C show that the major tyrosyl phosphorylated polypeptide of Flt4-transfected cells stimulated with PC-3 conditioned medium is the 125 kD Flt4 polypeptide (VEGFR-3), and also that the Flt4 stimulating activity is not adsorbed to heparin-sepharose.

FIGS. 10A–10C depict a comparison of the deduced amino acid sequences of PDGEL (SEQ ID NO:52), PDGF-B (SEQ ID NO:53), PlGF-1 (SEQ ID NO:54), VECF$_{165}$ (SEQ ID NO: 55), VECF$_{167}$ (SEQ ID NO:56), and Flt4 ligand (VEGFC SEQ ID NO: 33)

FIGS. 15A, 15B, and 15C show that VEGF-C stimulates endothelial cell migration in a three-dimensional collagen gel assay.

FIGS. 21A–C depict electrophoretic fractionations of the various forms of recombinant VEGF-C produced by transfected 293 EBNA cells. FIG. 21B depicts the electrophoretic fractionation, under non-reducing conditions, of polypeptides produced from mock (M) transfected cells, cells transformed with wild type (wt) VEGF-C cDNA, and cells transfected with a cDNA variant encoding VEGF-C-R102S. Each of the bands identified in FIG. 21B was excised and electrophoretically fractionated in a separate lane under reducing conditions. Fractionation of bands corresponding to wt VEGF-C are depicted in FIG. 21A; fractionation of bands corresponding to the R102S variant are depicted in FIG. 21C.

FIG. 22A shows the VEGF-C forms secreted into the media; FIG. 22B shows the VEGF-C forms retained by the cells. Mock (M) transfected cells served as a control.

FIG. 25 illustrates the cloning strategy for inserting a DNA encoding a truncated VEGF-C containing amino acid residues 104–213 SEQ ID NO: 33 into the *Pichia pastoris* expression vector pHIL-S1.

FIG. 26B depicts the results of a Western blot wherein NIH 3T3 cells expressing VEGFR-3 (Flt4), and PAE cells expressing VEGFR-2 (KDR), were stimulated with 5× concentrated medium from Pichia yeast transfected with a VEGF-C cDNA-containing vector (+), with a vector lacking an insert (–), or stimulated with the positive control vanadate. The stimulated cells were lysed and immunoprecipitated with VEGFR-specific antibodies, and the immunoprecipitates were blotted and probed with anti-phosphotyrosine antibodies.

and Δ is the site of a 12 bp deletion in the mouse cDNA, relative to the human cDNA.

Figure 31A:
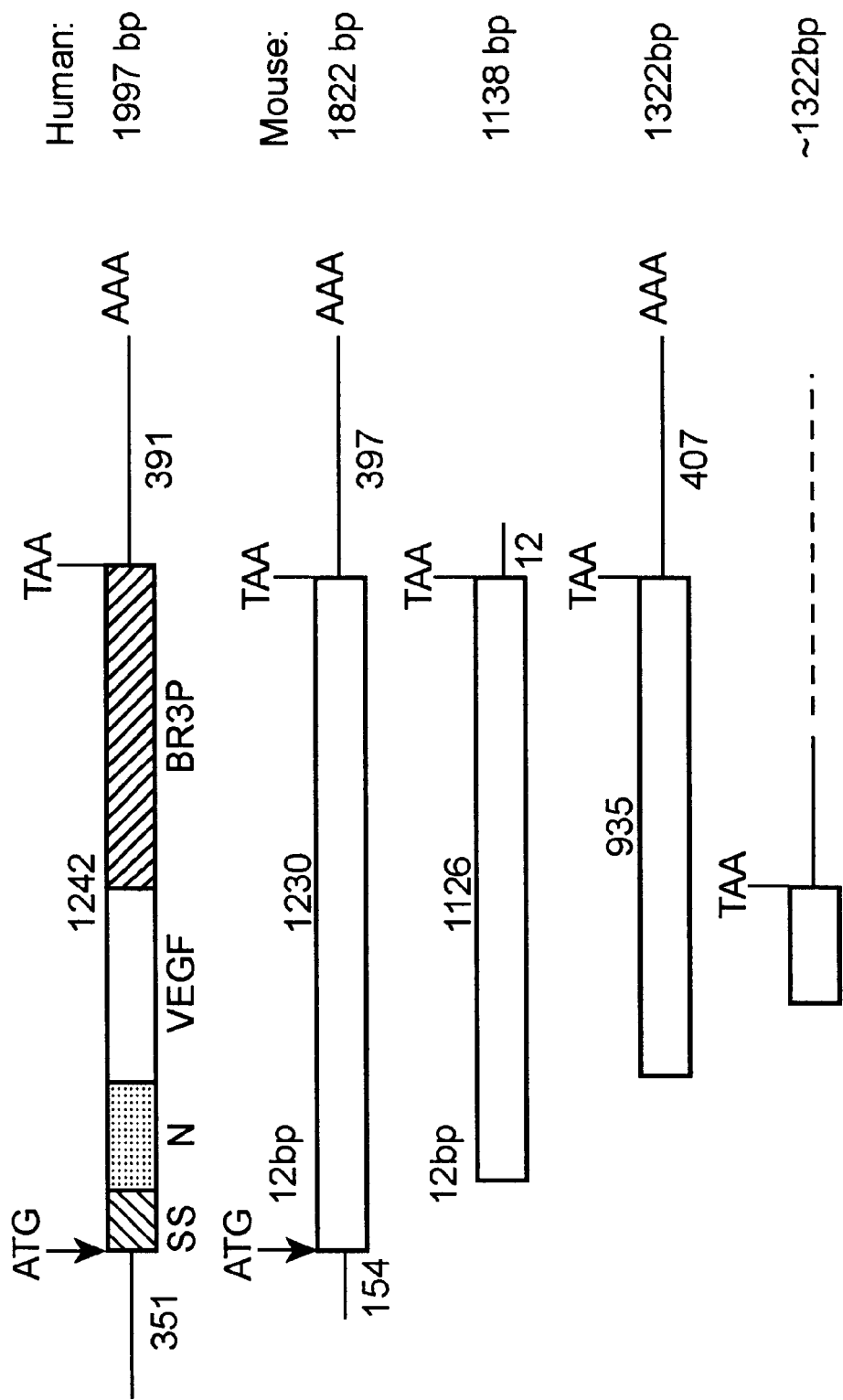
FIG. 31A provides a schematic illustration of the structure of mouse VEGF-C cDNA clones. The human VEGF-C cDNA structure is shown on the top line, with the signal sequence (SS), N-terminal propeptide (N), VEGF- and Balbiani Ring 3. protein (BR3P) homologous regions indicated. The lengths of the 5' and 3' noncoding regions and the long open reading frame are given in base pairs. The "ATG" and "TAA" in FIG. 31A indicate the translational start and stop codons, respectively; AAA is the polyadenylation sequence.

FIG. 31B presents a comparison of the human SEQ ID NO: 33 and mouse SEQ ID NO: 41 VEGF-C amino acid sequences. The amino acid sequence of mouse VEGF-C is presented on the top line and differences in the human sequence are marked below it. The sequences have been labeled to depict the regions shown in FIG. 32A. The arrow indicates the putative cleavage site for the signal peptidase; BR3P motifs, as well as a CR/SC motif, are boxed; and conserved cysteine residues are marked in bold above the sequence. Arginine residue 158 is also marked in bold. The numbering refers to mouse VEGF-C residues.

FIG. 32A presents SDS-PAGE-fractionated samples immunoprecipitated or affinity-purified from various $^{35}$S-labeled media. In the left panel, control medium from Bosc23 cells containing vector only, medium from cells expressing human VEGF-C, and medium from cells expressing mouse VEGF-C were independently precipitated with human VEGFR-3-Extracellular Domain coupled to sepharose. In the right panel, similar conditioned media were subjected to precipitation with anti-VEGF-C antibodies. mwm: molecular weight markers; m—mouse; h—human; α—anti.

Figure 32B:
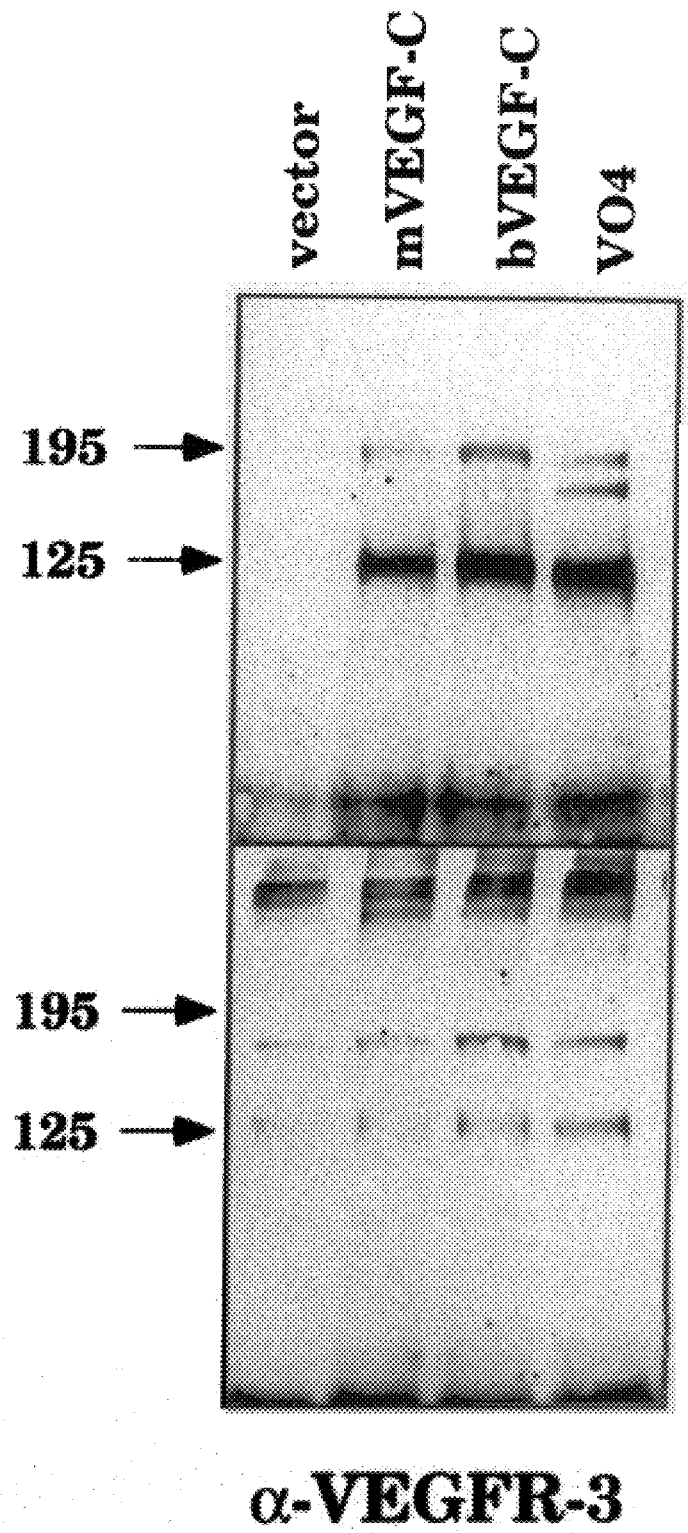
Figure 32C:
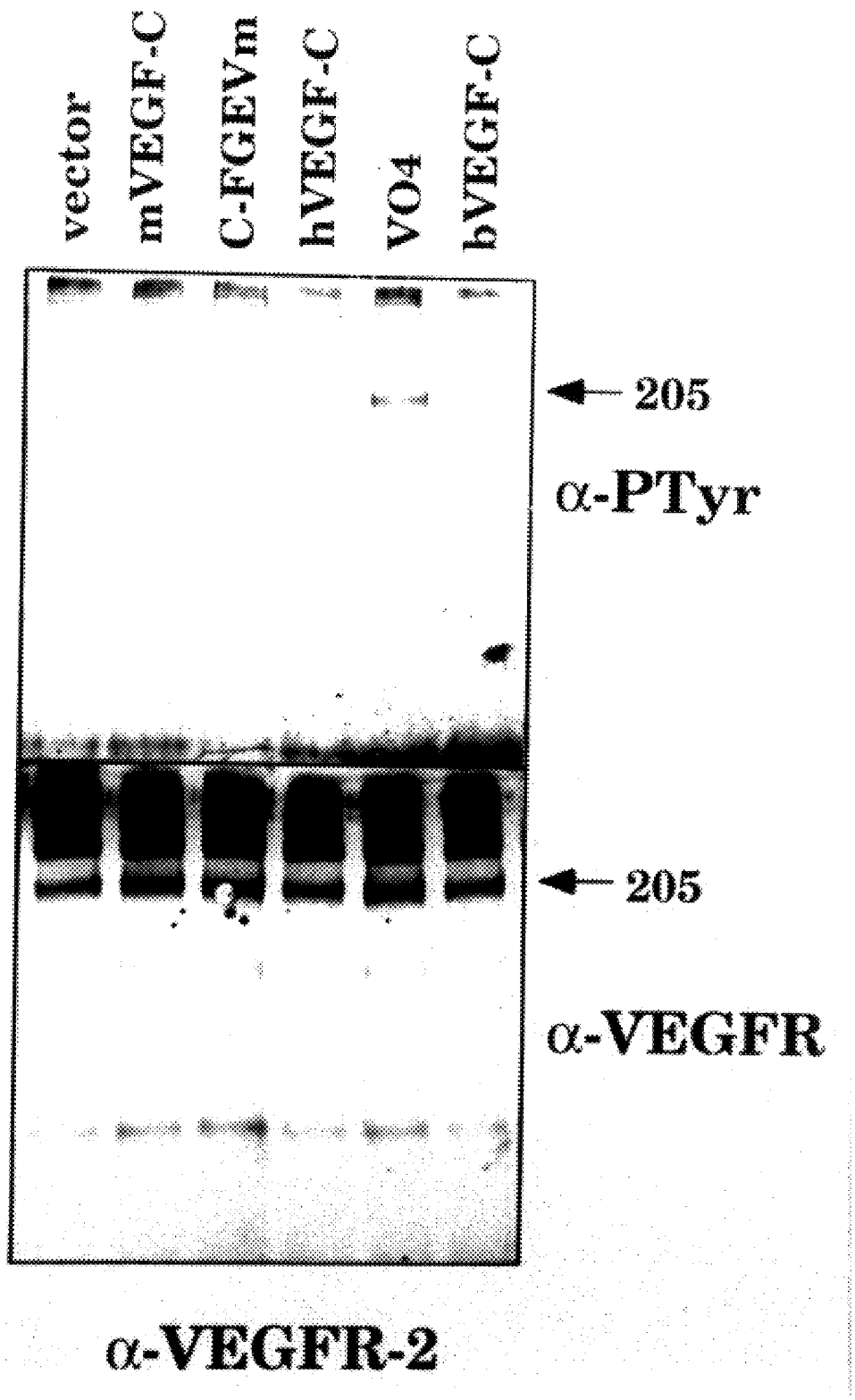

FIGS. 32B and 32C shows Western blots of gel-fractionated immunoprecipitates from lysates made from NIH 3T3 cells expressing VEGFR-3 that had been stimulated by contact with VEGF-C-containing lysates (or a vector control), as a measure of VEGF-C-induced receptor autophosphorylation. Western blots were probed with anti-phosphotyrosine (α-PTyr) or anti-receptor antisera (anti-VEGFR-3 and anti-VEGFR-2), as indicated. As a control, receptor autophosphorylation was induced by pervanadate treatment (VO4). The arrows and numbers refer to the apparent molecular weights of the tyrosyl phosphorylated receptor polypeptide bands. bVEGF: human baculoviral VEGF-C protein; C-FGEVm: lysate from cells harboring a mouse VEGF-C cDNA cloned into the vector in an antisense orientation.

Figure 33A:
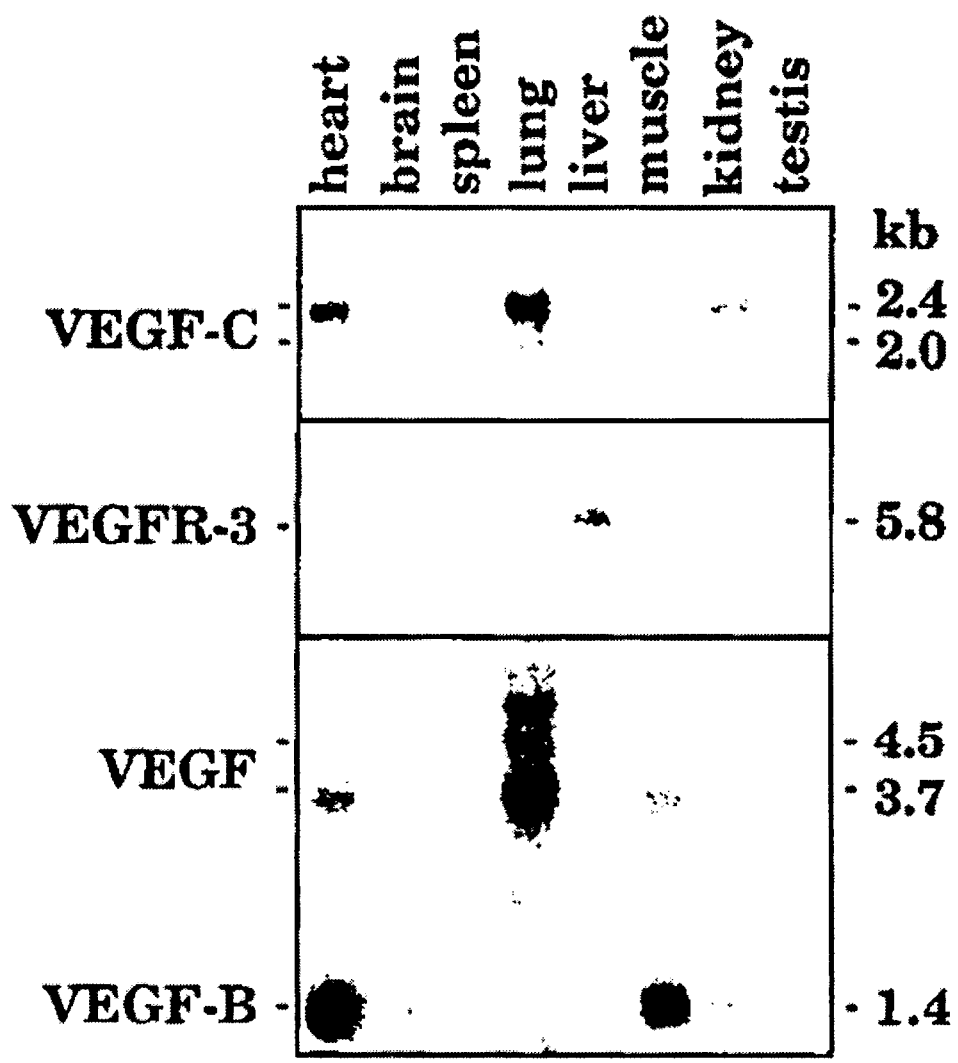

FIG. 33A depicts Northern blots of mRNA isolated from the indicated tissues of adult mice, probed with a VEGF-C probe (top panel), a VEGFR-3 probe (middle panel), and with a pool of the VEGF and VEGF-B probes (lower panel). The sizes of the RNA bands are indicated in kilobases (kb) to the right.

Figure 33B:
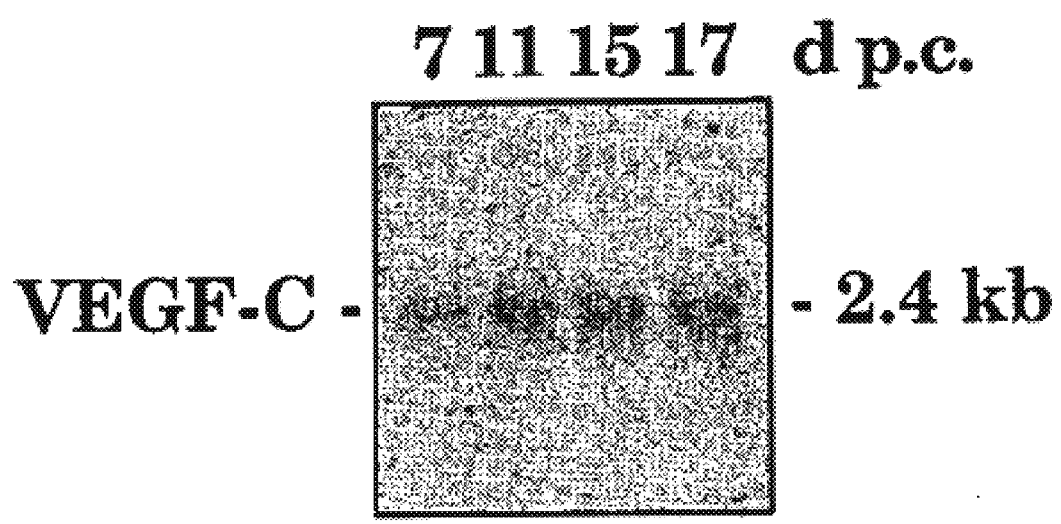

FIG. 33B depicts a Northern blot of mouse embryonic mRNA isolated at the indicated gestational ages and probed with a VEGF-C probe.

Figure 34A:
Figure 34B:
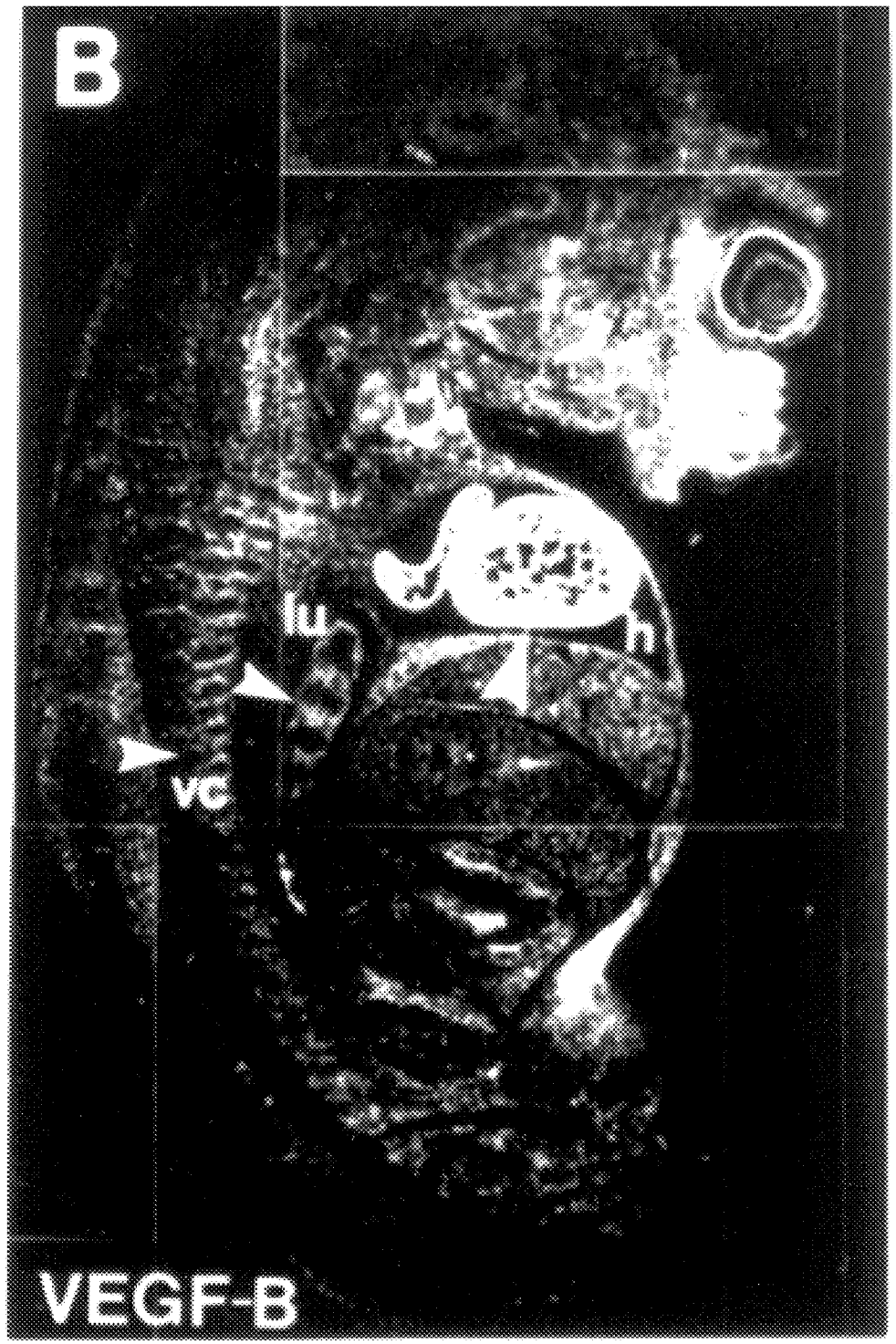
Figure 34C:
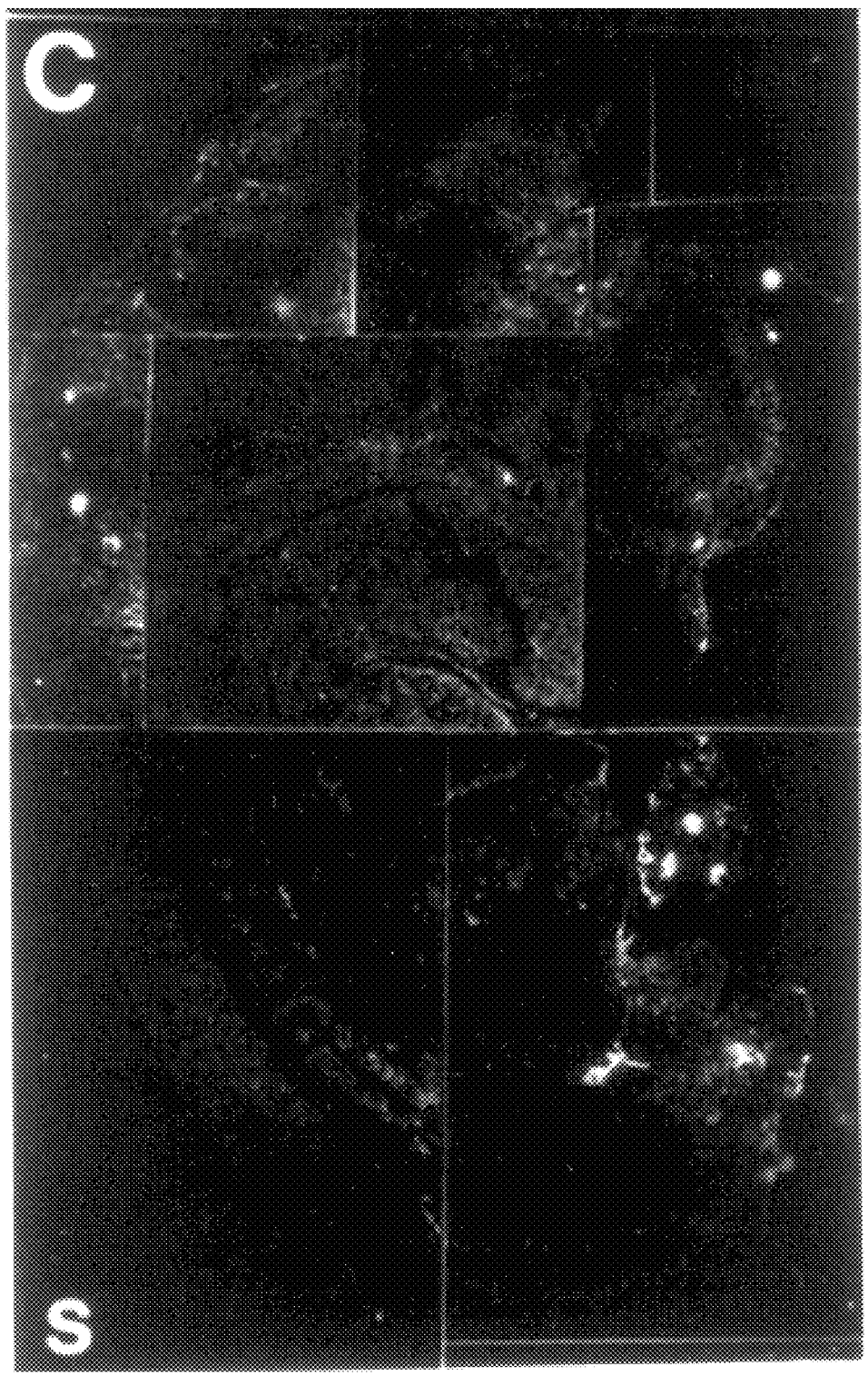
Figure 34D:
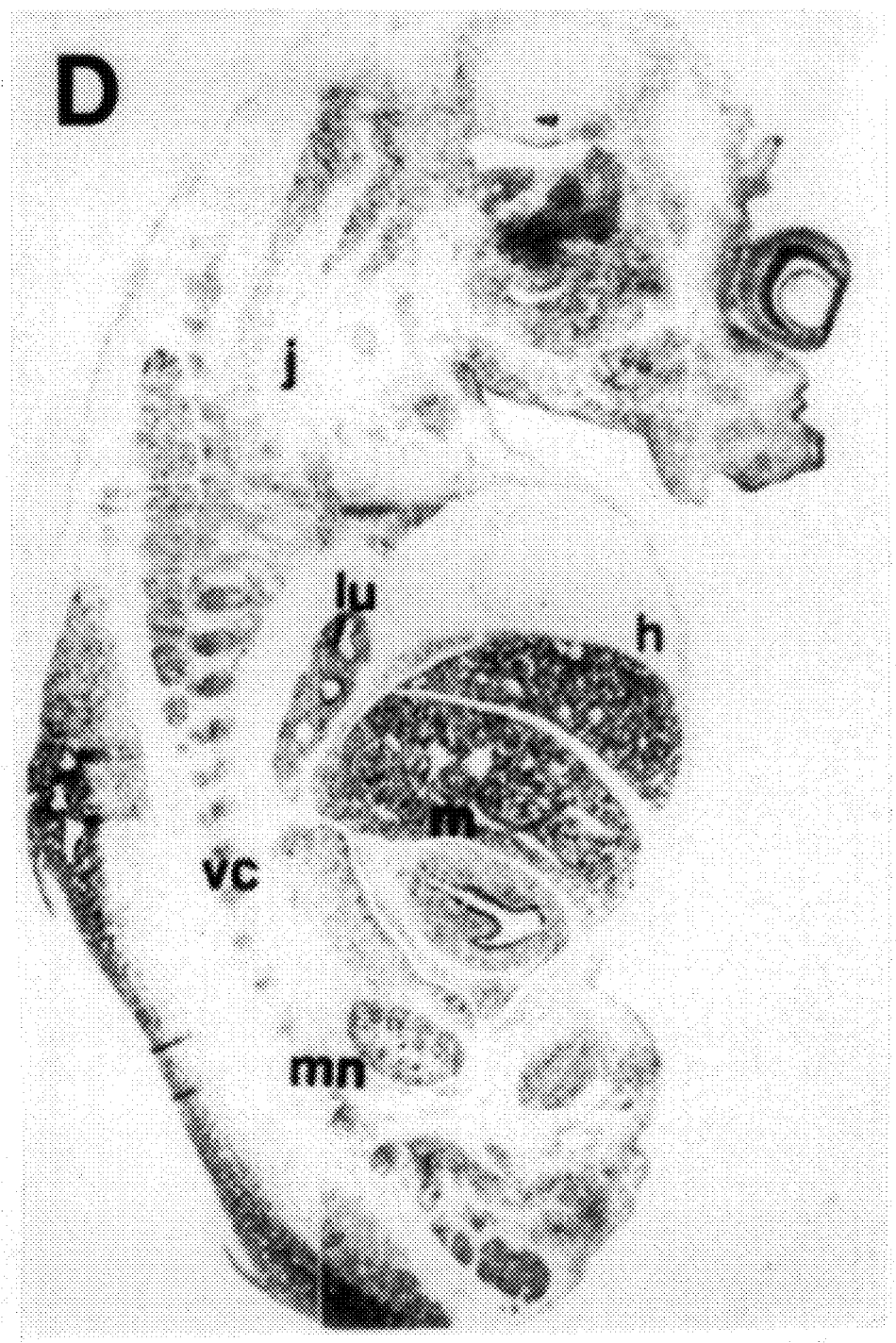

FIGS. 34A–D depict photomicrographs of in situ hybridizations revealing the expression of VEGF-C and VEGF-B mRNAs in a parasagittal section of a 12.5 day mouse embryo. FIG. 34A: VEGF-C probe; j—jugular veins, mn—metanephros, m—mesenterium (arrowheads), vc—intervertebral vessels, lu—lung (arrowheads). FIG. 34B: VEGF-B probe; h—heart, nasopharyngeal area (arrowheads). FIG. 34C: VEGF-C sense strand probe serving as a control. FIG. 34D: bright-field photomicrograph of the same field shown in FIG. 34C.

Figure 35A:
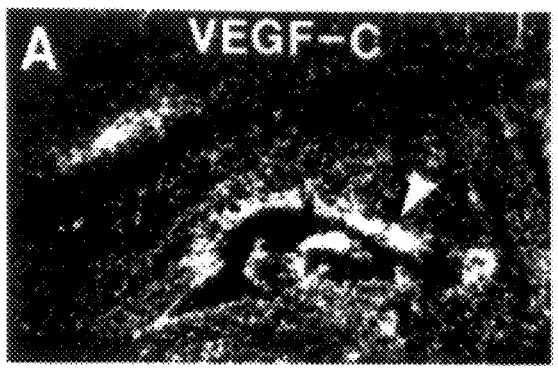
Figure 35B:
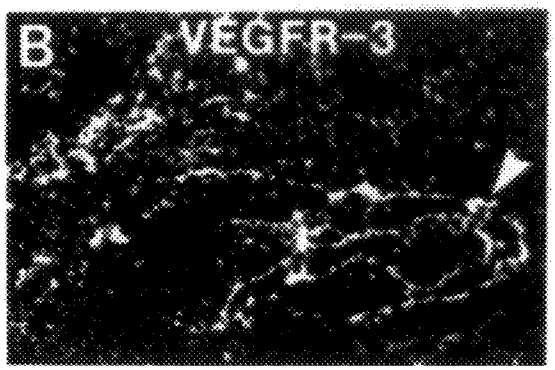
Figure 35C:
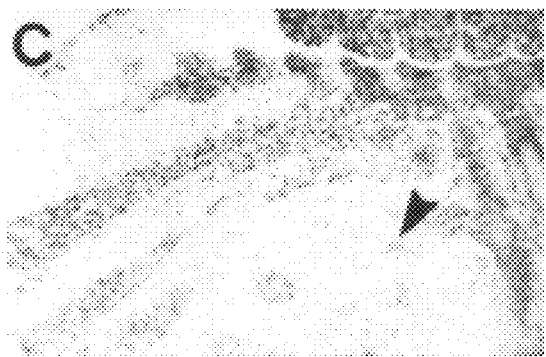
Figure 35D:
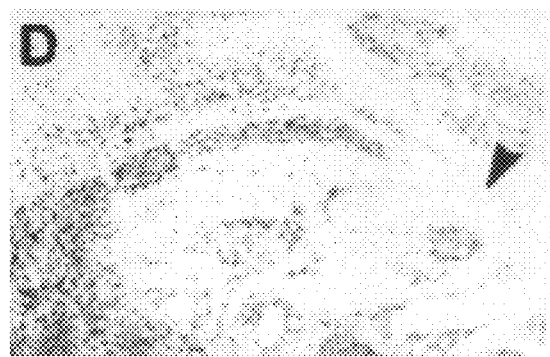
Figure 35E:
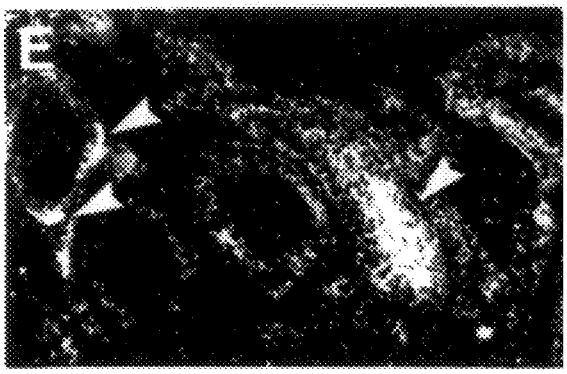
Figure 35F:
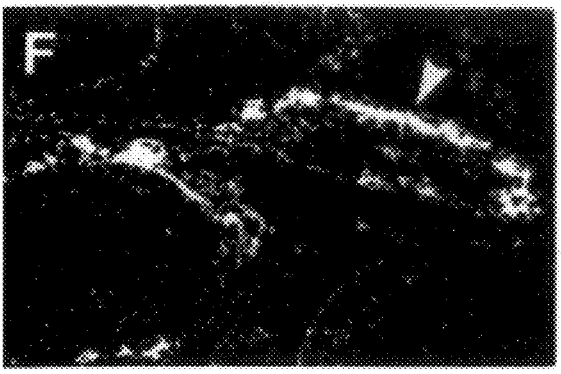
Figure 35G:
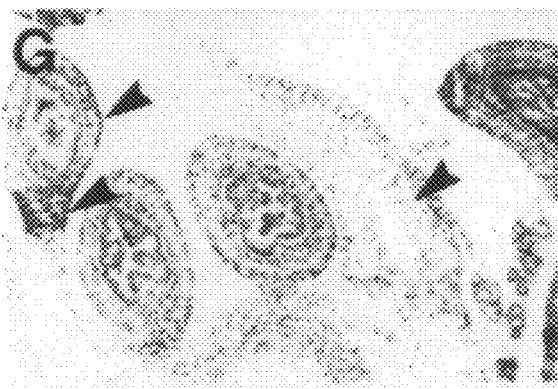
Figure 35H:
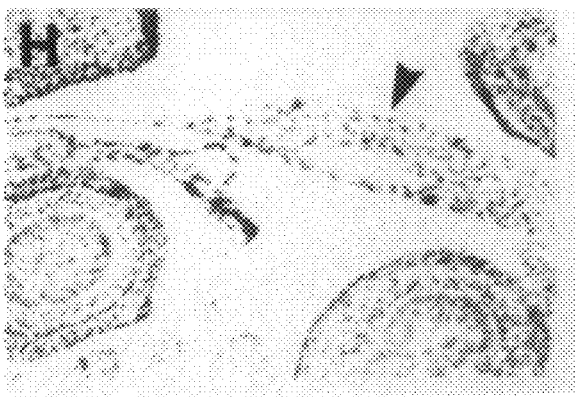

FIGS. 35A–H depict sections of mouse embryos providing comparisons of VEGF-C and VEGFR-3 expression in the jugular vessels and the mesenteric area. FIGS. 35A and 35C show expression of VEGF-C transcripts in the mesenchyme around the large sac-like structures in the jugular area (arrowheads). FIGS. 35B and 35D show expression of VEGFR-3 transcripts in the jugular venous sacs. FIGS. 35E and 35G show VEGF-C mRNA distribution in the mesenteric region of a 14.5 day p.c. embryo, as well as around the gut. FIGS. 35F and 35H show VEGFR-3 mRNA in the mesenteric region of a 14.5 day embryo, as well as the gut area, developing lymphatic vessels, and venules.

Figure 36A:
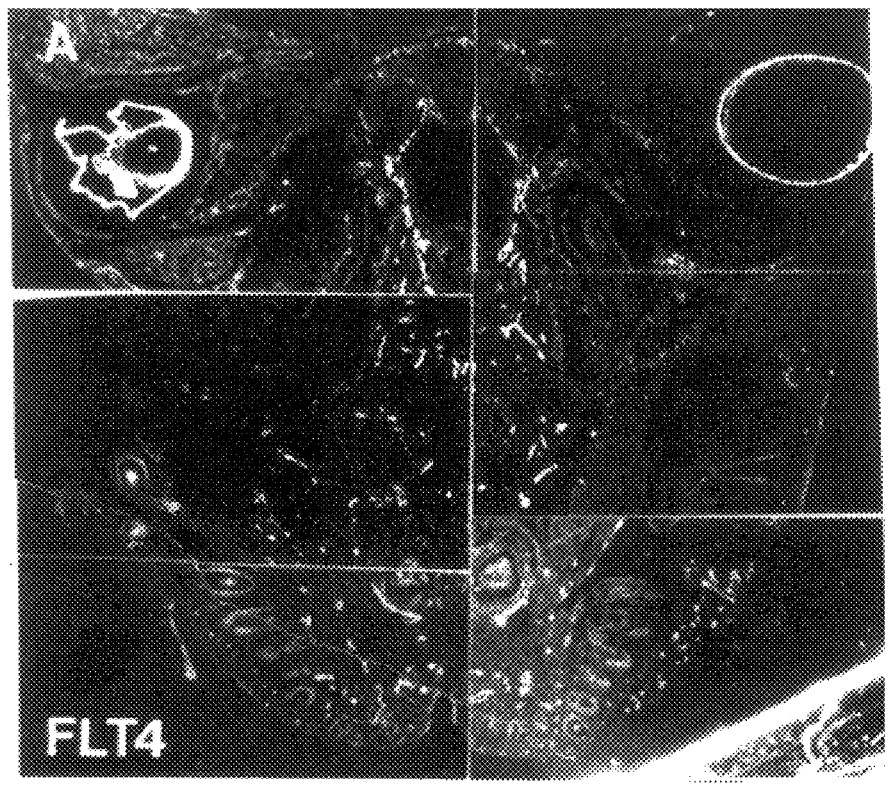
Figure 36B:
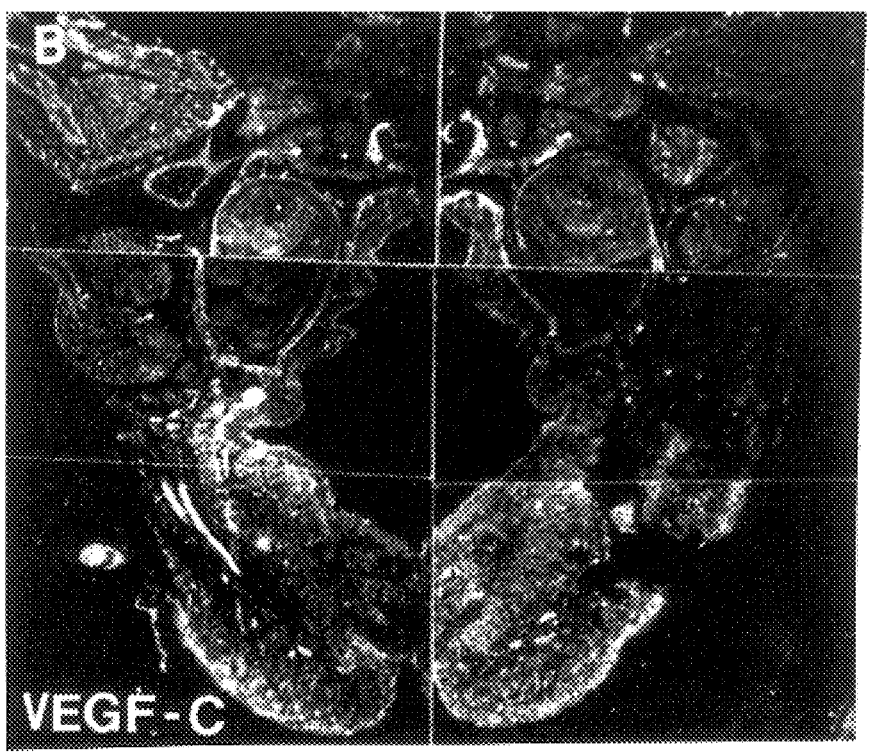
Figure 36C:

FIGS. 36A–D depict photomicrographs showing FLT4 and VEGF-C in situ hybridization of the cephalic region of a 16-day p.c. mouse embryo. A section of the cephalic region hybridized with the Flt4 probe (FIG. 36A) shows the developing snout, nasal structures and eyes. A more caudally located section shows hybridization with the VEGF-C probe (FIG. 36B). The round structures on both sides in the upper part represent the developing molars. In the upper (dorsal) part on both sides of the midline, the caudal portion of the developing conchae are seen. These structures also are shown in higher magnification darkfield (FIG. 36C) and lightfield (FIG. 36D) microscopy.

Figure 37:
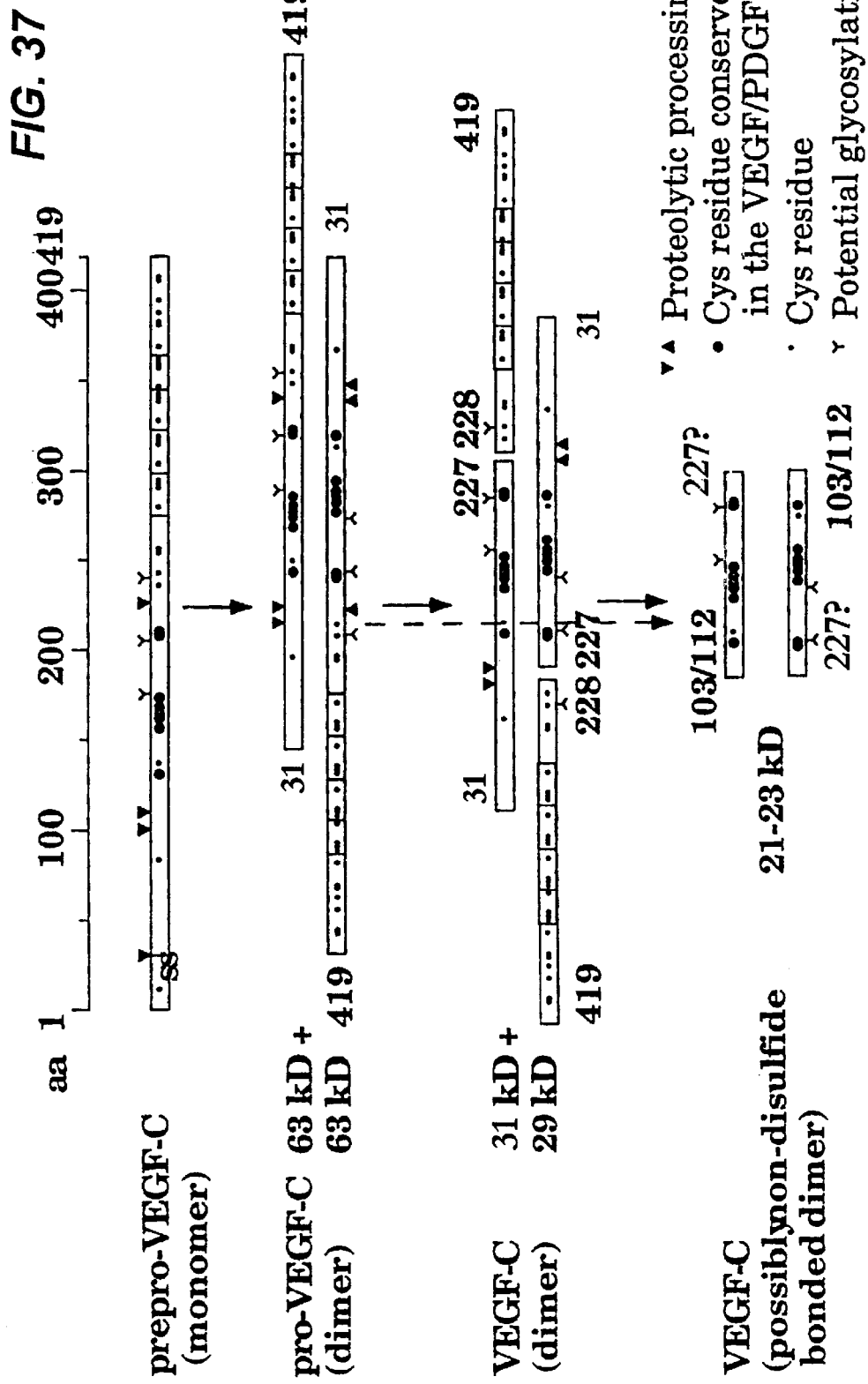

FIG. 37 presents a schematic illustration of VEGF-C processing, including the major forms of VEGF-C.

DETAILED DESCRIPTION OF THE INVENTION

Described herein is the isolation of a novel vascular endothelial growth factor and the cloning of a DNA encoding this novel growth factor from a cDNA library prepared from the human prostatic adenocarcinoma cell line PC-3. The isolated cDNA encodes a protein which is proteolytically processed and secreted to cell culture medium. The secreted protein, designated VEGF-C, binds to the extracellular domain of Flt4 and induces tyrosine autophosphorylation of Flt4 and VEGFR-2. VEGF-C also stimulates the migration of endothelial cells in collagen gel.

The present invention also is directed to novel growth factor polypeptides which are ligands for the Flt4 receptor tyrosine kinase (VEGFR-3). Ligands of the invention are members of a family of platelet-derived growth factors/vascular endothelial growth factors which promote mitosis and proliferation of vascular endothelial cells and/or mesodermal cells. As described in greater detail in Examples 4 and 5, ligands recognizing the Flt4 receptor tyrosine kinase were purified from a PC-3 prostatic adenocarcinoma cell line (ATCC CRL1435). When applied to a population of cells expressing the Flt4 receptor, ligands of the invention stimulate autophosphorylation, resulting in receptor activation.

A ligand according to the invention may be expressed as a larger precursor which is cleaved to produce the ligand. A coexpressed region in some cases results from alternative splicing of RNA of the ligand gene. Such a co-expressed region may be a function of the particular expression system used to obtain the ligand. The skilled artisan understands that in recombinant production of proteins, additional sequence may be expressed along with a functional peptide depending upon the particular recombinant construct used to express the protein, and subsequently removed to obtain the desired ligand. In some cases the recombinant ligand can be made lacking certain residues of the endogenous/natural ligand. Moreover, it is well-known in that conservative replacements may be made in a protein which do not alter the function of the protein. Accordingly, it is anticipated that such alterations are within the scope of the claims. Moreover, it is anticipated that one or more VEGF-C precursors (the largest putative native secreted VEGF-C precursor having the complete amino acid sequence from residue 32 to residue 419 of SEQ ID NO: 33) is capable of stimulating the Flt4 ligand without any further processing, in a manner similar to that in which VEGF stimulates its receptor in its unprocessed form after the secretion and concomitant release of the signal sequence.

Results reported herein show that Flt4 (VEGFR-3) transmits signals for the VEGF-C novel growth factor. This conclusion is based on the specific binding of VEGF-C to recombinant Flt4EC (Flt4 extracellular domain) protein and the induction of VEGFR-3 autophosphorylation by medium from VEGF-C transfected cells. In contrast, neither VEGF nor PLGF showed specific binding to VEGFR-3 or induced its autophosphorylation.

As set forth in greater detail below, the putative prepro-VEGF-C has a deduced molecular mass of 46,883; a putative prepro-VEGF-C processing intermediate has an observed molecular weight of about 32 kD; and mature VEGF-C isolated form conditioned media has a molecular weight of about 23 kD as assessed by SDS-Page under reducing conditions. A major part of the difference in the observed molecular mass of the purified and recombinant VEGF-C and the deduced molecular mass of the prepro-VEGF-C encoded by the VEGF-C open reading frame (ORF) is attributable to proteolytic removal of sequences at the amino-terminal and carboxyl-terminal regions of the prepro-VEGF-C polypeptide. However, proteolytic cleavage of the putative 102 amino acid leader sequence is not believed to account for the entire difference between the deduced molecular mass of 46,883 and the observed mass of about 23 kD, because the deduced molecular weight of a polypeptide consisting of amino acids 1–317 of SEQ ID NO: 33 is 35,724 kD. It is believed that a portion of the observed difference in molecular weights is attributable to proteolytic removal of amino acid residues in the amino and carboxyl terminal regions of the VEGF-C precursor. By extrapolation from studies of the structure of PDGF (Heldin et al., *Growth Factors,* 8:245–52 (1993)), it may be that the region critical for receptor binding and activation by VEGF-C is contained within amino acids residues 104–213, which are found in the secreted form of the VEGF-C protein (i.e., the form lacking the putative prepro leader sequence and some carboxyterminal sequences). The 23 kD polypeptide binding VEGFR-3 is likely to represent the VEGF-homologous domain. After biosynthesis, the nascent VEGF-C polypeptide may be glycosylated at three putative N-linked glycosylation sites identified in the deduced VEGF-C amino acid sequence. Polypeptides containing modifications, such as N-linked glycosylations, are intended as aspects of the invention.

The carboxyl terminal amino acid sequences, which increase the length of the VEGF-C polypeptide in comparison with other ligands of this family, show a pattern of spacing of cysteine residues reminiscent of the Balbiani ring 3 protein (BR3P) sequence (Dignam et al., *Gene,* 88:133–40 (1990); Paulsson et al., *J. Mol. Biol.,* 211:331–49 (1990)). This novel C-terminal silk protein-like structural motif of VEGF-C may fold into an independent domain, which, on the basis of the considerations above, is at least partially cleaved off after biosynthesis. Interestingly, at least one cysteine motif of the BR3P type is also found in the carboxyl terminus of VEGF. In our experiments both the putative precursor and cleaved ligand were detected in the cell culture media, although processing was apparently cell-associated on the basis of the pulse-chase experiments. The determination of the amino-terminal and carboxy-terminal sequences of VEGF-C isolates allows the identification of the proteolytic processing sites. The generation of antibodies against different parts of the pro-VEGF-C molecule will allow the exact determination of the precursor-product relationship and ratio, their cellular distribution, and the kinetics of processing and secretion.

VEGF-C has a conserved pattern of eight cysteine residues, which may participate in the formation of intra- and interchain disulfide bonds, creating an antiparallel dimeric biologically active molecule, similar to PDGF. Mutational analysis of the cysteine residues involved in the interchain disulfide bridges has shown that, in contrast to PDGF, VEGF dimers need to be held together by these covalent interactions in order to maintain biological activity. Disulfide linking of the VEGF-C polypeptide chains was evident in the analysis of VEGF-C in nonreducing conditions.

VEGFR-3, which distinguishes between VEGF and VEGF-C, is closely related in structure to VEGFR-1 and VEGFR-2. Finnerty et al., *Oncogene,* 8:2293–98 (1993); Galland et al., *Oncogene,* 8:1233–40 (1993); Pajusola et al., *Cancer Res.,* 52:5738–43 (1992). However, the mature form of VEGFR-3 differs from the two other VEGFRs in that it is proteolytically cleaved in the extracellular domain into two disulfide-linked polypeptides. Pajusola et al., *Oncogene,* 9:3545–55 (1994). Another difference is that 4.5 and 5.8 kb VEGFR-3 mRNAs encode polypeptides differing in their C-termini and apparently in their signalling properties due to the use of alternative 3' exons. Borg et al., *Oncogene,* 10:973–84 (1995); Pajusola et al., *Oncogene,* 8:2931–37 (1993).

Besides VEGFR-3, VEGFR-2 tyrosine kinase also is activated in response to VEGF-C. VEGFR-2 mediated signals cause striking changes in the morphology, actin reorganization and membrane ruffling of porcine aortic endothelial cells overexpressing this receptor. In these cells, VEGFR-2 also mediated ligand-induced chemotaxis and mitogenicity. Waltenberger et al., *J. Biol. Chem.,* 269:26988–95 (1994). Similarly, the receptor chimera CSF-1R/VEGFR-3 was mitogenic when ectopically expressed in NIH 3T3 fibroblastic cells, but not in porcine aortic endothelial cells (Pajusola et al., 1994). Consistent with such results, the bovine capillary endothelial (BCE) cells, which express VEGFR-2 mRNA but very little or no VEGFR-1 or VEGFR-3 mRNAs, showed enhanced migration when stimulated with VEGF-C. Light microscopy of the BCE cell cultures in collagen gel also suggested that VEGF-C stimulated the proliferation of these cells. The data thus indicate that the VEGF ligands and receptors show a great specificity in their signalling, which may be cell-type-dependent.

The expression pattern of the VEGFR-3 (Kaipainen et al., *Proc. Natl. Acad. Sci. (USA),* 92:3566–70 (1995)) suggests that VEGF-C may function in the formation of the venous and lymphatic vascular systems during embryogenesis. Constitutive expression of VEGF-C in adult tissues shown herein further suggests that this gene product also is involved in the maintenance of the differentiated functions of the lymphatic endothelium where VEGFR-3 is expressed (Kaipainen et al., 1995). Lymphatic capillaries do not have well-formed basal laminae and an interesting possibility remains that the silk-like BR3P motif is involved in producing a supramolectilar structure which could regulate the availability of VEGF-C in tissues. However, as shown here, VEGF-C also activates VEGFR-2, which is abundant in proliferating endothelial cells of vascular sprouts and branching vessels of embryonic tissues, but not so abundant in adult tissues. Millauer et al., *Nature,* 367:576–78 (1993). These data have suggested that VEGFR-2 is a major regulator of vasculogenesis and angiogenesis. VEGF-C may thus have a unique effect on lymphatic endothelium and a more redundant function, shared with VEGF, in angiogenesis and possibly in regulating the permeability of several types of endothelia. Because VEGF-C stimulates VEGFR-2 and promotes endothelial migration, VEGF-C may be useful as an inducer of angiogenesis of blood and lymphatic vessels in wound healing, in tissue transplantation, in eye diseases, and in the formation of collateral vessels around arterial stenoses and into injured tissues after infarction.

Taken together, these results show an increased complexity of signalling in the vascular endothelium. They reinforce the concept that when organs differentiate and begin to perform their specific functions, the phenotypic heterogeneity of endothelial cells increases in several types of functionally and morphologically distinct vessels. However, upon stimulation by suitable angiogenic stimuli, endothelial cells can re-enter the cell cycle, migrate, withdraw from the cell cycle and subsequently differentiate again to form new vessels that are functionally adapted to their tissue environment. This process of angiogenesis, concurrent with tissue development and regeneration, depends on the tightly controlled balance between positive and negative signals for endothelial cell proliferation, migration, differentiation and survival.

Previously-identified growth factors promoting angiogenesis include the fibroblast growth factors, hepatocyte growth factor/scatter factor, PDGF and TGF-α. (See e.g., Folkman, *Nature Med.*, 1:27–31 (1995); Friesel et al., *FASEB J.*, 9:919–25 (1995); Mustonen et al., *J. Cell. Biol.*, 129:895–98 (1995). However, VEGF has been the only growth factor relatively specific for endothelial cells. The newly identified factors VEGF-B and VEGF-C thus increase our understanding of the complexity of the specific and redundant positive signals for endothelial cells involved in vasculogenesis, angiogenesis, permeability, and perhaps also other endothelial functions.

Also described herein is the localization of the VEGF-C gene in human chromosomes by analysis of somatic cell hybrids and fluorescence in situ hybridization (FISH). Southern blotting and polymerase chain reaction analysis of somatic cell hybrids and fluorescence in situ hybridization of metaphase chromosomes were used to assess the chromosomal localization of the VEGF-C gene. The VEGF-C gene was located on chromosome 4q34, close to the human aspartylglucosaminidase gene previously mapped to 4q34–35. The VEGF-C locus at 4q34 is a candidate target for mutations leading to vascular malformations or cardiovascular diseases. Expression studies using Northern blotting show abundant VEGF-C expression in heart and skeletal muscle; other tissues, such as placenta ovary, small intestine, thyroid gland, kidney, prostate, spleen, testis and large intestine also express this gene. Whereas PlGF is predominantly expressed in the placenta, the expression patterns of VEGF, VEGF-B and VEGF-C overlap in many tissues, which suggests that they may form heterodimers and interact to exert their physiological functions.

Targeted mutagenesis leading to inactivation of the VEGF receptor loci in the mouse genome has shown that VEGFR-1 is necessary for the proper organization of endothelial cells forming the vascular endothelium, while VEGFR-2 is necessary for the generation of both endothelial and hematopoietic cells. This suggests that the four genes of the VEGF family can be targets for mutations leading to vascular malformations or cardiovascular diseases.

The following Examples illustrate preferred embodiments of the invention, wherein the isolation, characterization, and function of Flt4 ligands and ligand-encoding nucleic acids according to the invention are shown.

EXAMPLE 1

Production of pLTRFlt4l Expression Vector

Figure 2A:
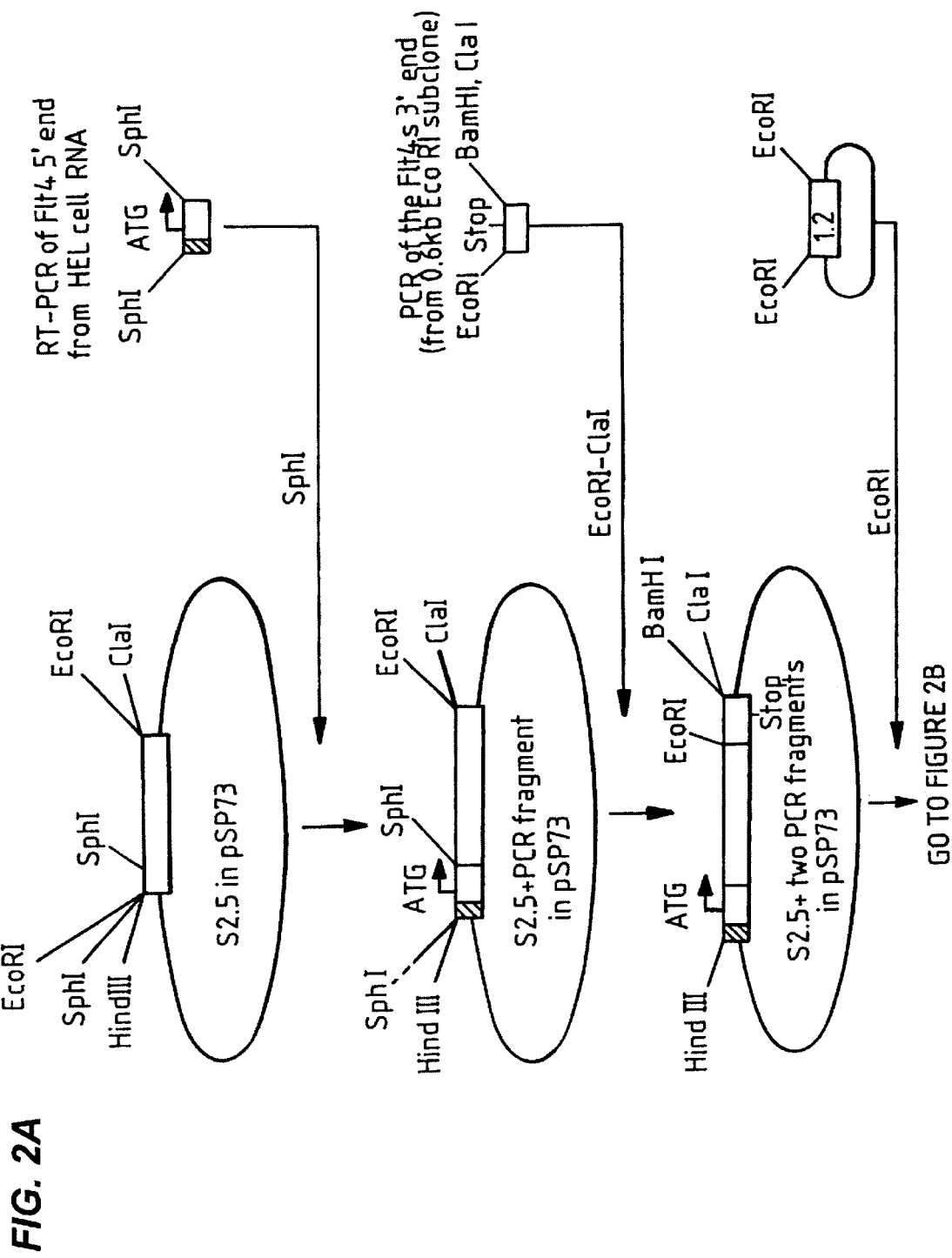
FIGS. 2A and 2B schematically depict the construction of the pLTRFlt4l expression vector.
Figure 2B:
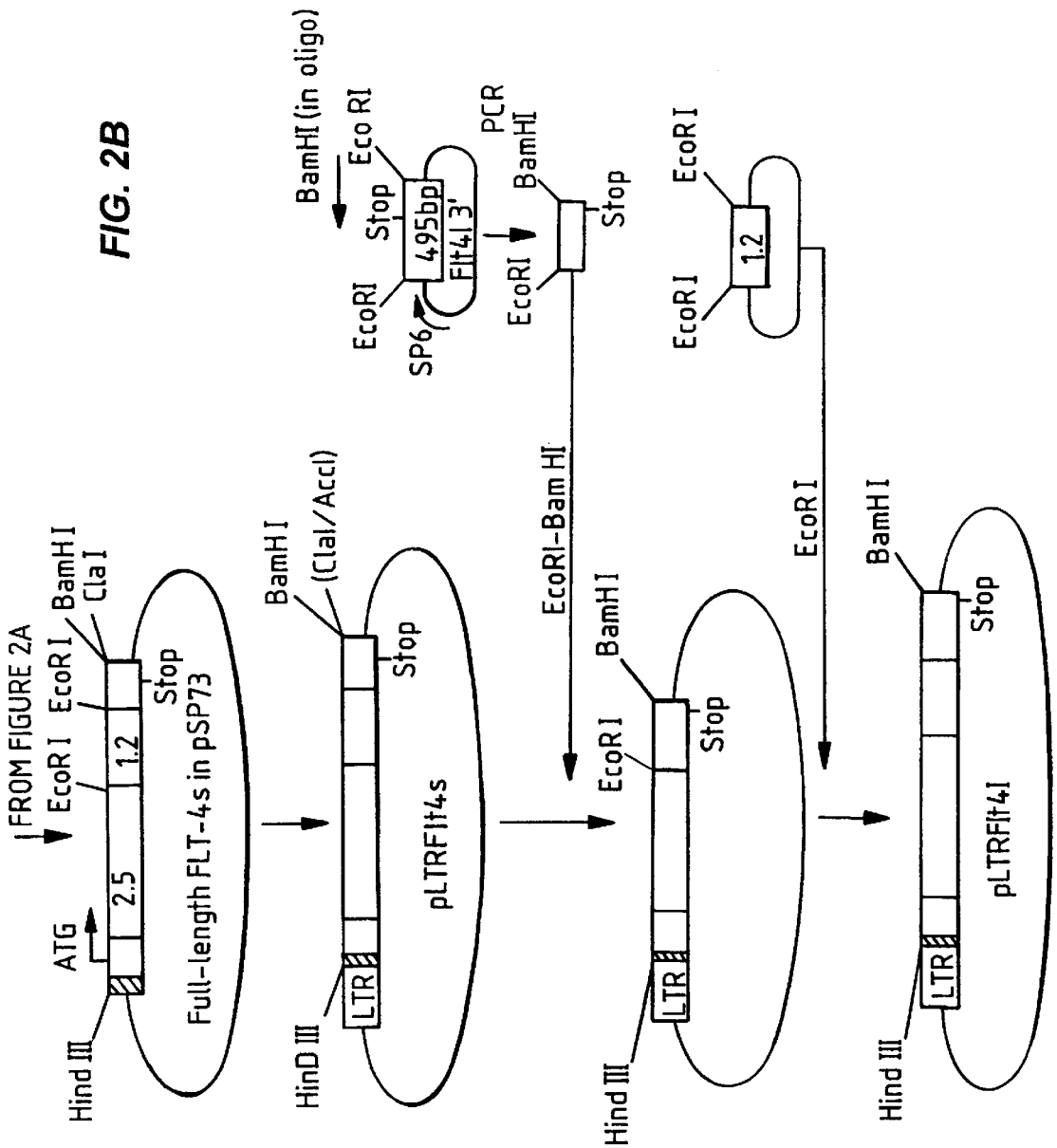

Construction of the LTR-Flt4l vector is schematically shown in FIGS. 2A and 2B. The full-length Flt4s cDNA (Genbank Accession No. X68203, SEQ ID NO: 36) was assembled by first subcloning the S2.5 fragment, reported in Pajusola et al., *Cancer Res.*, 52:5738–5743 (1992), incorporated by reference herein, containing base pairs 56–2534 of the Flt4s into the EcoRI site of the pSP73 vector (Promega, Madison, Wis.).

Since cDNA libraries used for screening of Flt4 cDNAs did not contain the extreme 5' protein-coding sequences, inverse PCR was used for the amplification of the 5' end of Flt4 corresponding to the first 12 amino acid residues (MQRGAALCLRLW). Poly(A)$^+$ RNA was isolated from human HEL erythroleukemia cells and double-stranded cDNA, were synthesized using an Amersham cDNA Synthesis System Plus kit (Amersham Corp., Buckinghamshire, U.K.) and a gene-specific primer: 5'-TGTCCTCGCTGTCCTTGTCT-3' (SEQ ID NO: 1), which was located 195 bp downstream of the 5' end of clone S2.5. Double-stranded cDNA was treated with T4 DNA polymerase to blunt the ends and cDNA was purified by filtration with Centricon 100 filters (Amicon Inc., Beverly, Mass.). Circularization of the blunt-ended cDNA was performed by ligation in a total volume of 150 microliters. The reaction mixture contained a standard ligation buffer, 5% PEG-8000, 1 mM DTT and 8 U of T4 DNA ligase (New England Biolabs, Beverly, Mass.). Ligation was carried out at 16° C. for 16 hours. Fifteen microliters of this reaction mix were used in a standard PCR reaction (100 μl total volume) containing 100 ng of Flt4-specific primers introducing SacI and PstI restriction sites, and 1 unit of Taq DNA polymerase (Perkin Elmer Cetus). Two rounds of PCR were performed using 33 cycles per round (denaturation at 95° C. for 1 minute, annealing at 55° C. for 2 minutes, and elongation at 72° C. for 4 minutes). The PCR mixture was treated sequentially with the SacI and PstI restriction enzymes, and after purification with MagicPCR Preps (Promega), DNA fragments were subcloned into the pGEM3Zf(+) vector for sequencing (Promega). The sequence corresponded to the 5' end of the Flt4s cDNA clone deposited in the Genbank Database as Accession No. X68203.

Figure 1:
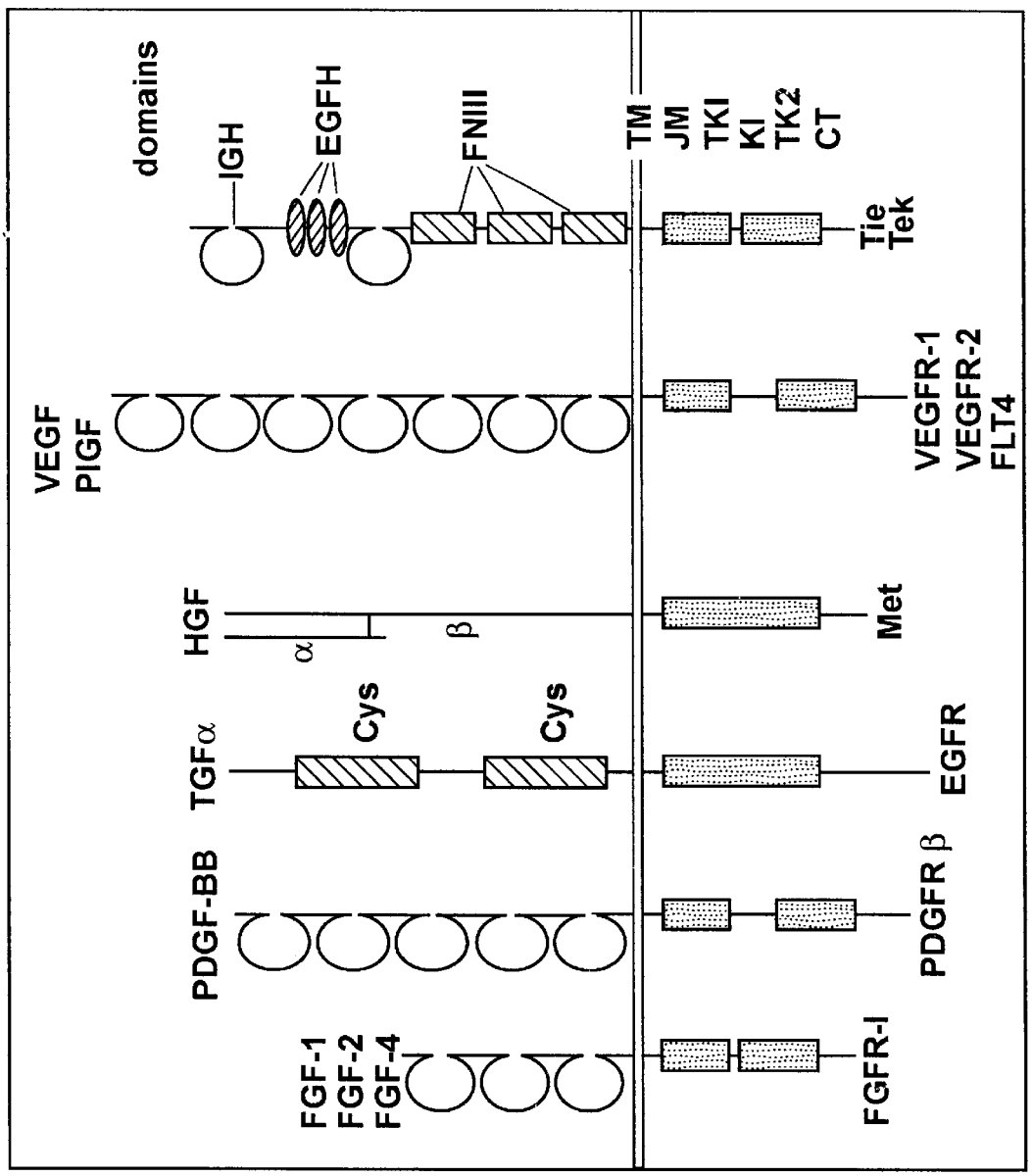
FIG. 1 is a schematic diagram showing major endothelial cell receptor tyrosine kinases and growth factors involved in vasculogenesis and angiogenesis.

The sequence encoding the first 12 amino acid residues was added to the expression construct by ligating an SphI-digested PCR fragment amplified using reverse transcription-PCR of poly(A)$^+$ RNA isolated from the HEL cells. The forward primer had the following sequence: 5'-ACAT<u>GCATGC</u> CACCATGCAG CGGGGCGCCG CGCTGTGCCT GCGACTGTGG CTCTGCCTGG GACTCCTGGA-3' (SEQ ID NO: 2) (SphI site underlined, translational start codon marked in bold). The translation start codon is immediately downstream from an optimized Kozak consensus sequence. Kozak, *Nucl. Acids Res.*, 15: 8125–8148, 1987). The reverse primer, 5'-ACAT<u>GCATGC</u> CCCGCCGGT CATCC-3' (SEQ ID NO: 3) (SphI site underlined), to the 5' end of the S2.5 fragment, thus replacing the unique SphI fragment of the S2.5 plasmid. The resulting vector was digested with EcoRI and ClaI and ligated to a 138 bp PCR fragment amplified from the 0.6 kb EcoRI fragment (base pairs 3789 to 4416 in the Genbank X68203 sequence) which encodes the 3' end of Flt4s shown in FIG. 1 of Pajusola et al., *Cancer Res.*, 52:5738–5743 (1992), using the oligonucleotides 5'-CG<u>GAATTC</u>CC CAT-GACCCCA AC-3' (SEQ ID NO: 4) (forward primer, EcoRI site underlined) and 5'-CC<u>ATCGAT</u>GG ATCCTACCTG AAGCCGCTTT CTT-3' (SEQ ID NO: 5) (reverse primer, ClaI site underlined). The coding domain was completed by ligation of the 1.2 kb EcoRI fragment (base pairs 2535–3789 of the sequence found in Gen Bank Acc. No. X68203) into the above construct. The complete cDNA was subcloned as a HindIII-ClaI(blunted) fragment (this ClaI site was also included in the 3' primer used to construct the 3' end of the coding sequence) to the pLTRpoly expression vector reported in Mäkelä et al., *Gene,* 118: 293–294 (1992) (Genbank accession number X60280, SEQ ID NO: 37), incorporated by reference herein, using its HindIII-AccI (blunted) restriction sites.

The long form of Flt4 was produced by replacing the 3'-end of the short form as follows: The 3' region of the Flt4l cDNA was PCR-amplified using a gene-specific oligonucleotide (SEQ ID NO: 7, see below) and a PGEM 3Z vector-specific (SP6 promoter) oligonucleotide 5'-ATTTAGGTGACACTATA-3' (SEQ ID NO: 6) as reverse and forward primers, respectively. The template for PCR was an Flt4l cDNA clone containing a 495 bp EcoRI fragment extending downstream of the EcoRI site at nucleotide 3789 of the Genbank X68203 sequence (the sequence downstream of this EcoRI site is deposited as the Flt4 long form 3' sequence having Genbank accession number S66407 (SEQ ID NO: 38)). The gene-specific oligonucleotide contains a BamHI restriction site located right after the end of the coding region and has the following sequence: 5'-CCATCGATGGATCCCGATGCTGCTTAGTAGCTGT-3' (SEQ ID NO: 7) (BamI site is underlined). The PCR product was digested with EcoRI and BamIH and transferred in frame to the LTRFlt4s vector fragment from which the coding sequences downstream of the EcoRI site at base pair 2535 (see sequence X68203) had been removed by EcoRI-BamHI digestion. The resulting clone was designated pLTRFlt4l. Again, the coding domain was completed by ligation of the 1.2 kb EcoRI fragment (base pairs 2535–3789 of sequence X68203) back into the resulting construct.

EXAMPLE 2

Production and Analysis of Flt4l Transfected Cells

NIH 3T3 cells (60% confluent) were co-transfected with 5 micrograms of the pLTRFlt4l construct and 0.25 micrograms of the pSV2neo vector containing the neomycin phosphotransferase gene (Southern et al., *J. Mol. Appl. Genet.,* 1:327 (1982)), using the DOTAP liposome-based transfection reagents (Boehringer-Mannheim, Mannheim, Germany). One day after transfection, the cells were transferred into selection media containing 0.5 mg/ml geneticin (GIBCO, Grand Island, N.Y.). Colonies of geneticin-resistant cells were isolated and analyzed for expression of the Flt4 proteins. Cells were lysed in boiling lysis buffer containing 3.3% SDS 125 mM Tris, pH 6.8. Protein concentrations of the samples were measured by the BCA method (Pierce, Rockford, Ill.). About 50 micrograms of protein from each lysate were analyzed for the presence of Flt4 by 6% SDS-polyacrylamide gel electrophoresis (SDS-PAGE) and immunoblotting using antisera against the carboxyl terminus of Flt4. Signals on Western blots were revealed using the ECL method (Amersham).

For production of anti-Flt4 antiserum, the Flt4 cDNA fragment encoding the 40 carboxy-terminal amino acid residues of the short form: NH2-PMTPTTYKG SVDN-QTDSGM VLASEEFEQI ESRHRQESGFR-COOH (SEQ ID NO: 8) was cloned as a 657 bp EcoRI-fragment into the pGEX-1λT bacterial expression vector (Pharmacia-LKB, Inc., Uppsala, Sweden) in frame with the glutathione-S-transferase coding region. The resultant GST-Flt4S fusion protein was produced in *E. coli* and purified by affinity chromatography using a glutathione-Sepharose 4B column.

The purified protein was lyophilized, dissolved in phosphate-buffered saline (PBS), mixed with Freund's adjuvant and used for immunization of rabbits at bi-weekly intervals using methods standard in the art (Harlow et al., *Antibodies: A Laboratory Manual* (Cold Spring Harbor Laboratory Press, 1988)). Antisera were used, after the fourth booster immunization, for immunoprecipitation of Flt4 from transfected cells. Cell clones expressing Flt4 were also used for ligand stimulation analysis.

EXAMPLE 3

Figure 3:
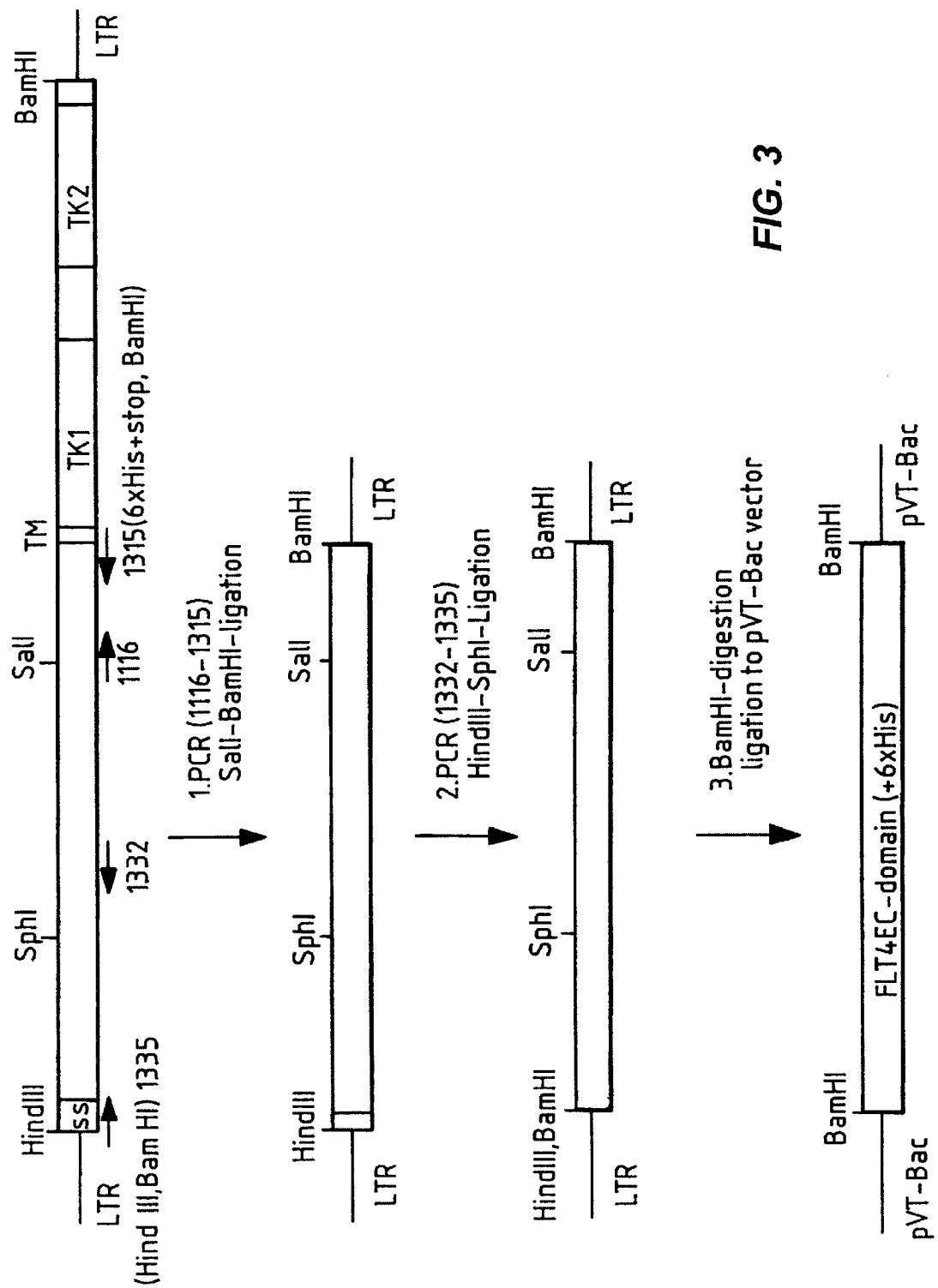
FIG. 3 schematically depicts the construction of the baculovirus vector encoding a secreted soluble Flt4 extracellular domain (Flt4EC).

Construction of a Flt4 EC Baculovirus Vector and Expression and Purification of its Product The construction of an Flt4 extracellular domain (EC) baculovirus vector is schematically depicted in FIG. 3. The Flt4-encoding cDNA was prepared in both a long form and a short form, each being incorporated in a vector under control of the Moloney murine leukemia virus LTR promoter. The nucleotide sequence of the short form of the Flt4 receptor is available from the Genbank database as Accession No. X68203 and the specific 3' segment of the long form cDNA is available under GenBank Accession No. S66407.

The ends of a cDNA segment encoding the Flt4 extracellular domain (EC) were modified as follows: The 3' end of the Flt4 cDNA sequence (Genbank Accession Number X68203) which encodes the extracellular domain was amplified using primer 1116 (5'-CTGGA GTCGACTTGGCGGACT-3'; SEQ ID NO:. 9, SalI site underlined) and primer 1315 (5'-CGC GGATCCCTAGTGATGGTGATGGTGATGTCTACCTTC-GATCATGCTGCCCTTAT CCTC-3'; (SEQ ID NO: 10, BamHI site underlined). The sequence at the 5' end of primer 1315 is not complementary to the flt4 coding region. Inspection of the sequence that is complementary to this region of prier 1315 reveals in a 5' to 3' order, a stop codon, six contiguous histidine codons (for subsequent chromatographic purification of the encoded polypeptide using a Nc-NTA column; Qiagen, Hilden, Germany), and an added BamHI site. The amplified fragment was digested with SalI and BamHI and used to replace a unique SalI-BamHI fragment in the LTRFlt4 vector shown in FIG. 3. The SalI-BamHI fragment that was replaced encodes the Flt4 transmembrane and cytoplasmic domains. The result was a modified LTF Flt4 vector.

The 5' end without the Flt4 signal sequence encoding region was amplified by PCR using the primer 1335 (5'-CCC AAGCTTGGATCCAAGTGGCTACTCCATGACC-3'; (SEQ ID NO: 11) the primer contains added HindIII (AAGCTT) and BamHI (GGATCC) restriction sites, which are underlined). The second primer used to amplify the region encoding the Flt4 signal sequence was primer 1332 5'-GTTGCCTGTGATGTGCACCA-3'; SEQ ID NO: 12). The amplified fragment was digested with HindIII and SphI (the HindIII site (AAGCTT) is underlined in primer 1335 and the SphI site is within the amplified region of the Flt4l cDNA). The resultant HindIII-SphI fragment was used to replace a HindIII-SphI fragment in the modified LTRFlt4l vector described immediately above (the HindIII site is in the 5' junction of the Flt4 insert with the pLTRpoly portion of the vector, the SphI site is in the Flt4 cDNA). The resultant Flt4EC insert was then ligated as a BamHI fragment into the BamHI site in the pVTBac plasmid described in Tessier et al., *Gene* 98:177–183 (1991), incorporated herein by reference. The relative orientation of the insert was confirmed by partial sequencing so that the open reading frame of the signal sequence-encoding portion of the vector was adjacent to, and in frame with, the Flt4 coding region sequence. The Flt4EC construct was transfected together with baculovirus genomic DNA into SF-9 cells by lipofection. Recombinant virus was purified, amplified and used for infection of High-Five cells (Invitrogen, San Diego, Calif.) using methods standard in the art. The Flt4 extracellular domain (Flt4EC) was purified from the culture medium of the infected High-Five cells using Ni-NTA affinity chromatography according to manufacturer's instructions (Qiagen) for binding and elution of the 6xHis tag encoded in the COOH-terminus of the recombinant Flt4 extracellular domain.

EXAMPLE 4

Isolation of an Flt4 Ligand from Conditioned Media

A human Flt4 ligand according to the invention was isolated from media conditioned by: a PC-3 prostatic adenocarcinoma cell line (ATCC CRL 1435) in Harris F-12 Nutrient mixture (GIBCO) containing 7% fetal calf serum (FCS). The cells were grown according to the supplier's instructions. In order to prepare the conditioned media, confluent PC-3 cells were cultured for 7 days in Ham's F-12 Nutrient mixture (GIBCO) in the absence of fetal bovine serum (FBS). Medium was then cleared by centrifugation at 10,000 g for 20 minutes. The medium was then screened to determine its ability to induce tyrosine phosphorylation of Flt4 by exposure to NIH 3T3 cells which had been transfected with Flt4-encoding cDNA using the pLTRFlt4l vector. For receptor stimulation experiments, subconfluent NIH 3T3 cells were starved overnight in serum-free DMEM medium (GIBCO) containing 0.2% bovine serum albumin (BSA). The cells were stimulated with the conditioned media for 5 minutes, washed twice with cold PBS containing 100 micromolar vanadate, and lysed in RIPA buffer (10 mM Tris pH 7.5, 50 mM NaCl, 0.5% sodium deoxycholate, 0.5% Nonidet P40 (BDH, Poole, England), 0.1% SDS, 0.1 U/ml Aprotinin (Boehringer Mannheim), 1 mM vanadate) for receptor immunoprecipitation analysis. The lysates were centrifuged for 20 minutes at 15,000×g. The supernatants were incubated for 2 hours on ice with 3 microliters of the antiserum against the Flt4 C-terminus described in Example 2. See also Pajusola et al., *Oncogene*, 8:2931–2937 (1993), incorporated by reference herein.

After a two hour incubation in the presence of anti-Flt4 antiserum, protein A-Sepharose (Pharmacia) was added and incubation was continued for 45 minutes with rotation. The immunoprecipitates were washed three times with the immunoprecipitation buffer and twice with 10 mM Tris, pH 7.5, before analysis by SDS-PAGE. Polypeptides were transferred to nitrocellulose and analyzed by Western blotting using Flt4- or phosphotyrosine-specific antisera and the ECL method (Amersham Corp.). Anti-phosphotyrosine monoclonal antibodies (anti-PTyr; PY20) were purchased from Transduction Laboratories (Lexington, Ky.). In some cases, the filters were restained with a second antibody after stripping. The stripping of the filters was done for 30 minutes at 50° C. in 100 mM 2-mercaptoethanol, 2% SDS, 62.5 mM Tris-HCl pH 6.7 with occasional agitation.

Figure 4:
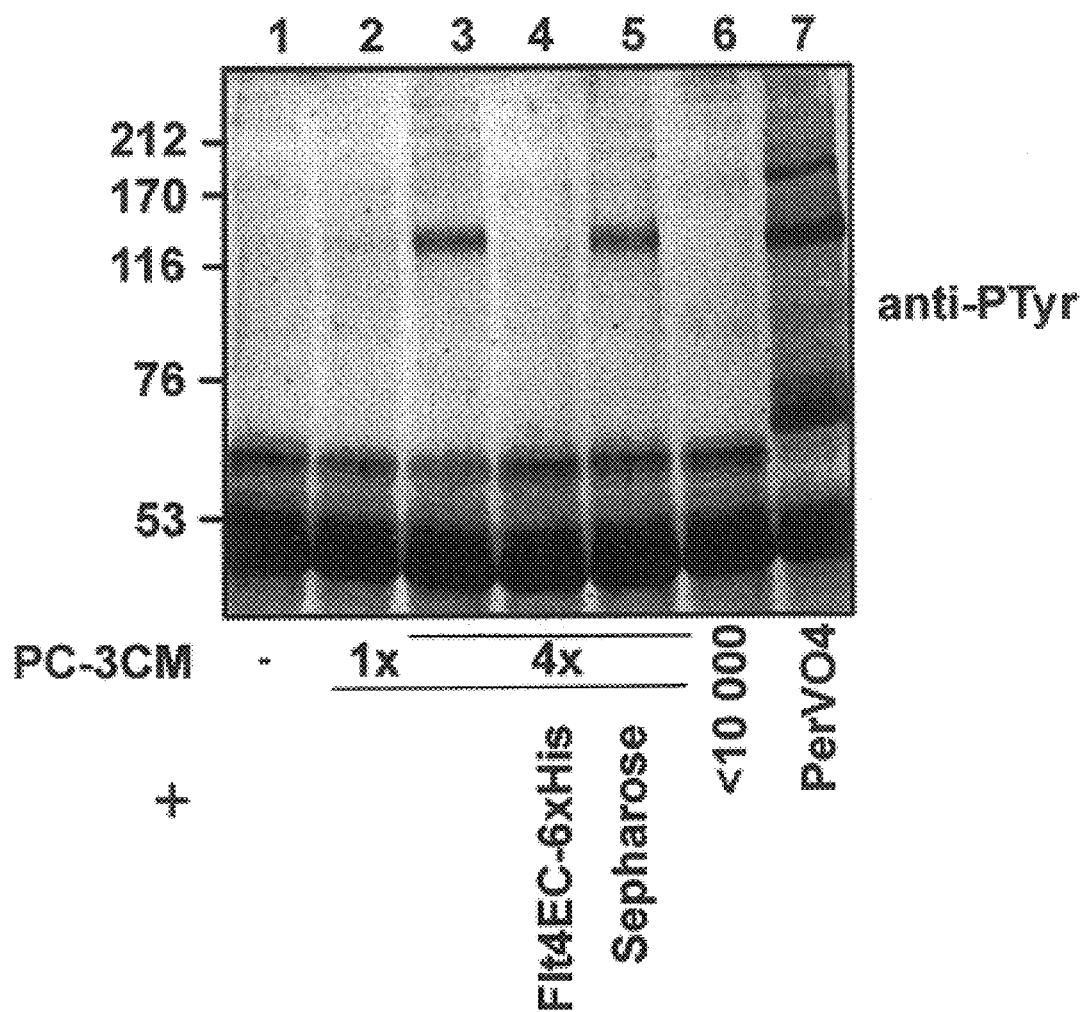
FIG. 4 shows results of stimulation of Flt4 autophosphorylation by conditioned medium from PC-3 cell cultures.

As shown in FIG. 4, the PC-3 conditioned medium stimulated tyrosine phosphorylation of a 125 kD polypeptide when Flt4-expressing NIH 3T3 cells were treated with the indicated preparations of media, lysed, and the lysates were immunoprecipitated with anti-Flt4 antiserum followed by SDS-PAGE, Western blotting, and staining using anti-PTyr antibodies. The resulting band was weakly phosphorylated upon stimulation with unconcentrated PC-3 conditioned medium (lane 2). The 125 kD band comigrated with the tyrosine phosphorylated, processed form of the mature Flt4 from pervanadate-treated cells (compare lanes 2 and 7 of FIG. 4, see also FIG. 5A). Comigration was confirmed upon restaining with anti-Flt4 antibodies as is also shown in FIG. 5A (panel on the right). In order to show that the 125 kD polypeptide is not a non-specific component of the conditioned medium reactive with anti-phosphotyrosine antibodies, 15 microliters of conditioned medium were separated by SDS-PAGE, blotted on nitrocellulose, and the blot was stained with anti-PTyr antibodies. No signal was obtained (FIG. 5B). Also, unconditioned medium failed to stimulate Flt4 phosphorylation, as shown in FIG. 4, lane 1.

FIG. 5C shows a comparison of the effects of PC-3 CM stimulation (+) on untransfected (lanes 4 and 5), FGFR-4-transfected (lanes 8 and 9) and Flt4-transfected NIH 3T3 cells (lanes 1–3, 6 and 7). These results indicate that neither untransfected NIH 3T3 cells nor NIH 3T3 cells transfected with FGFR-4 showed tyrosine phosphorylation of a protein of about 125 kD upon stimulation with the conditioned medium from PC-3 cells. Analysis of stimulation by PC-3 CM pretreated with Heparin-Sepharose CL-6B (Pharmacia) for 2 hours at room temperature (lane 3) showed that the Flt4 ligand does not bind to heparin.

As shown in FIG. 4, lane 3, stimulating activity was considerably increased when the PC-3 conditioned medium was concentrated four-fold using a Centricon-10 concentrator (Amicon). FIG. 4, lane 4, shows that pretreatment of the concentrated PC-3 conditioned medium with 50 microliters of the Flt4 extracellular domain coupled to CNBr-activated sepharose CL-4B (Pharmacia; about 1 mg of Flt4EC domain/ml sepharose resin) completely abolished Flt4 tyrosine phosphorylation. Similar pretreatment of the conditioned medium with unsubstituted sepharose CL-4B did not affect stimulatory activity, as shown in FIG. 4, lane 5. Also, the flow through obtained after concentration, which contained proteins of less than 10,000 molecular weight, did not stimulate Flt4 phosphorylation, as shown in FIG. 4, lane 6.

Figure 8:
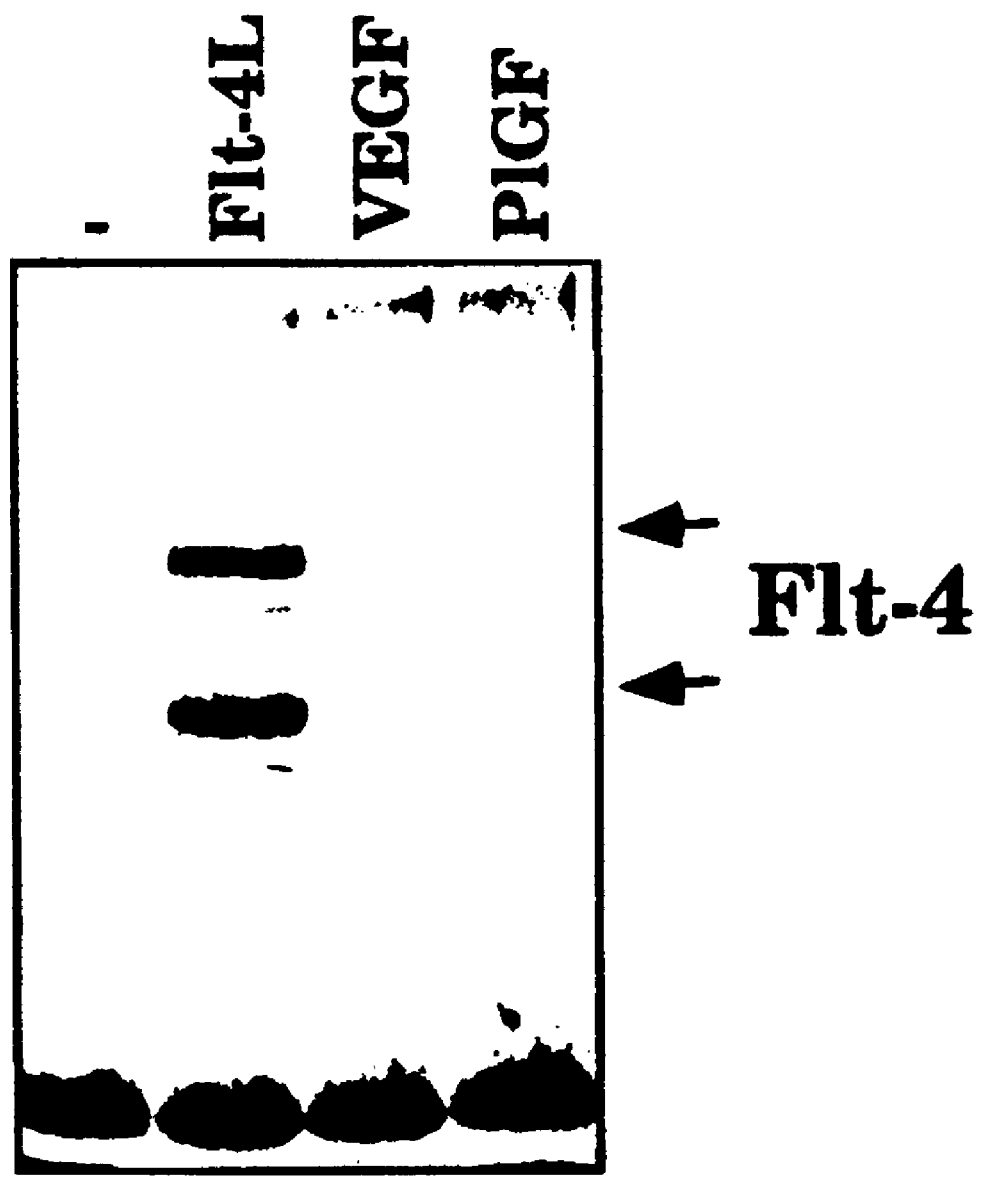
FIG. 8 shows results of Western analysis of Flt4 autophosphorylation induced by either the Flt4 ligand (VEGF-C), VEGF, or PlGF.

In another experiment, a comparison of Flt4 autophosphorylation in transformed NIH 3T3 cells expressing LTRFlt4l was conducted, using unconditioned medium, medium from PC-3 cells expressing the Flt4 ligand, or unconditioned medium containing either 50 ng/ml of VEGF165 or 50 ng/ml of PlGF-1. The cells were lysed, immunoprecipitated using anti-Flt4 antiserum and analyzed by Western blotting using anti-phosphotyrosine antibodies. As shown in FIG. 8, only the PC-3 conditioned medium expressing the Flt4 ligand (lane Flt-4L) stimulated Flt4 autophosphorylation.

The foregoing data show that PC-3 cells produce a ligand which binds to the extracellular domain of Flt4 and activates this receptor.

EXAMPLE 5

Purification of the Flt4 Ligand

The ligand expressed by human PC-3 cells as characterized in Example 4 was purified and isolated using a recombinantly-produced Flt4 extracellular domain (Flt4EC) in affinity chromatography.

Two harvests of serum-free conditioned medium, comprising a total of 8 liters, were collected from 500 confluent 15 cm diameter culture dishes containing confluent layers of PC-3 cells. The conditioned medium was clarified by centrifugation at 10,000×g and concentrated 80-fold using an Ultrasette Tangential Flow Device (Filtron, Northborough, Mass.) with a 10 kD cutoff Omega Ultrafiltration membrane according to the manufacturer's instructions. Recombinant Flt4 extracellular domain was expressed in a recombinant baculovirus cell system and purified by affinity chromatography on Ni-agarose (Ni-NTA affinity column obtained from Qiagen). The purified extracellular domain was coupled to CNBr-activated Sepharose CL-4B at a concentration of 5 mg/ml and used as an affinity matrix for ligand affinity chromatography.

Concentrated conditioned medium was incubated with 2 ml of the recombinant Flt4 extracellular domain-Sepharose affinity matrix in a rolling tube at room temperature for 3 hours. All subsequent purification steps were at +4° C. The affinity matrix was then transferred to a column with an inner diameter of 15 mm and washed successively with 100 ml of PBS and 50 ml of 10 mM Na-phosphate buffer (pH 6.8). Bound material was eluted step-wise with 100 mM glycine-HCl, successive 6 ml elutions having pHs of 4.0, 2.4, and 1.9. Several 2 ml fractions of the eluate were collected in tubes containing 0.5 ml 1 M Na-phosphate (pH 8.0). Fractions were mixed immediately and dialyzed in 1 mM Tris-HCl (pH 7.5). Aliquots of 75 µl each were analyzed for their ability to stimulate tyrosine phosphorylation of Flt4. The ultrafiltrate, 100 µl aliquots of the concentrated conditioned medium before and after ligand affinity chromatography, as well as 15-fold concentrated fractions of material released from the Flt4 extracellular domain-Sepharose matrix during the washings were also analyzed for their ability to stimulate Flt4 tyrosine phosphorylation.

Figure 6:
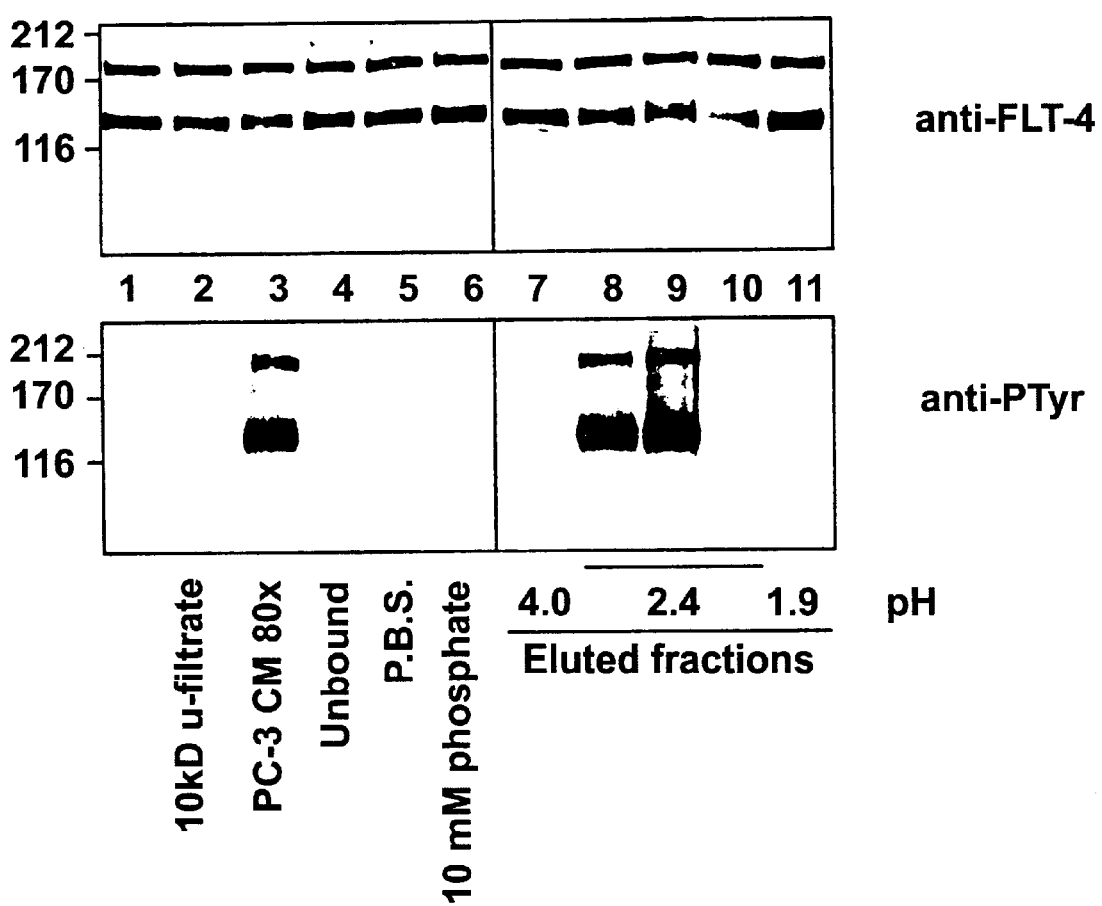
FIG. 6 shows Western immunoblotting analysis of the Flt4 Ligand activity isolated from PC-3 conditioned medium.

As shown in FIG. 6, lane 3, the concentrated conditioned medium induced prominent tyrosine phosphorylation of Flt4 in transfected NIH 3T3 cells overexpressing Flt4. This activity was not observed in conditioned medium taken after medium was exposed to the Flt4 Sepharose affinity matrix described above (FIG. 6, lane 4). The specifically-bound Flt4-stimulating material was retained on the affinity matrix after washing in PBS, 10 mM Na-phosphate buffer (pH 6.8), and at pH 4.0 (FIG. 6, lanes 5–7, respectively), and it was eluted in the first two 2 ml aliquots at pH 2.4 (lanes 8 and 9). A further decrease of the pH of the elution buffer did not cause release of additional Flt4-stimulating material (FIG. 6, lane 11). FIG. 6, lane 1 depicts a control wherein Flt4-expressing cells were treated with unconditioned medium; lane 2 depicts the results following treatment of Flt4-expressing cells with the ultrafiltrate fraction of conditioned medium containing polypeptides of less than 10 kD molecular weight.

Figure 7:
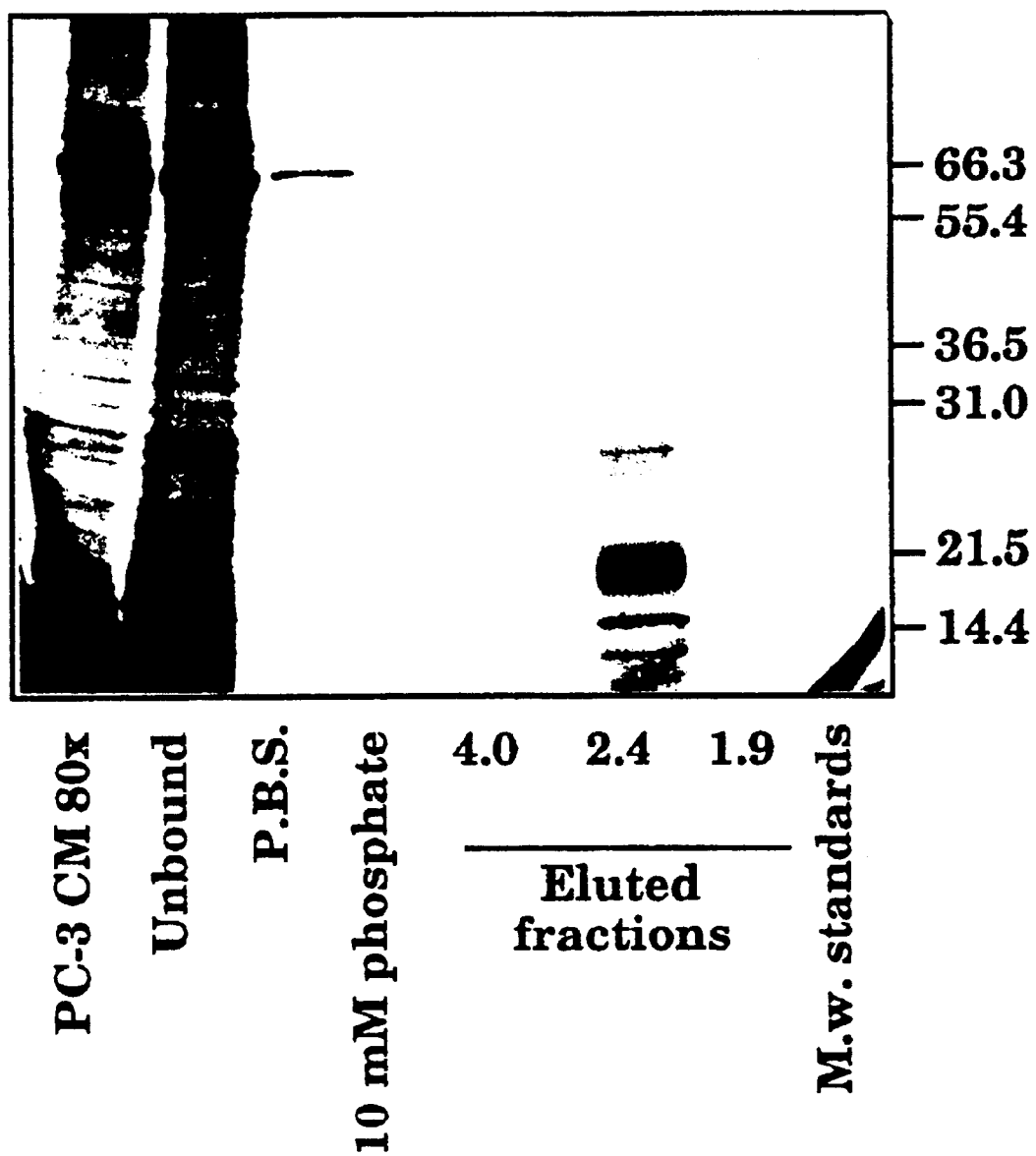
FIG. 7 shows results of gel electrophoresis of chromatographic fractions from the affinity purification of Flt4 ligand (VEGF-C) isolated from PC-3 conditioned medium.

Small aliquots of the chromatographic fractions were concentrated in a SpeedVac concentrator (Savant, Farmingdale, N.Y.) and subjected to SDS-PAGE under reducing conditions with subsequent silver staining of the gel a standard technique in the art. As shown in FIG. 7, the major polypeptide, having a molecular weight of approximately 23 kD (reducing conditions), was detected in the fractions containing Flt4 stimulating activity (corresponding to lanes 8 and 9 in FIG. 6). That polypeptide was not found in the other chromatographic fractions. On the other hand, all other components detected in the two active fractions were also distributed in the starting material and in small amounts in the other washing and eluting steps after their concentration. Similar results were obtained in three independent affinity purifications, indicating that the 23 kD polypeptide specifically binds to Flt4 and induces tyrosine phosphorylation of Flt4.

Fractions containing the 23 kD polypeptide were combined, dried in a SpeedVac concentrator and subjected to SDS-PAGE in a 12.5% gel. The proteins from the gel were then electroblotted to Immobilon-P (PVDF) transfer membrane (Millipore, Marlborough, Mass.) and visualized by staining of the blot with Coomassie Blue R-250. The region containing only the stained 23 kD band was cut from the blot and subjected to N-terminal amino acid sequence analysis in a Prosite Protein Sequencing System (Applied Biosystems, Foster City, Calif.). The data were analyzed using a 610A Data Analysis System (Applied Biosystems). Analysis revealed a single N-terminal sequence of $NH_2$-XEEIKFAAAHYNTEILK-COOH (SEQ ID NO: 13).

EXAMPLE 6

Construction of PC-3 Cell cDNA Library in a Eukaryotic Expression Vector

Human poly(A)$^+$ RNA was isolated from five 15 cm diameter dishes of confluent PC-3 cells by a single step method using oligo(dT) (Type III, Collaborative Biomedical Products, Becton-Dickinson Labware, Bedford, Mass.) cellulose affinity chromatography (Sambrook et al., 1989). The yield was 70 micrograms. Six micrograms of the Poly(A)$^+$ RNA were used to prepare an oligo(dT)-primed cDNA library in the mammalian expression vector pcDNA I and the Librarian kit of Invitrogen according to the instructions included in the kit. The library was estimated to contain about $10^6$ independent recombinants with an average insert size of approximately 1.8 kb.

EXAMPLE 7

Amplification of the Unique Nucleotide Sequence Encoding the Flt4 Ligand

Figure 9:
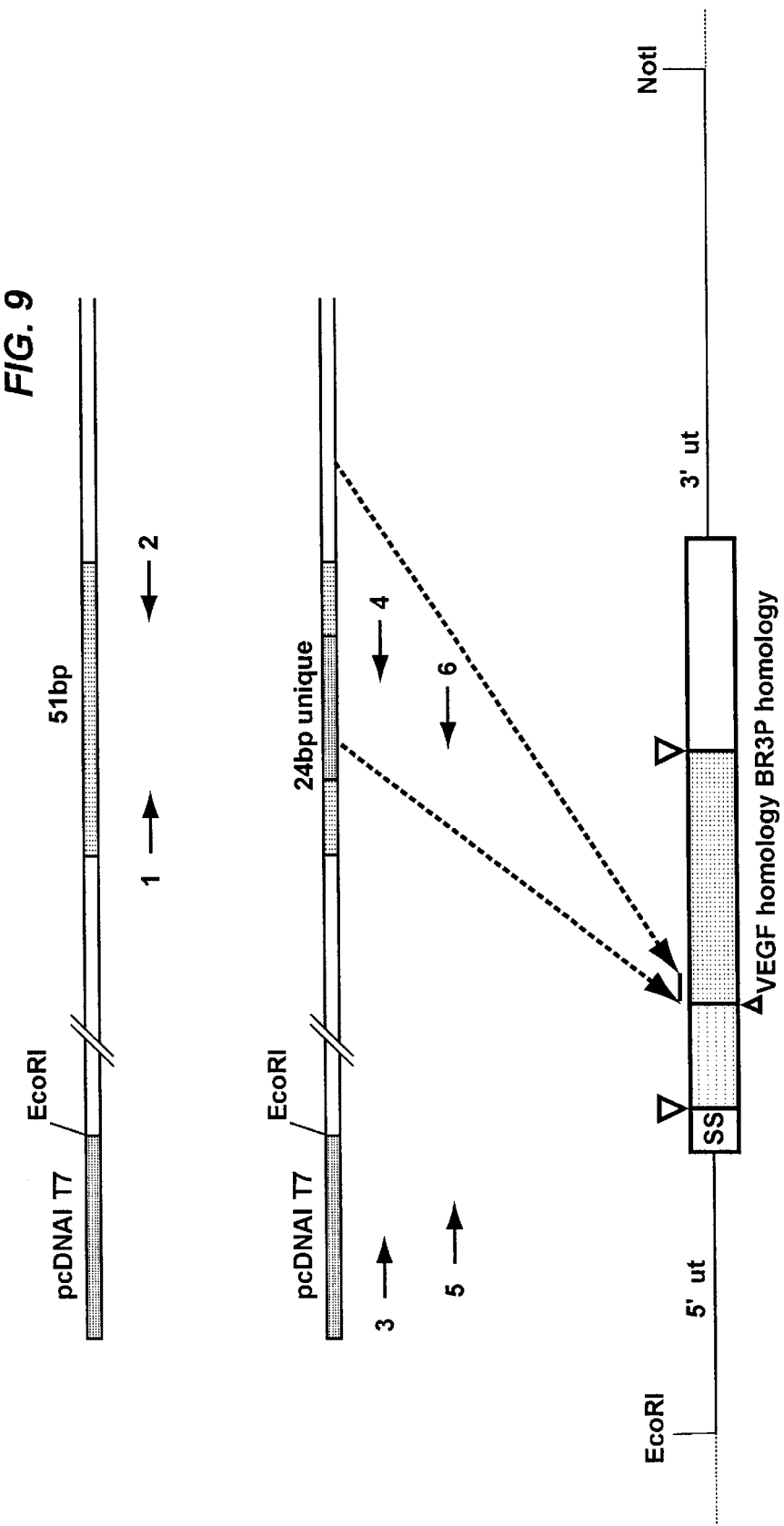
FIG. 9 schematically depicts the cloning and analysis of the Flt4 ligand, VEGF-C. The VEGF homologous region (dark shaded box) and amino and carboxyl terminal propeptides (light shaded and unshaded boxes, respectively) as well as putative signal sequence (ss) are depicted between 5' and 3' untranslated (ut) nucleic acid regions. The cleavage sites for the signal sequence and the amino and carboxyl terminal propeptides are indicated with triangles.

Degenerate oligonucleotides were designed based on the N-terminal amino acid sequence of the isolated human Flt4 ligand and were used as primers in a polymerase chain reaction (PCR) to amplify cDNA encoding the Flt4 ligand from a PC-3 cell library. The overall strategy is schematically depicted in FIG. 9, where the different primers have been marked with arrows.

The PCR was carried out using 1 microgram of DNA from the amplified PC-3 cDNA library and a mixture of 48 sense-strand primers present in equal proportions, the primer sequences collectively comprising the sequence 5'-GCAGARGARACNATHAA-3' (SEQ ID NO: 14) (wherein R is A or G, N is A,G,C or T and H is A, C or T), encoding amino acid residues 2–6 (EETIK, SEQ ID NO: 15) and 384 antisense-strand primers present in equal proportions, the anti-sense strand primers collectively comprising the sequence 5'-GCAYTTNARDATYTCNGT-3' (SEQ ID NO: 16) (wherein Y is C or T and D is A, G or T), corresponding to amino acid residues 14–18 (TEILK, SEQ ID NO: 17). Three extra nucleotides (GCA) were added to the 5'-terminus of each primer to increase annealing stability. Two successive PCR runs were carried out using 1 U per reaction of DynaZyme (F-500L, Finnzymes, Espoo, Finland), a thermostable DNA polymerase, in a buffer supplied by the manufacturer (10 mM Tris-HCl, pH 8.8 at 25° C., 1.5 mM $MgCl_2$, 50 mM KCl, 0.1% Triton-X100), at an extension temperature of 72° C. The first PCR run was carried out for 43 cycles. The first three cycles were run at an annealing temperature of 33° C. for 2 minutes, and the remaining cycles were run at 42° C. for 1 minute.

The region of the gel containing a weak band of the expected size (57 bp) was cut out from the gel and eluted. The eluted material was reamplified for 30 cycles using the same primer pairs described above at 42° C. for 1 minute. The amplified fragment was cloned into a pCR II vector (Invitrogen) using the TA cloning kit (Invitrogen) and sequenced using the radioactive dideoxynucleotide sequencing method of Sanger. Six clones were analyzed and all six clones contained the sequence encoding the expected peptide (amino acid residues 104–120 of the Flt4 ligand precursor). Nucleotide sequence spanning the region from the third nucleotide of codon 6 to the third nucleotide of codon 13 (the extension region) was identical in all six clones: 5'-ATTCGCTGCAGCACACTACAAC-3' (SEQ ID NO: 18) and thus represented an amplified product from the unique sequence encoding part of the amino terminus of the Flt4 ligand.

EXAMPLE 8

Amplification of the 5'-end of the cDNA Encoding the Flt4 Ligand

Based on the unique nucleotide sequence encoding the N-terminus of the isolated human Flt4 ligand, two pairs of nested primers were designed to amplify, in two nested PCR reactions, the complete 5'-end of the corresponding cDNAs from one microgram of DNA of the above-described PC-3 cDNA library. First, amplification was performed with an equal mixture of 4 primers collectively defining the sequence 5'-TCNGTGTTGTAGTGTGCTG-3' (SEQ ID NO: 19), which is the antisense-strand primer corresponding to amino acid residues 9–15 (AAHYNTE, SEQ ID NO: 20), and sense-strand primer 5'-TAATACGACTCACTATA-GGG-3' (SEQ ID NO: 21), corresponding to the T7 RNA promoter of the pcDNAI vector used for construction of the library. "Touchdown" PCR was used as disclosed in Don et al., *Nucl. Acids Res.*, 19:4008 (1991), incorporated by reference herein. The annealing temperature of the two first cycles was 62° C. and subsequently the annealing temperature was decreased in every other cycle by 1° C. until a final temperature of 53° C. was reached, at which temperature 16 additional cycles were conducted. Annealing time was 1 minute and extension at each cycle was conducted at 72° C. for 1 minute. Multiple amplified DNA fragments were obtained in the first reaction. The products of the first amplification (1 μl of a 1:100 dilution in water) were used in the second amplification reaction employing a pair of nested primers comprising an antisense-strand primer 5'-GTTGTAGTGTGCTGCAGCGAATTT-3'; SEQ ID NO: 22) encoding amino acid residues 6–13 (KFAAAHYN, SEQ ID NO: 23) of the Flt4 ligand, and a sense-strand primer (5'-TCACTATAGGGAGACCCAAGC-3'; SEQ ID NO: 24), corresponding to nucleotides 2179–2199 of the pcDNAI vector. The sequences of these sense and antisense primers overlapped with the 3' ends of the corresponding primers used in the first PCR. "Touchdown" PCR was carried out by decreasing the annealing temperature from 72° C. to 66° C. and continuing with 18 additional cycles at 66° C. The annealing time was 1 minute and extension at each cycle was carried out at 72° C. for 2 minutes. One major product of about 220 bp and three minor products of about 270 bp, 150 bp, and 100 bp were obtained.

The amplified fragment of approximately 220 bp was excised from an agarose gel, cloned into a pCRII vector using the TA cloning kit (Invitrogen), and sequenced. Three recombinant clones were analyzed and they contained the sequence 5'TCACTATAGGGAGACCCAAG CTTGGTAC-CGAGCTCGGATCCACTAGTAACGGCCGC-CAGTGTGGTGGAATTCGACGAACTCATGACT-GTACTCTACCCAGAATATTGGAAAATGTACAA-GTGTCAGCTAAGGCAAGGAGGCTGGCAACATAAC-AGAGAACAGGCCAACCTCAACTCAAGGACAGAA-GAGACTATAAAATTCGCTGCAGCACACTACAAC 3' (SEQ ID NO: 25). The beginning of the sequence represents the pcDNAI vector and the underlined sequence represents the amplified product of the 5'-end of the insert.

EXAMPLE 9

Amplification of the 3'-end of cDNA Encoding the Flt4 Ligand

Based upon the amplified 5'-sequence of the clones encoding the amino terminus of the 23 kD human Flt4 ligand, two pairs of non-overlapping nested primers were designed to amplify the 3'-portion of the Flt-4-ligand-encoding cDNA clones. The sense-strand primer 5'-ACAGAGAACAGGCCAACC-3' (SEQ ID NO: 26), corresponding to nucleotides 152–169 of the amplified 5'-sequences of the Flt4 ligand (SEQ ID NO: 25), and antisense-strand primer 5'-TCTAGCATTTAGGTGACAC-3' (SEQ ID NO: 27) corresponding to nucleotides 2311–2329 of the pcDNAI vector were used in a first "touchdown" PCR. The annealing temperature of the reaction was decreased 1° C. every two cycles from 72° C. to 52° C., at which temperature 15 additional cycles were carried out. The annealing time was 1 minute and extension at each cycle was carried out at 72° C. for 3 minutes. DNA fragments of several sizes were obtained in the first amplification. Those products were diluted 1:200 in water and reamplified in PCR using the second pair of primers: 5'-AAGAGACTATAAAATTCGCTGCAGC-3' (SEQ ID NO: 28) and 5'-CCCTCTAGATGCATGCTCGA-3' (SEQ ID NO: 29) (antisense-strand primer corresponding to nucleotides 2279–2298 of the pcDNAI vector). Two DNA fragments were obtained, having sizes of 1350 bp and 570 bp. Those fragments were cloned into a pCRII vector and the inserts of the clones were sequenced. Both of these fragments were found to contain sequences encoding an amino acid sequence homologous to the VEGF sequence.

EXAMPLE 10

Screening the PC-3 Cell cDNA Library Using the 5' PCR Fragment of Flt4 Ligand cDNA A 219 bp 5'-terminal fragment of human Flt4 ligand cDNA was amplified by PCR using the 5' PCR fragment described above and primers 5'-GTTGTA-GTGTGCTGCAGCGAATTT-3' (antisense-strand primer, SEQ ID NO: 30) and 5'-TCACTATAGGG-AGACCCAAGC-3' (SEQ ID NO: 31) (sense-primer corresponding to nucleotides 2179–2199 of the pcDNAI vector). The amplified product was subjected to digestion with EcoRI (Boehringer Mannheim) to remove the portion of the DNA sequence amplified from the pcDNAI vector and the resulting 153 bp fragment encoding the 5' end of the Flt4 ligand was labeled with [$^{32}$P]-dCTP using the Klenow fragment of *E. coli* DNA polymerase I (Boehringer Mannheim). That fragment was used as a probe for hybridization screening of the amplified PC-3 cell cDNA library.

Filter replicas of the library were hybridized with the radioactively labeled probe at 42° C. for 20 hours in a solution containing 50% formamide, 5×SSPE, 5×Denhardt's solution, 0.1 % SDS and 0.1 mg/ml denatured salmon sperm DNA. Filters were washed twice in 1×SSC, 0.1% SDS for 30 minutes at room temperature, then twice for 30 minutes at 65° C. and exposed overnight.

On the basis of autoradiography, 10 positive recombinant bacterial colonies hybridizing with the probe were chosen from the library. Plasmid DNA was purified from these colonies and analyzed by EcoRI and NotI digestion and agarose gel electrophoresis followed by ethidium bromide staining. The ten plasmid clones were divided into three groups on the basis of the presence of insert sizes of approximately 1.7, 1.9 and 2.1 kb, respectively. Inserts of plasmids from each group were sequenced using the T7 oligonucleotide as a primer and walking primers for subsequent sequencing reactions.

Sequence analysis showed that all clones contain the open reading frame encoding the NH2-terminal sequence of the 23 kD human Flt4 ligand. Dideoxy sequencing was continued using walking primers in the downstream direction. A complete human cDNA sequence and deduced amino acid sequence from a 2.1 kb clone is set forth in FIG. 9. A putative cleavage site of a "prepro" leader sequence is located between resides 102 and 103 of SEQ ID NO: 33. When compared with sequences in the GenBank Database, the predicted protein product of this reading frame was found to be homologous with the predicted amino acid sequences of the PDGF/VEGF family of growth factors, as shown in FIGS. 10A–10C.

Plasmid pFLT4-L, containing the 2.1 kb human cDNA clone in pcDNAI vector, has been deposited with the American Type Culture Collection, 12301 Parklawn Drive, Rockville, Md. 20852 as accession number 97231.

EXAMPLE 11

Stimulation of Flt4 Autophosphorylation by the Protein Product of the Flt4 Ligand Vector The 2.1 kb human cDNA insert of plasmid pFlt4-L, which contains the open reading frame encoding the sequence shown in SEQ ID NO: 32–33 (human VEGF-C, see below), was cut out from the pcDNAI vector using HindIII and NotI restriction enzymes, isolated from a preparative agarose gel, and ligated to the corresponding sites in the pREP7 expression vector (Invitrogen). The pREP7 vector containing the pFlt4-L insert was transfected into 293-EBNA cells (Invitrogen) using the calcium phosphate transfection method (Sambrook et al., 1989). About 48 hours after transfection the medium of the transfected cells was changed to DMEM medium lacking fetal calf serum and incubated for 36 h. The conditioned medium was then collected, centrifuged at 5000×g for 20 minutes, the supernatant was concentrated 5-fold using Centriprep 10 (Amicon) and used to stimulate NIH 3T3 cells expressing LTRFlt4(the Flt4 receptor), as in Example 4. The cells were lysed, immunoprecipitated using anti-Flt4 antiserum and analyzed by Western blotting using anti-phosphotyrosine antibodies.

Figure 11:
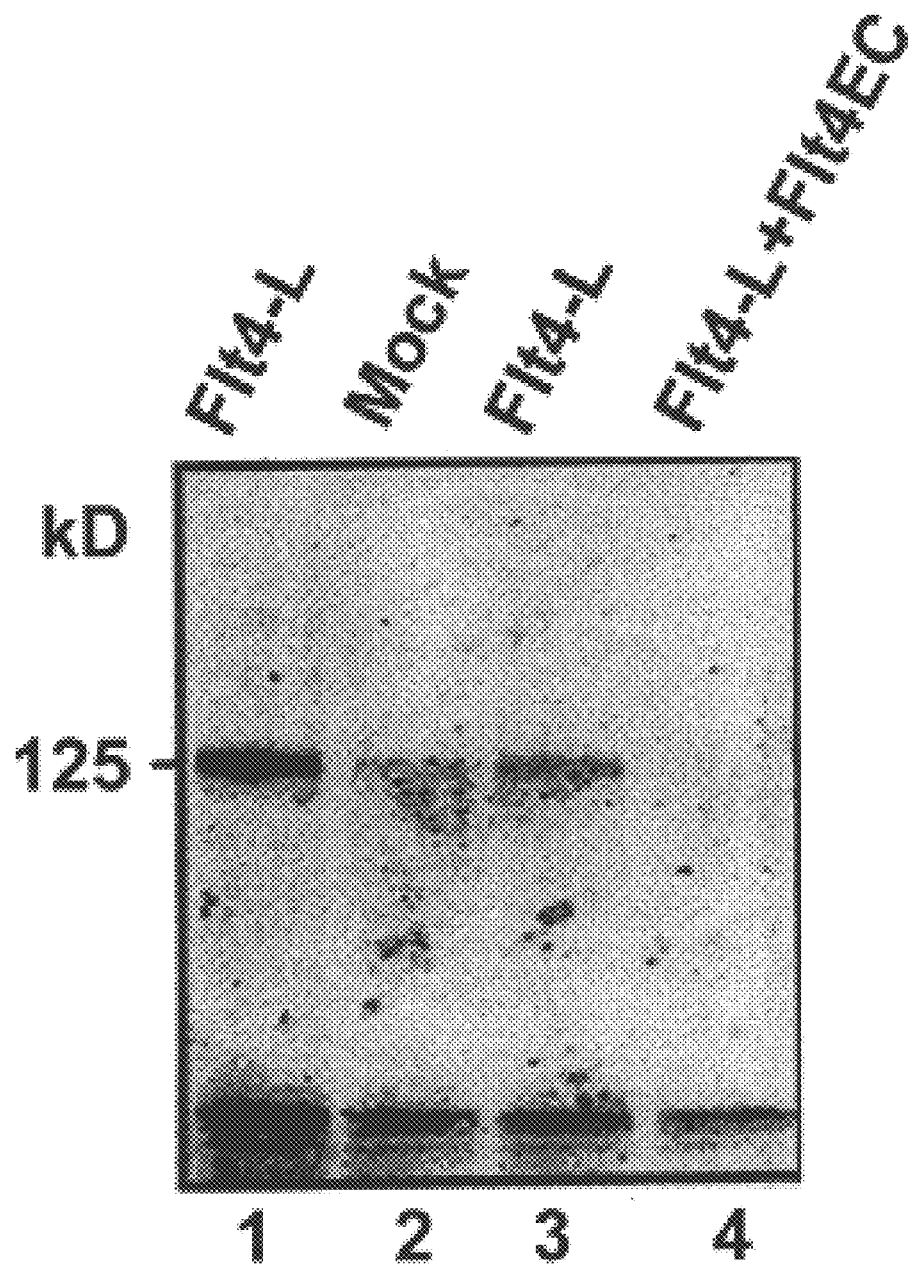
FIG. 11 shows the stimulation of autophosphorylation of the Flt4 receptor by conditioned medium from cells transfected with the pREP7 expression vector containing the VEGF-C-encoding cDNA insert of plasmid FLT4-L.

As can be seen from FIG. 11, lanes 1 and 3, the conditioned medium from two different dishes of the transfected cells stimulated Flt4 autophosphorylation in comparison with the medium from mock-transfected cells, which gave only background levels of phosphorylation of the Flt4 receptor (lane 2). When the concentrated conditioned medium was pre-absorbed with 20 microliters of a slurry of Flt4EC domain coupled to Sepharose (see example 4), no phosphorylation was obtained (lane 4), showing that the activity responsible for Flt4 autophosphorylation was indeed the Flt4 ligand. Thus, these results demonstrate that an expression vector having an approximately 2.1 kb insert and containing an open reading frame as shown in SEQ ID NO: 32 is expressed as a biologically active Flt4 ligand (VEGF-C) in transfected cells. The sequence encoded by that open reading frame is shown in SEQ ID NO: 33.

The deduced molecular weight of a polypeptide consisting of the complete amino acid sequence in SEQ ID NO: 33 (residues 1 to 419) is 46,883. The deduced molecular weight of a polypeptide consisting of amino acid residues 103 to 419 of SEQ ID NO: 33 is 35,724. The Flt4 ligand purified from PC-3 cultures had an observed molecular weight of about 23 kD as assessed by SDS-PAGE under reducing conditions. Thus, it appears that the Flt4 ligand mRNA is translated into a precursor polypeptide, from which the mature ligand is derived by proteolytic cleavage. Also, the Flt4 ligand may be glycosylated at three putative N-linked glycosylation sites conforming to the consensus which can be identified in the deduced Flt4 ligand amino acid sequence (N-residues underlined in FIGS. 10A–10C).

The carboxyl terminal amino acid sequences, which increase the predicted molecular weight of the Flt4 ligand subunit in comparison with other ligands of this family, show a pattern of spacing of cysteine residues reminiscent of the Balbiani ring protein 3 (BR3P) sequence (Dignam et al., *Gene*, 88:133–140 (1990)), as depicted schematically in FIG. 9. Such a sequence may encode an independently folded domain present in a Flt4 ligand precursor and it may be involved, for example, in the regulation of secretion, solubility, stability, cell surface localization or activity of the Flt4 ligand. Interestingly, at least one cysteine motif of the BR3P type is also found in the VEGF carboxy terminal amino acid sequences.

Thus, the Flt4 ligand mRNA appears first to be translated into a precursor from the mRNA corresponding to the cDNA insert of plasmid FLT4-L, from which the mature ligand is derived by proteolytic cleavage. To define the mature Flt4 ligand polypeptide, one first expresses the cDNA clone (which is deposited in the pcDNAI expression vector) in cells, such as COS cells. One uses antibodies generated against encoded peptides, fragments thereof, or bacterial Flt4 fusion proteins, such as a GST-fusion protein, to raise antibodies against the VEGF-homologous domain and the amino- and carboxyl-terminal propeptides of Flt4 ligand. One then follows the biosynthesis and processing of the Flt4 ligand in the transfected cells by pulse-chase analysis using radioactive cysteine for labelling-of the cells, immunoprecipitation and gel electrophoresis. Using antibodies against the three domains of the product encoded by the cDNA insert of plasmid FLT4-L, material for radioactive or non-radioactive amino-terminal sequence analysis is isolated. The determination of the amino-terminal sequence of the mature VEGF-C polypeptide allows for identification of the amino-terminal proteolytic processing site. The determination of the amino-terminal sequence of the carboxyl-terminal propeptide will give the carboxyl-terminal processing site. This is confirmed by site-directed mutagenesis of the amino acid residues adjacent to the cleavage sites, which would prevent the cleavage.

On the other hand, the Flt4 ligand is characterized by progressive 3' deletions in the 3' coding sequences of the Flt4 ligand precursor clone, introducing a stop codon resulting in carboxy-terminal truncations of its protein product. The activities of such truncated forms are assayed by, for example, studying Flt4 autophosphorylation induced by the truncated proteins when applied to cultures of cells, such as NIH 3T3 cells expressing LTRFlt4. By extrapolation from studies of the structure of the related platelet derived growth factor (PDGF, Heldin et al., *Growth Factors*, 8:245–252 (1993)) one determines that the region critical for receptor activation by the Flt4 ligand is contained within its first approximately 180 amino acid residues of the secreted VEGF-C protein lacking the putative 102 amino acid prepro leader, and apparently within the first approximately 120 amino acid residues.

On the other hand, the difference between the molecular weights observed for the purified ligand and deduced from the open reading frame of the Flt4 precursor clone may be due to the fact that the soluble ligand was produced from an alternatively spliced mRNA which would also be present in the PC-3 cells, from which the isolated ligand was derived. To isolate such alternative cDNA clones one uses cDNA fragments of the deposited clone and PCR primers made according to the sequence provided as well as techniques standard in the art to isolate or amplify alternative cDNAs from the PC-3 cell cDNA library. One may also amplify using reverse transcription (RT)-PCR directly from the PC-3 mRNA using the primers provided in the sequence of the cDNA insert of plasmid FLT4-L. Alternative cDNA sequences are determined from the resulting cDNA clones. One can also isolate genomic clones corresponding to the Flt4 ligand mRNA transcript from a human genomic DNA library using methods standard in the art and to sequence such clones or their subcloned fragments to reveal the corresponding exons. Alternative exons can then be identified by a number of methods standard in the art, such as heteroduplex analysis of cDNA and genomic DNA, which are subsequently characterized.

EXAMPLE 12

Expression of the Gene Encoding VEGF-C in Human Tumor Cell Lines

Figure 12:
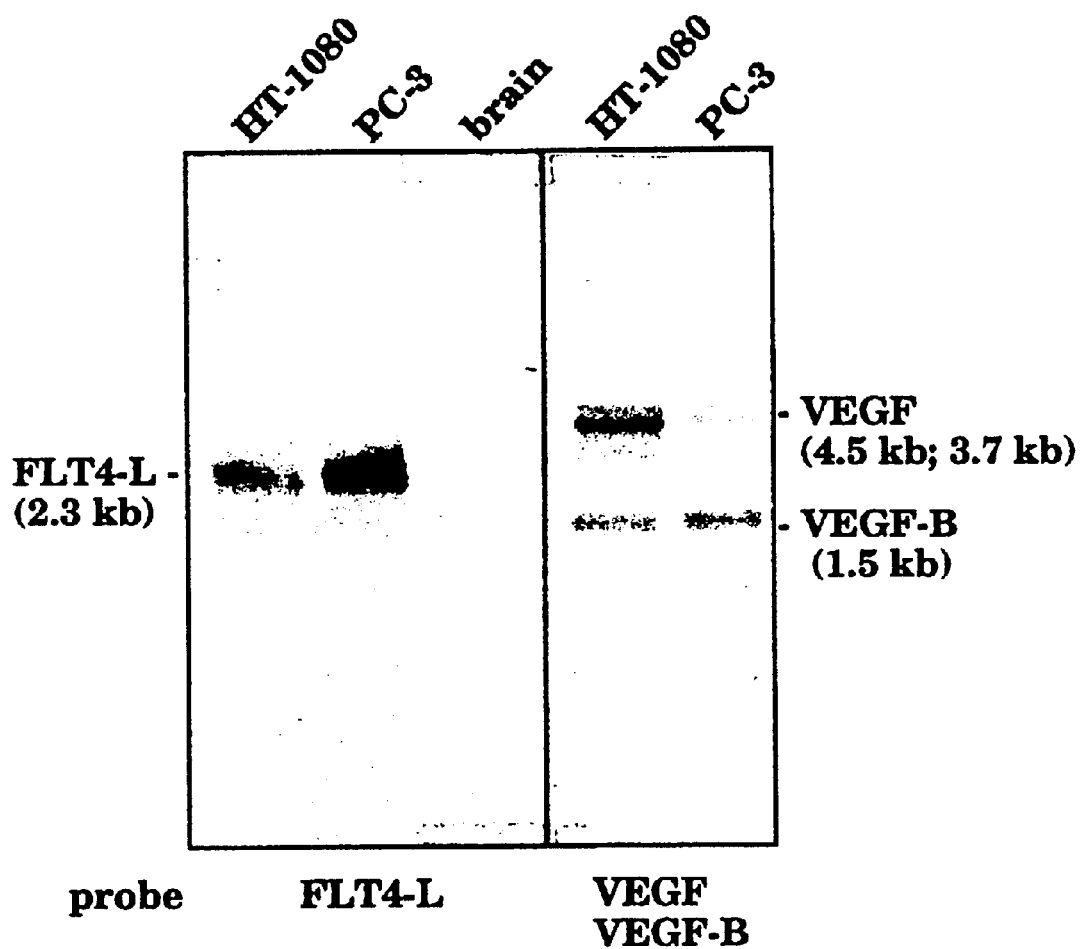
FIG. 12 shows Northern blotting analysis of the genes encoding VEGF, VEGF-B, AND VEGF-C (indicated by "FLT4-L") in two human tumor cell lines.

Expression of transcripts corresponding to the Flt4 ligand (VEGF-C) was analyzed by hybridization of Northern blots containing isolated poly(A)+ RNA from HT-1080 and PC-3 human tumor cell lines. The probe was the radioactively labelled insert of the 2.1 kb cDNA clone (pFlt4-L/VEGF-C) specific activity $10^8$–$10^9$ cpm/mg of DNA). The blot was hybridized overnight at 42° C. using 50% formamide, 5×SSPE buffer, 2% SDS, 10×Denhardt's solution, 100 mg/ml salmon sperm DNA and $1 \times 10^6$ cpm of the labelled probe/ml. The blot was washed at room temperature for 2×30 minutes in 2×SSC containing 0.05% SDS, and then for 2×20 min at 52° C. in 0.1×SSC containing 0.1% SDS. The blot was then exposed at −70° C. for three days using intensifying screens and Kodak XAR film. Both cell lines expressed an Flt4 ligand mRNA of about 2.4 kb, as well as VEGF and VEGF-B mRNAs (FIG. 12).

EXAMPLE 13

VEGF-C Chains Are Proteolytically Processed after Biosynthesis and Disulfide Linked The predicted molecular mass of a secreted human VEGF-C polypeptide, as deduced from the VEGF-C open reading frame, is 46,883 kD, suggesting that VEGF-C mRNA may be first translated into a precursor, from which the ligands of 21/23 kD and 29/32 kD are derived by proteolytic cleavage.

This possibility was explored by metabolic labelling of 293 EBNA cells expressing VEGF-C. Initially, 293 EBNA cells were transfected with the VEGF-C construct. Expression products were labeled by the addition of 100 µCi/ml of Pro-mix™ L-[$^{35}$S] in vitro cell labelling mix (Amersham) to the culture medium devoid of cysteine and methionine. After two hours, the cell layers were washed twice with. PBS and the medium was then replaced with DMEM-0.2% BSA. After 1, 3, 6, 12 and 24 hours of subsequent incubation, the culture medium was collected, clarified by centrifugation, and concentrated, and human VEGF-C was bound to 30 µl of a slurry of Flt4EC-Sepharose overnight at +4° C., followed by three washes in PBS, two washes in 20 mM Tris-HCl (pH 7.5), alkylation, SDS-PAGE and autoradiography. Alkylation was carried out by treatment of the samples with 10 mM 1,4 Dithiothreitol (Boehringer-Mannheim, Mannheim, Germany) for one hour at 25° C., and subsequently with 30 mM iodoacetamide (Fluka, Buchs, Switzerland).

Figure 13A:
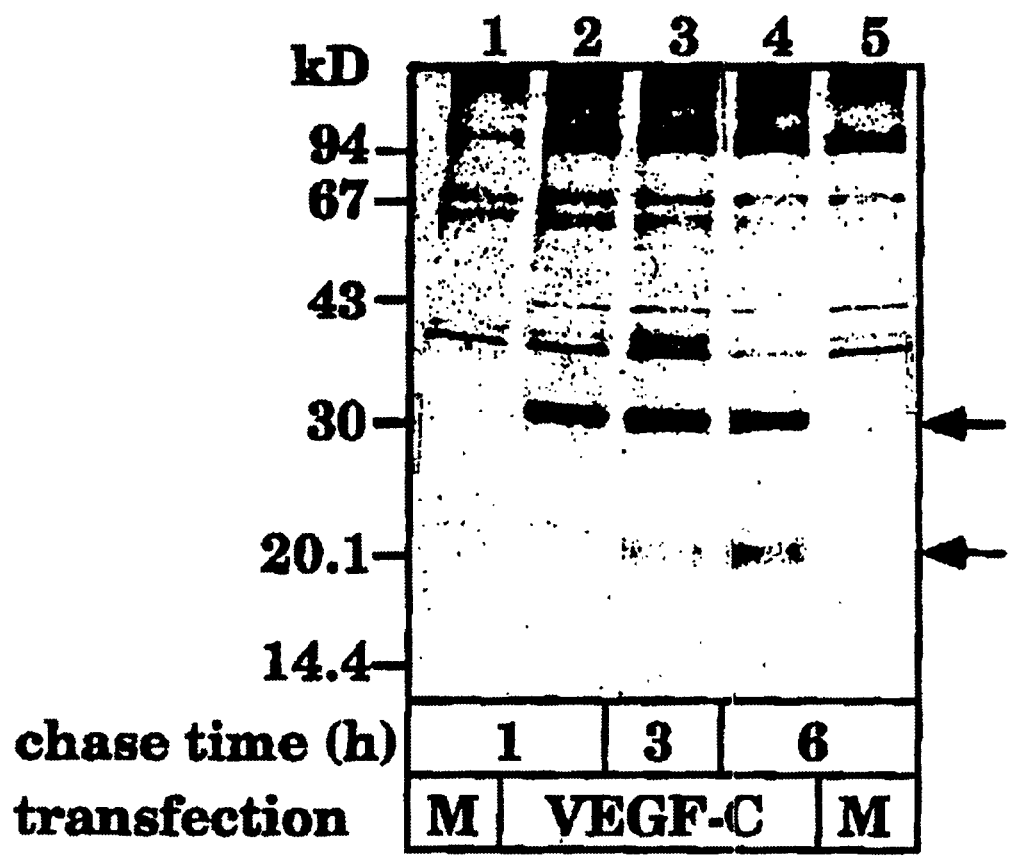
FIG. 13A is an autoradiograph showing recombinant VEGF-C isolated following a pulse-chase experiment and electrophoresed via SDS-PAGE under reducing conditions.

These experiments demonstrated that a putative precursor polypeptide of 32 kD apparent molecular mass was bound to the Flt4EC affinity matrix from the conditioned medium of metabolically labelled cells transfected with a human VEGF-C expression vector (FIG. 13A). Increased amounts of a 23 kD receptor binding polypeptide accumulated in the culture medium during a subsequent chase period of three hours, but not thereafter (lanes 2–4 and data not shown), suggesting that the 23 kD form is produced by proteolytic processing, which is cell-associated and incomplete, at least in the transiently transfected cells. The arrows in FIG. 13A indicate the 32 kD and 23 kD polypeptides of secreted VEGF-C. Subsequent experiments showed that the 32 kD VEGF-C form contains two components migrating in the absence of alkylation as polypeptides of 29 and 32 kD (FIGS. 21–23).

Figure 13B:
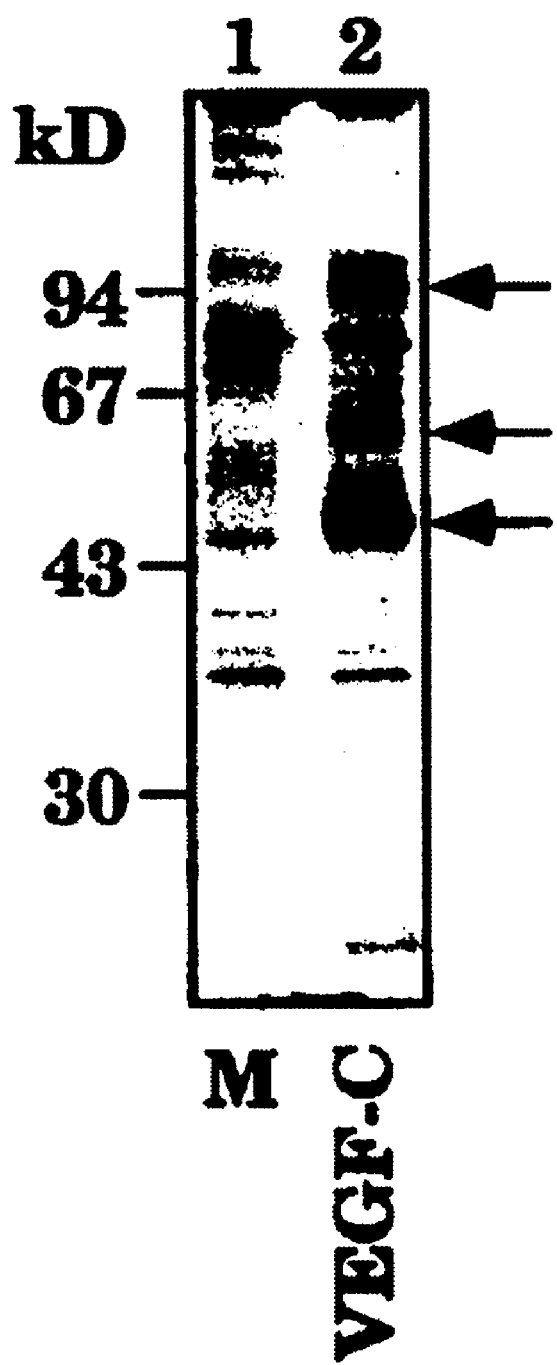
FIG. 13B is a photograph of polyacrylamide gel showing that recombinant VEGF-C forms are disulfide-linked in nonreducing conditions.

In a related experiment, human VEGF-C isolated using Flt4EC-Sepharose after a 4 h continuous metabolic labelling was analyzed by polyacrylamide gel electrophoresis in non-reducing conditions (FIG. 13B). Higher molecular mass forms were observed under nonreducing conditions, suggesting that the VEGF-C polypeptides can form disulfide-linked dimers and/or multimers (arrows in FIG. 13B).

EXAMPLE 14

Stimulation Of VEGFR-2 Autophosphorylation by VEGF-C

Conditioned medium (CM) from 293 EBNA cells transfected with the human VEGF-C vector also was used to stimulate porcine aortic endothelial (PAE) cells expressing VEGFR-2. Pajusola et al., Oncogene, 9:3545–55 (1994); Waltenberger et al., J. Biol. Chem., 269:26988–26995 (1994). The cells were lysed and immunoprecipitated using VEGFR-2-specific antiserum (Waltenberger et al., 1994).

PAE-KDR cells (Waltenberger et al., 1994) were grown in Ham's F12 medium-10% fetal calf serum (FCS). Confluent NIH 3T3-Flt4 cells or PAE-KDR cells were starved overnight in DMEM or Ham's F12 medium, respectively, supplemented with 0.2% bovine serum albumin (BSA), and then incubated for 5 min with the analyzed media. Recombinant human VEGF (R&D Systems) and PDGF-BB, functional as stimulating agents, were used as controls. The cells were washed twice with ice-cold Tris-Buffered Saline (TBS) containing 100 mM sodium orthovanadate and lysed in RIPA buffer-containing 1 mM phenylmethylsulfonyl fluoride (PMSF), 0.1 U/ml aprotinin and 1 mM sodium orthovanadate. The lysates were sonicated, clarified by centrifugation at 16,000×g for 20 min and incubated for 3–6 h on ice with 3–5 µl of antisera specific for Flt4 (Pajusola et al., 1993), VEGFR-2 or PDGFR-β (Claesson-Welsh et al., J. Biol. Chem. 264:1742–1747 (1989); Waltenberger et al., 1994). Immunoprecipitates were bound to protein A-Sepharose, washed three times with RIPA buffer containing 1 mM PMSF, 1 mM sodium orthovanadate, washed twice with 10 mM Tris-HCl (pH 7.4), and subjected to SDS-PAGE using a 7% gel. Polypeptides were transferred to nitrocellulose by Western blotting and analyzed using PY20 phosphotyrosine-specific monoclonal antibodies (Transduction Laboratories) or receptor-specific antiserum and the ECL detection method (Amersham Corp.).

Figure 14A:
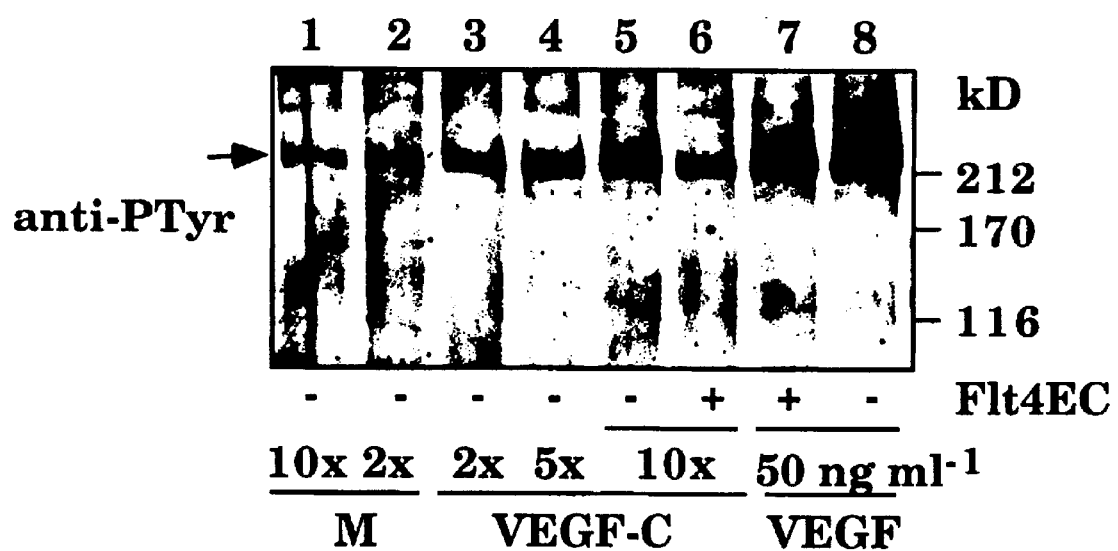
FIGS. 14A and 14B depict Western blots showing that VEGF-C stimulates autophosphorylation of VEGFR-2 (KDR) but has no effect on PDGFR-β phosphorylation.
Figure 14B:
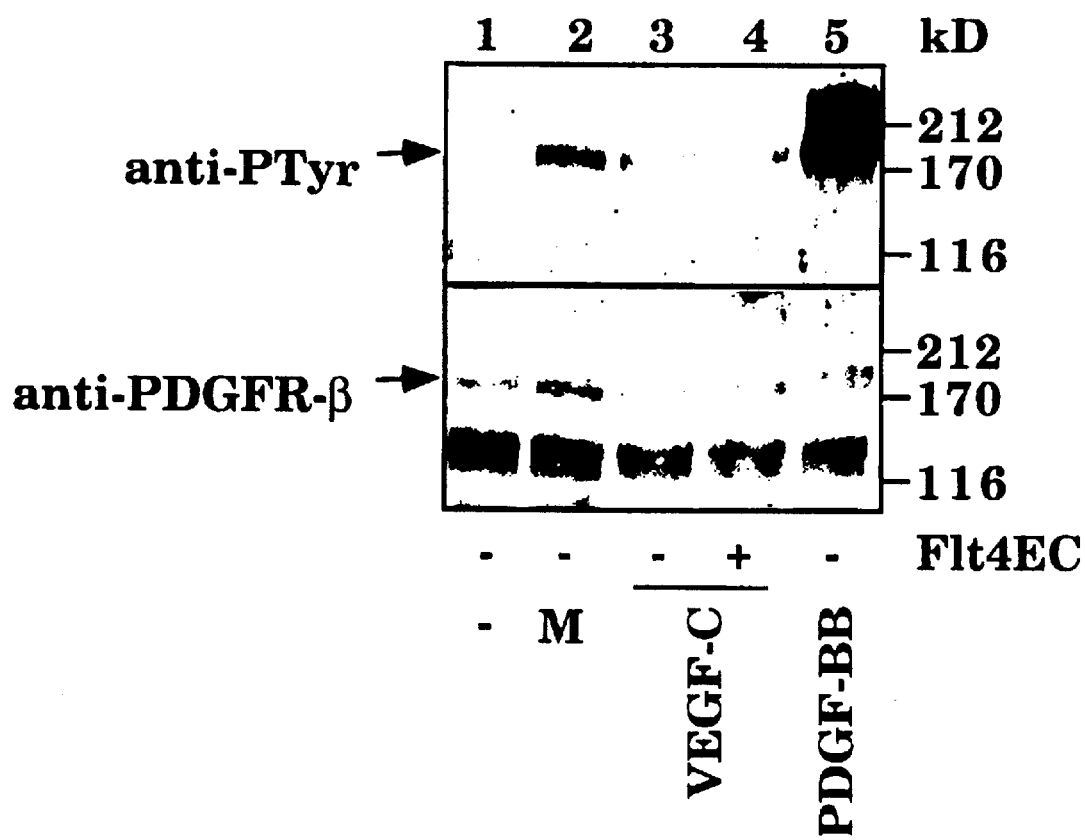

The results of the experiment are presented in FIGS. 14A and 14B. As shown in FIG. 14A, PAE cells expressing VEGFR-2 were stimulated with 10- or 2-fold concentrated medium from mock-transfected 293-EBNA cells (lanes 1 and 2), or with 2-, 5- or 10-fold concentrated medium from 293-EBNA cell cultures expressing the recombinant VEGF-C (lanes 3–6). VEGFR-2 was immunoprecipitated with specific antibodies and analyzed by SDS-PAGE and Western blotting using phosphotyrosine antibodies. For comparison, the stimulations were carried out with non-conditioned medium containing 50 ng/ml of purified recombinant VEGF (lanes 7 and 8). Lanes 6 and 7 show stimulation with VEGF-C- or VEGF-containing media pretreated with Flt4EC. As depicted in FIG. 14B, PDGFR-β-expressing NIH 3T3 cells were stimulated with non-conditioned medium (lane 1), 5-fold concentrated CM from mock-transfected (lane 2) or VEGF-C-transfected (lanes 3 and 4) cells, or with non-conditioned medium containing 50 ng/ml of recombinant human PDGF-BB (lane 5). Medium containing VEGF-C was also pretreated with recombinant Flt4EC (lane 4). PDGFR-β was immunoprecipitated with specific antibodies and analyzed by SDS-PAGE and Western blotting using phosphotyrosine antibodies with subsequent stripping and reprobing of the membrane with antibodies specific for PDGFR-β.

Referring again to FIG. 14A, a basal level of tyrosine phosphorylation of VEGFR-2 was detected in cells stimulated by CM from the mock-transfected cells. A further concentration of this medium resulted in only a slight enhancement of VEGFR-2 phosphorylation (lanes 1 and 2). CM containing recombinant VEGF-C stimulated tyrosine autophosphorylation of VEGFR-2 and the intensity of the autophosphorylated polypeptide band was increased upon concentration of the VEGF-C CM (lanes 3–5). Furthermore, the stimulating effect was abolished after pretreatment of the medium with the Flt4EC affinity matrix (compare lanes 1, 5 and 6). The maximal effect of VEGF-C in this assay was comparable to the effect of recombinant VEGF added to unconditioned medium at concentration of 50 ng/ml (lane 8). Pretreatment of the medium containing VEGF with Flt4EC did not abolish its stimulating effect on VEGFR-2 (compare lanes 7 and 8). These results suggest that the VEGF-C expression vector encodes a ligand not only for Flt4 (VEGFR-3), but also for VEGFR-2.

In order to further confirm that the stimulating effect of VEGF-C on tyrosine phosphorylation of VEGFR-3 and VEGFR-2 was receptor-specific, we analyzed the effect of VEGF-C on tyrosine phosphorylation of PDGF receptor β (PDGFR-β) which is abundantly expressed on fibroblastic cells. As can be seen from FIG. 14B, a weak tyrosine phosphorylation of PDGFR-β was detected upon stimulation of Flt4-expressing NIH 3T3 cells with CM from the mock-transfected cells (compare lanes 1 and 2). A similar low level of PDGFRβ phosphorylation was observed when the cells were incubated with CM from the VEGF-C transfected cells, with or without prior treatment with Flt4EC (lanes 3 and 4). In contrast, the addition of 50 ng/ml of PDGF-BB induced a prominent tyrosine autophosphorylation of PDGFRβ (lane 5).

EXAMPLE 15

VEGF-C Stimulates Endothelial Cell Migration in Collagen Gel

CM from cell cultures transfected with the VEGF-C expression vector was placed in a well made in collagen gel and used to stimulate the migration of bovine capillary endothelial (BCE) cells in the three-dimensional collagen gel as follows.

BCE cells (Folkman et al., *Proc. Natl. Acad. Sci. (USA)*, 76:5217–5221 (1979) were cultured as described in Pertovaara et al., *J. Biol. Chem.*, 269:6271–74 (1994). The collagen gels were prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. The tissue culture plates (5 cm diameter) were coated with about 1 mm thick layer of the solution, which was allowed to polymerize at 37° C. BCE cells were seeded on top of this layer. For the migration assays, the cells were allowed to attach inside a plastic ring (1 cm diameter) placed on top of the first collagen layer. After 30 min., the ring was removed and unattached cells were rinsed away. A second layer of collagen and a layer of growth medium (5% newborn calf serum (NCS)), solidified by 0.75% low melting point agar (FMC BioProducts, Rockland, Me.), were added. A well (3 mm diameter) was punched through all the layers on both sides of the cell spot at a distance of 4 mm, and the sample or control media were pipetted daily into the wells. Photomicrographs of the cells migrating out from the spot edge were taken after six days through an Olympus CK 2 inverted microscope equipped with phase-contrast optics. The migrating cells were counted after nuclear staining with the fluorescent dye bisbenzimide (1 mg/ml, Hoechst 33258, Sigma).

Figure 15A:
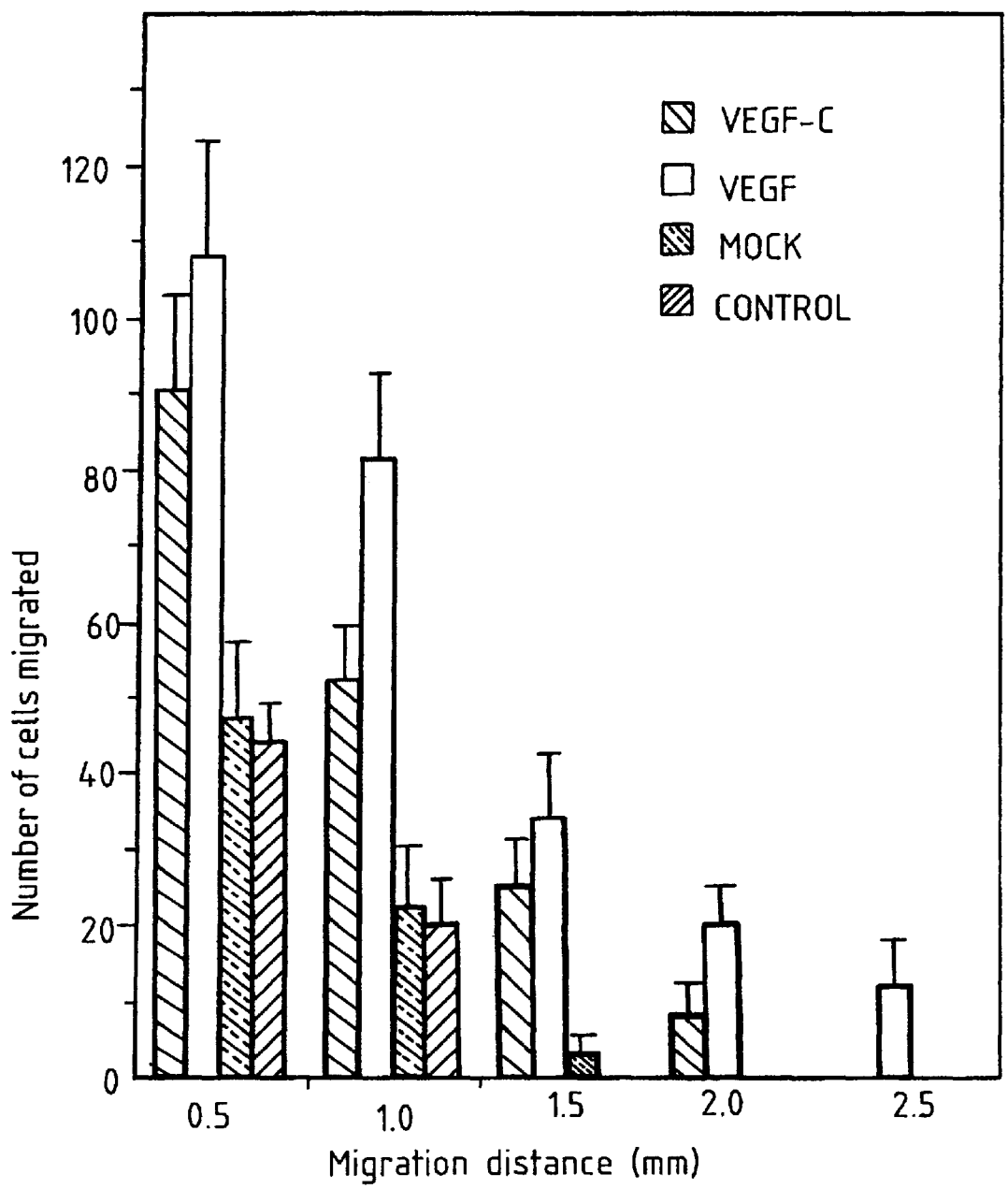
Figure 15B:
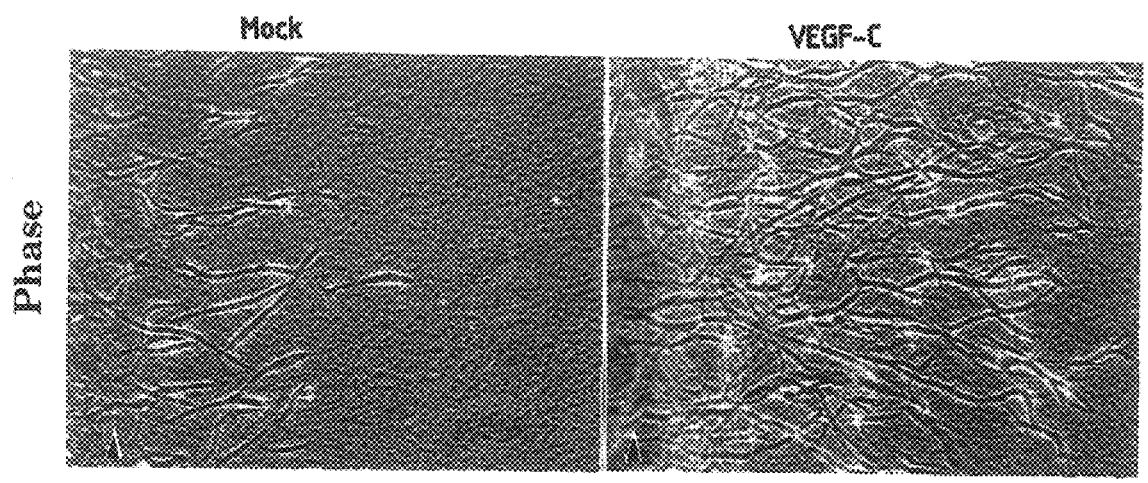

FIG. 15A depicts a comparison of the number of cells migrating at different distances from the original area of attachment towards wells containing media conditioned by the non-transfected (control) or transfected (mock; VEGF-C; VEGF) cells, 6 days after addition of the media. The number of cells migrating out from the original ring of attachment was counted in five adjacent 0.5 mm×0.5 mm squares using a microscope ocular lens grid and 10×magnification. Cells migrating further than 0.5 mm were counted in a similar way by moving the grid in 0.5 mm steps. The experiments were carried out twice with similar results, and medium values from the one of the experiments are presented with standard error bars. The photographs in FIGS. 15B and 15C depict phase-contrast microscopy and fluorescent microscopy of the nuclear staining of BCE cells migrating towards the wells containing media conditioned by the mock-transfected cells or by VEGF-C-transfected cells. The areas shown is approximately 1 mm×1.5 mm, and arrows indicate the borders of the original ring of attachment.

After 6 days of treatment, the cultures were stained and cells at different distances outside of the original ring of attachment were counted using fluorescent nuclear staining and detection with a fluorescence microscope equipped with a grid. A comparison of the numbers of migrating cells in successive 0.5 mm×0.5 mm areas is shown in FIG. 15A. As can be seen from the columns, VEGF-C-containing CM stimulated cell migration more than medium conditioned by the non-transfected or mock-transfected cells but less than medium from cells transfected with a VEGF expression vector. An example of typical phase contrast and fluorescent microscopic fields of cultures stimulated with medium from mock-transfected or VEGF-C transfected cells is shown in FIGS. 15B and 15C. Daily addition of 1 ng of FGF2 into the wells resulted in the migration of approximately twice the number of cells when compared to the stimulation by CM from VEGF-transfected cells.

EXAMPLE 16

VEGF-C is Expressed In Multiple Tissues

Figure 16A:
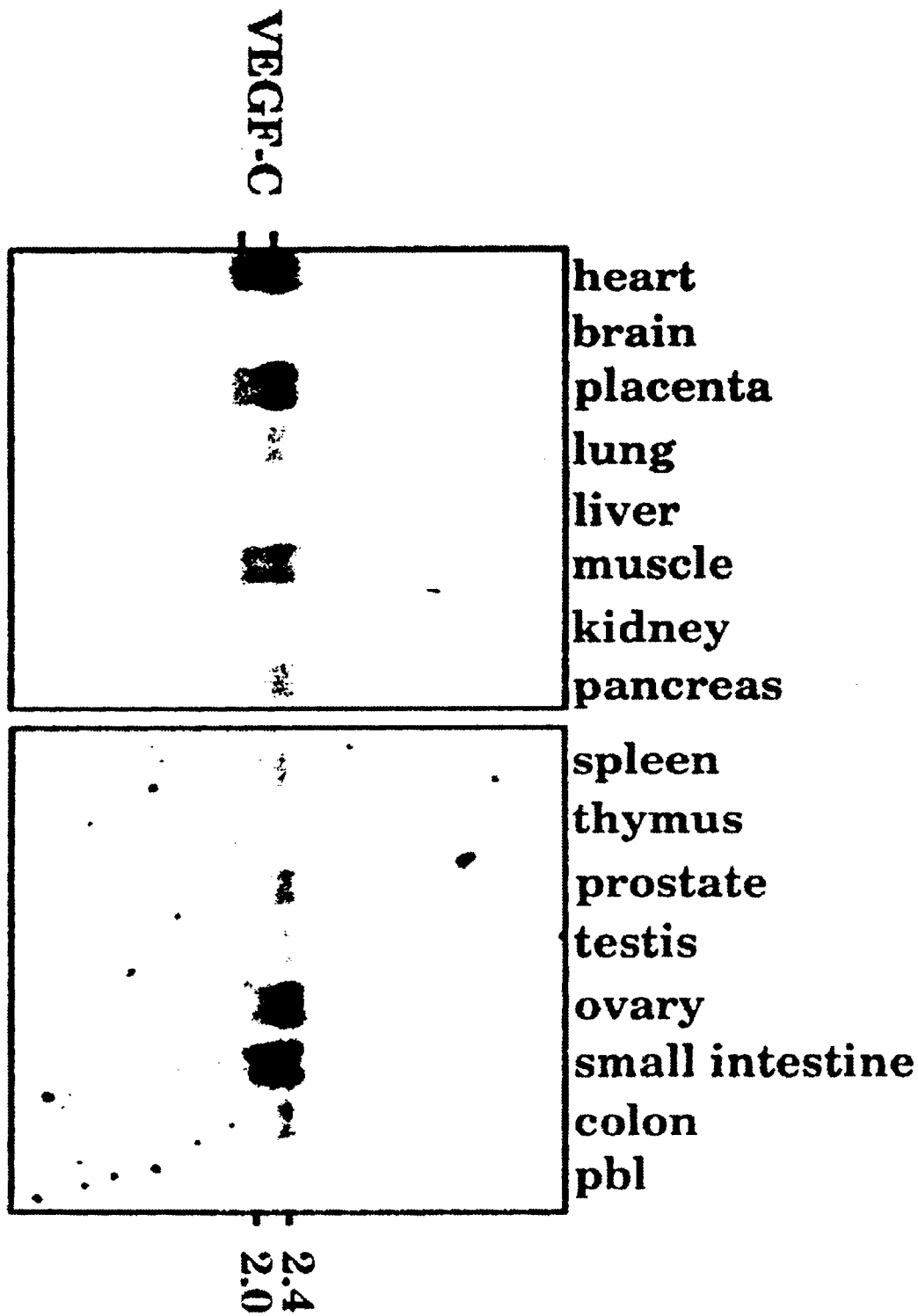
FIG. 16A shows the expression of VEGF-C mRNA in human adult tissues.
Figure 16B:
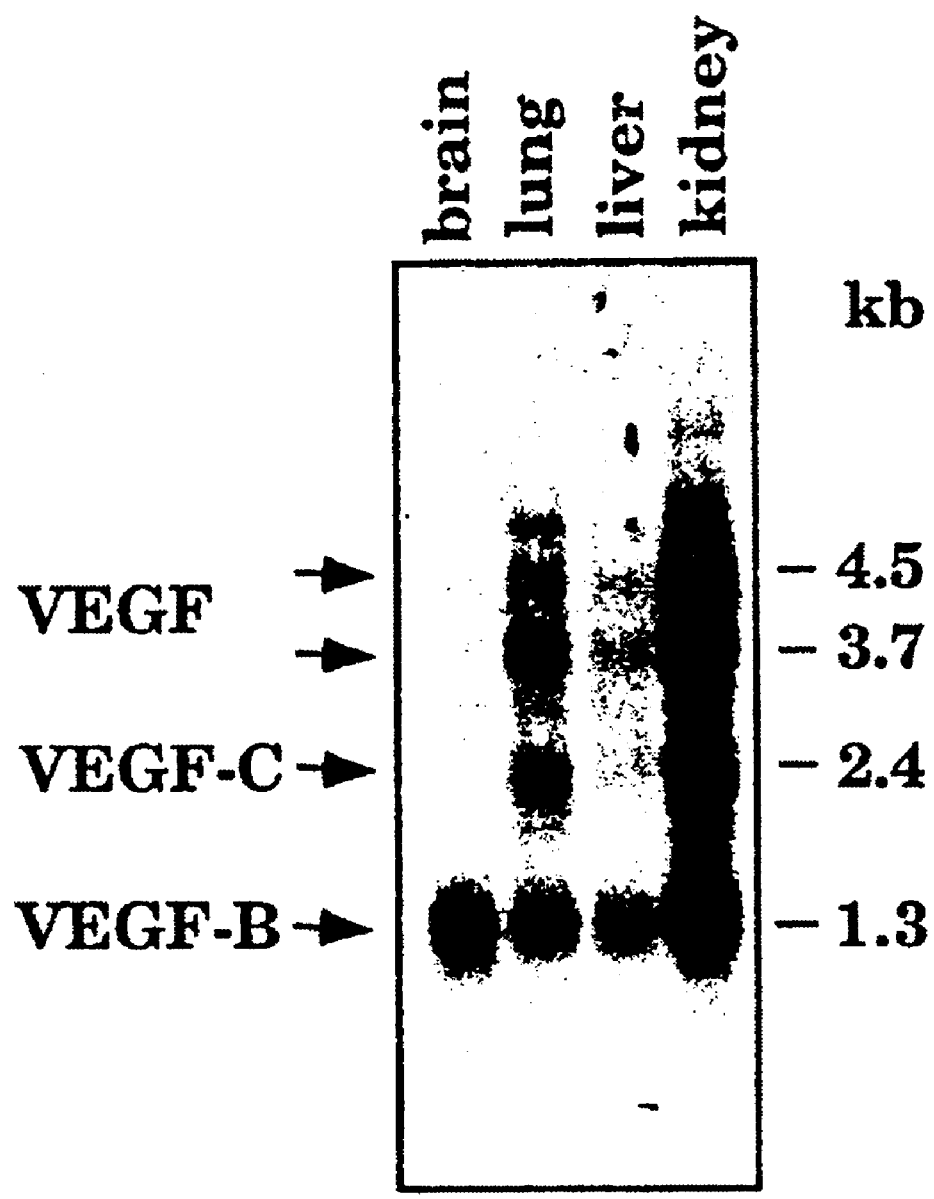
FIG. 16B shows the expression of VEGF, VEGF-B, and VEGF-C in selected human fetal tissues.

Northern blots containing 2 micrograms of isolated poly (A)$^+$ RNA from multiple human tissues (blot from Clontech Laboratories, Inc., Palo Alto, Calif.) were probed with radioactively labelled insert of the 2.1 kb VEGF-C cDNA clone. Northern blotting and hybridization analysis showed that the 2.4 kb RNA and: smaller amounts of a 2.0 kb mRNA are expressed in multiple human tissues, most prominently in the heart, placenta, muscle, ovary and small intestine (FIG. 16A). Very little VEGF-C RNA was seen in the brain, liver or thymus and peripheral blood leukocytes (PBL) appeared negative. A similar analysis of RNA from human fetal tissues (FIG. 16B) shows that VEGF-C is highly expressed in the kidney and lung and to a lesser degree in the liver, while essentially no expression is detected in the brain. Interestingly, VEGF expression correlates with VEGF-C expression in these tissues, whereas VEGF-B is highly expressed in all tissues analyzed.

EXAMPLE 17

The VEGF-C Gene Localizes to Chromosome 4q34

A DNA panel of 24 interspecies somatic cell hybrids, which had retained one or two human chromosomes, was used for the chromosomal localization of the VEGF-C gene (Bios Laboratories, Inc., New Haven, Conn.). Primers were designed to amplify an about 250 bp fragment of the VEGF-C gene from somatic cell hybrid DNA. The primers and conditions for polymerase chain reaction (PCR) were 5'-TGAGTGATIIGTAGCTGCTGTG-3' (forward) [SEQ ID NO: 34] and 5'-TATTGCAGCAACCCCCACATCT-3' (reverse) [SEQ ID NO: 35] for VEGF-C (94° C., 60s/62° C., 45s/72° C., 60s). The PCR products were evaluated by electrophoresis in 1% agarose gels and visualized by ethidium bromide staining in ultraviolet light. [$\alpha$-$^{32}$P]-dCTP-labelled cDNA inserts of a plasmid representing the complete VEGF-C coding domain was used as a probe in Southern blotting and hybridization analysis of the somatic cell hybrid DNAs as instructed by the supplier (Bios Laboratories).

The cell lines for fluorescence in situ hybridization (FISH) were obtained from the American Type Culture Collection (Rockville, Md.). Purified DNA from P1 clones 7660 and 7661 (VEGF-C) (Genome Systems, Inc., St. Louis, Mo.) were confirmed positive by Southern blotting of EcoRI-digested DNA followed by hybridization with the VEGF-C cDNA. The P1 clones were then labelled by nick translation either with biotin-11-dUTP, biotin-14-ATP (Sigma Chemical Co., St. Louis, Mo.) or digoxigenin 11-dUTP (Boehringer Mannheim GmbH, Mannheim, Germany) according to standard protocols. PHA-stimulated peripheral blood lymphocyte cultures were treated with 5-bromodeoxyuridine (BrdU) at an early replicating phase to induce G-banding. See Takahashi et al., *Human Genet.*, 86:14–16 (1995); Lemieux et al., *Cytogenet. Cell Genet.*, 59:311 –12 (1992). The FISH procedure was carried out in 50% formamide, 10% dextran sulphate in 2×SSC using well-known procedures. See e.g., Rytkönnen et al., *Cytogenet Cell Genet.*, 68:61–63 (1995); Lichter et al., *Proc. Natl. Acad. Sci.* (USA), 85:9664–68 (1988). Repetitive sequences were suppressed with 50-fold excess of Cot-1 DNA (BRL, Gaithersburg, Md.) compared with the labeled probe. Specific hybridization signals were detected by incubating the hybridized slides in labelled antidigoxigenin antibodies, followed by counterstaining with 0.1 mmol/L 4,6-diamino-2-phenylindole. Probe detection for two-color experiments was accomplished by incubating the slides in fluorescein isothiocyanate (FITC)-anti-digoxigenin antibodies (Sigma Chemical Co.) and Texas red-avidin (Vector Laboratories, Burlingame, Calif.) or rhodamine-anti-digoxigenin and FITC-avidin.

Multi-color digital image analysis was used for acquisition, display and quantification of hybridization signals of metaphase chromosomes. The system contains a PXL camera (Photometrics Inc., Tucson, Ariz.) attached to a PowerMac 7100/Av workstation. IPLab software controls the camera operation, image acquisition and Ludl Filter wheel. At least 50 nuclei were scored. Overlapping nuclei and clusters of cells were ignored. A slide containing normal lymphocyte metaphase spreads and interphase nuclei was included in each experiment to control for the efficiency and specificity of the hybridization.

In order to determine the chromosomal localization of the human VEGF-C gene, DNAs from human rodent somatic cell hybrids containing defined sets of human chromosomes were analyzed by Southern blotting and hybridization with the VEGF-C cDNA probe. Among 24 DNA samples on the hybrid panel, representing different human chromosomes, human-specific signals were observed only in hybrids which contained human chromosome 4. The results were confirmed by PCR of somatic cell hybrid DNA using VEGF-C specific primers, where amplified bands were obtained only from DNAs containing human chromosome 4.

Figure 17:
FIG. 17 schematically depicts the chromosomal localization of the VEGF-C gene.

A genomic P1 plasmid for VEGF-C was isolated using specific primers and PCR and verified by Southern blotting and hybridization using a VEGF-C specific cDNA probe. The chromosomal localization of VEGF-C was further studied using metaphase FISH. Using the P1 probe for VEGF-C in FISH a specific hybridization to the 4q34 chromosomal band was detected in 40 out of 44 metaphases (FIG. 17). Double-fluorochrome hybridization using a cosmid probe specific for the aspartylglucosaminidase (AGA) gene showed that VEGF-C is located just proximal to the AGA gene previously mapped to the 4q34–35 chromosomal band.

Biotin labelled VEGF-C P1 and digoxigenin labeled AGA cosmid probes were hybridized simultaneously to metaphase chromosomes. This experiment demonstrated that the AGA gene is more telomerically located than the VEGF-C gene. The foregoing example demonstrates the utility of polynucleotides of the invention as chromosomal markers.

EXAMPLE 18

Figure 18:
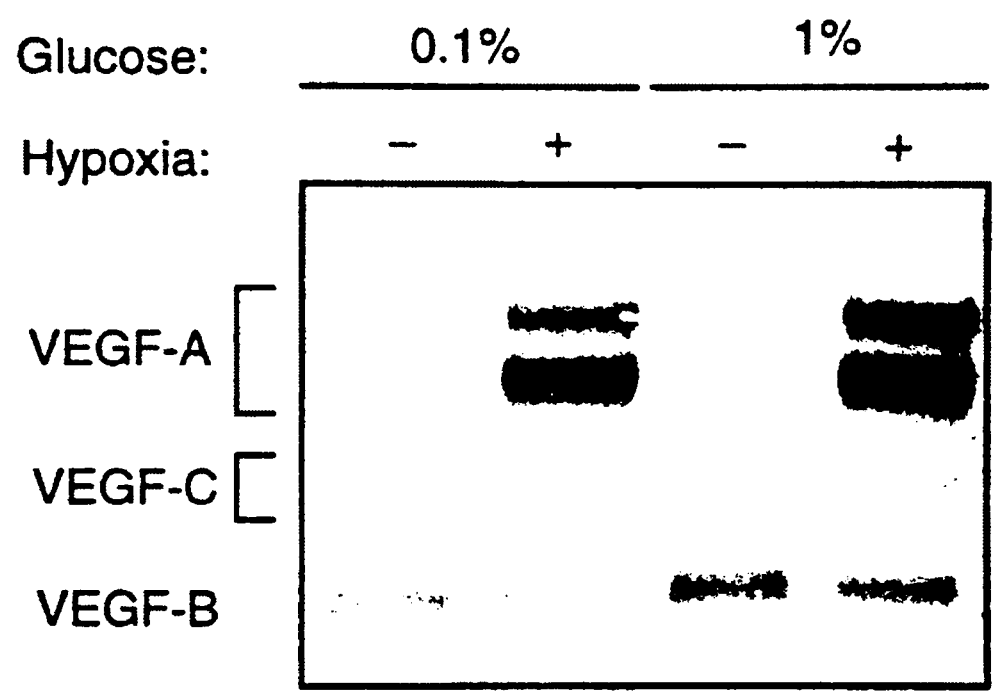
FIG. 18 is a Northern blot hybridization study showing the effects of hypoxia on the mRNA expression of VEGF (VEGF-A), VEGF-B and VEGF-C.

Effect of Glucose Concentration and Hypoxia on VEGF, VEGF-B and VEGF-C mRNA Levels in C6 Glioblastoma Cells Confluent cultures of C6 cells (ATCC CCL 107) were grown on 10 cm diameter tissue culture plates containing 2.5 ml of DMEM and 5% fetal calf serum plus antibiotics. The cultures were exposed for 16 hours to normoxia in a normal cell culture incubator containing 5% $CO_2$ (FIG. 18: lanes marked −) or hypoxia (FIG. 18: lanes marked +) by closing the culture plates in an airtight glass chamber and burning a piece of wood inside until the flame was extinguished due to lack of oxygen. Polyadenylated RNA was isolated (as in the other examples), and 8 micrograms of the RNA was electrophoresed and blot-hybridized with a mixture of the VEGF, VEGF-B and VEGF-C probes (see FIG. 12). The results show that hypoxia strongly induces VEGF (VEGF-A) mRNA expression (compare lanes − and +), both in low and high glucose, but has no significant effect on the VEGF-B mRNA levels. The VEGF-C mRNA isolated from hypoxic cells runs slightly faster in gel electrophoresis and an extra band of faster mobility can be seen below the upper mRNA band. This observation suggests that hypoxia affects VEGF-C RNA processing. One explanation for this observation is that VEGF-C mRNA splicing is altered, affecting the VEGF-C open reading frame and resulting in an alternative VEGF-C protein being produced by hypoxic cells. Such alternative forms of VEGF-C and VEGF-C-encoding polynucleotides are contemplated as an aspect of the invention. This data indicates screening and diagnostic utilities for polynucleotides and polypeptides of the invention, such as methods whereby a biological sample is screened for the hypoxia-induced form of VEGF-C and/or VEGF-C mRNA. The data further suggests a therapeutic indication for antibodies and/or other inhibitors of the hypoxia-induced form of VEGF-C or the normal form of VEGF-C.

EXAMPLE 19

Pulse-chase Labeling and Immunoprecipitation of VEGF-C Polypeptides from 293 Cells Transfected with VEGF-C Expression Vector The following VEGF-C branched amino-terminal peptide, designated PAM126, was synthesized for production of anti-VEGF-C antiserum:

$NH_2$-E-E-T-I-K-F-A-A-A-H-Y-N-T-E-I-L-K-COOH (SEQ ID NO: 39). In particular, PAM126 was synthesized as a branched polylysine structure K3PA4 having four peptide acid (PA) chains attached to two available lysine (K) residues. The synthesis was performed on a 433A Peptide Synthesizer (Applied Biosystems) using Fmoc-chemistry and TentaGel S MAP RAM10 resin mix (RAPP Polymere GmbH, Tubingen, Germany), yielding both cleavable and resin-bound peptides. The cleavable peptide was purified via reverse phase HPLC and was used together with the resin-bound peptide in immunizations. The correctness of the synthesis products were confirmed using mass-spectroscopy (Lasermatt).

The peptide was dissolved in phosphate buffered saline (PBS), mixed with Freund's adjuvant, and used for immunization of rabbits at bi-weekly intervals using methods standard in the art (Harlow and Lane, *Antibodies, a laboratory manual*, Cold Spring Harbor Laboratory Press (1988)). Antisera obtained after the fourth booster immunization was used for immunoprecipitation of VEGF-C in pulse-chase experiments, as described below.

For pulse-chase analysis, 293 cells transfected with a VEGF-C expression vector (i.e., the FLT4-L cDNA inserted into the pREP7 expression vector as described above) were incubated for 30 minutes in methionine-free, cysteine-free, serum-free DMEM culture medium at 37° C. The medium was then changed, and 200 µCi of $^{35}$S-methionine and $^{35}$S-cysteine (Promix, Amersham, Buckinghamshire, England) was added. The cell layers were incubated in this labeling medium for two hours, washed with PBS, and incubated for 0, 15, 30, 60, 90, 120, or 180 minutes in serum-free DMEM (chase). After the various chase periods, the medium was collected, the cells were again washed two times in PBS, and lysed in immunoprecipitation buffer. The VEGF-C polypeptides were analyzed from both the culture medium and from the cell lysates by immunoprecipitation, using the VEGF-C-specific antiserum raised against the $NH_2$-terminal peptide (PAM126) of the 23 kD VEGF-C form. Immunoprecipitated polypeptides were analyzed via SDS-PAGE followed by autoradiography.

Figure 19:
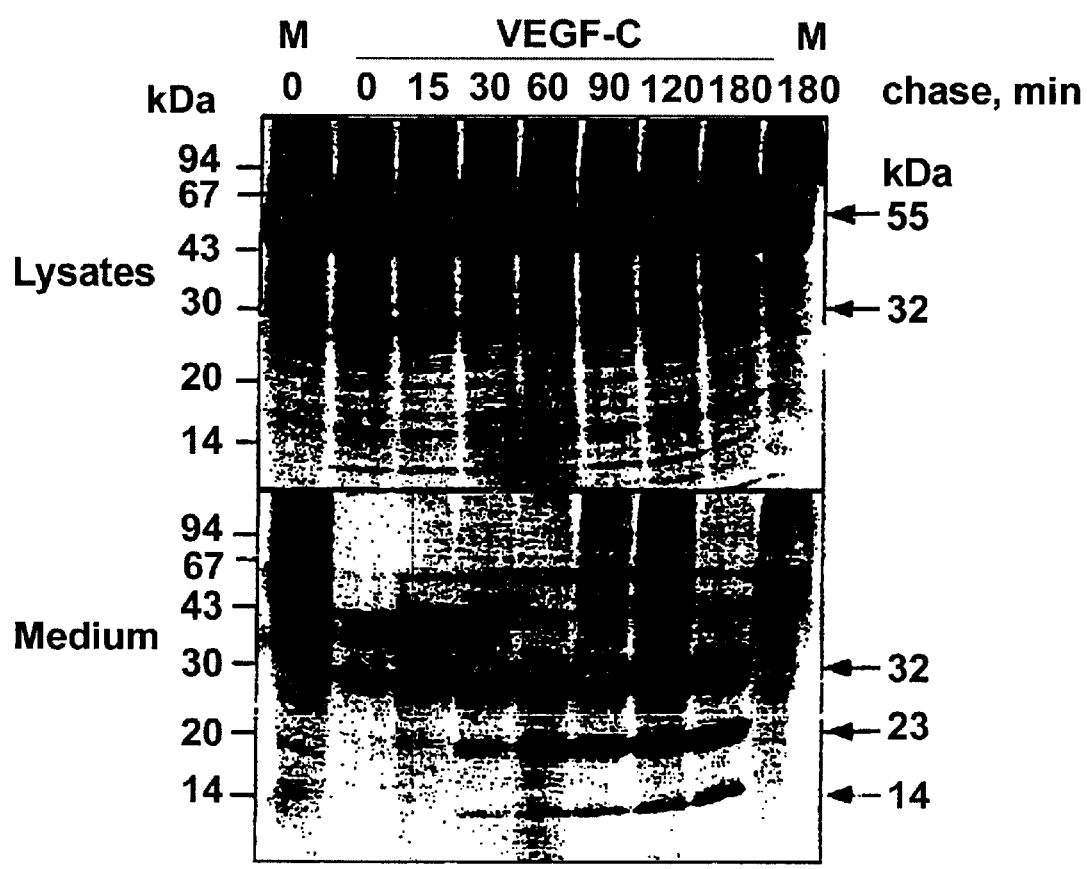
FIG. 19 depicts autoradiograms from a pulse-chase immunoprecipitation experiment wherein cells transfected with a VEGF-C expression vector (VEGF-C) and mock transfected cells (M) were pulse-labeled with radioactive amino acids and chased for varying lengths of time.

Referring to FIG. 19, the resultant autoradiograms demonstrate that immediately after a 2 hour labeling (chase time 0), the VEGF-C vector-transfected cells contained a radioactive 55 kD polypeptide band, which is not seen in mock-transfected cells (M). This 55 kD polypeptide band gradually diminishes in intensity with increasing chase periods, and is no longer detected in the cells by 180 minutes of chase. A 32 kD polypeptide band also is observed in VEGF-C transfected cells (and not mock-transfected cells). This 32 kD band disappears with similar kinetics to that of the 55 kD band. Simultaneously, increasing amounts of 32 kD (arrow) and subsequently 23 kD (arrow) and 14 kD polypeptides appear in the medium.

Collectively, the data from the pulse-chase experiments indicate that the 55 kD intracellular polypeptide represents a pro-VEGF-C polypeptide, which is not secreted from cells, but rather is first proteolytically cleaved into the 32 kD form. The 32 kD form is secreted-and simultaneously further processed by proteolysis into the 23 kD and 14 kD forms. Without intending to be limited to a particular theory, it is believed that processing of the VEGF-C precursor occurs as removal of a signal sequence, removal of the COOH-terminal domain (BR3P), and removal of an amino terminal peptide, resulting in a VEGF-C polypeptide having the TEE . . . amino terminus.

At high resolution, the 23 kD polypeptide band appears as a closely spaced polypeptide doublet, suggesting heterogeneity in cleavage or glycosylation.

EXAMPLE 20

Isolation of Mouse cDNA Clones Encoding VEGF-C

To clone a mouse variant of VEGF-C, approximately $1 \times 10^6$ bacteriophage lambda clones of a commercially-available 12 day mouse embryonal cDNA library (lambda EXlox library, Novagen, catalog number 69632-1) were screened with a radiolabeled fragment of human VEGF-C cDNA containing nucleotides 495 to 1661 of SEQ ID NO: 32. One positive clone was isolated.

A 1323 bp EcoRI/HindIII fragment of the insert of the isolated mouse cDNA clone was subcloned into the corresponding sites of the pBluescript SK+ vector (Stratagene) and sequenced. The cDNA sequence of this clone was homologous to the human VEGF-C sequence reported herein, except that about 710 bp of 5'-end sequence present in the human clone was not present in the mouse clone.

For further screening of mouse cDNA libraries, a HindIII-BstXI (HindIII site is from the pBluescript SK+ polylinker) fragment of 881 bp from the coding region of the mouse cDNA clone was radiolabeled and used as a probe to screen two additional mouse cDNA libraries. Two additional cDNA clones from an adult mouse heart ZAP II cDNA library (Stratagene, catalog number 936306) were identified. Three additional clones also were isolated from a mouse heart 5'-stretch-plus cDNA library in λgt11 (Clontech Laboratories, Inc., catalog number ML5002b). Of the latter three clones, one was found to contain an insert of about 1.9 kb. The insert of this cDNA clone was subcloned into EcoRI sites of pBluescript SK+ vector and both strands of this clone were completely sequenced, resulting in the nucleotide and deduced amino acid sequences shown in SEQ ID NOs: 40 and 41.

It is contemplated that the polypeptide corresponding to SEQ ID NO: 41 is processed into a mature mouse VEGF-C protein, in a manner analogous to the processing of the human VEGF-C prepropeptide. Putative cleavage sites for the mouse protein are identified using procedures outlined above for identification of cleavage sites for the human VEGF-C polypeptide.

The foregoing example demonstrates the utility of polynucleotides of the invention for-identifying and isolating polynucleotides encoding other non-human mammalian variants of VEGF-C. Such identified and isolated polynucleotides, in turn, can be expressed (using procedures similar to those described in preceding examples) to produce recombinant polypeptides corresponding to non-human mammalian variants of VEGF-C.

EXAMPLE 21

N-terminal Peptide Sequence Analyses of Recombinant VEGF-C

Cells (293 EBNA) transfected with VEGF-C cDNA (see Example 13) secrete several forms of recombinant VEGF-C (FIG. 21A, lane IP). In the absence of alkylation, the three major, proteolytically-processed forms of VEGF-C migrate in SDS-PAGE as proteins with apparent molecular masses of 32/29 kD (doublet), 21 kD and 15 kD. Two minor polypeptides exhibit approximate molecular masses of 63 and 52 kD, respectively. One of these polypeptides is presumably a glycosylated and non-processed form; the other polypeptide is presumably glycosylated and partially processed.

To determine sites of proteolytic cleavage of the VEGF-C precursor, an immunoaffinity column was used to purify VEGF-C polypeptides from the conditioned medium of 293 EBNA cells transfected with VEGF-C cDNA. To prepare the immunoaffinity column, a rabbit was immunized with a synthetic peptide corresponding to the amino-terminus of mature VEGF-C secreted from the PC-3 cell line (amino acids 104–120 in SEQ ID NO: 33: $H_2N$-EETIKFAAAHYNTEILK; see PAM126 in Example 19). The IgG fraction was isolated from the serum of the immunized rabbit using protein A Sepharose (Pharmacia). The isolated IgG fraction was covalently bound to CNBr-activated Sepharose CL-4B (Pharmacia) using standard techniques at a concentration of 5 mg IgG/ml of Sepharose. This immunoaffinity matrix was used to isolate processed VEGF-C from 1.2 liters of the conditioned medium (CM).

The purified material eluted from the column was analyzed by gel electrophoresis and Western blotting. Fractions containing VEGF-C polypeptides were combined, dialyzed against 10 mM Tris HCl, vacuum-dried, electrotransferred to Immobilon-P (polyvinylidene difluoride or PVDF) transfer membrane (Millipore, Marlborough, Mass.) and subjected to N-terminal amino acid sequence analysis.

The polypeptide band of 32 kD yielded two distinct sequences: $NH_2$-FESGLDLSDA . . . and $NH_2$-AVVMTQTPAS . . . (SEQ ID NO: 51), the former corresponding to the N-terminal part of VEGF-C after cleavage of the signal peptide, starting from amino acid 32 (SEQ ID NO: 33), and the latter corresponding to the kappa-chain of IgG, which was present in the purified material due to "leakage" of the affinity matrix during the elution procedure.

In order to obtain the N-terminal peptide sequence of the 29 kD form of VEGF-C, a construct (VEGF-C NHis) encoding a VEGF-C variant was generated. In particular, the construct encoded a VEGF-C variant that fused a 6×His tag to the N-terminus of the secreted precursor (i.e., between amino acids 31 and 33 in SEQ ID NO: 33). The phenylalanine at position 32 was removed to prevent possible cleavage of the tag sequence during secretion of VEGF-C. The VEGF-C NHis construct was cloned into pREP7 as a vector; the construction is described more fully in Example 28, below.

Figure 27A:
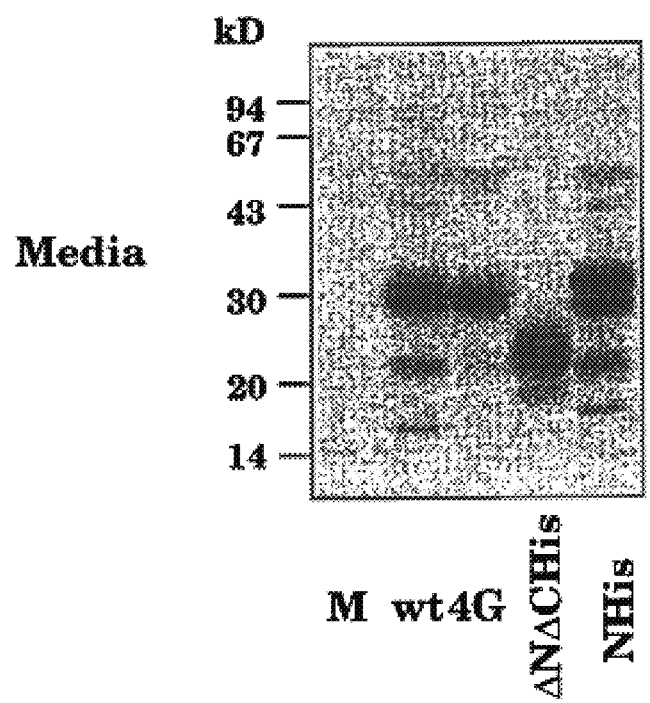
FIGS. 27A–B present gel electrophoretograms of human VEGF-C (wt) and VEGF-C variants secreted (FIG. 27A) or retained (FIG. 27B) by the host 293 EBNA cells. Mock (M) transfected cells served as a control. Molecular weight markers are indicated on the left in kilodaltons (kD).
Figure 27B:
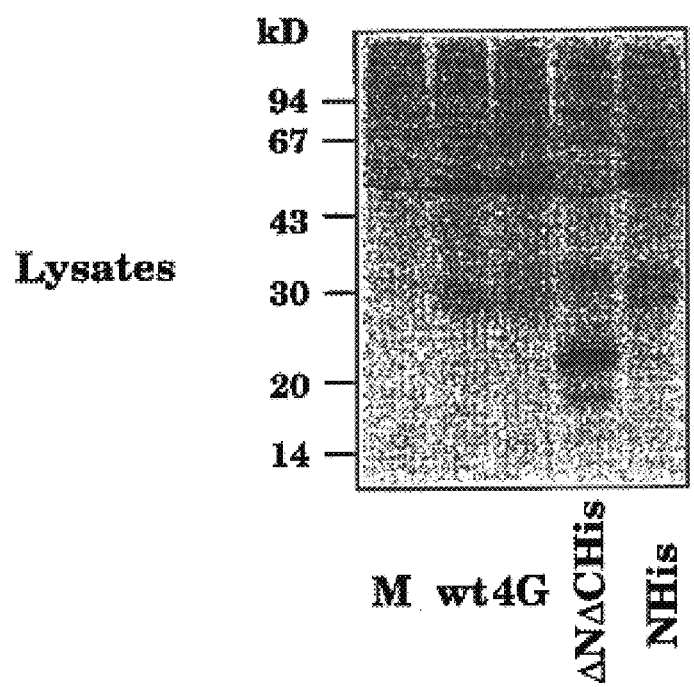

The calcium phosphate co-precipitation technique was used to transfect VEGF-C NHis into 293 EBNA cells. Cells were incubated in DMEM/10% fetal calf serum in 15 cm cell culture dishes (a total of 25 plates). The following day, the cells were reseeded into fresh culture dishes (75 plates) containing the same medium and incubated for 48 hours. Cell layers were then washed once with PBS and DMEM medium lacking FCS was added. Cells were incubated in this medium for 48 hours and the medium was collected, cleared by centrifugation at 5000×g and concentrated 500× using an Ultrasette Tangential Flow Device (Filtron, Northborough, Mass.), as described in Example 5 above. VEGF-C NHis was purified from the concentrated conditioned medium using TALONY™ Metal Affinity Resin (Clontech Laboratories, Inc.) and the manufacturer's protocol for native protein purification using imidazole-containing buffers. The protein was eluted with a solution containing 20 mM Tris-HCl (pH 8.0), 100 mM NaCl, and 200 mM imidazole. The eluted fractions containing purified VEGF-C NHis were detected by immunoblotting with Antiserum 882 (antiserum from rabbit 882). Fractions containing VEGF-C NHis were combined, dialyzed and vacuum-dried. As can be seen in FIG. 27, due to the presence of the 6×His tag at the N-terminus of this form of VEGF-C, the upper component of the major doublet of the VEGF-CNHis migrates slightly slower than the 32 kD form of wild type VEGF-C, thereby improving the separation of the VEGF-CNHis 32 kD variant from the 29 kD band using SDS-PAGE. Approximately 15 µg of the purified VEGF-C were subjected to SDS-PAGE under reducing conditions, electrotransferred to Immobilon-P (PVDF) transfer membrane (Millipore, Inc., Marlborough, Mass.) and the band at 29 kD was subjected to N-terminal amino acid sequence analysis. This sequence analysis revealed an N-terminal sequence of $H_2N$-SLPAT . . . , corresponding to amino acids 228–232 of VEGF-C (SEQ ID NO: 33).

The polypeptide band of 21 kD yielded the sequence $H_2N$-AHYNTEILKS . . . , corresponding to an amino-terminus starting at amino acid 112 of SEQ ID NO: 33. Thus, the proteolytic processing site which results in the 21 kD form of VEGF-C produced by transfected 293 EBNA cells apparently occurs nine amino acid residues downstream of the cleavage site which results in the 23 kD form of VEGF-C secreted by PC-3 cells.

The N-terminus of the 15 kD form was identical to the N-terminus of the 32 kD form ($NH_2$-FESGLDLSDA . . .). The 15 kD form was not detected when recombinant VEGF-C was produced by COS cells. This suggests that production of this form is cell lineage specific.

EXAMPLE 22

Dimeric and Monomeric Forms of VEGF-C

The composition of VEGF-C dimers was analyzed as follows. Cells (293 EBNA cells), transfected with the pREP7 VEGF-C vector as described in Example 11, were metabolically labelled with Pro-mix L-[$^{35}$S] labelling mix (Amersham Corp.) to a final concentration of 100 µCi/ml.

In parallel, a VEGF-C mutant, designated "R102S", was prepared and analyzed. To prepare the DNA encoding VEGF-C-R102S, the arginine codon at position 102 of SEQ ID NO: 33 was replaced with a serine codon. This VEGF-C-R102S-encoding DNA, in a pREP7 vector, was transfected into 293 EBNA cells and expressed as described above. VEGF-C polypeptides were immunoprecipitated using antisera 882 (obtained by immunization of a rabbit with a polypeptide corresponding to residues 104–120 of SEQ ID NO: 33 (see previous Example)) and antisera 905 (obtained by immunization of a rabbit with a polypeptide corresponding to a portion of the prepro-VEGF-C leader: H₂N-ESGLDLSDAEPDAGEATAYASK (residues 33 to 54 of SEQ ID NO: 33).

The immunoprecipitates from each cell culture were subjected to SDS-PAGE under non-denaturing conditions (FIG. 21B). Bands 1–6 were cut out from the gel, soaked for 30 minutes in 1×gel-loading buffer containing 200 mM β-mercaptoethanol, and individually subjected to SDS-PAGE under denaturing conditions (FIGS. 21A and 21C, lanes 1–6).

As can be seen from FIGS. 21A–C, each high molecular weight form of VEGF-C (FIG. 21B, bands 1–4) consists of at least two monomers bound by disulfide bonds (Compare FIGS. 21A and 21C, lanes 1–4, in the reducing gels). The main component of bands 1–3 is the doublet of 32/29 kD, where both proteins are present in an equimolar ratio. The main fraction of the 21 kD form is secreted as either a monomer or as a homodimer connected by means other than disulfide bonds (bands 6 and lanes 6 in FIGS. 21A–C).

The R102S mutation creates an additional site for N-linked glycosylation in VEGF-C at the asparagine residue at position 100 in SEQ ID NO: 33. Glycosylation at this additional glycosylation site increases the apparent molecular weight of peptides containing the site, as confirmed in FIGS. 21A–C and FIGS. 22A–B. The additional glycosylation lowers the mobility of forms of VEGF-C-R102S that contain the additional glycosylation site, when compared to peptides of similar primary structure corresponding to VEGF-C. FIGS. 21A–C and FIGS. 22A–B reveal that the VEGF-C-R102S polypeptides corresponding to the 32 kD and 15 kD forms of wt VEGF-C exhibit increased apparent molecular weights, indicating that each of these peptides contains the newly introduced glycosylation site. In particular, the VEGF-C-R102S peptide corresponding to the 15 kD peptide from VEGF-C comigrates on a gel with the 21 kD form of the wild type (wt) VEGF-C, reflecting a shift on the gel to a position corresponding to a greater apparent molecular weight. (Compare lanes 4 in FIGS. 21A and 21C).

Figure 22A:
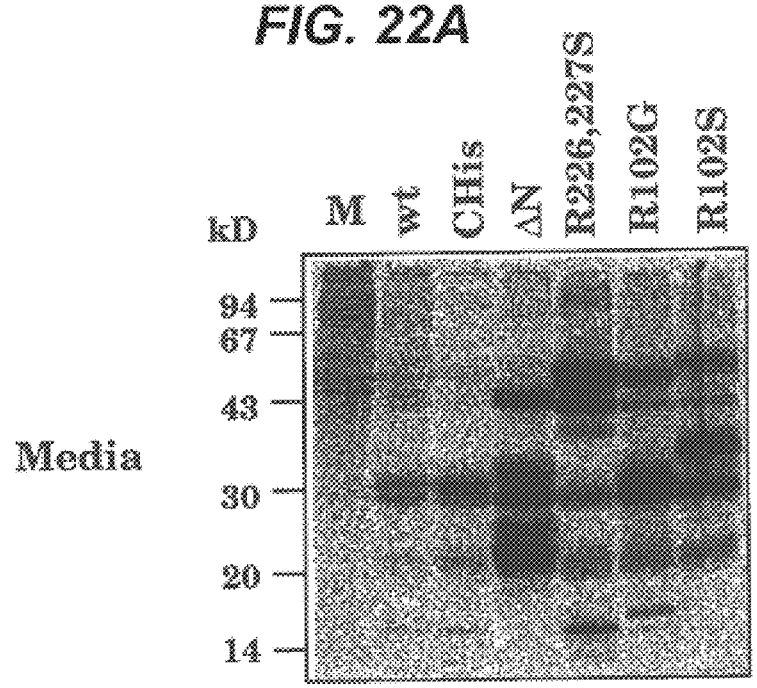
FIGS. 22A–B depict the forms and sizes of wild type and mutant recombinant VEGF-Cs, as revealed by non-reducing gel electrophoresis.
Figure 22B:
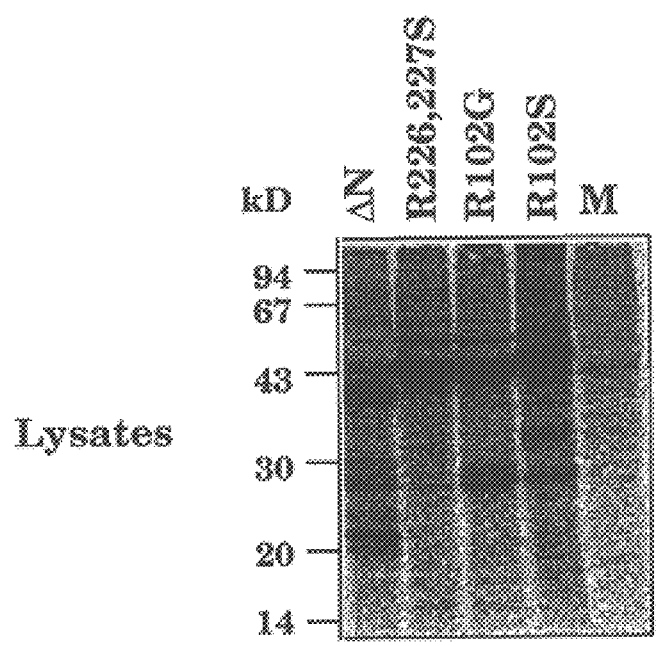

In a related experiment, another VEGF-C mutant, designated "R226,227S," was prepared and analyzed. To prepare a DNA encoding VEGF-C-R226,227S, the arginine codons at positions 226 and 227 of SEQ ID NO: 33 were replaced with serine codons by site-directed mutagenesis. The resultant DNA was transfected into 293 EBNA cells as described above and expressed and analyzed under the same conditions as described for VEGF-C and VEGF-C-R102S. In the conditioned medium from the cells expressing VEGF-C-R226,227S, no 32 kD form of VEGF-C was detected. These results indicate that a C-terminal cleavage site of wild-type VEGF-C is adjacent to residues 226 and 227 of SEQ ID NO: 33, and is destroyed by the mutation of the arginines to serines. Again, the mobility of the 29 kD component of the doublet was unchanged (FIGS. 22A–B).

Taken together, these data indicate that the major form of the processed VEGF-C is a heterodimer consisting of (1) a polypeptide of 32 kD containing amino acids 32–227 of the prepro-VEGF-C (amino acids 32 to 227 in SEQ ID NO: 33) attached by disulfide bonds to (2) a polypeptide of 29 kD beginning with amino acid 228 in SEQ ID NO: 33. These data are also supported by a comparison of the pattern of immunoprecipitated, labelled VEGF-C forms using antisera 882 and antisera 905.

Figure 23A:
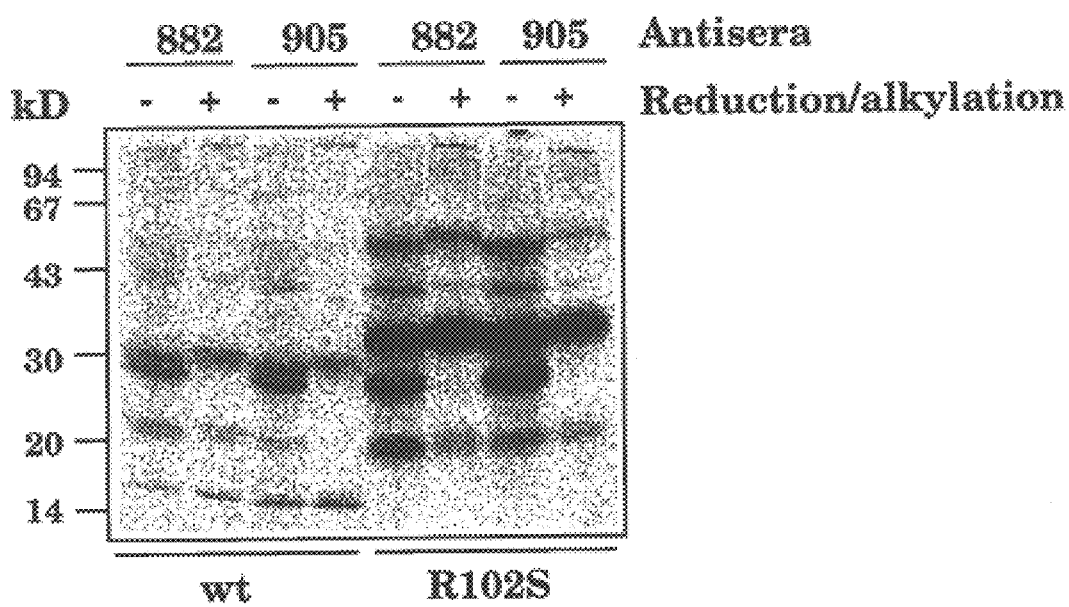
FIGS. 23A–B present a comparison of the pattern of immunoprecipitated, labelled VEGF-C forms using antisera 882 and antisera 905. Adjacent lanes contain immunoprecipitates that were (lanes marked +) or were not (lanes marked –) subjected to reduction and alkylation.
Figure 23B:
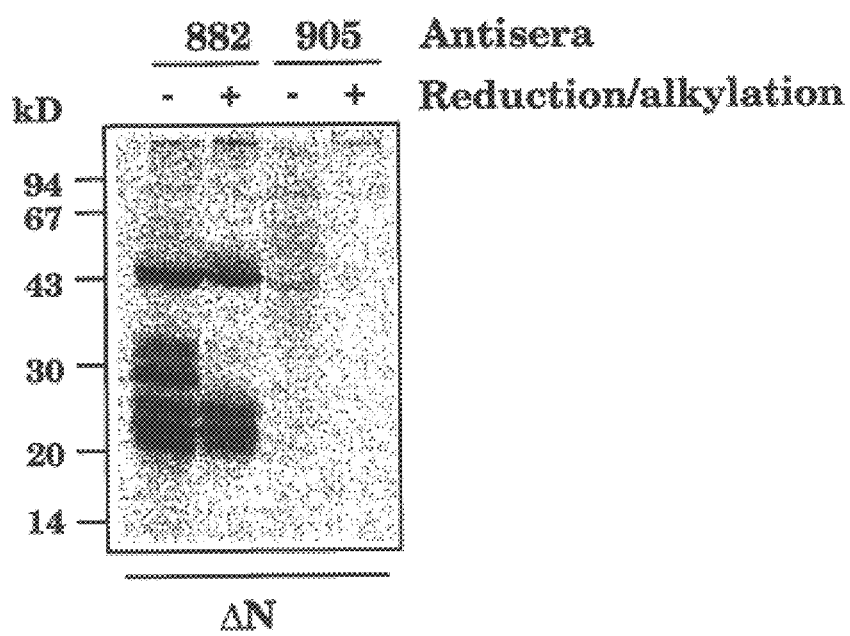
Figures 24A, 24B:
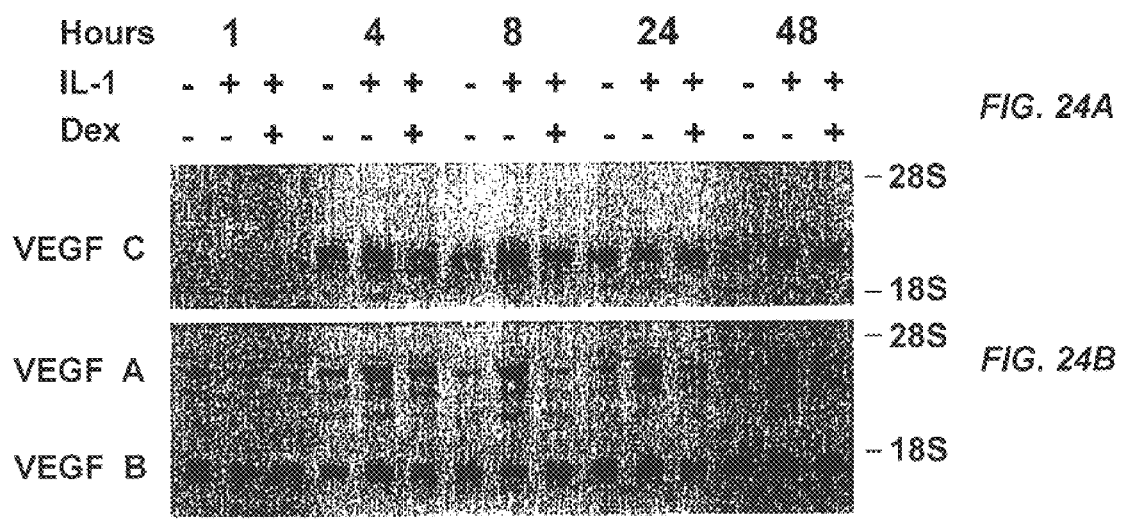
FIGS. 24A–B present Northern blots of total RNA isolated from cells grown in the presence or absence of interleukin-1 (IL-1) and/or dexamethasone (DEX) for the indicated times. For FIG. 25B, the Northern blot was probed with radiolabeled DNA from a VEGF 581 bp cDNA covering bps 57–638 (Genbank Acc. No. X15997), and a human VEGF-B$_{167}$ cDNA fragment (nucleotides 1/382, Genbank Acc. No. U48800). For FIG. 24A, the Northern blot was probed with radiolabeled DNA from a human full-length VEGF-C cDNA (Genbank Acc. No. X94216). 18S and 28S-rRNA markers.

When VEGF-C immunoprecipitation was carried out using conditioned medium, both antisera (882 and 905) recognized some or all of the three major processed forms of VEGF-C (32/29 kD, 21 kD and 15 kD). When the conditioned medium was reduced by incubation in the presence of 10 mM dithiothreitol for two hours at room temperature with subsequent alkylation by additional incubation with 25 mM iodoacetamide for 20 minutes at room temperature, neither antibody precipitated the 29 kD component, although antibody 882 still recognized polypeptides of 32 kD, 21 kD and 15 kD. These results are consistent with the nature of the peptide antigen used to elicit the antibodies contained in antisera 882, a peptide containing amino acids 2–18 of SEQ ID NO: 33. On the other hand, antisera 905 recognized only the 32 kD and 15 kD polypeptides, which include sequence of the peptide (amino acids 33 to 54 of SEQ ID NO: 33) used for immunization to obtain antisera 905. Taking into account the mobility shift of the 32 kD and 15 kD forms, the immunoprecipitation results with the R102S mutant were similar (FIGS. 23A–B). The specificity of antibody 905 is confirmed by the fact that it did not recognize a VEGF-C ΔN variant form wherein the N-terminal propeptide spanning residues 32–102 of the unprocessed polypeptide had been deleted (FIG. 23B).

The results of these experiments also demonstrate that the 21 kD polypeptide is found (1) in heterodimers with other molecular forms (see FIGS. 21A–C and FIGS. 22A–B), and (2) secreted as a monomer or a homodimer held by bonds other than disulfide bonds (FIGS. 21A and 21B, lanes 6).

The experiments disclosed in this example demonstrate that several forms of VEGF-C exist. A variety of VEGF-C monomers were observed and these monomers can vary depending on the level and pattern of glycosylation. In addition, VEGF-C was observed as a multimer, for example a homodimer or a heterodimer. The processing of VEGF-C is schematically presented in FIG. 37 (disulfide bonds not shown). All forms of VEGF-C are within the scope of the present invention.

EXAMPLE 23

In Situ Hybridization of Mouse Embryos

To analyze VEGF-C mRNA distribution in different cells and tissues, sections of 12.5 and 14.5-day post-coitus (p.c.) mouse embryos were prepared and analyzed via in situ hybridization using labeled VEGF-C probes. In situ hybridization of tissue sections was performed as described Västrik et al., *J. Cell Biol.*, 128:1197–1208 (1995). A mouse VEGF-C antisense RNA probe was generated from linearized pBluescript II SK+ plasmid (Stratagene Inc., La Jolla, Calif.), containing a cDNA fragment corresponding to nucleotides 499–979 of a mouse VEGF-C cDNA (SEQ ID NO: 40). This clone was obtained from a partial clone isolated from the Novagen library (see the 1322 bp cDNA clone of FIG. 31A), from which the 3' noncoding region and the BR3P repeats had been removed by exonuclease III treatment. Radiolabeled RNA was synthesized using T7 polymerase and [³⁵S]-UTP (Amersham). Mouse VEGF-B antisense and sense RNA probes were synthesized in a similar manner from linearized pCRII plasmid containing the mouse VEGF-B cDNA insert as described Olofsson et al., *Proc. Natl. Acad. Sci. (USA)*, 93:2576–2581 (1996). The high stringency wash was for 45 minutes at 65° C. in a solution containing 30 mM DTT and 4×SSC. The slides were exposed for 28 days, developed and stained with hematoxylin. For comparison, similar sections were hybridized with a VEGFR-3 probe and the 12.5-day p.c. embryos were also probed for VEGF-B mRNA.

FIGS. 34A–D show darkfield (FIGS. 34A–C) and lightfield (FIG. 34D) photomicrographs of 12.5 day p.c. embryo sections probed with the antisense (FIG. 34A) and sense (FIGS. 34C–D) VEGF-C probes. FIG. 34A illustrates a parasagittal section, where VEGF-C mRNA is particularly prominent in the mesenchyme around the vessels surrounding the developing metanephros (mn). In addition, hybridization signals were observed between the developing vertebrae (vc), in the developing lung mesenchyme (lu), in the neck region and developing forehead. The specificity of these signals is evident from the comparison with VEGF-B expression in an adjacent section (FIG. 34B), where the myocardium gives a very strong signal and lower levels of VEGF-B mRNA are detected in several other tissues. Both genes appear to be expressed in between the developing vertebrae (vc), in the developing lung (lu) and forehead. Hybridization of the VEGF-C sense probe showed no specific expression within these structures (FIG. 34C).

FIGS. 35A–D show a comparison of the expression patterns of VEGF-C and VEGFR-3 in 12.5 day p.c. mouse embryos in the jugular region, where the developing dorsal aorta and cardinal vein are located. This is the area where the first lymphatic vessels sprout from venous sac-like structures according to a long-standing theory. Sabin, *Am. J. Anat.*, 9:43–91 (1909). As can be seen from FIGS. 35A–D, an intense VEGF-C signal is detected in the mesenchyme surrounding the developing venous sacs (FIGS. 35A and 35C) which are positive for VEGFR-3 (FIGS. 35B and 35D).

The mesenterium supplies the developing gut with blood and contains developing lymphatic vessels. The developing 14.5 day p.c. mesenterium is positive for VEGF-C mRNA, with particularly high expression in connective tissue surrounding certain vessels (arrowheads in FIGS. 35A–H). This signal in FIG. 35E should be distinguished from the false positive reflection of light from red blood cells within the vessel, shown with an asterisk. The adjacent mesenterial VEGFR-3 signals shown in FIG. 35F originate from small capillaries of the mesenterium (arrowheads). Therefore, there appears to be a paracrine relationship between the production of the mRNAs for the two growth factors. This data indicates that VEGF-C is expressed in a variety of tissues. Moreover, the pattern of expression is consistent with a role for VEGF-C in venous and lymphatic vessel development. Further, the data reveals that VEGF-C is expressed in non-human animals.

EXAMPLE 24

Analysis of VEGF, VEGF-B, and VEGF-C mRNA Expression in Fetal and Adult Tissues

A human fetal tissue Northern blot containing 2 µg of polyadenylated RNAs from brain, lung, liver and kidney (Clontech Inc.) was hybridized with a pool of the following probes: a human full-length VEGF-C cDNA insert (Genbank Acc. No. X94216), a human VEGF-B$_{167}$ cDNA fragment (nucleotides 1–382, Genbank Acc. No. U48800) obtained by PCR amplification; and a human VEGF 581 bp cDNA fragment covering base pairs 57–638 (Genbank Acc. No. X15997). Blots were washed under stringent conditions, using techniques standard in the art.

Mouse embryo multiple tissue Northern blot (Clontech Inc.) containing 2 µg of polyadenylated RNAs from 7, 11, 15 and 17 day postcoital (p.c.) embryos was hybridized with mouse VEGF-C cDNA fragment (base pairs 499–656). A mouse adult tissue Northern blot was hybridized with the probes for human VEGF, VEGF-B$_{167}$, VEGF-C and with a VEGFR-3 cDNA fragment (nucleotides 1–595; Genbank Acc. No. X68203).

In adult mouse tissues, both 2.4 kb and 2.0 kb mRNA signals were observed with the VEGF-C probe, at an approximately 4:1 ratio. The most conspicuous signals were obtained from lung and heart RNA, while kidney, liver, brain, and skeletal muscle had lower levels, and spleen and testis had barely visible levels (FIG. 33A). As in the human tissues, VEGF mRNA expression in adult mice was most abundant in lung and heart RNA, whereas the other samples showed less coordinate regulation with VEGF-C expression. Skeletal muscle and heart tissues gave the highest VEGF-B mRNA levels from adult mice, as previously reported Olofsson et al., *Proc. Natl. Acad. Sci. (USA)*, 93:2576–2581 (1996). Comparison with VEGFR-3 expression showed that the tissues where VEGF-C is expressed also contain mRNA for its cognate receptor tyrosine kinase, although in the adult liver VEGFR-3 mRNA was disproportionally abundant.

To provide a better insight into the regulation of the VEGF-C mRNA during embryonic development, polyadenylated RNA isolated from mouse embryos of various gestational ages (7–17 day p.c.) was hybridized with the mouse VEGF-C probe. These analyses showed that the amount of 2.4 kb VEGF-C mRNA is relatively constant throughout the gestational period (FIG. 33B).

EXAMPLE 25

Regulation of mRNAs for VEGF Family Members by Serum, Interleukin-1 and Dexamethasone in Human Fibroblasts in Culture Human IMR-90 fibroblasts were grown in DMEM medium containing 10% FCS and antibiotics. The cells were grown to 80% confluence, then starved for 48 hours in 0.5% FCS in DMEM. Thereafter, the growth medium was changed to DMEM containing 5% FCS, with or without 10 ng/ml Interleukin-1 (IL-1) and with or without 1 mM dexamethasone, as indicated in FIGS. 25A–B. The culture plates were incubated with these additions for the times indicated, and total cellular RNA was isolated using the TRIZOL kit (GIBCO-BRL). About 20 µg of total RNA from each sample was electrophoresed in 1.5% formaldehyde-agarose gels as described in Sambrook et al., supra (1989). The gel was used for Northern blotting and hybridization with radiolabeled insert DNA from the human VEGF (VEGF-A) clone (a 581 bp cDNA covering bps 57–638, Genbank Acc. No. 15997) and a human VEGF-B$_{167}$ cDNA fragment (nucleotides 1–382, Genbank Acc. No. U48800) (FIG. 25B). Subsequently, the Northern blots were probed with radiolabelled insert from the VEGF-C cDNA plasmid (FIG. 25A). Primers were labelled using a standard technique involving enzymatic extension reactions of random primers, as would be understood by one of ordinary skill in the art. The mobilities of the 28S and 18S ribosomal RNA bands are indicated, based on UV photography of ethidium bromide stained RNA before the transfer.

As can be seen in FIGS. 25A–B, very low levels of VEGF-C and VEGF-A are expressed by the starved IMR-90 cells as well as cells after 1 hour of stimulation. In contrast, abundant VEGF-B mRNA signal is visible under these conditions. After a 4 hours of serum stimulation, there is a strong induction of VEGF-C and VEGF mRNAs, which are further increased in the IL-1 treated sample. The effect of IL-1 seems to be abolished in the presence of dexamethasone. A similar pattern of enhancement is maintained in the 8 hour sample, but a gradual down-regulation of all signals occurs for both RNAs in the 24 hour and 48 hour samples. In contrast, VEGF-B mRNA levels remain constant and thus show remarkable stability throughout the time period. The results are useful in guiding efforts to use VEGF-C in methods for treating a variety of disorders.

EXAMPLE 26

Expression and Analysis of Recombinant VEGF-C

The mouse VEGF-C cDNA was expressed as a recombinant protein and the secreted protein was analyzed for its receptor binding properties. The binding of mouse VEGF-C to the human VEGFR-3 extracellular domain was studied by using media from Bosc23 cells transfected with mouse VEGF-C cDNA in a retroviral expression vector.

The 1.8 kb mouse VEGF-C cDNA was cloned as an EcoRI fragment into the retroviral expression vector pBabe-puro containing the SV40 early promoter region Morgenstern et al., *Nucl. Acids Res.*, 18:3587–3595 (1990), and transfected into the Bosc23 packaging cell line by the calcium-phosphate precipitation method Pearet et al., *Proc. Natl. Acad. Sci. (USA)*, 90:8392–8396 (1994). For comparison, Bosc23 cells also were transfected with the previously-described human VEGF-C construct in the pREP7 expression vector. The transfected cells were cultured for 48 hours prior to metabolic labelling. Cells were changed into DMEM medium devoid of cysteine and methionine, and, after 45 minutes of preincubation and medium change, Pro-mix™ L-[$^{35}$] in vitro cell labelling mix (Amersham Corp.), in the same medium, was added to a final concentration of about 120 $\mu$Ci/ml. After 6 hours of incubation, the culture medium was collected and clarified by centrifugation.

For immunoprecipation, 1 ml aliquots of the media from metabolically-labelled Bosc23 cells transfected with empty vector or mouse or human recombinant VEGF-C, respectively, were incubated overnight on ice with 2 $\mu$l of rabbit polyclonal antiserum raised against an N-terminal 17 amino acid peptide of mature human VEGF-C (H$_2$N-EETIKFAAAHYNTEILK) (SEQ ID NO: 33, residues 104–120). Thereafter, the samples were incubated with protein A sepharose for 40 minutes at 4° C. with gentle agitation. The sepharose beads were then washed twice with immunoprecipation buffer and four times with 20 mM Tris-HCl, pH 7.4. Samples were boiled in Laemmli buffer and analyzed by 12.5% sodium dodecyl sulfate polyacrylamide gel electrophoresis (SDS-PAGE).

Immunoprecipation of VEGF-C from media of transfected and metabolically-labelled cells revealed bands of approximately 30–32×10$^3$ M$_r$ (a doublet) and 22–23×10$^3$ M$_r$ in 12.5% SDS-PAGE. These bands were not detected in samples from nontransfected or mock-transfected cells as shown in FIG. 32A (i.e., lanes marked "vector"). These results show that antibodies raised against human VEGF-C recognize the corresponding mouse ligand.

For receptor binding experiments, 1 ml aliquots of media from metabolically-labelled Bosc23 cells were incubated with VEGFR-3 extracellular domain covalently coupled to sepharose for 4 hours at 4° C. with gentle mixing. The VEGFR-3 extracellular domain is described in co-owned, co-pending U.S. patent application Ser. No. 08/340,011, incorporated herein by reference. The sepharose beads were washed four times with ice-cold phosphate buffered saline (PBS), and the samples were analyzed by gel electrophoresis as described in Joukov et al., *EMBO J.*, 15:290–298 (1996).

As can be seen from FIG. 32A, similar 30–32×10$^3$ M$_r$ doublet and 22–23×10$^3$ M$_r$ polypeptide bands were obtained in the receptor binding assay as compared to the immunoprecipitation assay. Thus, mouse VEGF-C binds to human VEGFR-3. The slightly faster mobility of the mouse VEGF-C polypeptides may be caused by the four amino acid residue difference observed in sequence analysis (residues H88-E91, FIGS. 32B and 32C).

The capacity of mouse recombinant VEGF-C to induce VEGFR-3 autophosphorylation was also investigated. For the VEGFR-3 receptor stimulation experiments, subconfluent NIH 3T3-VEGFR-3 cells, Pajusola et al., *Oncogene*, 9:3545–3555 (1994), were starved overnight in serum-free medium containing 0.2% BSA. In general, the cells were stimulated with the conditioned medium from VEGF-C vector-transfected cells for 5 minutes, washed three times with cold PBS containing 200 $\mu$M vanadate, and lysed in RIPA buffer for immunoprecipation analysis. The lysates were centrifuged for 25 minutes at 16000×g and the resulting supernatants were incubated for 2 hours on ice with the specific antisera, followed by immunoprecipation using protein A-sepharose and analysis in 7% SDS-PAGE. Polypeptides were transferred to nitrocellulose and analyzed by immunoblotting using anti-phosphotyrosine (Transduction Laboratories) and anti-receptor antibodies, as described by Pajusola et al., *Oncogene*, 9:3545–3555 (1994). Filter stripping was carried out at 50° C. for 30 minutes in 100 mM 2-mercaptoethanol, 2% SDS, 62.5 mM Tris-HCl, pH 6.7, with occasional agitation. U.S. patent application Ser. No. 08/340,011. The results of the experiment are shown in FIGS. 32B and 32C. The results demonstrate that culture medium containing mouse VEGF-C stimulates the autophosphorylation of VEGFR-3 to a similar extent as human baculoviral VEGF-C or the tyrosyl phosphatase inhibitor pervanadate.

VEGFR-2 stimulation was studied in subconfluent porcine aortic endothelial (PAE) cells expressing VEGFR-2 (PAE-VEGFR-2) Waltenberger et al., *J. Biol. Chem.*, 269:26988–26995 (1994), which were starved overnight in serum-free medium containing 0.2% BSA. Stimulation was carried out and the lysates prepared as described above. For receptor immunoprecipation, specific antiserum for VEGFR-2 (Waltenberger et al., *J. Biol. Chem.*, 269:26988–26995 (1994) was used. The immunoprecipitates were analyzed as described for VEGFR-3 in 7% SDS-PAGE followed by Western blotting with anti-phosphotyrosine antibodies, stripping of the filter, and re-probing it with anti-VEGFR-2 antibodies (Santa Cruz).

Mouse VEGF-C appeared to be a potent inducer of VEGFR-3 autophosphorylation, with the 195×10$^3$ M$_r$ precursor and proteolytically cleaved 125×103 M$_r$ tyrosine kinase polypeptides of the receptor (Pajusola et al., *Oncogene*, 9.3545–3555 (1994)), being phosphorylated. VEGFR-2 stimulation was first tried with unconcentrated medium from cells expressing recombinant VEGF-C, but immunoblotting analysis did not reveal any receptor autophosphorylation.

To further determine whether mouse recombinant VEGF-C can also induce VEGFR-2 autophosphorylation as has been previously reported for human VEGF-C (Joukov et al., *EMBO J.*, 15:290–298 (1996)), PAE cells expressing VEGFR-2 were stimulated with tenfold concentrated medium from cultures transfected with mouse VEGF-C expression vector and autophosphorylation was analyzed. For comparison, cells treated with tenfold concentrated medium containing human recombinant VEGF-C (Joukov et al., (1996)), unconcentrated medium from human VEGF-C baculovirus infected insect cells, or pervanadate (a tyrosyl phosphatase inhibitor) were used. As can be seen from FIGS. 32B and 32C, in response to human baculoviral VEGF-C as well as pervanadate treatment, VEGFR-2 was prominently phosphorylated, whereas human and mouse recombinant VEGF-C gave a weak and barely detectable enhancement of autophosphorylation, respectively. Media from cell cultures transfected with empty vector or VEGF-C cloned in the antisense orientation did not induce autophosphorylation of VEGFR-2. Therefore, mouse VEGF-C binds to VEGFR-3 and activates this receptor at a much lower concentration than needed for the activation of VEGFR-2. Nevertheless, the invention comprehends methods for using the materials of the invention to take advantage of the interaction of VEGF-C with VEGFR-2, in addition to the interaction between VEGF-C and VEGFR-3.

EXAMPLE 27

VEGF-C T103-S213 Fragment Expressed in Pichia Yeast Stimulates Autophosphorylation of Flt4 (VEGFR-3) and KDR (VEGFR-2)

A truncated form of human VEGF-C cDNA was constructed wherein (1) the sequence encoding residues of the putative mature VEGF-C amino terminus $H_2N$-E(104)ETIK (SEQ ID NO: 33, residues 104 et seq.) was fused to the yeast PHO1 signal sequence, and (2) a stop codon was introduced after amino acid 213 ($H_2N$- . . . RCMS; i.e., after codon 213 of SEQ ID NO: 32). The resultant truncated cDNA construct was then inserted into the *Pichia pastoris* expression vector pHIL-S1. The engineering of this construct is schematically illustrated in FIG. 25. For the cloning, an internal BglII site in the VEGF-C coding sequence was mutated without change of the encoded polypeptide sequence.

Figure 26A:
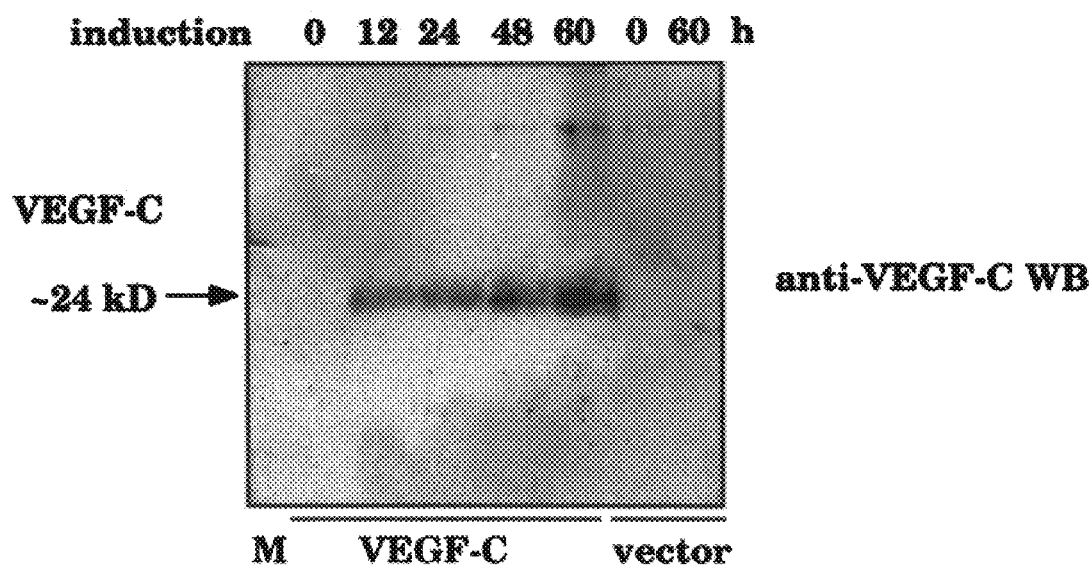
FIGS. 26A–B show VEGF-C expression in *P. pastoris* cultures transfected with a VEGF-C cDNA, with vector alone, or mock-(M) transfected, following induction with methanol for various periods of time as indicated. About 10 μl of medium was analyzed by gel electrophoresis followed by Western blotting and detection with anti-VEGF-C antiserum.

This VEGF-C expression vector was then transfected into Pichia cells and positive clones were identified by screening for the expression of VEGF-C protein in the culture medium by Western blotting. One positive clone was grown in a 50 ml culture, and induced with methanol for various periods of time from 0 to 60 hours. About 10 µl of medium was analyzed by gel electrophoresis, followed by Western blotting and detection with anti-VEGF-C antiserum, as described above. As can be seen in FIG. 26A, an approximately 24 kD polypeptide (note the band spreading due to glycosylation) accumulates in the culture medium of cells transfected with the recombinant VEGF-C construct, but not in the medium of mock-transfected cells or cells transfected with the vector alone.

Figure 26B:
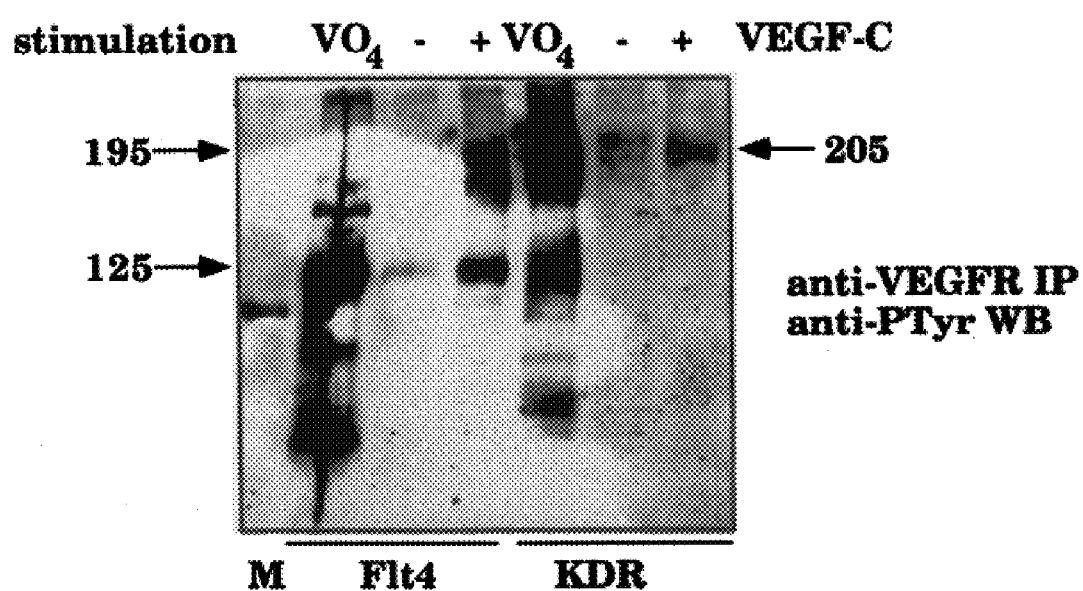

The medium containing the recombinant VEGF-C protein was concentrated by Centricon 30 kD cutoff ultrafiltration and used to stimulate NIH 3T3 expressing Flt4 (VEGFR-3) and porcine aortic endothelial (PAE) cells expressing KDR (VEGFR-2). The stimulated cells were lysed and immunoprecipitated using VEGFR-specific antisera and the immunoprecipitates were analyzed by Western blotting using anti-phosphotyrosine antibodies, chemiluminescence, and fluorography. As a positive control for maximal autophosphorylation of the VEGFRs, vanadate ($VO_4$) treatment of the cells for 10 min was used. As can be seen from the results shown in FIG. 26B, medium from Pichia cultures secreting this recombinant VEGF-C polypeptide induces autophosphorylation of both Flt4l polypeptides of 195 kD and 125 kD as well as the KDR polypeptide of about 200 kD. Vanadate, on the other hand, induces heavy tyrosyl phosphorylation of the receptor bands in addition to other bands probably coprecipitating with the receptors.

These results demonstrate that a VEGF-homologous domain of VEGF-C consisting of amino acid residues 104E -213S (SEQ ID NO: 33, residues 104–213) can be recombinantly produced in yeast and is capable of stimulating the autophosphorylation of Flt4 (VEGFR-3) and KDR (VEGFR-2). Recombinant VEGF-C fragments such as the fragment described herein, which are capable of stimulating Flt4 or KDR autophosphorylation are intended as aspects of the invention; methods of using these fragments are also within the scope of the invention.

EXAMPLE 28

Properties of the Differentially Processed Forms of VEGF-C

The following oligonucleotides were used to generate a set of VEGF-C variants:

5'-TCTCTTCTGTGCTTGAGTTGAG-3' (SEQ ID NO: 42), used to generate VEGF-C R102S (arginine mutated to serine at position 102 (SEQ ID NO: 33));

5'-TCTCTTCTGTCCCTGAGTTGAG-3' (SEQ ID NO: 43), used to generate VEGF-C R102G (arginine mutated to glycine at position 102 (SEQ ID NO: 33));

5'-TGTGCTGCAGCAAATTTTATAGTCTCTTCTGTG-GCGGCGGCGGCGGCGGGCGCCTCGCGA-GGACC-3' (SEQ ID NO: 44), used to generate VEGF-C ΔN (deletion of N-terminal propeptide corresponding to amino acids 32–102 (SEQ ID NO: 33));

5'-CTGGCAGGGAACTGCTAATAATGGAATGAA-3' (SEQ ID NO: 45), used to generate VEGF-C R226, 227S (arginine codons mutated to serines at positions 226 and 227 (SEQ ID NO: 33));

5 '-GGGCTCCGCGTCCGAGAGGTCGAGTCCG-GACTCGTGATGGT GATGGTGATGGGCGGCG-GCGGCG GCGGGCGCCTCGCGAGGACC-3' (SEQ ID NO: 46), used to generate VEGF-C NHis (this construct encodes a polypeptide with a 6xHis tag fused to the N-terminus of the secreted precursor (amino acid 32 of SEQ ID NO: 33)).

Some of the foregoing VEGF-C variant constructs were further modified to obtain additional constructs. For example, VEGF-C R102G in pALTER and oligonucleotide 5'-GTATTATAATGTCCTCCACCAAATTTTATAG-3' (SEQ ID NO: 47) were used to generate VEGF-C 4G, which encodes a polypeptide with four point mutations: R102G, A110G, A111G, and A112G (alanines mutated to glycines at positions 110–112 (SEQ ID NO: 33). These four mutations are adjacent to predicted sites of cleavage of VEGF-C expressed in PC-3 and recombinantly expressed in 293 EBNA cells.

Another construct was created using VEGF-C ΔN and oligonucleotide 5'-GTTCGCTGCCTGACACTGTGGTAGTG-TTGCTGGCGGCCGCTAGTGATGGTGATGGTGATGA-ATAATGGAATGAACTTGTCTGTAAACATCCAG-3' (SEQ ID NO: 48) to generate VEGF-C ΔNΔCHis. This construct encodes a polypeptide with a deleted N-terminal propeptide (amino acids 32–102); a deleted C-terminal propeptide (amino acids 226–419 of SEQ ID NO: 33); and an added 6xHis tag at the C-terminus.

All constructs were further digested with HindIII and NotI, subcloned into HindIII/NotI digested pREP7 vector, and used to transfect 293 EBNA cells. About 48 hours after transfection, the cells were either metabolically labelled with $^{35}$S as described above, or starved in serum-free medium for 2 days. Media were then collected and used in subsequent experiments. As can be seen from FIGS. 27A–B, wild type (wt) VEGF-C, VEGF-C NHis and VEGF-C ΔNΔCHis were expressed to similar levels in 293 EBNA cells. At the same time, expression of the VEGF-C 4G polypeptide was considerably lower, possibly due to the changed conformation and decreased stability of the translated product. However, all the above VEGF-C variants were secreted from the cells (compare FIGS. 27A and 27B). The conditioned media from the transfected and starved cells were concentrated 5-fold and used to assess their ability to stimulate tyrosine phosphorylation of Flt4 (VEGFR-3) expressed in NIH 3T3 cells and KDR (VEGFR-2) expressed in PAE cells.

Figure 28A:
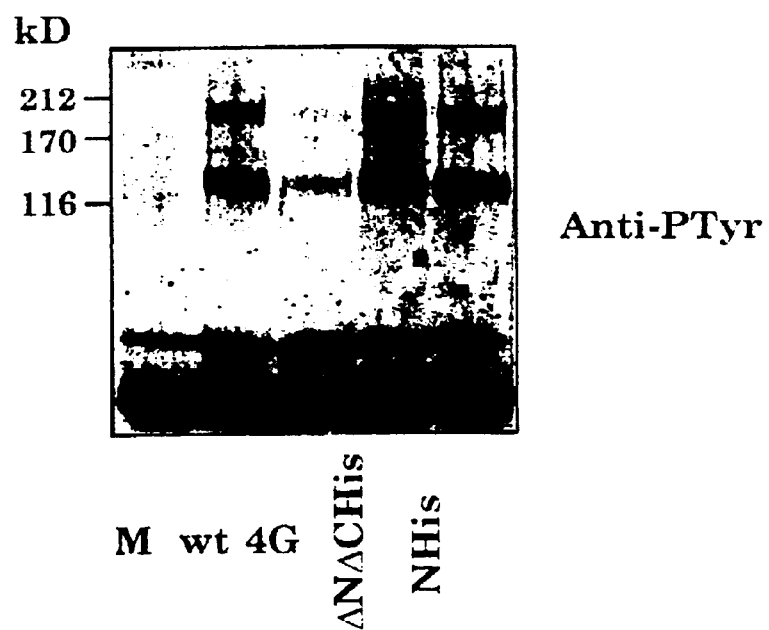
FIGS. 28A–B show Western blots of VEGFRs that were stimulated to autophosphorylate by wild type (wt) VEGF-C, as well as three VEGF-C polypeptide variants. Cell lysates (NIH 3T3 for VEGFR-3 and PAE for VEGFR-2) were subjected to receptor-specific antisera and the receptors were immunoprecipitated. Immunoprecipitates were then gel-fractionated and blotted for Western analyses. Western blots were probed with anti-phosphotyrosine antibodies.
Figure 28B:
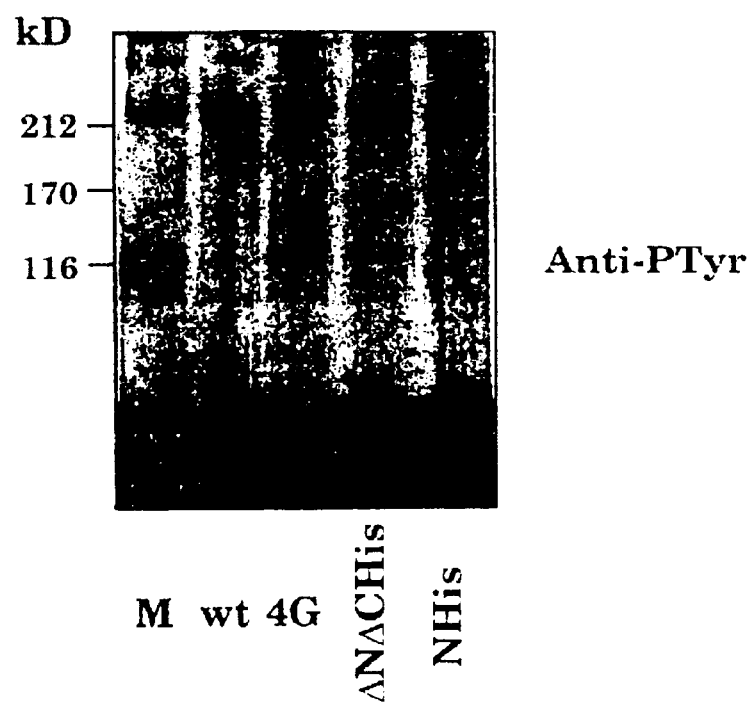
Figure 29A:
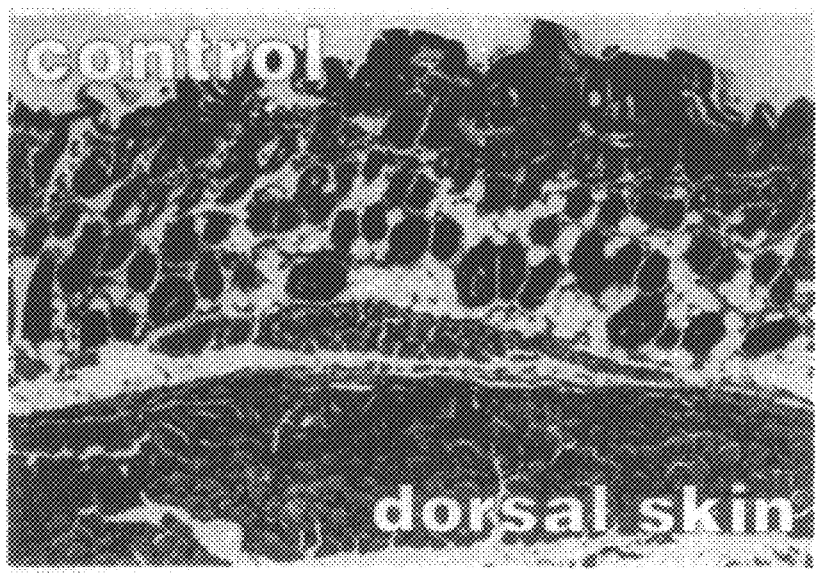
FIGS. 29A–D are photomicrographs of hematoxylin-eosin stained sections of K14-VEGF-C transgenic and control mouse littermate tissues. Areas shown are from the dorsal skin and snout, as indicated. The white arrows show the endothelium-lined margin of the lacunae devoid of red cells.
Figure 29B:
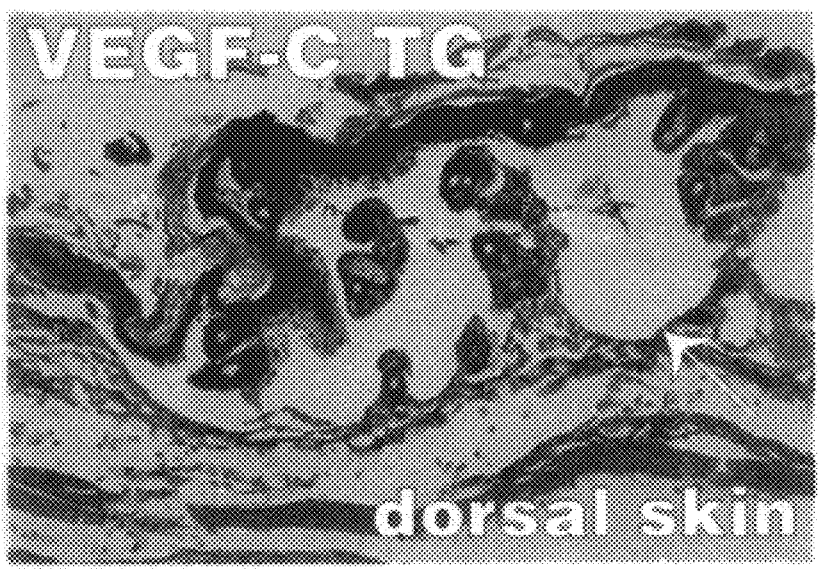
Figure 29C:
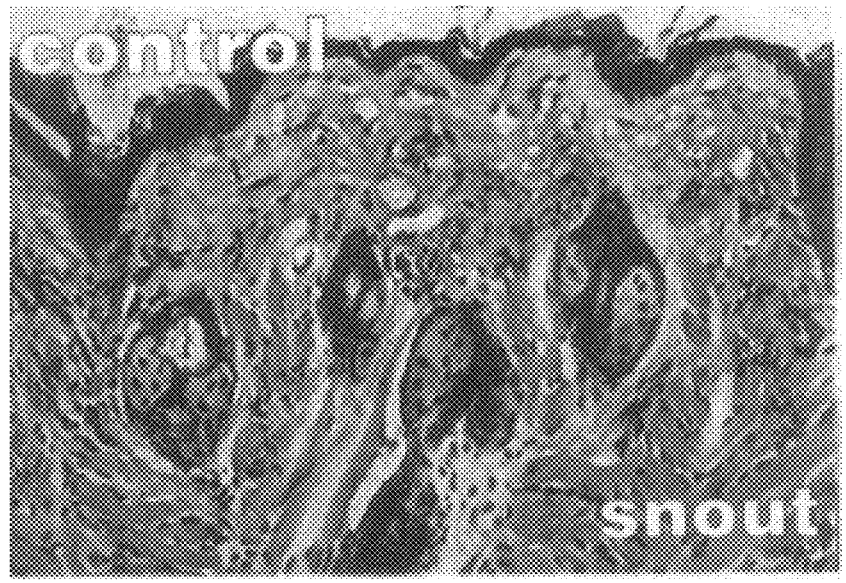
Figure 29D:
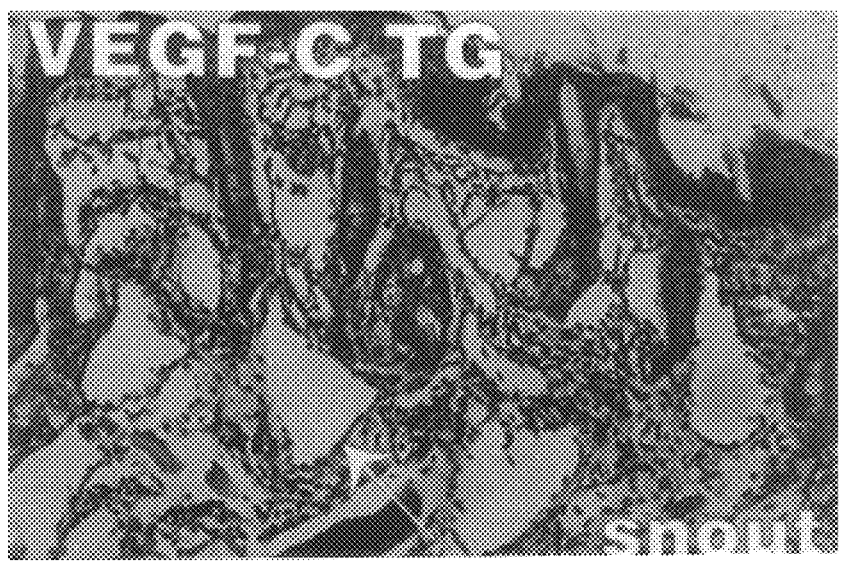
Figure 30:
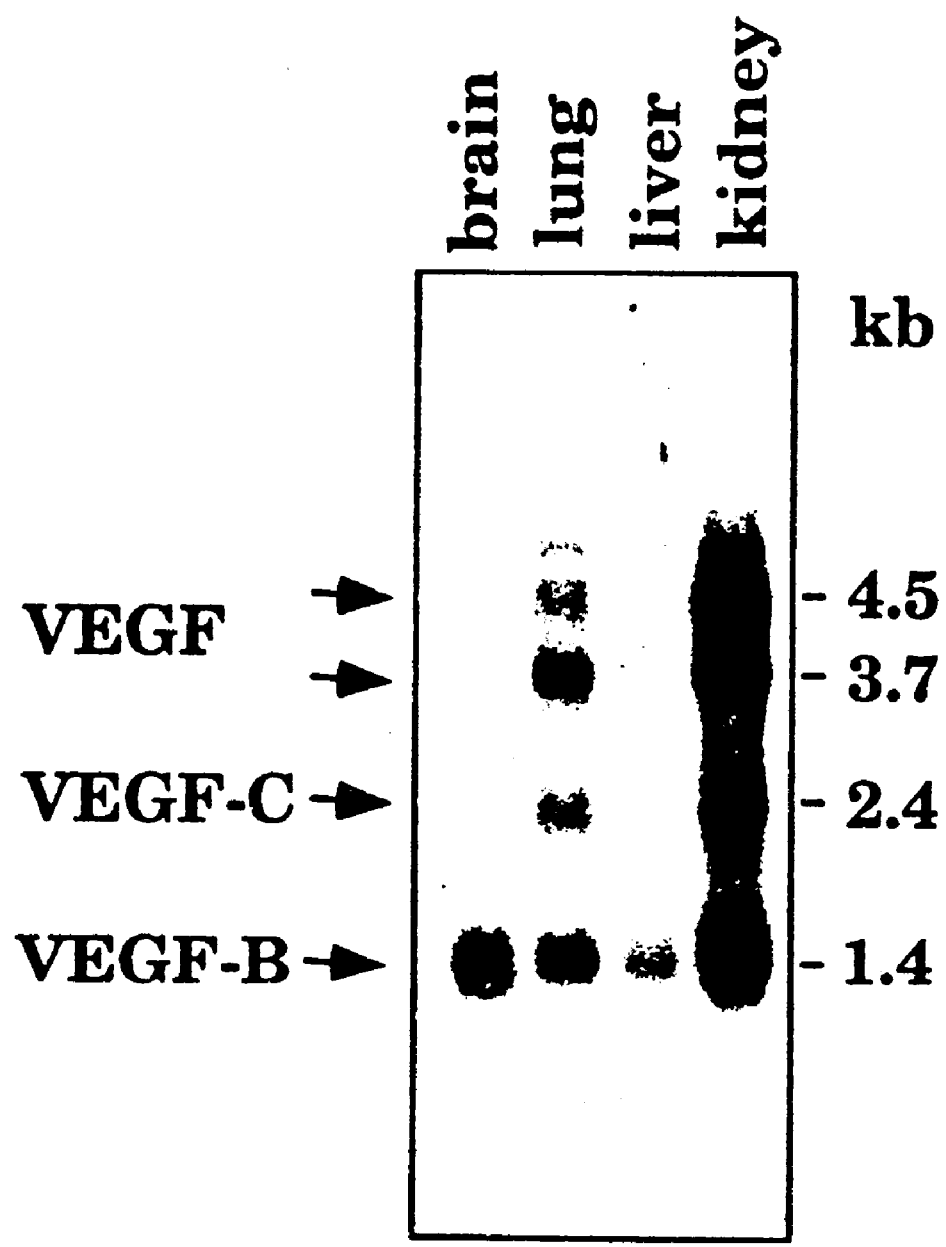
FIG. 30 presents a Northern blot of polyadenylated RNA from the indicated tissues, hybridized with a pool of VEGF, VEGF-B$_{167}$, and VEGF-C probes. Estimated transcript sizes are shown on the right in kilobases (kb).

FIGS. 28A–B show that wt VEGF-C, as well as all three mutant polypeptides, stimulate tyrosine phosphorylation of VEGFR-3. The most prominent stimulation is by the short mature VEGF-C ΔNΔCHis. This mutant, as well as VEGF-C NHis, also stimulated tyrosine phosphorylation of VEGFR-2. Thus, despite the fact that a major component of secreted recombinant VEGF-C is a dimer of 32/29 kD, the active part of VEGF-C responsible for its binding to VEGFR-3 and VEGFR-2 is localized between amino acids 102 and 226 (SEQ ID NO: 33) of the VEGF-C precursor. Analysis and comparison of binding properties and biological activities of these VEGF-C proteins and variants, using assays such as those described herein, will provide data concerning the significance of the observed major 32/29 kD and 21–23 kD VEGF-C processed forms. The data indicate that constructs encoding amino acid residues 103–225 of the VEGF-C precursor (SEQ ID NO: 33) generate a recombinant ligand that is functional for both VEGFR-3 and VEGFR-2.

The data from this and preceding examples demonstrate that numerous fragments of the VEGF-C polypeptide retain biological activity. A naturally occurring VEGF-C polypeptide spanning amino acids 103–226 (or 103–227) of SEQ ID NO: 33, produced by a natural processing cleavage defining the C-terminus, has been shown to be active. The foregoing example demonstrates that a fragment with residues 104–213 of SEQ ID NO: 33 retains biological activity.

In addition, data from Example 21 demonstrates that a VEGF-C polypeptide having its amino terminus at position 112 of SEQ ID NO: 33 retains activity. Additional experiments have shown that a fragment lacking residues 1–112 of SEQ ID NO: 33 retains biological activity.

In a related experiment, a stop codon was substituted for the lysine at position 214 of SEQ ID NO: 33 (SEQ ID NO: 32, nucleotides 991–993). The resulting recombinant polypeptide still was capable of inducing Flt4 autophosphorylation, indicating that a peptide spanning amino acid residues 113–213 of SEQ ID NO: 33 is biologically active.

Sequence comparisons of members of the VEGF family of polypeptides provides an indication that still smaller fragments of the polypeptide depicted in SEQ ID NO: 33 will retain biological activity. In particular, eight highly conserved cysteine residues of the VEGF family of polypeptides define a region from residues 131–211 of SEQ ID NO: 33 (see FIGS. 32B and 32C) of evolutionary signficance; therefore, a polypeptide spanning from about residue 131 to about residue 211 is expected to retain VEGF-C biological activity. In fact, a polypeptide which retains the conserved motif RCXXCC (e.g., a polypeptide comprising from about residue 161 to about residue 211 of SEQ ID NO: 33 is postulated to retain VEGF-C biological activity. To maintain native conformation of these fragments, it may be preferred to retain about 1–2 additional amino acids at the carboxy-terminus and 1–2 or more amino acids at the amino terminus.

Beyond the preceding considerations, evidence exists that smaller fragments and/or fragment variants which lack the conserved cysteines nonetheless will retain VEGF-C biological activity. In particular, VEGF-C that has been reduced and alkylated (processes that interfere with the chemistry of cysteine residues) retains biological activity. Consequently, the materials and methods of the invention include all VEGF-C fragments and variants that retain at least one biological activity of VEGF-C, regardless of the presence or absence of members of the conserved set of cysteine residues.

EXAMPLE 29

Expression of Human VEGF-C Under the Human K14 Keratin Promoter in Transgenic Mice Induces Abundant Growth of Lymphatic Vessels in the Skin The FLT4 receptor tyrosine kinase is relatively specifically expressed in the endothelia of lymphatic vessels. Kaipainen et al., *Proc. Natl. Acad. Sci. (USA)*, 92: 3566–3570 (1995). Furthermore, the VEGF-C growth factor stimulates the FLT4 receptor, showing at least 10 to 100 fold less activity towards the KDR receptor of blood vessels (Joukov et al., *EMBO J.*, 15: 290–298 (1996); Kukk et al., submitted for publication).

Experiments were conducted in transgenic mice to analyze the specific effects of VEGF-C overexpression in tissues. The human K14 keratin promoter is active in the basal cells of stratified squamous epithelia (Vassar et al., *Proc. Natl. Acad. Sci. (USA)*, 86:1563–1567 (1989)) and was used as the expression control element in the recombinant VEGF-C transgene. The vector containing the K14 keratin promoter is described in Vassar et al., *Genes Dev.,* 5:714–727 (1991) and Nelson et al., *J. Cell Biol.* 97:244–251 (1983).

Figure 20:
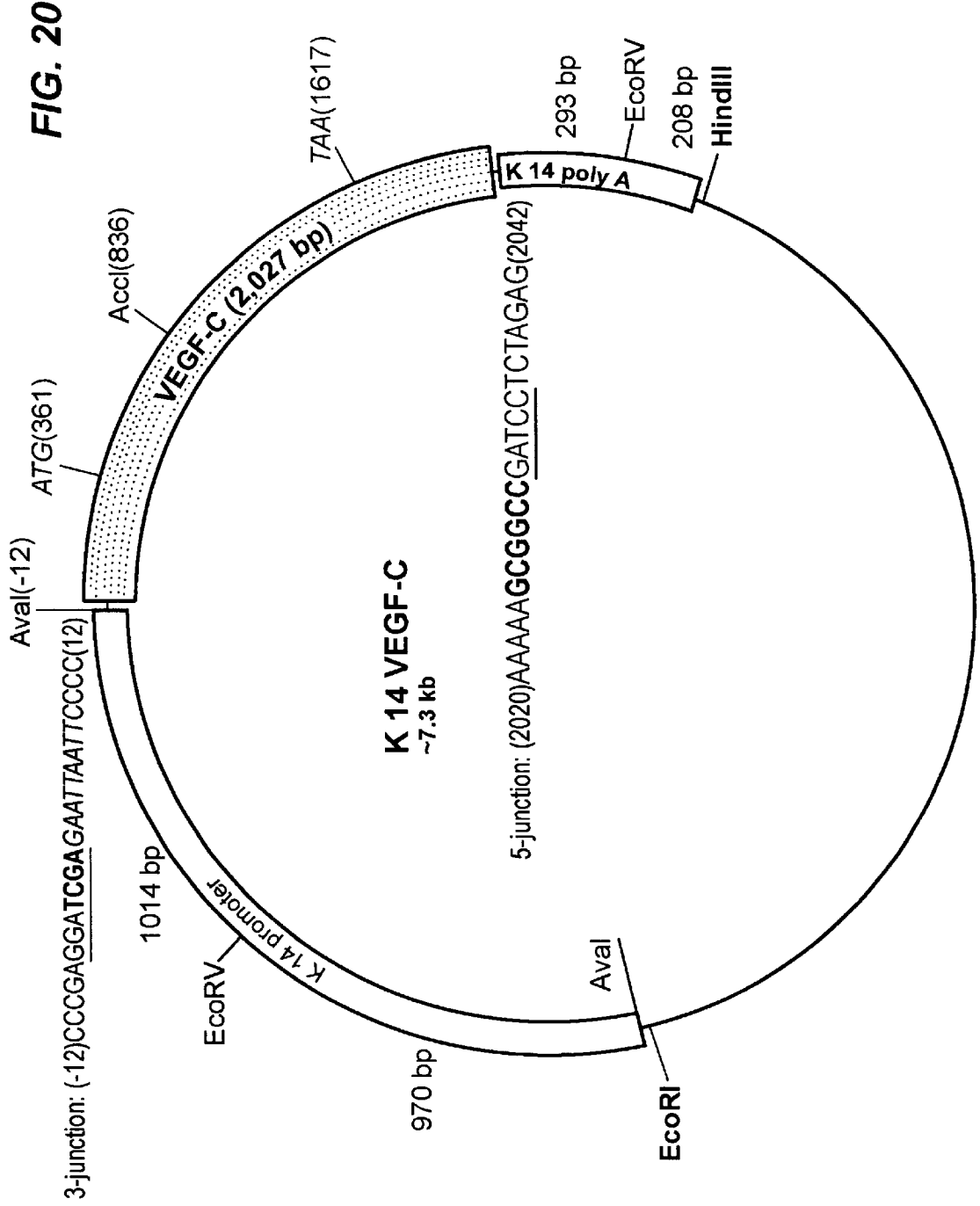
FIG. 20 is a schematic map of the K14-VEGF-C vector construct. The junction sequences depicted therein are set forth in Seq. ID. NO:51 and 52.

The recombinant VEGF-C transgene was constructed using the human full length VEGF-C cDNA (GenBank Acc. No. X94216). This sequence was excised from a pCI-neo vector (Promega) with XhoI/NotI, and the resulting 2027 base pair fragment containing the open reading frame and stop codon (nucleotides 352–1611 of SEQ ID NO: 32) was isolated. The isolated fragment was then subjected to an end-filling reaction using the Klenow fragment of DNA polymerase. The blunted fragment was then ligated to a similarly opened BamHI restriction site in the K14 vector. The resulting construct contained the EcoRI site derived from the polylinker of the pCI-neo vector. This EcoRI site was removed using standard techniques (a Klenow-mediated fill-in reaction following partial digestion of the recombinant intermediate with EcoRI) to facilitate the subsequent excision of the DNA fragment to be injected into fertilized mouse oocytes. The resulting clone, designated K14-VEGF-C, is illustrated in FIG. 20.

The EcoRI-HindIII fragment from clone K14 VEGF-C containing the K14 promoter, VEGF-C cDNA, and K14 polyadenylation signal was isolated and injected into fertilized oocytes of the FVB-NIH mouse strain. The injected zygotes were transplanted to oviducts of pseudopregnant C57BL/6×DBA/2J hybrid mice. The resulting founder mice were analyzed for the presence of the transgene by polymerase chain reaction of tail DNA using the primers: 5'-CATGTACGAACCGCCAG-3' (SEQ ID NO: 49) and 5'-AATGACCAGAGAGAGGCGAG-3' (SEQ ID NO: 50). In addition, the tail DNAs were subjected to EcoRV digestion and subsequent Southern analysis using the EcoRI-HindIII fragment injected into the mice. Out of 8 pups analyzed at 3 weeks of age, 2 were positive, having approximately 40–50 copies and 4–6 copies of the transgene in their respective genomes.

The mouse with the high copy number transgene was small, developed more slowly than its litter mates and had difficulty eating (i.e., suckling). Further examination showed a swollen, red snout and poor fur. Although fed with a special liquid diet, it suffered from edema of the upper respiratory and digestive tracts after feeding and had breathing difficulties. This mouse died eight weeks after birth and was immediately processed for histology, immunohistochemistry, and in situ hybridization.

Histological examination showed that in comparison to the skin of littermates, the dorsal dermis of K14-VEGF-C transgenic mice was atrophic and connective tissue was replaced by large lacunae devoid of red cells, but lined with a thin endothelial layer (white arrows in FIGS. 29A–D). These distended vessel-like structures resembled those seen in human lymphangiomas. The number of skin adnexal organs and hair follicles were reduced. In the snout region, an increased number of vessels was also seen. Therefore, VEGF-C overexpression in the basal epidermis is capable of promoting the growth of extensive vessel structure in the underlying skin, including large vessel lacunae. The vessel morphology indicates that VEGF-C stimulates the growth of vessels having features of lymphatic vessels.

The foregoing in vivo data indicates utilities for both (i) VEGF-C polypeptides and polypeptide variants having VEGF-C biological activity, and (ii) anti-VEGF-C antibodies and VEGF-C antagonists that inhibit VEGF-C activity (e.g., by binding VEGF-C or interfering with VEGF-C/ receptor interactions. For example, the data indicates a therapeutic utility for VEGF-C polypeptides in patients wherein growth of lymphatic tissue may be desirable (e.g., in patients following breast cancer or other surgery where lymphatic tissue has been removed and where lymphatic drainage has therefore been compromised, resulting in swelling; or in patients suffering from elephantiasis). The data indicates a therapeutic utility for anti-VEGF-C antibody substances and VEGF-C antagonists for conditions wherein growth-inhibition of lymphatic tissue may be desirable (e.g., treatment of lymphangiomas). Accordingly, methods of administering VEGF-C and VEGF-C variants and antagonists are contemplated as methods and materials of the invention.

EXAMPLE 30

Expression of VEGF-C and FLT4 in the Developing Mouse

Embryos from a 16-day post-coitus pregnant mouse were prepared and fixed in 4% paraformaldehyde (PFA), embedded in paraffin, and sectioned at 6 μm. The sections were placed on silanated microscope slides and treated with xylene, rehydrated, fixed for 20 minutes in 4% PFA, treated with proteinase K (7 mg/ml; Merck, Darmstadt, Germany) for 5 minutes at room temperature, again fixed in 4% PFA and treated with acetic anhydride, dehydrated in solutions with increasing ethanol concentrations, dried and used for in situ hybridization.

In situ hybridization of sections was performed as described (Västrik et al., *J. Cell Biol.*, 128:1197–1208 (1995)). A mouse VEGF-C antisense RNA probe was generated from linearized pBluescript II SK+ plasmid (Stratagene Inc.), containing a fragment corresponding to nucleotides 499–979 of mouse VEGF-C cDNA, where the noncoding region and the BR3P repeat were removed by Exonuclease III treatment. The fragment had been cloned into the EcoRI and HindIII sites of pBluescript II SK+. Radiolabeled RNA was synthesized using T7 RNA Polymerase and [$^{35}$S]-UTP (Amersham, Little Chalfont, UK). About two million cpm of the VEGF-C probe was applied per slide. After an overnight hybridization, the slides were washed first in 2×SSC and 20–30 mM DDT for 1 hour at 50° C. Treatment continued with a high stringency wash, 4×SSC and 20 mM DTT and 50% deionized formamide for 30 minutes at 65° C. followed by RNase A treatment (20 μg/ml) for 30 minutes at 37° C. The high stringency wash was repeated for 45 minutes. Finally, the slides were dehydrated and dried for 30 minutes at room temperature. The slides were dipped into photography emulsion and exposed for 4 weeks. Slides were developed using Kodak D-16 developer, counterstained with hematoxylin and mounted with Permount (FisherChemical).

For in situ hybridizations of Flt4 sequences, a mouse Flt4 cDNA fragment covering bp 1–192 of the published sequence (Finnerty et al., *Oncogene*, 8:2293–2298 (1993)) was used, and the above-described protocol was followed, with the following exceptions. Approximately one million cpm of the Flt4 probe were applied to each slide. The stringent washes following hybridization were performed in 1×SSC and 30 mM DTT for 105 minutes.

Figure 36D:
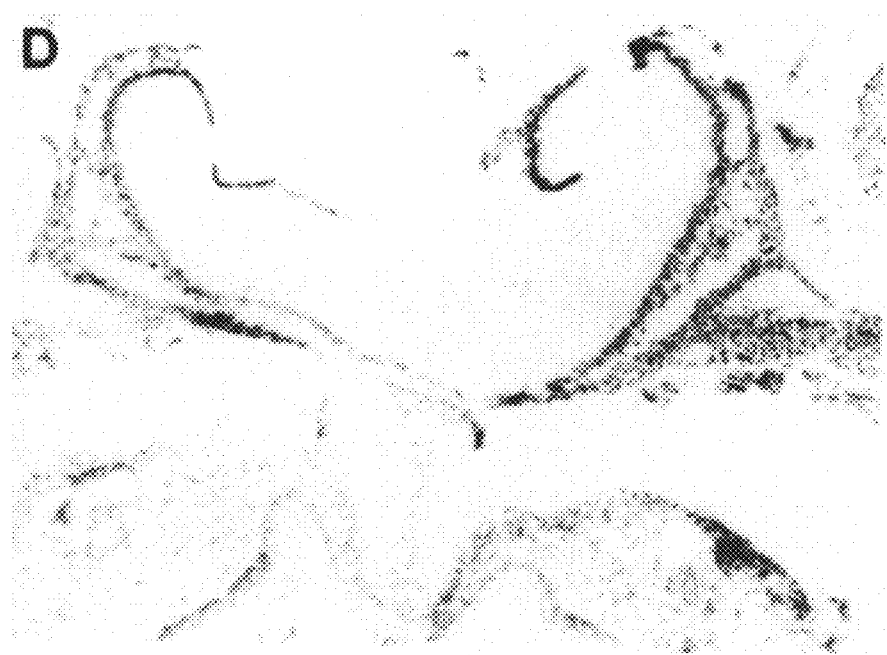

The figure shows photomicrographs of the hybridized sections in dark field microscopy (FIGS. 36A–C) and light field microscopy (FIG. 36D). Magnifications used for photography were 4× for FIGS. 36A–B and 10× for FIGS. 36C–D. The transverse sections shown are from the cephalic region and the area shown for VEGF-C and FLT4 are about 14 sections apart, FLT4 being more cranially located in the embryo. In FIG. 36A (Flt4 probe), the developing nasopharyngeal cavity is in the midline in the upper, posterior part; in the anterior part of FIG. 36A is the snout with emerging fibrissal follicles and, in the midline, the forming nasal cavity. On both sides, the retinal pigment gives a false positive signal in dark field microscopy. The most prominently FLT4-hybridizing structures appear to correspond to the developing lymphatic and venous endothelium. Note that a plexus-like endothelial vascular structure surrounds the developing nasopharyngeal mucous membrane. In FIG. 36B, the most prominent signal is obtained from the posterior part of the developing nasal conchae, which in higher magnification (FIGS. 36C–D) show the epithelium surrounding loose connective tissue/forming cartilage. This structure gives a strong in situ hybridization signal for VEGF-C. Also in FIG. 36B, more weakly hybridizing areas can be seen around the snout, although this signal is much more homogeneous in appearance. Thus, the expression of VEGF-C is strikingly high in the developing nasal conchae.

The conchae are surrounded with a rich vascular plexus, important in nasal physiology as a source for the mucus produced by the epithelial cells and for warming inhaled air. It is suggested that VEGF-C is important in the formation of the concheal venous plexus at the mucous membranes, and that it may also regulate the permeability of the vessels needed for the secretion of nasal mucus. Possibly, VEGF-C and its derivatives, and antagonists, could be used in the regulation of the turgor of the conchal tissue and mucous membranes and therefore the diameter of the upper respiratory tract, as well as the quantity and quality of mucus produced. These factors are of great clinical significance in inflammatory (including allergic) and infectious diseases of the upper respiratory tract. Accordingly, the invention contemplates the use of the materials of the invention, including VEGF-C, Flt4, and their derivatives, in methods of diagnosing and treating inflammatory and infectious conditions affecting the upper respiratory tract, including nasal structures.

DEPOSIT OF BIOLOGICAL MATERIALS

Plasmid FLT4-L has been deposited with the American Type Culture Collection (ATCC), 12301 Parklawn Dr., Rockville Md. 20952 (USA), pursuant to the provisions of the Budapest Treaty, and has been assigned a deposit date of Jul. 24, 1995 and ATCC accession number 97231.

While the present invention has been described in terms of specific embodiments, it is understood that variations and modifications will occur to those in the art. Accordingly, only such limitations as appear in the appended claims should be placed on the invention.

What is claimed is:

1. A purified and isolated polypeptide that binds to the extracellular domain of human Flt4 receptor tyrosine kinase (Flt4EC), said polypeptide including a contiguous portion of SEQ ID NO: 33 that is sufficient to bind human Flt4EC, wherein said contiguous portion includes eight cysteine residues that are conserved in human vascular endothelial growth factor (VEGF), human platelet derived growth factor A (PDGF-A), and human platelet derived growth factor B (PDGF-B), and wherein said polypeptide lacks any portion of SEQ ID NO: 33 that has one or more cysteine motifs of a Balbiani ring 3 protein (BR3P).

2. A polypeptide according to claim 1 further comprising a detectable label.

3. A composition comprising a polypeptide according to claim 1 in a pharmaceutically-acceptable diluent, adjuvant, excipient or carrier.

4. A purified and isolated mammalian polypeptide that binds to the extracellular domain of human Flt4 receptor tyrosine kinase (Flt4EC), said polypeptide including a contiguous portion of a mammalian Flt4 ligand precursor polypeptide that is sufficient to bind human Flt4EC, wherein said mammalian Flt4 ligand precursor polypeptide is encoded by a DNA which hybridizes to a non-coding strand complementary to nucleotides 352 to 1611 of SEQ ID NO: 32 under the following hybridization conditions: hybridization at 42° C. in a hybridization solution comprising 50% formamide, 5×SSC, 20 mM Na.PO$_4$, pH 6.8; and washing in 0.2×SSC at 55° C., wherein said contiguous portion includes eight cysteine residues that are conserved in human vascular endothelial growth factor (VEGF), human platelet derived growth factors A and B (PDGF-A, PDGF-B), human placenta growth factor (PlGF-1), and human vascular endothelial growth factor B (VEGF-B), and wherein said polypeptide lacks any portion of the mammalian Flt4 ligand precursor polypeptide that has one or more cysteine motifs of a Balbiani ring 3 protein (BR3P).

5. A purified and isolated polypeptide according to claim 4, said polypeptide having a molecular weight of approximately 32 kD as determined by SDS-PAGE under reducing conditions.

6. A purified and isolated polypeptide according to claim 5, wherein said polypeptide stimulates tyrosine phosphorylation of human Flt4 receptor tyrosine kinase in a host cell expressing said Flt4 receptor tyrosine kinase.

7. A purified and isolated polypeptide according to claim 5, said polypeptide comprising an amino acid sequence set forth in SEQ ID NO: 13.

8. A purified and isolated polypeptide that binds to the extracellular domain of human Flt4 receptor tyrosine kinase, said polypeptide being encoded by plasmid pFLT4-L, deposited as ATCC Accession Number 97231, said polypeptide lacking the carboxyl terminal portion of the amino acid sequence encoded by plasmid pFLT4-L that contains cysteine motifs of a Balbiani ring 3 protein (BR3P).

9. A purified and isolated polypeptide that binds to the extracellular domain of human Flt4 receptor tyrosine kinase, said polypeptide having an amino acid sequence consisting of a portion of the amino acid sequence set forth in SEQ ID NO: 33, said portion including from residue 161 of SEQ ID NO: 33 to residue 211 of SEQ ID NO: 33, said portion lacking at least carboxy-terminal residues of SEQ ID NO: 33 beyond residue 227.

10. A purified and isolated polypeptide according to claim 9 wherein said portion of the amino acid sequence set forth in SEQ ID NO: 33 includes from residue 131 of SEQ D NO: 33 to residue 211 of SEQ ID NO: 33.

11. A purified and isolated polypeptide according to claim 9 wherein said portion of the amino acid sequence set forth in SEQ ID NO: 33 includes from residue 113 of SEQ ID NO: 33 to residue 213 of SEQ ID NO: 33.

12. A purified and isolated polypeptide according to claim 9 wherein said portion of the amino acid sequence set forth in SEQ ID NO: 33 includes amino acids 103 to 217 of SEQ ID NO: 33.

13. A purified and isolated polypeptide according to claim 9 wherein said portion of the amino acid sequence set forth in SEQ ID NO: 33 includes amino acids 103 to 225 of SEQ ID NO: 33.

14. A purified and isolated polypeptide according to claim 9 wherein said portion of the amino acid sequence set forth in SEQ ID NO: 33 includes amino acids 32 to 227 of SEQ ID NO: 33.

15. A purified and isolated polypeptide that binds to the extracellular domain of human Flt4 receptor tyrosine kinase, said polypeptide comprising a portion of the amino acid sequence in SEQ ID NO: 33 effective to permit said binding, said polypeptide lacking at least carboxy-terminal residues of SEQ ID NO: 33 beyond residue 227.

16. A polypeptide according to claim 15 wherein said portion of the amino acid sequence in SEQ ID NO: 33 is a continuous portion having as its amino terminal residue an amino acid between residues 30 and 162 of SEQ ID NO: 33 and having as its carboxy terminal residue an amino acid between residues 210 and 228 of SEQ ID NO: 33.

17. A polypeptide according to claim 15 wherein said portion of the amino acid sequence in SEQ ID NO: 33 is a continuous portion having as its amino terminal residue an amino acid between residues 102 and 132 of SEQ ID NO: 33 and having as its carboxy terminal residue an amino acid between residues 210 and 228 of SEQ ID NO: 33.

18. A polypeptide according to claim 15 wherein said portion of the amino acid sequence in SEQ ID NO: 33 is a continuous portion having, as its amino terminal residue, residue 103 of SEQ ID NO: 33; and having, as its carboxy terminal residue, an amino acid between residues 216 and 228 of SEQ ID NO: 33.

19. A purified protein comprising a first polypeptide linked to a second polypeptide, wherein at least one of said first polypeptide and said second polypeptide is a polypeptide according to claim 15, 16, 17, or 18, and wherein said purified protein binds to the extracellular domain of Flt4 receptor tyrosine kinase.

20. A purified protein comprising a first polypeptide linked to a second polypeptide, wherein each of said first polypeptide and said second polypeptide is a polypeptide according to claim 15, 16, 17, or 18, and wherein said purified protein binds to the extracellular domain of Flt4 receptor tyrosine kinase.

21. A polypeptide according to any one of claims 15–18, wherein said polypeptide further includes a polyhistidine amino acid sequence.

22. A polypeptide according to claim 15 having an apparent molecular weight of approximately 32 kD as assessed by SDS-PAGE under reducing conditions.

23. A polypeptide according to claim 15 that binds the extracellular domain of Flt4 receptor tyrosine kinase and stimules Flt4 phosphorylation in mammalian cells expressing Flt4 receptor tyrosine kinase.

24. A purified and isolated polypeptide according to claim 15 wherein said portion of the amino acid sequence in SEQ ID NO: 33 is a continuous portion having, as its amino terminal residue, residue 103 of SEQ ID NO: 33; and having, as its carboxyl terminal residue, an amino acid between residues 221 and 228 of SEQ ID NO: 33.

25. A purified polypeptide according to claim 15, wherein the amino acid sequence of said polypeptide consists of a portion of the amino acid sequence in SEQ ID NO: 33.

26. A purified polypeptide according to claim 25 wherein said polypeptide has an apparent molecular weight of approximately 21–23 kD as assessed by SDS-PAGE under reducing conditions.

27. A purified polypeptide according to claim 25 wherein said polypeptide has an apparent molecular weight of about 32 kD as assessed by SDS-PAGE under reducing conditions.

28. A purified protein comprising a first polypeptide linked to a second polypeptide, wherein at least one of said first polypeptide and said second polypeptide is a polypeptide according to claim 25, and wherein said protein is capable of binding to the extracellular domain of human Flt4 receptor tyrosine kinase.

29. A purified protein according to claim 28 wherein said first polypeptide is covalently linked to said second polypeptide.

30. A purified protein according to claim 28 wherein the amino acid sequence of at least one of said first polypeptide and said second polypeptide is an amino acid sequence selected from the group consisting of:

(a) amino acids 161 to 211 of SEQ ID NO: 33;
(b) amino acids 131 to 211 of SEQ ID NO: 33;
(c) amino acids 113 to 213 of SEQ ID NO: 33;
(d) amino acids 113 to 227 of SEQ ID NO: 33;

(e) amino acids 103 to 217 of SEQ ID NO: 33;
(f) amino acids 103 to 225 of SEQ ID NO: 33;
(g) amino acids 103 to 227 of SEQ ID NO: 33; and
(h) amino acids 32 to 227 of SEQ ID NO: 33.

31. A purified protein according to claim 28 wherein the amino acid sequences of said fist polypeptide and said second polypeptide are selected from the group consisting of:
(a) amino acids 161 to 211 of SEQ ID NO: 33;
(b) amino acids 131 to 211 of SEQ ID NO: 33;
(c) amino acids 113 to 213 of SEQ ID NO: 33;
(d) amino acids 113 to 227 of SEQ ID NO: 33;
(e) amino acids 103 to 217 of SEQ ID NO: 33,
(e) amino acids 103 to 225 of SEQ ID NO: 33;
(g) amino acids 103 to 227 of SEQ ID NO: 33;
(g) amino acids 32 to 227 of SEQ ID NO: 33; and
(i) amino acids 228 to 419 of SEQ ID NO: 33.

32. A purified and isolated polypeptide that binds to the extracellular domain of human Flt4 receptor tyrosine kinase, said polypeptide comprising a portion of SEQ ID NO: 33 effective to permit said binding, said portion of SEQ ID NO: 33 lacking at least carboxy terminal residues of SEQ ID NO: 33 having cysteine motifs of a Balbiani ring 3 protein.

33. A purified polypeptide that binds to the extracellular domain of human Flt4 receptor tyrosine kinase, said polypeptide produced by a method comprising the steps of:
(a) expressing a nucleic acid in a host cell; and
(b) purifying a polypeptide that binds to the extracellular domain of human Flt4 receptor tyrosine kinase from said host cell or from a growth medium of said host cell;
wherein said nucleic acid comprises a nucleotide sequence encoding a portion of the amino acid sequence in SEQ ID NO: 33 effective to permit such binding, and wherein said polypeptide lacks at least the carboxy-terminal portion of SEQ ID NO: 33 that is characterized by cysteine motifs of a Balbiani ring 3 protein.

34. A purified and isolated polypeptide according to claim 33, wherein said purifying comprises an affinity purification procedure wherein the affinity purification matrix comprises a polypeptide comprising the extracellular domain of Flt4 receptor tyrosine kinase.

35. A polypeptide according to claim 33, that has an apparent molecular weight of approximately 32 kD as assessed by SES-PAGE under reducing conditions.

36. A polypeptide according to claim 33 wherein said portion of the amino acid sequence in SEQ ID NO: 33 encoded by said polynucleotide is a continuous portion having as its amino terminal residue an amino acid between residues 30 and 162 of SEQ ID NO: 33 and having as its carboxy terminal residue an amino acid between residues 210 and 228 of SEQ ID NO: 33.

37. A polypeptide according to claim 33 wherein said portion of the amino acid sequence in SEQ ID NO: 33 encoded by said polynucleotide is a continuous portion having as its amino terminal residue an amino acid between residues 102 and 132 of SEQ ID NO: 33 and having as its carboxy terminal residue an amino acid between residues 210 and 228 of SEQ ID NO: 33.

38. A polypeptide according to claim 33 wherein said portion of the amino acid sequence in SEQ ID NO: 33 encoded by said polynucleotide is a continuous portion having, as its amino terminal residue, residue 103 of SEQ ID NO: 33, and having, as its carboxy terminal residue, an amino acid between residues 216 and 228 of SEQ ID NO: 33.

39. A purified and isolated polypeptide having the amino acid sequence of residues 1 to 415 of SEQ ID NO: 41.

40. A purified and isolated polypeptide that binds to the extracellular domain of an Flt4 receptor tyrosine kinase, said polypeptide comprising a contiguous portion of the amino acid sequence of SEQ ID NO: 41 effective to permit such binding,
said contiguous portion including eight cysteine residues of SEQ ID NO: 41 that are conserved in human vascular endothelial growth factor (VEGF), human platelet derived growth factors A and B (PDGF-A, PDGF-B), human placenta growth factor (PlGF-1), and human vascular endothelial growth factor B (VEGF-B).

41. A purified polypeptide that binds to the extracellular domain of human Flt4 receptor tyrosine kinase, said polypeptide produced by a method comprising the steps of:
(a) expressing a nucleic acid in a host cell, said nucleic acid comprising a nucleotide sequence encoding a portion of the amino acid sequence in SEQ ID NO: 41 effective to permit such binding; and
(b) purifying a polypeptide that binds to the extracellular domain of human Flt4 receptor tyrosine kinase from said host cell or from a growth medium of said host cell, wherein said polypeptide lacks at least the carboxy-terminal portion of SEQ ID NO: 41 that is characterized by cysteine motifs of a Balbiani ring 3 protein.

42. A composition comprising a polypeptide according to any one of claims 4, 8–11, 15–18, 24, 32, 33, and 36–37 in a pharmaceutically-acceptable diluent, adjuvant, excipient, or carrier.

43. A method of modulating the activity of human Flt4 receptor tyrosine kinase comprising administering to a person in need of modulation of Flt4 receptor tyrosine kinase activity a composition according to claim 42.

44. A method of modulating the activity of human Flt4 receptor tyrosine kinase comprising contacting cells that express human Flt4 receptor tyrosine kinase with a polypeptide according to any one of claims 4, 8–11, 15–18, 24, 32, 33 and 36–37.

45. A method of modulating the growth of mammalian endothelial cells comprising the steps of:
exposing mammalian endothelial cells to a polypeptide according to any one of claims 4, 8–11, 15–18, 24, 32, 33 and 36–37, in an amount effective to modulate the growth of mammalian endothelial cells, wherein the mammalian endothelial cells comprise cells that express Flt4 receptor tyrosine kinase.

46. A method for detecting endothelial cells that express Flt4 in a biological tissue comprising the steps of
exposing a biological tissue comprising endothelial cells to a polypeptide according to any one of claims 4, 8–11, 15–18, 24, 32, 33 and 36–37, under conditions wherein said polypeptide binds to endothelial cells; and
detecting said polypeptide bound to endothelial cells in said biological tissue, thereby detecting said endothelial cells.

* * * * *